United States Patent
Haynes et al.

(10) Patent No.: US 10,344,077 B2
(45) Date of Patent: Jul. 9, 2019

(54) HIV-1 NEUTRALIZING ANTIBODIES AND USES THEREOF (V3 ANTIBODIES)

(71) Applicant: Duke University, Durham, NC (US)

(72) Inventors: Barton F. Haynes, Durham, NC (US); Ryan Meyerhoff, Durham, NC (US); M. Anthony Moody, Durham, NC (US); Hua-Xin Liao, Durham, NC (US); Todd Bradley, Durham, NC (US); Mattia Bonsignori, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

(21) Appl. No.: 15/559,361

(22) PCT Filed: Mar. 21, 2016

(86) PCT No.: PCT/US2016/023380
§ 371 (c)(1),
(2) Date: Sep. 18, 2017

(87) PCT Pub. No.: WO2016/149698
PCT Pub. Date: Sep. 22, 2016

(65) Prior Publication Data
US 2018/0072797 A1    Mar. 15, 2018

Related U.S. Application Data

(60) Provisional application No. 62/261,233, filed on Nov. 30, 2015, provisional application No. 62/260,100, filed on Nov. 25, 2015, provisional application No. 62/222,175, filed on Sep. 22, 2015, provisional application No. 62/191,054, filed on Jul. 10, 2015, provisional application No. 62/135,309, filed on Mar. 19, 2015.

(51) Int. Cl.
*A61K 48/00* (2006.01)
*C07K 16/10* (2006.01)
*A61K 39/00* (2006.01)

(52) U.S. Cl.
CPC .......... *C07K 16/1063* (2013.01); *A61K 48/00* (2013.01); *A61K 2039/505* (2013.01); *C07K 2317/21* (2013.01); *C07K 2317/30* (2013.01); *C07K 2317/31* (2013.01); *C07K 2317/52* (2013.01); *C07K 2317/56* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,458,704 B2 | 12/2008 | Naoi | |
| 8,637,036 B2 * | 1/2014 | Mascola | C07K 16/1063 424/160.1 |
| 8,784,821 B1 | 7/2014 | Kufer et al. | |
| 8,795,667 B2 | 8/2014 | Johnson et al. | |
| 2005/0037000 A1 | 2/2005 | Stavenhagen et al. | |
| 2005/0064514 A1 | 3/2005 | Stavenhagen et al. | |
| 2009/0060910 A1 | 3/2009 | Johnson et al. | |
| 2010/0093979 A1 | 4/2010 | Lazar | |
| 2010/0174053 A1 | 7/2010 | Johnson et al. | |
| 2011/0081347 A1 | 4/2011 | Gorlatov | |
| 2012/0237523 A1 | 9/2012 | Mascola et al. | |
| 2013/0295121 A1 | 11/2013 | Johnson et al. | |
| 2014/0088295 A1 | 3/2014 | Smith et al. | |
| 2014/0099318 A1 | 4/2014 | Huang et al. | |
| 2014/0170149 A1 | 6/2014 | Neijssen et al. | |
| 2014/0205607 A1 | 7/2014 | Mascola et al. | |
| 2014/0206846 A1 | 7/2014 | Beckmann | |
| 2014/0314784 A1 | 10/2014 | Bedian et al. | |
| 2014/0328836 A1 | 11/2014 | Johnson et al. | |
| 2015/0152183 A1 | 6/2015 | Chamberlain et al. | |

FOREIGN PATENT DOCUMENTS

| | | | |
|---|---|---|---|
| EP | 2158221 A2 | 3/2010 | |
| EP | 2376109 A1 | 10/2011 | |
| EP | 2601216 B1 | 6/2013 | |
| EP | 2714079 B1 | 4/2014 | |
| WO | WO-2004/063351 A2 | 7/2004 | |
| WO | WO-2010/080538 A1 | 7/2010 | |
| WO | WO-2011/038290 A2 | 3/2011 | |
| WO | WO-2012/018687 A1 | 2/2012 | |
| WO | WO-2012/162068 A2 | 11/2012 | |
| WO | WO-2014/063059 A1 | 4/2014 | |
| WO | WO-2014/159940 A1 | 10/2014 | |
| WO | WO-2014/172366 A1 | 10/2014 | |
| WO | WO2014/172366 A1 * | 10/2014 | ............ C07K 19/00 |
| WO | WO-2015/021089 A1 | 2/2015 | |
| WO | WO-2015/026892 A1 | 2/2015 | |
| WO | WO-2015/026894 A2 | 2/2015 | |
| WO | WO-2016/149698 A2 | 9/2016 | |
| WO | WO-2016/196975 A1 | 12/2016 | |

OTHER PUBLICATIONS

Emini et al. (Nature, 1992, vol. 355, p. 728-730).*
Watkins et al. (PLoS, 2011, p. 1-7).*
Wardemann, H., et al., "Predominant Autoantibody Production by Early Human B Cell Precursors," Science, vol. 301, pp. 1374-1377, 5 pages total (2003).
Altschul, S. F., et al., "Basic Local Alignment Search Tool," Journal of Molecular Biology, vol. 215, pp. 403-410 (May 15, 1990).
Altschul, S. F., et al., "Issues in Searching Molecular Sequence Ddatabases," Nature Genetics, vol. 6, pp. 119-129 (Feb. 1994).
Atwell, S., et al., "Stable Heterodimers from Remodeling the Domain Interface of a Homodimer Using a Phage Display Library," Journal of Molecular Biology, vol. 270, pp. 26-35 (Apr. 25, 1997).
Bai, S., et al., "A Guide to Rational Dosing of Monoclonal Antibodies," Clinical Pharmacokinetics, vol. 51, No. 2, pp. 119-135 (Feb. 2012).
Barouch, D. H., et al., "Therapeutic Efficacy of Potent Neutralizing HIV-1-Specific Monoclonal Antibodies in SHIV-Infected Rhesus Monkeys," Nature, vol. 503, No. 7475, pp. 224-228 (Nov. 14, 2013)—Author Manuscript—24 total pages.

(Continued)

*Primary Examiner* — Agnieszka Boesen
(74) *Attorney, Agent, or Firm* — Wilmer Cutler Pickering Hale and Dorr LLP

(57) ABSTRACT

The invention is directed to HIV-1 neutralizing antibodies, CD4 binding site and V3 glycan antibodies, and methods for their uses.

24 Claims, 84 Drawing Sheets

Specification includes a Sequence Listing.

(56) References Cited

OTHER PUBLICATIONS

Bird, R. E., et al., "Single-Chain Antigen-Binding Proteins," Science, vol. 242, pp. 423-426 (Oct. 21, 1988).
Bonsignori, M., et al., "An Autoreactive Antibody from an SLE/HIV-1 Individual Broadly Neutralizes HIV-1," Journal of Clinical Investigation, vol. 124, No. 4, pp. 1835-1843 (Apr. 2014).
Bonsignori, M., et al., "Analysis of a Clonal Lineage of HIV-1 Envelope V2/V3 Conformational Epitope-Specific Broadly Neutralizing Antibodies and Their Inferred Unmutated Common Ancestors," Journal of Virology, vol. 85, No. 19, pp. 9998-10009 (Oct. 2011).
Byrne, H., et al., "A Tale of Two Specificities: Bispecific Antibodies for Therapeutic and Diagnostic Applications," Trends in Biotechnology, vol. 31, No. 11, pp. 621-632 (Nov. 2013).
Chen, K. S., et al, "Monoclonal Antibody Therapy for Malignant Glioma," Glioma, Advances in Experimental Medicine and Biology, Editor R. Yamanaka, vol. 746, pp. 121-141, 39 total pages (2012).
Chen, Y., et al., "Development of Polyether Urethane Intravaginal Rings for the Sustained Delivery of Hydroxychloroquine," Drug Design, Development and Therapy, vol. 8, pp. 1801-1815 (2014).
Chuang, G., et al., "Eliminating Antibody Polyreactivity Through Addition of N-Linked Glycosylation," Protein Science, vol. 24, pp. 1019-1030 (Mar. 2, 2015).
Corpet, F., "Multiple Sequence Alignment with Hierarchical Clustering," Nucleic Acids Research, vol. 16, No. 22, pp. 10881-10890 (Nov. 25, 1988).
Costa, et al., "Guidelines to cell engineering for monoclonal antibody production," European Journal of Pharmaceutics and Biopharmaceutics, vol. 74, No. 2, pp. 127-138 (Feb. 2010).
Doria-Rose, N. A., "HIV Neutralizing Antibodies: Clinical Correlates and Implications for Vaccines" The Journal of Infectious Diseases, vol. 201, No. 7, pp. 981-983 (Apr. 1, 2010).
Fahrner, R. L., et al., "Industrial Purification of Pharmaceutical Antibodies: Development, Operation, and Validation of Chromatography Processes," Biotechnology and Genetic Engineering Reviews, vol. 18, No. 1, pp. 301-327 (Jul. 18, 2001).
Gao, F., et al., "Cooperation of B Cell Lineages in Induction of HIV-1-Broadly Neutralizing Antibodies," Cell, vol. 158, No. 3, pp. 481-491 (Jul. 31, 2014)—Author Manuscript—15 total pages.
Garber, K., "Bispecific Antibodies Rise Again," Nature Reviews—Drug Discovery, vol. 13, pp. 799-801 (Nov. 2014).
Genbank Accession No. AGG22572.1, "immunoglobulin lambda light chain variable region, partial [*Homo sapiens*]", last downloaded from https://www.ncbi.nlm.nih.gov/ on Aug. 29, 2016 (1 total page).
Georgiev, I. S., et al., "Delineating Antibody Recognition in Polyclonal Sera from Patterns of HIV-1 Isolate Neutralization," Science, vol. 340, No. 6133, pp. 751-756, 7 total pages, DOI: 10.1126/science. 1233989 (May 10, 2013).
Hladik, F., et al., "Mucosal effects of tenofovir 1% gel," eLife, vol. 4, pp. 1-21 (Feb. 3, 2015).
Holliger, P. et al., "Specific Killing of Lymphoma Cells by Cytotoxic T-Cells Mediated by a Bispecific Diabody," Protein Engineering, vol. 9, No. 3, pp. 299-305 (1996).
Huston, J. S., et al., "Protein Engineering of Antibody Binding Sites: Recovery of Specific Activity in an Anti-Digoxin Single-Chain Fv Analogue Produced in *Escherichia coli*," Proceedings of the National Academy of Sciences of the United States of America, vol. 85, pp. 5879-5883 (Aug. 1988).
International Search Report and Written Opinion issued by United States Patent and Trademark Office for PCT/US2016/023380 dated Sep. 16, 2016 (11 total pages).
Kepler, T. B., "Reconstructing a B-Cell Clonal Lineage. I. Statistical Inference of Unobserved Ancestors," F1000Research, vol. 2, No. 103, pp. 1-12 (Apr. 3, 2013).
Kepler, T. B., et al., "Reconstructing a B-Cell Clonal Lineage. II. Mutation, Selection, and Affinity Maturation," Frontiers in Immunology, vol. 5, No. 170, pp. 1-10 (Apr. 22, 2014).
Kim, J. Y., et al., "CHO Cells in Biotechnology for Production of Recombinant Proteins: Current State and Further Potential," Applied Microbiology and Biotechnology, vol. 93, No. 3, pp. 917-930 (Feb. 2012).
Kipriyanov, S. M., et al., "Bispecific Tandem Diabody for Tumor Therapy with Improved Antigen Binding and Pharmacokinetics," Journal of Molecular Biology, vol. 293, No. 1, pp. 41-56 (Oct. 15, 1999).
Ko, S.-Y., et al., "Enhanced Neonatal Fc Receptor Function Improves Protection Against Primate SHIV Infection," Nature, vol. 514, No. 7524, pp. 642-645, (Oct. 30, 2014)—Author Manuscript—22 total pages.
Kostelny, S. A., et al., "Formation of a Bispecific Antibody by the use of Leucine Zippers," Journal of Immunology, vol. 148, No. 5, pp. 1547-1553 (Mar. 1, 1992).
Kuo, T. T., et al., "Neonatal Fc Receptor and IgG-based Therapeutics," mAbs, vol. 3, No. 5, pp. 422-430 (2011).
Li, M., et al., "Human Immunodeficiency Virus Type 1 env Clones from Acute and Early Subtype B Infections for Standardized Assessments of Vaccine-Elicited Neutralizing Antibodies," Journal of Virology, vol. 79, No. 16, pp. 10108-10125 (Aug. 2005).
Liao, H.-X., et al., "Co-Evolution of a Broadly Neutralizing HIV-1 Antibody and Founder Virus," Nature, vol. 496, No. 7446, pp. 469-476 (Apr. 25, 2013)—Author Manuscript—25 total pages.
Liao, H.-X., et al., "High-Throughput Isolation of Immunoglobulin Genes from Single Human B Cells and Expression as Monoclonal Antibodies," Journal of Virological Methods, vol. 158, Nos. 1-2, pp. 171-179, (Jun. 2009)—Author Manuscript—22 total pages.
Liao, H.-X., et al., "Initial Antibodies Binding to HIV-1 gp41 in Acutely Infected Subjects are Polyreactive and Highly Mutated," The Journal of Experimental Medicine, vol. 208, No. 11, pp. 2237-2249, 10 total pages (Oct. 24, 2011).
Liu, M., et al., "Polyreactivity and Autoreactivity among HIV-1 Antibodies," Journal of Virology, vol. 89, No. 1, doi:10.1128/JVI. 02378-14, pp. 784-798 (Jan. 2015).
Malcolm, R. K., et al., "Beyond HIV Microbicides: Multipurpose Prevention Technology Products," BJOG Royal College of Obstetricians and Gynaecologists, vol. 121, Suppl. 5, pp. 62-69 (Oct. 2014).
Mascola, J. R., et al., "HIV-1 Neutralizing Antibodies: Understanding Nature's Pathways," Immunological Reviews, vol. 254, No. 1, pp. 225-244, 29 total pages (Jul. 2013).
McCafferty, J., et al., "Phage Antibodies: Filamentous Phage Displaying Antibody Variable Domains," Nature, vol. 348, pp. 552-554 (Dec. 6, 1990).
Moldt, B., et al., "A Nonfucosylated Variant of the Anti-HIV-1 Monoclonal Antibody b12 Has Enhanced FcγRIIIa-Mediated Antiviral Activity In Vitro but Does Not Improve Protection Against Mucosal SHIV Challenge in Macaques," Journal of Virology, vol. 86, No. 11, pp. 6189-6196, (Jun. 2012).
Montefiori, D. C., "Chapter 26: Measuring HIV Neutralization in a Luciferase Reporter Gene Assay," HIV Protocols, Second Edition, vol. 485, pp. 395-405 (2009).
Moore, P. A., et al., "Application of Dual Affinity Retargeting Molecules to Achieve Optimal Redirected T-cell Killing of B-cell Lymphoma," Blood Journal, vol. 117, No. 17, pp. 4542-4551 (Apr. 28, 2011).
Nagorsen, D., et al., "Immunomodulatory Therapy of Cancer with T Cell-Engaging BiTE Antibody Blinatumomab," Experimental Cell Research, vol. 317, No. 9, pp. 1255-1260 (published online Mar. 16, 2011).
Needleman, S. B., et al., "A General Method Applicable to the Search for Similarities in the Amino Acid Sequence of Two Proteins," Journal of Molecular Biology, vol. 48, No. 3, pp. 443-453 (Mar. 28, 1970).
Pearson, W. R., et al., "Improved Tools for Biological Sequence Comparison," Proceedings of the National Academy of Sciences of the United States of America, vol. 85, No. 8, pp. 2444-2448 (Apr. 1988).
Ridgway, J. B. B., et al., "'Knobs-Into-Holes' Engineering of Antibody $C_H3$ Domains for Heavy Chain Heterodimerization," Protein Engineering, vol. 9, No. 7, pp. 617-621 (1996).

(56) References Cited

OTHER PUBLICATIONS

Robbie, G. J., et al., "A Novel Investigational Fe-Modified Humanized Monoclonal Antibody, Motavizumab-YTE, Has an Extended Half-Life in Healthy Adults," Antimicrobial Agents and Chemotherapy, vol. 57, No. 12, pp. 6147-6153 (Dec. 2013).
Romain, G., et al., "Antibody Fc Engineering Improves Frequency and Promotes Kinetic Boosting of Serial Killing Mediated by NK Cells," Blood Journal, vol. 124, No. 22, pp. 3241-3249, (Nov. 20, 2014).
Rouet, R., et al., "Bispecific Antibodies with Native Chain Structure," Nature Biotechnology, vol. 32, No. 2, 136-137 (Feb. 2014).
Rudicell, R. S., et al., "Enhanced Potency of a Broadly Neutralizing HIV-I Antibody in Vitro Improves Protection against Lentiviral Infection In Vivo," Journal of Virology, vol. 88, No. 21, pp. 12669-12682 (Nov. 2014).
Sarzotti-Kelsoe, M., et al., "Optimization and Validation of the TZM-bl Assay for Standardized Assessments of Neutralizing Antibodies Against HIV-1," Journal of Immunoligical Methods, vol. 409, pp. 131-146 (Jul. 2014)—Author Manuscript—37 total pages.
Scheid, J. F., et al., "Sequence and Structural Convergence of Broad and Potent HIV Antibodies that Mimic CD4 Binding," Science, vol. 333, No. 6049, pp. 1633-1637 (Sep. 16, 2011)—Author Manuscript—11 total pages.
Seaman, M. S., et al., "Tiered Categorization of a Diverse Panel of HIV-1 Env Pseudoviruses for Assessment of Neutralizing Antibodies," Journal of Virology, vol. 84, No. 3, pp. 1439-1452 (Feb. 2010).
Seimetz, D., et al., "Development and approval of the trifunctional antibody catumaxomab (anti-EpCAM × anti-CD3) as a targeted cancer immunotherapy," Cancer Treatment Reviews, vol. 36, No. 6, pp. 458-467 (Oct. 2010).
Shields, R. L., et al., "High Resolution Mapping of the Binding Site on Human IgG1 for FcγRI, FcγRII, FcγRIII, and FcRn and Design of IgG1 Variants with Improved Binding to the FcγR," Journal of Biological Chemistry, vol. 276, No. 9, pp. 6591-6604 (Mar. 2, 2001).
Shingai, M., et al., "Antibody Mediated Immunotherapy of Macaques Chronically Infected with SHIV Suppresses Viremia," Nature, vol. 503, No. 7475, pp. 277-280 (Nov. 14, 2013)—Author Manuscript—21 total pages.
Smith, T. F., et al., "Comparison of Biosequences," Advances in Applied Mathematics, vol. 2, No. 4, pp. 482-489, (Dec. 1981).
Songsivilai, S., et al., "Bispecific Antibody: A Tool for Diagnosis and Treatment of Disease,". Clinical and Experimental Immunology, vol. 79, No. 3, pp. 315-321 (Mar. 1990).
Stone, A., "Multipurpose Prevention Technologies for Reproductive and Sexual Health," Reproductive Health Matters, vol. 22, No. 44, pp. 213-217 (2014).
U.S. Appl. No. 62/260,100 entitled "HIV-1 Neutralizing Antibodies and Uses Thereof", filed Nov. 25, 2015 (140 total pages).
U.S. Appl. No. 62/170,558 entitled "Neutralizing Antibodies to HIV-1 ENV and Their Use", filed Jun. 3, 2015 (135 total pages).
Wardemann, H., et al., "Predominant Autoantibody Production by Early Human B Cell Precursors," Science, vol. 301, No. 5638, pp. 1374-1377 (Abstract Only—6 total pages) (Sep. 5, 2003).
Wu, C., et al., "Generation and Characterization of a Dual Variable Domain Immunoglobulin (DVD-Ig™) Molecule," Antibody Engineering, vol. 2, Eds, Kontermann, et al., Springer Berlin Heidelberg, 23 total pages including cover pages; table of contents and Chapter 19—pp. 239-250 (2010).
Xie, Z., et al., "A New Format of Bispecific Antibody: Highly Efficient Heterodimerization, Expression and Tumor Cell Lysis," Journal of Immunological Methods, vol. 296, Nos. 1-2 pp. 95-101 (Jan. 2005).
Yang, et al. "Passive Immunization against HIV/AIDS by Antibody Gene Transfer," Viruses, vol. 6, pp. 428-447 (2014).
Zalevsky, et al., "Enhanced Antibody Half-Life Improves in vivo Activity," Nature Biotechnology, vol. 28, No. 2, pp. 157-159 (Feb. 2010)—Author Manuscript—6 total pages.
Zhu, D., et al., "Biased Immunoglobulin Light Chain Use in the Chlamydophila psittaci Negative Ocular Adnexal Marginal Zone Lymphomas," American Journal of Hematology, vol. 88, No. 5, pp. 379-384 (May 2013)—Author Manuscript—15 total pages.

\* cited by examiner

| mAb | VH | D | JH | Mut Freq | HCDR3 length (AA) | HCDR3 | VL | JL | Mut Freq | LCDR3 length (AA) |
|---|---|---|---|---|---|---|---|---|---|---|
| DH542 | 1-2 | 3-22 | 4-1 | 12.8 | 20 | CTTGGWISLYYDSSYYPNFDHW | L2-23 | 2 | 6.6 | 10 |

| mAb | VH | D | JH | HCDR3 | VL | JL | LCDR3 |
|---|---|---|---|---|---|---|---|
| DH270 Lineage | 1-2 | 3-22 | 4 | 20 | λ2-23 | 2 | 10 |

Figure 2A

\>DH542_nt_HC (SEQ ID NO: 1)

CAGGTGCAGCTGGTGCAGTCTGGGGCTCAAATGAAGAACCCTGGGGCCT
CAGTGAAGGTCTCCTGCGCGCCTTCTGGATATACCTTCACCGACTTTTACA
TACATTGGTTGCGCCAGGCCCCTGGCCAGGGGCTTCAGTGGATGGGATG
GATGAACCCTCAGACTGGTCGCACAAACACTGCACGAAACTTTCAGGGG
AGGGTCACCATGACCAGGGACACGTCCATCGGCACAGCCTACATGGAGT
TGAGAAGCCTGACATCTGACGACACGGCCATATATTACTGTACGACAGG
GGGATGGATCAGTCTTTACTATGATAGTAGTTATTACCCCAACTTTGACC
ACTGGGGTCAGGGAACCCTGCTCACCGTCTCCTCAG

\>DH542_nt_LC (SEQ ID NO: 2)

ACCAGTCTGCTGACTCAGCCTGCCTCCGTGTCTGGGTCTCCTGGACAGTC
GATCACCATCTCCTGCACTGGAACCAAGTATGATGTTGGGAGTCATGACC
TTGTCTCCTGGTACCAACAGTACCCAGGCAAAGTCCCCAAATACATGATTT
ATGAAGTCAATAAACGGCCCTCAGGAGTTTCTAATCGCTTCTCTGGCTCC
AAATCTGGCAACACGGCCTCCCTGACAATCTCTGGGCTCCGGGCTGAGGA
CGAGGCTGACTATTATTGCTGTTCATTTGGAGGGAGTGCCACCGTGGTCT
GCGGCGGCGGGACCAAGGTGACCGTCCTAG

\>DH542_aa_HC (SEQ ID NO: 3)

QVQLVQSGAQMKNPGASVKVSCAPSGYTFTDFYIHWLRQAPGQGLQWM
GWMNPQTGRTNTARNFQGRVTMRDTSIGTAYMELRSLTSDDTAIYYCTT
GGWISLYYDSSYYPNFDHWGQGTLLTVSS

\>DH542_aa_LC (SEQ ID NO: 4)

TSLLTQPASVSGSPGQSITISCTGTKYDVGSHDLVSWYQQYPGKVPKYMIYE
VNKRPSGVSNRFSGSKSGNTASLTISGLRAEDEADYYCCSFGGSATVVCGGG
TKVTVL

Figure 2B

| HIV-1 Isolate | Clade | Tier | DH542 |
|---|---|---|---|
| Q23.17 | A | 1B | <0.023 |
| DJ263.8 | AG | 1B | 0.08 |
| C1080.c03 | AE | 2 | >50 |
| 6540.v4.c1 | AC | 2 | >50 |
| Q168.a2 | AD | 2 | >50 |
| 6101.1 | B | 2 | 0.03 |
| BG1168.1 | B | 2 | >50 |
| DU172.17 | C | 2 | 0.27 |
| DU156.12 | C | 2 | 0.07 |
| DU422.1 | C | 2 | 0.19 |
| 57128.vrc15 | D | | 2.0 |
| X1632-S2-B10 | G | 2 | >50 |
| Q679.d22 | A | | >50 |
| ZM106F.PB9 | C | | 0.05 |
| CNE58 | C | | 0.28 |
| 92RW020.2 | A | 2 | <0.023 |
| CAAN5342.A2 | B | 2 | 0.03 |
| JR-FL | B | 1B | 0.04 |
| PVO.4 | B | 2 | 0.14 |
| THRO4156.18 | B | 2 | >50 |
| TRJO4551.58 | B | 2 | 0.16 |
| TRO.11 | B | 2 | 0.06 |
| YU2 | B | | 0.06 |
| ZM55F.PB28a | C | | 0.05 |

| $IC_{50}$ (µg/ml) |
|---|
| 0.01-1 |
| 1.0-10.0 |
| 10.0-50.0 |
| >50 |

Figure 4A

Assay: Neutralization in TZM-bl cells
Viruses: Pseudoviruses were produced by transfection in 293T cells
Report Date: May 22, 2015
PGT121 and 10-1074 data from NVITAL. DH542 data from Duke

| | | | IC50 (ug/ml) in TZM-bl Cells[1] | | |
|---|---|---|---|---|---|
| Virus Name | Alt Virus Name | Clade | PGT121 | 10-1074 | DH542/293i |
| Q23.17 | Q23.17 | A | 0.0004 | 0.010 | 0.012 |
| Q769.d22 | Q769.d22 | A | >50 | >50 | >50 |
| 92RW020.2 | RW020.2 | A | 0.0005 | 0.002 | 0.012 |
| 6540.v4.c1 | 6540.v4.c1 | AC | >50 | >50 | >50 |
| Q168.a2 | Q168.a2 | AD | >50 | >50 | >50 |
| C1080.c03 | C1080.c3 | AE | >50 | >50 | >50 |
| DJ263.8 | DJ263.8 | AG | 0.148 | 0.008 | 0.083 |
| 6101.10 | 6101.10 | B | 0.001 | 0.030 | 0.034 |
| BG1168.1 | BG1168.01 | B | >50 | >50 | >50 |
| CAAN5342.A2 | CAAN.A2 | B | 0.003 | 0.014 | 0.052 |
| JR-FL | JRFL.JB | B | 0.008 | 0.020 | 0.040 |
| PVO.4 | PVO.04 | B | 0.255 | 0.044 | 0.143 |
| THRO4156.18 | THRO.18 | B | >50 | >50 | >50 |
| TRJO4551.58 | TRJO.58 | B | 5.08 | 0.086 | 0.163 |
| TRO.11 | TRO.11 | B | 0.004 | 0.022 | 0.064 |
| YU2 | YU2.DG | B | 0.155 | 0.089 | 0.062 |
| CNE58 | CNE58 | C | >50 | 0.097 | 0.281 |
| DU156.12 | DU156.12 | C | 0.0008 | 0.053 | 0.074 |
| DU172.17 | DU172.17 | C | 0.013 | 0.016 | 0.274 |
| DU422.1 | DU422.01 | C | 0.044 | 0.027 | 0.186 |
| ZM106F.PB9 | ZM106.9 | C | 0.0008 | 0.028 | 0.045 |
| ZM55F.PB28a | ZM55.28a | C | 0.078 | 0.002 | 0.053 |
| 57128.vrc15 | 57128.vrc15 | D | 4.17 | 0.252 | 1.99 |
| X1632-S2-B10 | X1632.S2.B10 | G | >50 | >50 | >50 |
| SVA-MLV | | non-HIV | >50 | >50 | >50 |

[1] Values are the antibody concentration (μg/ml) at which relative luminescence units (RLUs) were reduced 50% compared to virus control wells (no test sample).

Figure 4C

|  | PGT121 | 10-1074 | DH542/293i |
|---|---|---|---|
| # Viruses | 24 | 24 | 24 |
| Total VS Neutralized | | | |
| IC50 <50ug/ml | 16 | 17 | 17 |
| IC50 <10ug/ml | 16 | 17 | 17 |
| IC50 <1.0ug/ml | 14 | 17 | 16 |
| IC50 <0.1ug/ml | 11 | 16 | 11 |
| IC50 <0.01ug/ml | 8 | 3 | 0 |
| % VS Neutralized | | | |
| IC50 <50ug/ml | 67 | 71 | 71 |
| IC50 <10ug/ml | 67 | 71 | 71 |
| IC50 <1.0ug/ml | 58 | 71 | 67 |
| IC50 <0.1ug/ml | 46 | 67 | 46 |
| IC50 <0.01ug/ml | 33 | 13 | 0 |
| Median IC50 | 0.011 | 0.027 | 0.064 |
| Geometric Mean | 0.017 | 0.024 | 0.080 |
| % resistant virus | 33 | 29 | 29 |

Figure 4D

| ug/mL DH542 | SSA | SSB | Sm | RNP | Scl 70 | Jo 1 | dsDNA | Cent B | Histone |
|---|---|---|---|---|---|---|---|---|---|
| 50 | 28 | 15 | 7 | 19 | 4 | 28 | 28 | 17 | 40 |
| 25 | 16 | 8 | 5 | 14 | 4 | 15 | 16 | 12 | 25 |
| 12.5 | 9 | 9 | 5 | 9 | 2 | 10 | 11 | 8 | 17 |
| 6.25 | 9 | 5 | 2 | 8 | 1 | 7 | 6 | 7 | 14 |
Figure 6
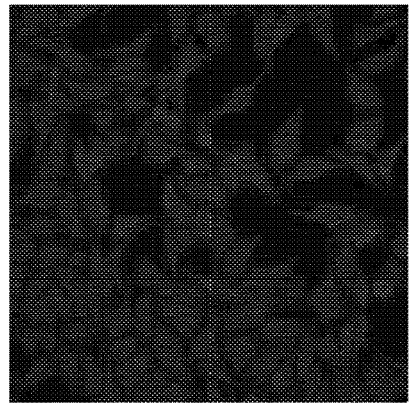
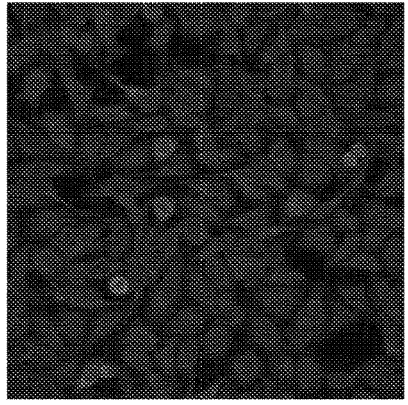
Figure 7

```
I4        ░░░░░░░░░ ░░░░░░░░░ ░░AACTMT GCACAGAAGT TTCAGGGCAG
I3        ░░░░░░░░░ ░░░░░░░░░ ░░AACAMT GCACAAAACT TTCAGGGCAG
DH542H    ░░░░░░░░░ ░░░░░░░░░ ░░AACACT GCACGAAACT TTCAGGGGAG
I2        ░░░░░░░░░ ░░░░░░░░░ ░░AATAAT GCACAAAACT TTCAGGGCAG
DH471H    ░░░░░░░░░ ░░░░░░░░░ ░░AATCAA GGACAAAACT TTCAGGGCAG
DH429H    ░░░░░░░░░ ░░░░░░░░░ ░░AATAAT GCACAAGATT TTCAGGGCAG
DH270H    ░░░░░░░░░ ░░░░░░░░░ ░░AACTCT CCACAGAAGT TTCAGGGCAG

....|....| ....|....| ....|....| ....|....| ....|....|
                   210        220        230        240        250
UCA       GGTCACCATG ACCAGGGACA CGTCCATCAG CACAGCCTAC ATGGAGCTGA
I5        GGTCACCATG ACCAGGGACA CGTCCATCAG CACAGCCTAC ATGGAGCTGA
I1        GGTCACCATG ACCAGGGACA CGTCCATCAG CACRGCCTAC ATGGAACTGA
DH473H    GGTCACCATG ACCAGGGAAA CGTCCGTCAG CACGGCCTAT ATGGAACTGA
DH391H    GGTCACGATG ACTACGGACA CGTCCATGAA TGTTGCCTAC ATGGAACTGA
I4        GGTCACCATG ACCAGGGACA CGTCCATCAG CACAGCCTAC ATGGAGCTGA
I3        GGTCACCATG ACCAGGGACA CGTCCATCGG CACAGCCTAC ATGGAGYTGA
DH542H    GGTCACCATG ACCAGGGACA CGTCCATCGG CACAGCCTAC ATGGAGTTGA
I2        GGTCACCATG ACCAGGGACA CGTCCATCGG CACAGCCTAC ATGGAGYTGA
DH471H    GGTCACCATG ACCAGGGACA CGTCCATCGG CACAGCCTAC ATGGAGTTGA
DH429H    GGTCACCCTG ACCAGGGACA CGTCCATCGG CACAGCCTAC ATGGAGCTGA
DH270H    GGTCACCATG ACCAGGGACA CGTCCATCAG CACAGCCTAC ATGGACCTGA

CDR3
               ....|....| ....|....| ....|....| ....|....| ....|....|
                   260        270        280        290        300
UCA       GCAGGCTGAG ATCTGACGAC ACGGCCGTGT ATTACTGTGC CACAGGGGGR
I5        GCAGVCTGAG ATCTGACGAC ACGGCCGTGT ATTACTGTGC CACAGGGGGR
I1        GAAGMCTGAG ATCTGACGAC ACGGCCGTCT ATTACTGTGC CACAGGGGGA
DH473H    GAAGACTGAG ATCTGACGAC ACGGCCGTCT ATTACTGTGC CAAAGCGGGA
DH391H    GAGGCTTGAG ATCTGACGAC ACGGCCGTCT ATTTCTGTGC CAGAGGGGGA
I4        GCAGVCTGAC ATCTGACGAC ACGGCCGTGT ATTACTGTGC CACAGGGGGR
I3        GVAGCCTGAC ATCTGACGAC ACGGCCGTVT ATTACTGTGC CACAGGGGGR
DH542H    GAAGCCTGAC ATCTGACGAC ACGGCCATAT ATTACTGTAC CACAGGGGGA
I2        GGAGCCTGAC ATCTGACGAC ACGGCCGTCT ATTACTGTGT CACAGGGGGR
DH471H    GGAGCCTCAC ATCTGACGAC ACGGCCGTCT ATTACTGTGT CACAGGGGCC
DH429H    GGAGGCTGAC ATCTGACGAC ACGGCCGTCT ATTACTGTGT CACAGGGGGG
DH270H    ACAGACTGAC GTCTGACGAC ACGGCCATGT ATTACTGTAC CACCGGGGGG

....|....| ....|....| ....|....| ....|....| ....|....|
                   310        320        330        340        350
UCA       TGGATCRGTC TTACTATCA TAGTAGTGGT TACCCTAACT TGACTACTG
I5        TGGATCRGTC TTACTATCA TAGTAGTGGT TACCCTAACT TGACTACTG
I1        TGGATCRGTC TTACGTTCA TTATAGTGGT TACCCTAACT TGACTCCTG
DH473H    TACATCGCCC TTACGTTCA CTATAGTGGT TACCCTAACT TTAATTCCTG
DH391H    TGGATCAGTC TCTACGTTCA TTACAGTTAT TACCCTAACT TGACTCGTG
I4        TGGATCRGTC TTACTATCA TAGTAGTGGT TACCCTAACT TGACTACTG
I3        TGGATCAGTC TTACTATCA TAGTAGTTAT TACCCTAACT TGACCACTG
DH542H    TGGATCAGTC TTACTATCA TAGTAGTTAT TACCCCAACT TGACCACTG
I2        TGGATCAGTC HTATTATCA TAGTAGTTAT TACCCTAACT TGACCACTG
DH471H    TGGATCAGTC ATTATTATCA TAGTAGTTAT TATCCTAACT TGACCACTG
DH429H    TGGATCAGTC CTTATTATCA TAGTAGTTAT TACCCTAATT TGACCACTG
DH270H    TGGATCGGTC TTACTCTGA TACTACTGGT TACCCTAACT TGACTACTG
```

Figure 8 cont.

```
              ....|....|  ....|....|  ....|....|  ..
                    360         370         380
UCA           GGGCCAGGGA  ACCCTGGTCA  CCGTCTCCTC  AG
I5            GGGCCAGGGA  ACCCTGGTCA  CCGTCTCCTC  AG
I1            GGGCCAGGGA  ACCCTGGTCA  CCGTCTCCTC  AG
DH473H        GGGCCAGGGA  ACCCTGGTCA  CCGTCTCCTC  AG
DH391H        GGGCCAGGGA  ACCCTGGTCT  CCGTCTCTTC  AG
I4            GGGCCAGGGA  ACCCTGGTCA  CCGTCTCCTC  AG
I3            GGGTCAGGGA  ACCCTGGTCA  CCGTCTCCTC  AG
DH542H        GGGTCAGGGA  ACCCTGCTCA  CCGTCTCCTC  AG
I2            GGGTCAGGGA  ACCCTGGTCA  CCGTCTCCTC  AG
DH471H        GGGTCAGGGA  ACCCTGGTCA  CCGTCTCCTC  AG
DH429H        GGGTCAGGGA  ACCCTGATCA  CCGTCTCCTC  AG
DH270H        GGGCCAGGGA  ACCCTGGTCA  CCGTCTCCTC  AG
```

Figure 8 cont.

DH270 lineage - Heavy chain amino acid sequences

```
                          CDR1
         ....|....| ....|....| ....|....| ....|....| ....|....|
              10         20         30         40         50
UCA(SEQ ID NO:17)   QVQLVQSGAE VKKPGASVKV SCKAS      MHWVRQA PGQGLEWMGW
I5(SEQ ID NO:18)    QVQLVQSGAE XKKPGASVKV SCKAS      IHWVRQA PGQGLEWMGW
I1(SEQ ID NO:19)    QVQLVQSGAE XKKPGASVKV SCKAS      IHWVRQA PGQGLEWMAW
DH473H(SEQ ID NO:20)EVQLVESGPE LKEPGASVKV SCKAS      IHWVRQA PGQGLEWMAW
DH391H(SEQ ID NO:21)QVQLVQSGAE LKKPGASVKV SCKAS      VHWLRQA PGQGLEWVAW
I4(SEQ ID NO:22)    QVQLVQSGAE MKKPGASVKV SCKAS      IHWVRQA PGQGLEWMGW
I3(SEQ ID NO:23)    QVQLVQSGAE MKNPGASVKV SCAXS      IHWVRQA PGQGLXWMGW
DH542H(SEQ ID NO:24)QVQLVQSGAQ MKNPGASVKV SCAPS      IHWLRQA PGQGLQWMGW
I2(SEQ ID NO:25)    QVQLVQSGAE MKNPGASVKV SCAXS      IHWVRLA PGQGLXWMGW
DH471H(SEQ ID NO:26)QVQLVQSGAE VKNPGASVKV SCAPS      IHWVRLA PGQGLEWLGW
DH429H(SEQ ID NO:27)EVQLVQSGAE MKNPGASVKV SCAAS      IHWVRLA PGHGLQWMGW
DH270H(SEQ ID NO:28)QVQLVQSGAE MKKPGASVRV SCKAS      IHWVRQA PGQGPEWMGW

CDR2                                              CDR3
         ....|....| ....|....| ....|....| ....|....| ....|....|
              60         70         80         90        100
UCA            NY AQKFQGRVTM TRDTSISTAY MELSRLRSDD TAVYYCARGX
I5             NX AQKFQGRVTM TRDTSISTAY MELSXLRSDD TAVYYCARGX
I1             XX ARKFQGRVTM TRDTSISXAY MELRXLRSDD TAVYYCARGG
DH473H         SF ARGFQGRVTM TRETSVSTAY MELRRLRSDD TAVYYCAKAG
DH391H         IS PRKFQGRVTM TTDTSMNVAY MELRGLRSDD TAVYFCARGG
I4             NX AQKFQGRVTM TRDTSISTAY MELSXLTSDD TAVYCATGX
I3             NX AQNFQGRVTM TRDTSIGTAY MEXXSLTSDD TAXYYCATGX
DH542H         NT ARNFQGRVTM TRDTSIGTAY MELRSLTSDD TAIYYCTTGG
I2             NN AQNFQGRVTM TRDTSIGTAY MEXRSLTSDD TAVYYCVTGX
DH471H         NQ GQNFQGRVTM TRDTSIGTAY MELRSLTSDD TAVYYCVTGA
DH429H         NN AQDFQGRVTL TRDTSIGTAY MELRRLTSDD TAVYYCVTGG
DH270H         NS PQKFQGRVTM TRDTSISTAY MDLNRLTSDD TAMYYCTTGG

....|....| ....|....| ....|..
              110        120
UCA      WIXLYYDSSG YPNFDYWGQG TLVTVSS
I5       WIXLYYDSSG YPNFDYWGQG TLVTVSS
I1       WIXLYVDYSG YPNFDSWGQG TLVTVSS
DH473H   YIALYVDYSG YPNFNSWGQG TLVTVSS
DH391H   WISLYVDYSY YPNFDSWGQG TLVSVSS
I4       WIXLYYDSSG YPNFDYWGQG TLVTVSS
I3       WISLYYDSSY YPNFDHWGQG TLVTVSS
DH542H   WISLYYDSSY YPNFDHWGQG TLLTVSS
I2       WISXYYDSSY YPNFDHWGQG TLVTVSS
DH471H   WISDYYDSSY YPNFDHWGQG TLVTVSS
DH429H   WISPYYDSSY YPNFDHWGQG TLITVSS
DH270H   WTGLYSDTSG YPNFDYWGQG TLVTVSS
```

Figure 8 cont.

DH270 lineage - Light chain nucleotide sequences

```
                           ....|....| ....|....| ....|....| ....|....| ....|....|
                                   10         20         30         40         50
UCA(SEQ ID NO:29)          CAGTCTGCCC TGACTCAGCC TGCCTCCGTG TCTGGGTCTC CTGGACAGTC
I5(SEQ ID NO:30)           CAGTCTGCCC TGACTCAGCC TGCCTCCGTG TCTGGGTCTC CTGGACAGTC
I1(SEQ ID NO:31)           CAGTCTGCCC TGACTCAGCC TGCCTCCGTG TCTGGGTCTC CTGGACAGTC
DH473H(SEQ ID NO:32)       CAGTCTGCCC TGACTCAGCC TGCCTCCGTG TCTGGGTCTC CTGGCCAGTC
DH391H(SEQ ID NO:33)       CAGCCTGTGC TGACTCAGCC TGCCTCCGTG TCTGGGTCTC CTGGACAGTC
I4(SEQ ID NO:34)           CAGTCTGCCC TGACTCAGCC TGCCTCCGTG TCTGGGTCTC CTGGACAGTC
I3(SEQ ID NO:35)           CAGTCTGYSC TGACTCAGCC TGCCTCCGTG TCTGGGTCTC CTGGACAGTC
DH542H(SEQ ID NO:36)       ACCAGTCTGC TGACTCAGCC TGCCTCCGTG TCTGGGTCTC CTGGACAGTC
I2(SEQ ID NO:37)           CAGTCTGYSC TGACTCAGCC TGCCTCCGTG TCTGGGTCTC CTGGACAGTC
DH471H(SEQ ID NO:38)       CTGCCTGTGC TGACTCAGCC TGCCTCCGTG TCTGGGTCTC CTGGGCAGTC
DH429H(SEQ ID NO:39)       CAGTCTGCCC TGACTCAGCC TGCCTCCGTG TCTGGGTCTC CTGGACAGTC
DH270H(SEQ ID NO:40)       CAGTCTGCCC TGACTCAGCC TGCCTCCGTG TCTGGGTCTC CTGGACAGTC

....|....| ....|....| ....|....| ....|....| ....|....|
                                   60         70         80         90        100
UCA                        GATCACCATC TCCTGCACTG GAACC
I5                         GATCACCATC TCCTGCACTG GAACC
I1                         GATCACCATC TCCTGCACTG GAACC
DH473H                     GATCACCATC TCCTGCACTG GAACC
DH391H                     GATCACCATC TCCTGCACTG GAAGC
I4                         GATCACCATC TCCTGCACTG GAACC
I3                         GATCACCATC TCCTGCACTG GAACC
DH542H                     GATCACCATC TCCTGCACTG GAACC
I2                         GATCACCATC TCCTGCACTG GAACC
DH471H                     GATCACCATC TCCTGCACTG GGACC
DH429H                     GATCACCATC TCCTGCACTG GAACC
DH270H                     GATCACCATC TCCTGCACTG GAACC

....|....| ....|....| ....|....| ....|....| ....|....|
                                  110        120        130        140        150
UCA                        GTCTCCTG GTACCAACAG CACCCAGGCA AAGCCCCCAA ACTCATGATT
I5                         GTCTCCTG GTACCAACAG CACCCAGGCA AAGCCCCCAA ACTCATGATT
I1                         GTCTCCTG GTACCAACAG CACCCAGGCA AAGCCCCCAA ACTCATGATT
DH473H                     GTCTCCTG GTACCAACAG CACCCAGGCA AAGCCCCCAA ACTCATTATT
DH391H                     GTGTCCTG GTACCAGCAG CACCCAGGCA AAGCCCCCAA ACTGATGATT
I4                         GTCTCCTG GTACCAACAG CACCCAGGCA AAGCCCCCAA ATACATGATT
I3                         GTCTCCTG GTACCAACAG CACCCAGGCA AAGCCCCCAA ATACATGATT
DH542H                     GTCTCCTG GTACCAACAG TACCCAGGCA AAGTCCCCAA ATACATGATT
I2                         GTCTCCTG GTACCAACAG CACCCAGGCA AAGCCCCCAA ATACATGATT
DH471H                     GTCTCCTG GTACCAGCAC CACCCAGGCA AAGCCCCCAA ATATTTGATT
DH429H                     GTCTCCTG GTTCCAACAG CACCCAGGCA AAGCCCCCAA ATACATGATT
DH270H                     GTCTCCTG GTATCAACAG CACCCAGGCA AAGTCCCCAA ATACATAATT

....|....| ....|....| ....|....| ....|....| ....|....|
                                  160        170        180        190        200
UCA                        TAT           AAGCGGCC CTCAGGGGTT TCTAATCGCT TCTCTGGCTC
I5                         TAT           AAGCGGCC CTCAGGGGTT TCTAATCGCT TCTCTGGCTC
I1                         TAT           AAGTGGCC CTCAGGGGTT TCTAATCGCT TCTCTGGCTC
DH473H                     TAT           CAGTGGCC CTCAGGGGTT TCTAAGCGCT TCTCTGGCTC
```

Figure 8 cont.

```
DH391H    TAT******  **AAGTGGGC CTCAGGGGTT TCTGATCGCT TCGCTGGCTC
I4        TAT******  **AAGCGGCC CTCAGGGGTT TCTAATCGCT TCTCTGGCTC
I3        TAT******  **AAGCGGCC CTCAGGAGTT TCTAATCGCT TCTCTGGCTC
DH542H    TAT******  **AAACGGCC CTCAGGAGTT TCTAATCGCT TCTCTGGCTC
I2        TAT******  **AAGTGGCC CTCAGGAGTT TCTCATCGCT TCTCTGGCTC
DH471H    TAT******  **AAGTGGCC CTCAGGAGTT TCTCATCGCT TCTCTGGCTC
DH429H    TAT******  **AAGTGGCC CTCAGGAGTT TCTCATCGCT TCTCTGGTTC
DH270H    TAT******  **AAGCGGCC CTCAGGGGTT TCTAATCGCT TCTCTGGCTC

....|....| ....|....| ....|....| ....|....| ....|....|
                 210        220        230        240        250
UCA       CAAGTCTGGC AACACGGCCT CCCTGACAAT CTCTGGGCTC CAGGCTGAGG
I5        CAAGTCTGGC AACACGGCCT CCCTGACAAT CTCTGGGCTC CAGGCTGAGG
I1        CAAGTCTGGC AACACGGCCT CCCTGACAAT CTCTGGGCTC CAGGCTGAGG
DH473H    CAAGTCTGGC AACACGGCCT CCCTGACAAT CTCTGGGCTC CAGGCTGAGG
DH391H    CAAGTCTGGC AACACGGCCT CCCTGACAAT CTCTAGACTC CAGGCTGAGG
I4        CAAGTCTGGC AACACGGCCT CCCTGACAAT CTCTGGGCTC CAGGCTGAGG
I3        CAAATCTGGC AACACGGCCT CCCTGACAAT CTCTGGGCTC CAGGCTGAGG
DH542H    CAAATCTGGC AACACGGCCT CCCTGACAAT CTCTGGGCTC CGGGCTGAGG
I2        CAAATCTGGC AACACGGCCT CCCTGACAAT CTCTGGGCTC CAGGCTGAGG
DH471H    CAAATCTGGC AACACGGCCT CCCTGACAAT CTCTGGGCTC CAGGTTGAGG
DH429H    CAAATCTGGC AACACGGCCT CCCTGACAAT CTCTGGGCTC CAGGCTGAGG
DH270H    CAAGTCTGGC AACACGGCCT CCCTGACAAT CTCTGGGCTC CAGGCTGAGG

CDR3
              ....|....| ....|....| ....|....| ....|....| ....|....|
                 260        270        280        290        300
UCA       ACGAGGCTGA TTATTACTGC TGCTCATATG CAGGTAGTAG CACTGTAWTA
I5        ACGAGGCTGA TTATTACTGY TGCTCATATG CAGGTAGTAG CACTGTAWTA
I1        ACGAGGCTVA TTATTACTGT TGCTCATATG CAGGTAGTAG CACTGTAATA
DH473H    ACGAGGCTCA TTATTACTGT TGCTCATATG CAGGTAGTAG CACTGTAATA
DH391H    ACGAGGCTAA TTACTTTTGT TGCTCATCTA CAAATAGTGC CACTGTCATA
I4        ACGAGGCTGA TTATTACTGY TGCTCATATG CAGGTAGTAG CACTGTADTW
I3        ACGAGGCTGA CTATTATTGC TGCTCATTTG GAGGTAGTGC CACTGTRCTC
DH542H    ACGAGGCTGA CTATTATTGC TGTTCATTTG GAGGCAGTGC CACCGTGGTC
I2        ACGAGGCTGA CTATTATTGC TGCTCATTCG GAGGTAGTGC CACTGTRCTC
DH471H    ACGAGGCTGA CTATTATTGC TGCTCATTCG GAGGTAGTGC CGCTGTGGTC
DH429H    ACGAGGCTGA CTATTATTGC TGCTCATTCG GAGGTAGTGC CACTGTAGTC
DH270H    ACGAGGCCAC TTATTACTGT TGTTCATATG CAGGTAGTAG CATTATATTT

....|....| ....|....| ....|....| .
                 310        320        330
UCA       TTCGGCGGAG GGACCAAGCT GACCGTCCTA G
I5        TTCGGCGGAG GGACCAAGCT GACCGTCCTA G
I1        TTCGGCGGAG GGACCAAGCT GACCGTCCTA G
DH473H    TTCGGCGGAG GGACCTCGCT GACCGTCCTA G
DH391H    TTCGGCGGAG GGACCAAGCT GACCGTCCTA G
I4        TTCGGCGGAG GGACCAAGCT GACCGTCCTA G
I3        TGCGGCGGAG GGACCAAGGT GACCGTCCTA G
DH542H    TGCGGCGGCG GGACCAAGGT GACCGTCCTA G
I2        TGCGGCGGAG GGACCAAGGT GACCGTCCTA G
DH471H    TGCGGCGGAG GGACCAAGGT GACCGTCCTA G
DH429H    TGCGGCGGAG GGACCAAGGT GACCGTCCTA G
DH270H    TTCGGCGGTG GGACCAAGCT GACCGTCATA G
```

Figure 8 cont.

DH270 lineage - Light chain amino acid sequences

```
                              CDR1
                 ....|....|....|....|....|....|....|....|....|....|
                     10        20        30        40        50
UCA(SEQ ID NO:41)   QSALTQPASV SGSPGQSITI SCTGT░░░░░ ░░░░VSWYQQ HPGKAPKLMI
I5(SEQ ID NO:42)    QSALTQPASV SGSPGQSITI SCTGT░░░░░ ░░░░VSWYQQ HPGKAPKLMI
I1(SEQ ID NO:43)    QSALTQPASV SGSPGQSITI SCTGT░░░░░ ░░░░VSWYQQ HPGKAPKLMI
DH473H(SEQ ID NO:44) QSALTQPASV SGSPGQSITI SCTGT░░░░░ ░░░░VSWYQQ HPGKAPKLII
DH391H(SEQ ID NO:45) QPVLTQPASV SGSPGQSITI SCTGS░░░░░ ░░░░VSWYQQ HPGKAPKLMI
I4(SEQ ID NO:46)    QSALTQPASV SGSPGQSITI SCTGT░░░░░ ░░░░VSWYQQ HPGKAPKYMI
I3(SEQ ID NO:47)    QSXLTQPASV SGSPGQSITI SCTGT░░░░░ ░░░░VSWYQQ HPGKAPKYMI
DH542H(SEQ ID NO:48) TSLLTQPASV SGSPGQSITI SCTGT░░░░░ ░░░░VSWYQQ YPGKVPKYMI
I2(SEQ ID NO:49)    QSXLTQPASV SGSPGQSITI SCTGT░░░░░ ░░░░VSWYQQ HPGKAPKYMI
DH471H(SEQ ID NO:50) LPVLTQPASV SGSPGQSITI SCTGT░░░░░ ░░░░VSWYQH HPGKAPKYLI
DH429H(SEQ ID NO:51) QSALTQPASV SGSPGQSITI SCTGT░░░░░ ░░░░VSWFQQ HPGKAPKYMI
DH270H(SEQ ID NO:52) QSALTQPASV SGSPGQSITI SCTGT░░░░░ ░░░░VSWYQQ HPGKVPKYII

CDR2                                              CDR3
         ....|....|....|....|....|....|....|....|....|....|
             60        70        80        90        100
UCA      Y░░░KRPSGV SNRFSGSKSG NTASLTISGL QAEDEADYYC CSYAGSSTVX
I5       Y░░░KRPSGV SNRFSGSKSG NTASLTISGL QAEDEADYYX CSYAGSSTVX
I1       Y░░░KWPSGV SNRFSGSKSG NTASLTISGL QAEDEAXYYC CSYAGSSTVI
DH473H   Y░░░QWPSGV SKRFSGSKSG NTASLTISGL QAEDEAHYYC CSYAGSSTVI
DH391H   Y░░░KWASGV SDRFAGSKSG NTASLTISRL QAEDEANYFC SSSTNSATVI
I4       Y░░░KRPSGV SNRFSGSKSG NTASLTISGL QAEDEADYYX CSYAGSSTVX
I3       Y░░░KRPSGV SNRFSGSKSG NTASLTISGL QAEDEADYYC CSFGGSATXV
DH542H   Y░░░KRPSGV SNRFSGSKSG NTASLTISGL RAEDEADYYC CSFGGSATVV
I2       Y░░░KWPSGV SHRFSGSKSG NTASLTISGL QAEDEADYYC CSFGGSATXV
DH471H   Y░░░KWPSGV SHRFSGSKSG NTASLTISGL QVEDEADYYC CSFGGSAAVV
DH429H   Y░░░KWPSGV SHRFSGSKSG NTASLTISGL QAEDEADYYC CSFGGSATVV
DH270H   Y░░░KRPSGV SNRFSGSKSG NTASLTISGL QAEDEATYYC CSYAGSSIIF
```

Figure 8 cont.

| Antibody | IC50 | IC80 | IC50 <50ug/ml | IC80 <5ug/ml | Antibody Specificity |
|---|---|---|---|---|---|
| PGT121 | 0.06 | 0.27 | 63% | 48% | V3-glycan |
| PGT128 | 0.07 | NA | 63% | NA | V3-glycan |
| DH270.IA1 | 0.07 | 0.22 | 63% | 61% | V3-glycan |
| DH420 | 0.06 | 0.22 | 63% | 60% | V3-glycan |
| VRC01 | 0.27 | 0.73 | 87% | 81% | VH1-2 CD4bs |
| CH31 | 0.10 | 0.42 | 83% | 80% | VH1-2 CD4bs (VRC01-like) |
| CH01 | 3.79 | NA | 46% | NA | V1V2-glycan |
| CH01+ CH31 | 3.73 | NA | 83% | NA | V1V2-glycan + VH1-2 CD4bs |
| CH103 | 4.54 | NA | 55% | NA | HCDR3 binder CD4 bs |
| CH98 | 4.20 | NA | 63% | NA | HCDR3 binder CD4 bs |
| DH493 | 5.98 | NA | 63% | NA | VH1-46 CD4bs (ANC131-like) |
| DH540 | 0.10 | NA | 90% | NA | N276-dependent CD4bs Ab (HJ16-like) |

Figure 9

| Antibody | IC50 | IC80 | IC50 <50ug/ml | IC80 <5ug/ml | Antibody Specificity |
|---|---|---|---|---|---|
| DH429 | 0.06 | 0.22 | 63% | 60% | V3-glycan |
| DH512 | 0.65 | 5.12 | 100% | 50% | MPER (10E8-like) |
| CH31 | 0.10 | 0.42 | 83% | 80% | VH1-2 CD4bs (VRC01-like) |
| CH01 | 3.79 | NA | 46% | NA | V1V2-glycan |
| CH01+ CH31 | 3.73 | NA | 93% | NA | V1V2-glycan + VH1-2 CD4bs |
| DH493 | 5.98 | NA | 83% | NA | VH1-46 CD4bs (ANC131-like) |
| DH540 | 0.10 | NA | 90% | NA | N276-dependent CD4bs Ab (HJ16-like) |

Figure 10

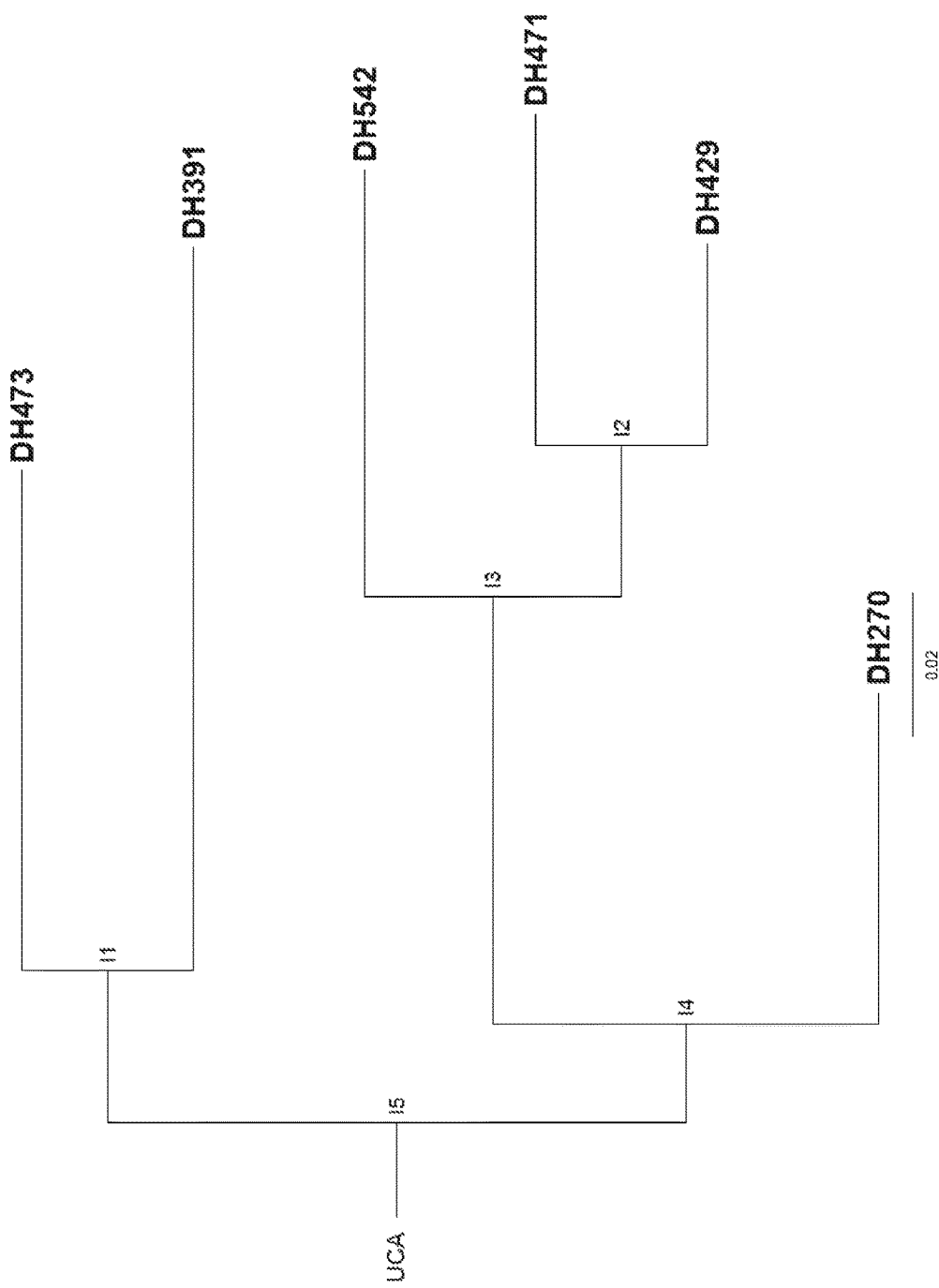

>DH511VH (SEQ ID NO: 53)

GAGGTTCAGCTGGTGGAGTCTGGGGGAGGCTTGGTGAAGCCGGGGGGGTCTCTTAGACTCCC
CGGTGCAGCCTCTGGTTTCACTTTCACCAACACGTGGATGAGTTGGGTCCGTCAGGCGCCAG
GGAAGGGACTGGAGTGGGTCGGTCGGATTAGCCGGAACAAAGATGGCGCGAAAACAGAGTAC
GCCGCACCCGTGAGAGGCAGATTCACCATCTCAAGAGATGACTCCAGAGACACATTGTATCT
GCAGATGACCAGCCTGAAAATAGAGGATTCAGGCCGGTATTTTGCACCGCAGATCTTGGGG
AGCCCGTGGTGTCACGATCCATTTTGAGTGGGGGTCTTATTATTATATGGACCTCTGG
GGCAAGGGGACCACGGTCACCGTCTCTTCA

>DH511VK (SEQ ID NO: 54)

GACATCCAGTTGACCCAGTCTCCATCTCCCCTGTCTGCGTCTGTGGGAGACACAGTCACTAT
CACTTGTCGGGCCAGCCAGAAGATTAGCGACTATTTGAACTGGTACCAACAGAAGCCGGGA
GAGCCCCCAAAATACTCATTTACGCTGCGTCCAAGTTGGGGAGTGGCGTCCCATCAAGGTTC
AGTGGCAGTGGATATGGCAGAGATTTCACTCTCACCATCACCGGTCTGCAGCCTGAAGATTT
TGCAACCTATTATTGTCAGGAGGCTTACAGTTCTACTCCCACGTTAACTTTTGGCCAGGGGA
CCAGGCTGGATCTCAAAC

>DH512VH (SEQ ID NO:55)

CAGGTGCAGCTGGTACAGTCTGGGGGAGGTCTGGTGAAGCCGGGGGGGTCCCTCACACTCTC
CTGTTCAGCCTCTGGATTCTTTTTCGATAATTCATGGATGGGGTGGGTCCGTCAGGCGCCAG
GGAAGGGACTGGAGTGGGTTGGCCGCATTAGAAGGCTCAAAGACGGTGCGACAGGAGAATAT
GGTGCAGCCGTGAAGGACAGATTCACCATTTCAAGAGATGACAGTAGAAATATGCTGTACCT
GCACATGAGGACCCTGAAAACCGAGGACTCAGGCACTTATTATTGTACCATGGATGAGGGA
CCCCAGTAACACGCTTCTTAGAATGGGGCTACTTCTATTATTATATGGCCGTTTGGGGCAGA
GGGACCACGGTCATCGTCTCTTCA

>DH512VK (SEQ ID NO:56)
GACATCGTGATGACCCAGTCTCCGTCCTCCGTGTCTGCATCTGTGGGAGACAGAGTCACCAT
CACTTGCCGGGCAAGTCAGAATATTAGAGACTATTTAAATTGGTATCAACATAAACCCGGGG
GATCCCCTAGACTCCTAATTTATGCTGCGTCAACTTTGCAAACTGGGGTCCCGTCCAGATTC
AGCGGCAGTGGATCTGGGAACCTTTTCACTCTCACCATTACCAATCTGCAACCTGAAGATTT
TGCAACTTATTATTGTCAAGAGAATTATAATACTATCCCCTCGCTCAGCTTTGGTCAGGGGA
CCAAGGTGGACATCAGGC

>DH513VH (SEQ ID NO:57)
GAGGTTCAGCTGGTGGAGTCTGGGGGAGGCTTGGTGAAGCCGGGGGGGTCTCTTAGACTCTC
CTGTGTAGCCTCTGGCTTCACTTTCAGCAACACGTGGATGAGTTGGGTCCGTCAGGCGCCAG
GGAAGGGACTGGAGTGGGTCGGTCGGATTAGCCGGAACAAAGATGGCGCGAAAACAGAGTAC
GCCGCACCCGTGAGAGGCAGATTCACCATCTCAAGAGATGACTCCAGAGACACATTGTATCT
GCAGATGAGCAGCCTGAAAATAGAGGATTCAGGCCGGTATTTTGCACCGCAGATCTTGGGG
AGGCCGTTGTGTCACGATTTTTGAGTGGGGGTCCTATTATTACTACATGGACTTCTGGGGC
AAGGGGACCACGGTCACCGTCTCTTCA

Figure 12A

>DH513VK (SEQ ID NO:58)

GACATTCAGATGACCCAATCTCCATCTCCCCTGTCTGCGTCTGTGGGAGACACAGTCACTAT
CACTTGCCGGGCCAGCCAGAAGATTAGCGACTATTTGAACTGGTACCAACAGAGGCCGGGGA
GAGCCCCCAAGATCCTCATTTACGCTGCGTCCAAGTTGGCAAGCGACGTCCCATCAAGATTT
AGTGGCAGTGGATATGGCAGAGATTTCACTCTCACCATAACCGGTCTGCAGCCTGAAGATTT
TGCAACCTATTATTGTCAGGAGGCTTACAGTTCTACCCCCACGTTAACTTTTGGCCAGGGGA
CCAGGCTGGATCTCAAAC

>DH514VH (SEQ ID NO:59)

GAGGTGCAGCTGGTGGAGTCTGGGGGCGGCTTGATAAAGCCGGGACAGTCACTCACACTATT
CTGTGTGGGCTTTGGATTCAACTTCGCTAACGACTGGATGGGCTGGGTCCGCCAGGCTCCAG
GGAAGGGACTGGAATGGGTTGGGCGTATAAGGAGACTGAAAGATGGTGCGAAAGCTGAATAT
GGATCTTCCGTGAAGGGTAGATTCACCATCTCAAGGGATGATTCCAAAAACACCCTATACTT
GCACATGAGCAGCCTCAAGGTCGAAGACACAGCCGTCTACTATTGCACCCGAGACGAGGGGG
CCCCAGTTACCCGGTTTCTGGAGTGGGGCTCCTATTACTACTACATGGCCGTCTGGGGCAAA
GGGACCACGGTCACCGTCTCTTCA

>DH514VK (SEQ ID NO:60)

GACATCCAGTTGACCCAGTCTCCAGCCTCTCTGTCTGCATCTGTAGGAGACACAGTGACTAT
CACTTGCCGGGCAAGTCAGAGTATAAAAGATTACATAAATTGGTATCAACACAAATCCGGGA
GCGCCCCTAGACTCCTGATTTATGCTGCGTCAACCTTACAAAGTGGAATCTCGTCAAGGTTC
ACTGGCAGTGGGTCTGGGACACAGTTCACTCTCACCATTAACAGTCTGCAACCTGAAGATTT
TGCGACTTATTATTGTCAAGAGGCTTATAACACCAACCCCACACTCTCCTTTGGTCAGGGGA
CCAGGGTGGACAAGAAGC

>DH515VH (SEQ ID NO:61)
GAGGTTCAGCTGGTGGAGTCTGGGGGCGGCTTGGTGAAGCCGGGACAGTCACTCACACTTTC
CTGTGTGGGCTTTGGATTCAATTTCGCTAACGACTGGATGGGCTGGGTCCGCCAGGCTCCAG
GGAAGGGACTGGAATGGGTTGGTCGAATAAGGAGACTAAAAGACGGTGCGACAACAGAATAT
TCTTCATCCGTGAAGGGGAGATTCAGTGTCTCAAGAGATGATTCAAGGAACACAGTATACTT
ACACATGAGTAGCCTCAAAGTCCAGGACATTGGCGTCTATTATTGTACTCGAGACGAGGGGG
CCCCGGTTACTCGATTTCTGGAGTGGGGCTCCTATTACTACTATATGGCCGTCTGGGGCAGA
GGGACCACGGTCACCGTCTCTTCA

>DH515VK (SEQ ID NO:62)
GACATCCAGATGACCCAGTCTCCAACCTCTCTGTCTGCATCTGTAGGAGACACAGTTGCTAT
CACTTGCCGGGCAAGTCAGAGTGTTAAAGATTATGTGAATTGGTATCAACACAAATCCGGGA
GCGCCCCTCGACTCCTGATTTATGCTGCCTCAGTCTTACATACTGGAGTCTCGTCAAGGTTC
ACTGGCAGTGGGTCTGGGACACAGTTCACTCTCACCATTAGCAGTCTACAACCTGAAGATTT
TGCTACTTATTATTGTCAAGAGGCTTATAACACCTATCCCACACTCTCCTTTGGTCAGGGGA
CCAGGGTGGACAGGAAAC

Figure 12A cont.

>DH516VH (SEQ ID NO:63)

GAGGTTCAGCTGGTGGAGTCTGGGGGAGGCTTGGTGAAGCCGGGGGGGTCTCTTAGACTCTC
CTGTGTAGCCTCTGGCTTCACTTTCAGCAACACGTGGATGAGTTGGGTCCGTCAGGCGCCAG
GGAAGGGACTGGAGTGGGTCGGTCGGATTAGCCGGAACAAAGATGGCGCGAAAACAGACTAC
GCCGCACCCGTGAGAGGCAGATTCACCATCTCCAGAGATGACTCCAGAGACACATTGTATCT
GCAGATGAGCAGCCTGAAAATAGAGGATTCAGGCCGGTATTTTTGCACCGCAGATCTTGGGG
AGGCCGTGGTGTCACGATTTTTTGAGTGGGGGTCCTATTATTACTACATGGACTTCTGGGGC
AAGGGGACCACGGTCACCGTCTCTTCA

>DH516VK (SEQ ID NO:64)

GATATTGTGATGACCCAGTCTCCACCTCCCCTGTCTGCGTCTGTGGGAGACACAGTCACTAT
CACTTGCCGGGCCAGCCAGAAGATTAGCGACTATTTGAACTGGTACCAACAGAGGCCGGGGA
GAGCCCCCAAAATACTCATTTACGCTGCGTCCAAGTTGGGAAGCGACGTCCCATCAAGGTTC
AGTGGCAGTGGATATGGCAGAGATTTCACTCTCACCATCACCGGTCTGCAGCCTGAAGATTT
TGCAACCTATTATTGTCAGGAGGCTTACAGTTCTACTCCCACGTTAAGTTTTGGCCAGGGGA
CCAGGCTGGATCTCAAAC

>DH517VH  (SEQ ID NO:65)
GAAAGGCAGGTGGTGGAATATGGGGGAGG TTGGTGAAGCCGGGGGGGTCTCTTAGACT TC
 TG TTACCGTTTGCCTTTGGGTTCAGGGCCCCCTGGAGGAGTTCTGTCCGTCACGCGCCTG
GGGGCGGAGCGGAGTGGGTCGGTCGGATTAGCCGGAACAAAGATGGCGCGAAAACAGAGTAC
GCCGCACCCGTGAGAGGCAGATTCACCATCTCAAGAGATGACTCCAGAGACACATTGTATCT
GCAGATGACCAGCCTGAAAATAGAGGATTCAGGCCGGTATTTTTGCACCGCAGATCTTGGGG
AGCCCGTGGTGTCACGATTTTTTGAGTGGGGGTCTTATTATTATTATATGGACCTCTGGGGC
AAGGGGACCACGGTCACCGTCTCTTCA

>DH517VL  (SEQ ID NO:66)
TCTTCTGAGCTGACTCAGGACCCCACTGTGTCTGTGGCCTTGGGCCAGACAGTCAAGATCAG
ATGCCAAGGAGCCAGCCTCAGAGACTGTTATGCGACCTGGTACCGGCAGAAGCCAGGACAGG
CCCCAACACTTCTCATTTATGATATAAATAAGAGGCCCTCAGGTATCCCAGACCGATTCTCT
GCCTCCTACTCAGGGAGCACTTCTTCCTTGACCATTATTGGGGCTCAGCCGGAAGATGAGGC
TGACTATTTTTGTGCTTCGCGGGACAGGAGTGGTGACCGTCTTGGCGTCTTCGGCGGTGGGA
CCAAACTGACCGTCCTG

>DH518VH (SEQ ID NO:67)
CAGCTGCAGGAGTCGGGTCCCAGACTGGTGAGGCCTTCGGAGACCCTGTCCCTCACCTGCAC
TGTATCTGGCTCTGGTGTCTCCGTCAGTCGTGGGAGTTATTATTGGGGCTGGATACGCCAGT
CCCCAGAAAAGGGACTCGAATGGATTGGAAGTGTCTATTCCACTACTAGTGGAAAAACCTAC
TACAACCCGTCCCTCAAGAGTCGAGTCACCTTTTCGAAGGACACGTCCCAGAACGCCTTCTC
CCTGACTCTGACGTCTATTACCGCCGCGGACACGGCCGTCTATTACTGTGCAAGACAATTTG
GCTTCATGGGGGCTTTTTGGAGTGGTATCCGCACTATTTTGACTTCTGGGGCCCGGGAATC
CAGGTCGTCGTGTCTTCT

*Figure 12A cont.*

>DH518VK (SEQ ID NO:68)
GACATTGTGATGACCCAGTCTCCATCCTACCTGTCTACATCTGTCGGTGACAGCATCACCAT
CACTTGCCGGGCAAGTCAGAGTATTAAAACATATGTAAATTGGTATCAACAAAGACCAGGGA
GAGCCCCTAAACTCCTCATCTATTCTTCATCCACTTTGCAACCTGGGGTCCCGTCAAGATTC
AGCGCCAGTGGATCTGGGACAGATTTCGTTCTCTCCATCACCAATTTGCAGTCTGAAGATTT
TGCAACTTACTACTGTCAACAGACCTACTACACCCCTCTACTTTTGGCCAGGGGACCACAC
TGGACATCAAG

>DH536VH (SEQ ID NO:69)

CAGGTGCAGCTGGTACAGTCTGGGGCTGAGGTGAAGAAGCCTGGGTCCTCGGTCAAGGTCTC
CTGCAAGGCCTCTGGAGGCTCCTTCTACACCTATACTATCAACTGGGTGCGACAGGCCCCTG
GACAAGGGCTTGAGTGGATGGGCAGGGTCACCACTATGTTTGGTGTAACACTTTACGCACAG
AAATTCCAGGGCAGAGTCACACTTACCGCGGACAAATCCACGAGCACAGCCTACATGGAACT
GAGCAGTCTAAGATCTGAGGACACGGCCGTCTATTATTGTGCGACAGATGGGCCTGACAATT
TTTGGAGTGGCTTGTCTCATGCTTTCGATCTCTGGGGCCAGGGGACAATGGTCACCGTCTCT
TCA

>DH536VL (SEQ ID NO:70)

CAGTCTGCCCTGACTCAGCCTGCCTCCGTGGCTGGGTCTCCTGGACAGTCGATCACCATCTC
CTGCACTGGAACCAGCAGTGACATTGGTGATTCTAAGTATGTCTCCTGGTACCAACAGTTCC
CAGGCAAAGCCCCCAAAGTCATGATTTATGAGGTCAGTTATCGGCCCTCAGGAGTCTCTAGC
CGCTTCTCTGGCTCCAAGTCTGGCAACACGGCCTCCCTGACCATCTCTGGACTCCAGACTGA
GGACGAGGCTGATTATTATTGCATGGCATATACAGGCACCTTCACTGCTATTTTCGGCGGAG
GGACCAAGCTGACCGTCCTG

>DH537VH (SEQ ID NO:71)

CAGGTGCAGCTGGTGCAGTCTGGGGCTGAGGTGAGGAAGGCTGGGTCGTCGGTGAAGGTCTC
CTGCAAGGCTTCTGGAGGCACCTTCACCAGCTATGGCTTCAGCTGGATACGGCAGGCCCCTG
GCCAAGGGCTTGAGTGGATGGGAAACGTCATCCCTGTCTTTGGTTCAACAAACTACGCACAG
AAATTTCAGGGCAGAGTCAGTATTACCGCGGACGAAGCCACGGGCACAGTCCACATGGACCT
CACCAGCCTGACATCTGACGACACGGCCGTTTATTACTGTGTGAGGTCGAGTAGAGAACTGC
CAACGTCAATGGAACGGTGGTTCGACCCCTGGGGCCAGGGAACCCAGGTCATTGTCTCCTCG

>DH537VK (SEQ ID NO:72)
GACATCCAGATGACCCAGTCTCCATCCTCCCTGTCTGCATCTGTGGGAGACAGCGTCACCAT
TACTTGCCGGGCAAGTCAGAGCATTAACACCTATTTAAATTGGTATCAGCAGAAACCAGGGA
AGGCCCCTAAACTCCTGATCTATTCTGCATCCAATTTACACAATGGGGTCCCATCGAGGTTC
AGTGGCAGTGGATCTGGGACATCTTTCACTCTCACCATCAACAATCTACAACCTGAAGATTT
TGCAACTTACTACTGTCAACAGAGTTACAGTGCCCCTTACACTTTTGGCCAGGGGACCAAGT
CAGACACCAAA

Figure 12A cont.

>DH511VH (SEQ ID NO:73)

EVQLVESGGGLVKPGGSLRLPGAASGFTFTNTWMSWVRQAPGKGLEWVGRISRNKDGAKTEY
AAPVRGRFTISRDDSRDTLYLQMTSLKIEDSGRYFCTADLGEPVVSRSIFEWGSYYYYMDLW
GKGTTVTVSS

>DH511VK (SEQ ID NO:74)

DIQLTQSPSPLSASVGDTVTITCRASQKISDYLNWYQQKPGRAPKILIYAASKLGSGVPSRF
SGSGYGRDFTLTITGLQPEDFATYYCQEAYSSTPTLTFGQGTRLDLK

>DH512VH (SEQ ID NO:75)

QVQLVQSGGGLVKPGGSLTLSCSASGFFFDNSWMGWVRQAPGKGLEWVGRIRRLKDGATGEY
GAAVKDRFTISRDDSRNMLYLHMRTLKTEDSGTYYCTMDEGTPVTRFLEWGYFYYYMAVWGR
GTTVIVSS

>DH512VK (SEQ ID NO:76)

DIVMTQSPSSVSASVGDRVTITCRASQNIRDYLNWYQHKPGGSPRLLIYAASTLQTGVPSRF
SGSGSGNLFTLTITNLQPEDFATYYCQENYNTIPSLSFGQGTKVDIR

>DH513VH (SEQ ID NO:77)

EVQLVESGGGLVKPGGSLRLSCVASGFTFSNTWMSWVRQAPGKGLEWVGRISRNKDGAKTEY
AAPVRGRFTISRDDSRDTLYLQMSSLKIEDSGRYFCTADLGEAVVSRFFEWGSYYYYMDFWG
KGTTVTVSS

>DH513 (SEQ ID NO:78)

VKDIQMTQSPSPLSASVGDTVTITCRASQKISDYLNWYQQRPGRAPKILIYAASKLASDVPS
RFSGSGYGRDFTLTITGLQPEDFATYYCQEAYSSTPTLTFGQGTRLDLK

>DH514VH (SEQ ID NO:79)

EVQLVESGGGLIKPGQSLTLFCVGFGFNFANDWMGWVRQAPGKGLEWVGRIRRLKDGAKAEY
GSSVKGRFTISRDDSKNTLYLHMSSLKVEDTAVYYCTRDEGAPVTRFLEWGSYYYYMAVWGK
GTTVTVSS

>DH514VK (SEQ ID NO:80)

DIQLTQSPASLSASVGDTVTITCRASQSIKDYINWYQHKSGSAPRLLIYAASTLQSGISSRF
TGSGSGTQFTLTINSLQPEDFATYYCQEAYNTNPTLSFGQGTRVDKK

Figure 12B

\>DH515VH (SEQ ID NO:81)

EVQLVESGGGLVKPGQSLTLSCVGFGFNFANDWMGWVRQAPGKGLEWVGRIRRLKDGATTEY
SSSVKGRFSVSRDDSRNTVYLHMSSLKVQDIGVYYCTRDEGAPVTRFLEWGSYYYYMAVWGR
GTTVTVSS

\>DH515VK (SEQ ID NO:82)

DIQMTQSPTSLSASVGDTVAITCRASQSVKDYVNWYQHKSGSAPRLLIYAASVLHTGVSSRF
TGSGSGTQFTLTISSLQPEDFATYYCQEAYNTYPTLSFGQGTRVDRK

\>DH516VH (SEQ ID NO:83)

EVQLVESGGGLVKPGGSLRLSCVASGFTFSNTWMSWVRQAPGKGLEWVGRISRNKDGAKTDY
AAPVRGRFTISRDDSRDTLYLQMSSLKIEDSGRYFCTADLGEAVVSRFFEWGSYYYYMDFWG
KGTTVTVSS

\>DH516VK (SEQ ID NO:84)

DIVMTQSPPPLSASVGDTVTITCRASQKISDYLNWYQQRPGRAPKILIYAASKLGSDVPSRF
SGSGYGRDFTLTITGLQPEDFATYYCQEAYSSTPTLSFGQGTRLDLK

\>DH517VH (SEQ ID NO:85)

ERQVVEYGGGLVKPGGSLRLSCLPFAFGFRAPWRSSVRHAPGGGAEWVGRISRNKDGAKTEY
AAPVRGRFTISRDDSRDTLYLQMTSLKIEDSGRYFCTADLGEPVVSRFFEWGSYYYYMDLWG
KGTTVTVSS

\>DH517VL (SEQ ID NO:86)

SSELTQDPTVSVALGQTVKIRCQGASLRDCYATWYRQKPGQAPTLLIYDINKRPSGIPDRFS
ASYSGSTSSLTIIGAQPEDEADYFCASRDRSGDRLGVFGGGTKLTVL

\>DH518VH (SEQ ID NO:87)

QLQESGPRLVRPSETLSLTCTVSGSGVSVSRGSYYWGWIRQSPEKGLEWIGSVYSTTSGKTY
YNPSLKSRVTFSKDTSQNAFSLTLTSITAADTAVYYCARQFGFMGGFLEWYPHYFDFWGPGI
QVVVSS

\>DH536VH (SEQ ID NO: 88)

QVQLVQSGAEVKKPGSSVKVSCKASGGSFYTYTINWVRQAPGQGLEWMGRVTTMFGVTLYAQ
KFQGRVTLTADKSTSTAYMELSSLRSEDTAVYYCATDGPDNFWSGLSHAFDLWGQGTMVTVS
S

Figure 12B cont.

>DH518VK (SEQ ID NO:89)

DIVMTQSPSYLSTSVGDSITITCRASQSIKTYVNWYQQRPGRAPKLLIYSSSTLQPGVPSRF
SASGSGTDFVLSITNLQSEDFATYYCQQTYYTPSTFGQGTTLDIK

>DH536VH (SEQ ID NO:90)

QVQLVQSGAEVKKPGSSVKVSCKASGGSFYTYTINWVRQAPGQGLEWMGRVTTMFGVTLYAQ
KFQGRVTLTADKSTSTAYMELSSLRSEDTAVYYCATDGPDNFWSGLSHAFDLWGQGTMVTVS
S

>DH536VL (SEQ ID NO:91)

QSALTQPASVAGSPGQSITISCTGTSSDIGDSKYVSWYQQFPGKAPKVMIYEVSYRPSGVSS
RFSGSKSGNTASLTISGLQTEDEADYYCMAYTGTFTAIFGGGTKLTVL

>DH537VH (SEQ ID NO:92)

QVQLVQSGAEVRKAGSSVKVSCKASGGTFTSYGFSWIRQAPGQGLEWMGNVIPVFGSTNYAQ
KFQGRVSITADEATGTVHMDLTSLTSDDTAVYYCVRSSRELPTSMERWFDPWGQGTQVIVSS

>DH537VK (SEQ ID NO:93)

DIQMTQSPSSLSASVGDSVTITCRASQSINTYLNWYQQKPGKAPKLLIYSASNLHNGVPSRF
SGSGSGTSFTLTINNLQPEDFATYYCQQSYSAPYTFGQGTKSDTK

Figure 12B cont.

| Region | R# | DH511 | DH511 mutation |
|---|---|---|---|
| CDRH3 | 92 | C | |
| | 93 | T | |
| | 94 | A | |
| | 95 | D | |
| | 96 | L | W |
| | 97 | G | W,F |
| | 98 | E | W |
| | 99 | P | W |
| | 100 | V | F,L |
| | 100a | V | W |
| | 100b | S | W |
| | 100c | R | W |
| | 100d | F | W |
| | 100e | F | W |
| | 100f | E | W |
| | 100g | W | |
| | 100h | G | W |
| | 100i | S | W |
| | 100j | Y | W |
| | 100k | Y | |
| | 100k | Y | W |
| | 100l | Y | |
| | 100m | M | |
| | 101 | D | |
| | 102 | L | |
| | 103 | W | |
| | 104 | G | |

Figure 13A

| Region | R# | DH512 | DH512 mutation |
|---|---|---|---|
| CDRH3 | 92 | C | |
| | 93 | T | |
| | 94 | M | |
| | 95 | D | |
| | 96 | E | W |
| | 97 | G | W,F |
| | 98 | T | W |
| | 99 | P | W |
| | 100 | V | F,L |
| | 100a | T | W |
| | 100b | R | W |
| | 100c | F | W |
| | 100d | L | W,F |
| | 100e | E | W |
| | 100f | W | |
| | 100g | G | W |
| | 100h | Y | W |
| | 100i | F | W |
| | 100j | Y | |
| | 100k | Y | W |
| | 100l | Y | |
| | 100m | M | |
| | 101 | A | |
| | 102 | V | |
| | 103 | W | |
| | 104 | G | |

Figure 13B

Mutations outside of CDRH3

| Region | R# | DH511 | DH511 mutation | Region | R# | DH512 | DH512 mutation |
|---|---|---|---|---|---|---|---|
| CDRH1 | 26 | G | W | CDRH1 | 26 | G | W |
| | 27 | F | | | 27 | F | |
| | 28 | T | W | | 28 | F | W |
| | 29 | F | | | 29 | F | |
| | 30 | S | | | 30 | D | |
| | 31 | N | W | | 31 | N | W |
| | 32 | T | | | 32 | S | |
| | 33 | W | | | 33 | W | |

| Region | R# | DH511 | DH511 mutation | Region | R# | DH512 | DH512 mutation |
|---|---|---|---|---|---|---|---|
| CDRH2 | 51 | I | | CDRH2 | 51 | I | |
| | 52 | S | W | | 52 | R | W |
| | 52a | R | | | 52a | R | |
| | 52b | N | W | | 52b | L | W |
| | 52c | K | W | | 52c | K | W |
| | 53 | D | W | | 53 | D | W |
| | 54 | G | | | 54 | G | |
| | 55 | A | | | 55 | A | |
| | 56 | K | | | 56 | T | |
| | 57 | T | | | 57 | G | |

| Region | R# | DH511 | DH511 mutation | Region | R# | DH512 | DH512 mutation |
|---|---|---|---|---|---|---|---|
| FR3 | 72 | D | | FR3 | 72 | D | |
| | 73 | D | W | | 73 | D | W |
| | 74 | S | W | | 74 | S | W |
| | 75 | R | W | | 75 | R | W |

Figure 13C

DH512 Nucleotide Sequence (SEQ ID NO: 95)

CAGGTGCAGCTGGTACAGTCTGGGGGAGGTCTGGTGAAGCCGGGGGGGTCCCTCACACTCTC
CTGTTCAGCCTCTGGATTCTTTTTCGATAATTCATGGATGGGGTGGGTCCGTCAGGCGCCAG
GGAAGGGACTGGAGTGGGTTGGCCGCATTAGAAGGCTCAAAGACGGTGCGACAGGAGAATAT
GGTGCAGCCGTGAAGGACAGATTCACCATTTCAAGAGATGACAGTAGAAATATGCTGTACCT
GCACATGAGGACCCTGAAAACCGAGGACTCAGGCACTTATTATTGTACCATGGATGAGGGA
CCCCAGTAACACGCTTCTTAGAATGGGGCTACTTCTATTATTATATGGCCGTTTGGGGCAGA
GGGACCACGGTCATCGTCTCTTCA

DH512 Translated (Amino Acid) Sequence (SEQ ID NO:96)

QVQLVQSGGGLVKPGGSLTLSCSASGFFFDNSWMGWVRQAPGKGLEWVGRIRRLKDGATGEY
GAAVKDRFTISRDDSRNMLYLHMRTLKTEDSGTYYC<u>TMDEGTPVTRFLEWGYFYYYMAVWGR</u>
GTTVIVSS

Amino Acid Sequences of DH512 Heavy Chain Mutants

>DH512_E96W (SEQ ID NO:97)

QVQLVQSGGGLVKPGGSLTLSCSASGFFFDNSWMGWVRQAPGKGLEWVGRIRRLKDGATGEY
GAAVKDRFTISRDDSRNMLYLHMRTLKTEDSGTYYC<u>TMDWGTPVTRFLEWGYFYYYMAVWGR</u>
GTTVIVSS

>DH512_G97W (SEQ ID NO:98)

QVQLVQSGGGLVKPGGSLTLSCSASGFFFDNSWMGWVRQAPGKGLEWVGRIRRLKDGATGEY
GAAVKDRFTISRDDSRNMLYLHMRTLKTEDSGTYYC<u>TMDEWTPVTRFLEWGYFYYYMAVWGR</u>
GTTVIVSS

>DH512_T98W (SEQ ID NO:99)

QVQLVQSGGGLVKPGGSLTLSCSASGFFFDNSWMGWVRQAPGKGLEWVGRIRRLKDGATGEY
GAAVKDRFTISRDDSRNMLYLHMRTLKTEDSGTYYC<u>TMDEGWPVTRFLEWGYFYYYMAVWGR</u>
GTTVIVSS

>DH512_P99W (SEQ ID NO:100)

QVQLVQSGGGLVKPGGSLTLSCSASGFFFDNSWMGWVRQAPGKGLEWVGRIRRLKDGATGEY
GAAVKDRFTISRDDSRNMLYLHMRTLKTEDSGTYYC<u>TMDEGTWVTRFLEWGYFYYYMAVWGR</u>
GTTVIVSS

>DH512_V100F (SEQ ID NO:101)

QVQLVQSGGGLVKPGGSLTLSCSASGFFFDNSWMGWVRQAPGKGLEWVGRIRRLKDGATGEY
GAAVKDRFTISRDDSRNMLYLHMRTLKTEDSGTYYC<u>TMDEGTPFTRFLEWGYFYYYMAVWGR</u>
GTTVIVSS

Figure 13D

>DH512_V100I (SEQ ID NO:102)

QVQLVQSGGGLVKPGGSLTLSCSASGFFFDNSWMGWVRQAPGKGLEWVGRIRRLKDGATGEY
GAAVKDRFTISRDDSRNMLYLHMRTLKTEDSGTYYCTMDEGTPITRFLEWGYFYYYMAVWGR
GTTVIVSS

>DH512_T100aW (SEQ ID NO:103)
QVQLVQSGGGLVKPGGSLTLSCSASGFFFDNSWMGWVRQAPGKGLEWVGRIRRLKDGATGEY
GAAVKDRFTISRDDSRNMLYLHMRTLKTEDSGTYYCTMDEGTPVWRFLEWGYFYYYMAVWGR
GTTVIVSS

>DH512_R100bW (SEQ ID NO:104)

QVQLVQSGGGLVKPGGSLTLSCSASGFFFDNSWMGWVRQAPGKGLEWVGRIRRLKDGATGEY
GAAVKDRFTISRDDSRNMLYLHMRTLKTEDSGTYYCTMDEGTPVTWFLEWGYFYYYMAVWGR
GTTVIVSS

>DH512_F100cW (SEQ ID NO:105)

QVQLVQSGGGLVKPGGSLTLSCSASGFFFDNSWMGWVRQAPGKGLEWVGRIRRLKDGATGEY
GAAVKDRFTISRDDSRNMLYLHMRTLKTEDSGTYYCTMDEGTPVTRWLEWGYFYYYMAVWGR
GTTVIVSS

>DH512_L100dW (SEQ ID NO:106)

QVQLVQSGGGLVKPGGSLTLSCSASGFFFDNSWMGWVRQAPGKGLEWVGRIRRLKDGATGEY
GAAVKDRFTISRDDSRNMLYLHMRTLKTEDSGTYYCTMDEGTPVTRFWEWGYFYYYMAVWGR
GTTVIVSS

>DH512_L100dF (SEQ ID NO:107)

QVQLVQSGGGLVKPGGSLTLSCSASGFFFDNSWMGWVRQAPGKGLEWVGRIRRLKDGATGEY
GAAVKDRFTISRDDSRNMLYLHMRTLKTEDSGTYYCTMDEGTPVTRFFEWGYFYYYMAVWGR
GTTVIVSS

>DH512_E100eW (SEQ ID NO:108)

QVQLVQSGGGLVKPGGSLTLSCSASGFFFDNSWMGWVRQAPGKGLEWVGRIRRLKDGATGEY
GAAVKDRFTISRDDSRNMLYLHMRTLKTEDSGTYYCTMDEGTPVTRFLWWGYFYYYMAVWGR
GTTVIVSS

>DH512_G100gW (SEQ ID NO:109)

QVQLVQSGGGLVKPGGSLTLSCSASGFFFDNSWMGWVRQAPGKGLEWVGRIRRLKDGATGEY
GAAVKDRFTISRDDSRNMLYLHMRTLKTEDSGTYYCTMDEGTPVTRFLEWWYFYYYMAVWGR
GTTVIVSS

Figure 13D cont.

\>DH512_Y100hW (SEQ ID NO:110)

QVQLVQSGGGLVKPGGSLTLSCSASGFFFDNSWMGWVRQAPGKGLEWVGRIRRLKDGATGEY
GAAVKDRFTISRDDSRNMLYLHMRTLKTEDSGTYYCTMDEGTPVTRFLEWGWFYYYMAVWGR
GTTVIVSS

\>DH512_F100iW (SEQ ID NO:111)

QVQLVQSGGGLVKPGGSLTLSCSASGFFFDNSWMGWVRQAPGKGLEWVGRIRRLKDGATGEY
GAAVKDRFTISRDDSRNMLYLHMRTLKTEDSGTYYCTMDEGTPVTRFLEWGYWYYYMAVWGR
GTTVIVSS

\>DH512_Y100kW (SEQ ID NO:112)

QVQLVQSGGGLVKPGGSLTLSCSASGFFFDNSWMGWVRQAPGKGLEWVGRIRRLKDGATGEY
GAAVKDRFTISRDDSRNMLYLHMRTLKTEDSGTYYCTMDEGTPVTRFLEWGYFYWYMAVWGR
GTTVIVSS

Figure 13D cont.

High Throughput Antibody Screen - CHAVI mAbs

Assay - Luc/TZM-bl
values represent IC50 in ug/ml          IC50

| Virus ID | Clade | Panel R DH542 L4 | Panel P DH542 | Panel P PGT128 | Panel M PGT121 | Panel H 10-1074 | Panel M DH270 | Panel M DH471 |
|---|---|---|---|---|---|---|---|---|
| 0260.v5.c36 | A | 0.363 | 0.378 | 0.037 | 0.056 | 0.130 | 2.32 | 2.18 |
| 0330.v4.c3 | A | 0.403 | 1.83 | 0.377 | 0.067 | 0.010 | >50 | 14.6 |
| 0439.v5.c1 | A | >50 | >50 | 1.38 | >25 | >50 | >50 | >50 |
| 3365.v2.c20 | A | 1.28 | 10.3 | >50 | 0.133 | 0.003 | >50 | >50 |
| 3415.v1.c1 | A | >50 | >50 | 0.010 | >25 | >50 | >50 | >50 |
| 3718.v3.c11 | A | >50 | >50 | >50 | 1.12 | >50 | >50 | >50 |
| 398-F1_F6_20 | A | 0.018 | 0.021 | 0.005 | 0.0007 | 0.017 | 0.038 | 0.036 |
| BB201.B42 | A | 16.5 | >50 | 0.004 | 0.0008 | 0.021 | >50 | >50 |
| BB539.2B13 | A | >50 | >50 | >50 | >25 | >50 | >50 | >50 |
| BG505.W6M.C2 | A | >50 | >50 | 0.048 | 0.024 | >50 | >50 | >50 |
| BI369.9A | A | 0.117 | 0.112 | 0.030 | 0.006 | 0.002 | 0.407 | 0.301 |
| BS208.B1 | A | 8.04 | 13.9 | >50 | >25 | 15.1 | >50 | >50 |
| KER2008.12 | A | 0.052 | 0.047 | >50 | 2.10 | 0.123 | 14.6 | 0.133 |
| KER2018.11 | A | >50 | >50 | >50 | >25 | >50 | >50 | >50 |
| KNH1209.18 | A | 0.033 | 0.028 | 0.009 | 0.0007 | 0.029 | 0.085 | 0.044 |
| MB201.A1 | A | >50 | >50 | 0.005 | 0.0006 | >50 | >50 | >50 |
| MB539.2B7 | A | >50 | >50 | 1.41 | >25 | >50 | >50 | >50 |
| MI369.A5 | A | 0.092 | 0.166 | 0.022 | 0.009 | 0.002 | 0.501 | 0.480 |
| MS208.A1 | A | >50 | >50 | >50 | >25 | >50 | >50 | >50 |
| Q23.17 | A | 0.016 | 0.019 | 0.010 | 0.0005 | 0.010 | 0.058 | 0.049 |
| Q259.17 | A | >50 | >50 | >50 | >25 | 1.94 | >50 | >50 |
| Q769.d22 | A | >50 | >50 | >50 | >25 | >50 | >50 | >50 |
| Q769.h5 | A | >50 | >50 | >50 | >25 | >50 | >50 | >50 |
| Q842.d12 | A | >50 | >50 | 0.042 | 0.007 | >50 | >50 | >50 |
| QH209.14M.A2 | A | >50 | >50 | >50 | >25 | >50 | >50 | >50 |
| RW020.2 | A | 0.012 | 0.012 | 0.004 | 0.0007 | 0.002 | 0.051 | 0.052 |
| UG037.8 | A | 0.129 | 0.058 | 0.023 | 0.031 | 0.031 | 1.53 | 0.290 |
| 246-F3.C10.2 | AC | >50 | >50 | 0.003 | >25 | >50 | >50 | >50 |
| 3301.V1.C24 | AC | 0.163 | 0.105 | 0.131 | 0.007 | 0.018 | 0.587 | 0.331 |
| 3589.V1.C4 | AC | >50 | >50 | 0.009 | >25 | >50 | >50 | >50 |
| 6540.v4.c1 | AC | >50 | >50 | 0.815 | >25 | >50 | >50 | >50 |
| 6545.V4.C1 | AC | >50 | >50 | >50 | >25 | >50 | >50 | >50 |
| 0815.V3.C3 | ACD | 0.095 | 0.131 | 0.025 | 0.016 | 0.008 | 0.635 | 0.508 |
| 6095.V1.C10 | ACD | >50 | >50 | >50 | >25 | >50 | >50 | >50 |
| 3468.V1.C12 | AD | 18.1 | >50 | >50 | 0.047 | 0.006 | >50 | >50 |
| Q168.a2 | AD | >50 | >50 | >50 | >25 | >50 | >50 | >50 |
| Q461.e2 | AD | >50 | >50 | >50 | >25 | >50 | >50 | >50 |
| 620345.c1 | AE | >50 | >50 | >50 | >25 | >50 | >50 | >50 |
| BJOX009000.02.4 | AE | >50 | >50 | 0.008 | 2.36 | >50 | >50 | >50 |
| BJOX010000.06.2 | AE | >50 | >50 | 1.97 | >25 | >50 | >50 | >50 |
| BJOX025000.01.1 | AE | >50 | >50 | >50 | >25 | >50 | >50 | >50 |
| BJOX028000.10.3 | AE | 22.7 | >50 | 0.025 | >25 | >50 | >50 | >50 |
| C1080.c3 | AE | >50 | >50 | 0.100 | >25 | >50 | >50 | >50 |

Figure 14A

| | | | | | | | | |
|---|---|---|---|---|---|---|---|---|
| C2101.c1 | AE | >50 | >50 | 0.014 | >25 | >50 | >50 | >50 |
| C3347.c11 | AE | >50 | >50 | 0.006 | >25 | >50 | >50 | >50 |
| C4118.09 | AE | >50 | >50 | >50 | >25 | >50 | >50 | >50 |
| CM244.ec1 | AE | >50 | >50 | 0.013 | >25 | >50 | >50 | >50 |
| CNE3 | AE | >50 | >50 | >50 | >25 | >50 | >50 | >50 |
| CNE5 | AE | >50 | >50 | 0.062 | >25 | >50 | >50 | >50 |
| CNE55 | AE | >50 | >50 | >50 | >25 | >50 | >50 | >50 |
| CNE56 | AE | >50 | >50 | 1.18 | >25 | >50 | >50 | >50 |
| CNE59 | AE | >50 | >50 | >50 | >25 | >50 | >50 | >50 |
| CNE8 | AE | >50 | >50 | 0.014 | >25 | >50 | >50 | >50 |
| M02138 | AE | >50 | >50 | >50 | >25 | >50 | >50 | >50 |
| R1166.c1 | AE | >50 | >50 | >50 | >25 | >50 | >50 | >50 |
| R2184.c4 | AE | >50 | >50 | 1.36 | >25 | >50 | >50 | >50 |
| R3265.c6 | AE | >50 | >50 | >50 | >25 | >50 | >50 | >50 |
| TH023.6 | AE |  | >50 | 0.071 | >25 | >50 | >50 | >50 |
| TH966.8 | AE | >50 | >50 | 0.009 | >25 | >50 | >50 | >50 |
| TH976.17 | AE | >50 | >50 | >50 | >25 | >50 | >50 | >50 |
| 235-47 | AG | 0.189 | 0.301 | >50 | 0.289 | 0.004 | 3.11 | 0.557 |
| 242-14 | AG | >50 | >50 | >50 | >25 | >50 | >50 | >50 |
| 263-8 | AG | 0.081 | 0.191 | 0.211 | 0.872 | 0.092 | >50 | 2.56 |
| 269-12 | AG | 0.035 | 0.036 | 0.010 | 0.236 | 0.004 | 2.74 | 0.184 |
| 271-11 | AG | >50 | >50 | >50 | 23.3 | >50 | >50 | >50 |
| 928-28 | AG | 1.00 | 2.12 | >50 | 16.8 | 0.530 | >50 | >50 |
| DJ263.8 | AG | 0.060 | 0.068 | >50 | 0.053 | 0.005 | 0.201 | 0.128 |
| T250-4 | AG | 16.2 | >50 | 0.004 | 0.0004 | 0.0009 | >50 | >50 |
| T251-18 | AG | 2.03 | 10.5 | >50 | 6.17 | 0.169 | >50 | >50 |
| T253-11 | AG | >50 | >50 | >50 | >25 | 2.70 | >50 | >50 |
| T255-34 | AG | >50 | >50 | >50 | 12.8 | 0.380 | >50 | >50 |
| T257-31 | AG | >50 | >50 | >50 | >25 | >50 | >50 | >50 |
| T266-60 | AG | 0.146 | 0.462 | 0.016 | 0.118 | 0.082 | 6.21 | 5.04 |
| T278-50 | AG | 2.45 | 11.6 | 0.039 | >25 | 0.247 | >50 | >50 |
| T280-5 | AG | 0.055 | 0.034 | 0.014 | 0.003 | 0.005 | 0.044 | 0.015 |
| T33-7 | AG | >50 | >50 | >50 | >25 | >50 | >50 | >50 |
| 3988.25 | B | 0.046 | 0.018 | 0.004 | 0.0008 | 0.016 | 0.090 | 0.054 |
| 5768.04 | B | 0.039 | 0.164 | 1.41 | 0.293 | 0.314 | >50 | 5.23 |
| 6101.10 | B | 0.028 | 0.024 | 0.003 | 0.0009 | 0.030 | 0.124 | 0.104 |
| 6535.3 | B | 0.046 | 0.029 | 0.011 | 0.0008 | 0.018 | 0.102 | 0.059 |
| 7165.18 | B | 0.100 | 0.068 | 0.012 | 0.014 | 0.008 | 0.281 | 0.163 |
| 45_01dG5 | B | 0.028 | 0.029 | 0.010 | 0.0008 | 0.007 | 0.099 | 0.090 |
| 89.6.DG | B | 0.042 | 0.035 | 0.010 | 0.007 | 0.002 | 0.267 | 0.321 |
| AC10.29 | B | 0.021 | 0.018 | 0.010 | 0.029 | 0.025 | 1.18 | 0.025 |
| ADA.DG | B | 0.124 | 0.030 | 0.010 | 0.031 | 0.003 | 0.463 | 0.231 |
| Bal.01 | B | 0.042 | 0.045 | 0.117 | 0.0009 | 0.003 | 0.176 | 0.131 |
| BaL.26 | B | 0.049 | 0.060 | 0.050 | 0.010 | 0.004 | 0.221 | 0.113 |
| BG1168.01 | B | >50 | >50 | >50 | >25 | >50 | >50 | >50 |
| BL01.DG | B |  | 15.5 | >50 | >25 | 5.28 | >50 | >50 |
| BR07.DG | B | >50 | >50 | 0.636 | 0.396 | 0.015 | >50 | >50 |
| BX08.16 | B |  | 0.020 | 0.007 | 0.0008 | 0.008 | 0.074 | 0.078 |
| CAAN.A2 | B | 0.033 | 0.027 | 0.124 | 0.003 | 0.014 | 0.088 | 0.106 |

Figure 14A cont.

| | | | | | | | | |
|---|---|---|---|---|---|---|---|---|
| CNE10 | B | 1.35 | 10.1 | 0.010 | 0.0009 | 0.006 | >50 | >50 |
| CNE12 | B | 0.053 | 0.049 | 0.016 | 0.002 | 0.025 | 0.128 | 0.083 |
| CNE14 | B | 0.027 | 0.021 | 0.013 | 0.0008 | 0.019 | 0.066 | 0.043 |
| CNE4 | B | 0.582 | 2.99 | 0.898 | 6.42 | 0.102 | >50 | 33.9 |
| CNE57 | B | 0.044 | 0.048 | 0.008 | 0.005 | 0.006 | 0.135 | 0.081 |
| HO86.8 | B | >50 | >50 | >50 | >25 | >50 | >50 | >50 |
| HT593.1 | B | >50 | >50 | >50 | >25 | 0.704 | >50 | >50 |
| HXB2.DG | B | 6.92 | >50 | >50 | >25 | 3.91 | >50 | >50 |
| JRCSF.JB | B | 0.041 | 0.046 | 0.011 | 0.020 | 0.004 | 1.17 | 0.100 |
| JRFL.JB | B | 0.024 | 0.019 | 0.010 | 0.008 | 0.020 | 0.075 | 0.033 |
| MN.3 | B | >50 | >50 | >50 | >25 | 1.29 | >50 | >50 |
| PVO.04 | B | 0.102 | 0.079 | 0.013 | 0.113 | 0.044 | 0.447 | 0.299 |
| QH0515.01 | B | 0.383 | 0.907 | >50 | 9.88 | 0.200 | >50 | >50 |
| QH0692.42 | B | 0.238 | 0.212 | 0.039 | 0.891 | 0.185 | 3.96 | 1.40 |
| REJO.67 | B | >50 | >50 | >50 | 13.3 | >50 | >50 | >50 |
| RHPA.7 | B | 0.054 | 0.059 | 0.032 | 0.010 | 0.007 | 0.285 | 0.116 |
| SC422.8 | B | 0.078 | 0.092 | 0.384 | 0.165 | 0.043 | 0.646 | 0.321 |
| SF162.LS | B | 0.009 | 0.009 | 0.006 | 0.0007 | 0.003 | 0.036 | 0.022 |
| SS1196.01 | B | 0.025 | 0.021 | 0.011 | 0.0008 | 0.011 | 0.080 | 0.067 |
| THRO.18 | B | >50 | >50 | >50 | >25 | >50 | >50 | >50 |
| TRJO.58 | B | 0.146 | 0.137 | 0.019 | 7.82 | 0.086 | >50 | 0.335 |
| TRO.11 | B | 0.060 | 0.044 | 0.019 | 0.001 | 0.022 | 0.189 | 0.116 |
| WITO.33 | B | 16.1 | >50 | >50 | 0.705 | 0.213 | >50 | >50 |
| X2278.C2.B6 | B | 0.033 | 0.038 | 0.012 | 0.004 | 0.015 | 0.855 | 0.108 |
| YU2.DG | B | 0.109 | 0.135 | 0.085 | 0.079 | 0.089 | 0.634 | 0.524 |
| BJOX002000.03.2 | BC | 0.024 | 0.021 | 0.018 | 0.008 | 0.011 | 0.096 | 0.046 |
| CH038.12 | BC | 0.039 | 0.039 | 0.007 | 0.002 | 0.019 | 0.217 | 0.093 |
| CH070.1 | BC | 0.113 | 0.091 | 0.028 | 0.010 | 0.048 | 0.621 | 0.310 |
| CH117.4 | BC | >50 | >50 | >50 | >25 | >50 | >50 | >50 |
| CH119.10 | BC | 0.055 | 0.049 | 0.020 | 0.017 | 0.020 | 0.235 | 0.077 |
| CH181.12 | BC | 0.123 | 0.102 | 0.022 | 0.012 | 0.011 | 0.773 | 0.320 |
| CNE15 | BC | >50 | >50 | >50 | >25 | >50 | >50 | >50 |
| CNE19 | BC | 0.010 | 0.030 | >50 | 0.0008 | 0.027 | >50 | 0.093 |
| CNE20 | BC | 1.18 | 4.32 | 0.002 | <0.0003 | 0.002 | >50 | >50 |
| CNE21 | BC | 0.071 | 0.060 | 0.012 | 0.002 | 0.014 | 0.535 | 0.129 |
| CNE40 | BC | >50 | >50 | >50 | 0.321 | 0.964 | >50 | >50 |
| CNE7 | BC | >50 | >50 | 0.034 | 0.013 | 0.048 | >50 | >50 |
| 286.36 | C | 0.023 | 0.027 | 0.011 | 0.0009 | 0.009 | 0.119 | 0.069 |
| 288.38 | C | 0.041 | 0.048 | 0.011 | 0.004 | 0.024 | 0.148 | 0.114 |
| 0013095-2.11 | C | >50 | >50 | >50 | >25 | 5.84 | >50 | >50 |
| 001428-2.42 | C | 2.37 | 18.2 | 0.037 | 0.007 | 0.008 | >50 | >50 |
| 0077_V1.C16 | C | >50 | >50 | >50 | >25 | >50 | >50 | >50 |
| 00836-2.5 | C | >50 | >50 | >50 | >25 | >50 | >50 | >50 |
| 0921.V2.C14 | C | 1.74 | 3.86 | >50 | >25 | >50 | >50 | >50 |
| 16055-2.3 | C | >50 | >50 | >50 | 1.18 | >50 | >50 | >50 |
| 16845-2.22 | C | 1.00 | 1.12 | 0.121 | 7.98 | 0.318 | >50 | 13.1 |
| 16936-2.21 | C | 0.034 | 0.072 | 0.023 | 0.002 | 0.003 | 0.725 | 0.380 |
| 25710-2.43 | C | 0.099 | 0.120 | 0.020 | 0.019 | 0.011 | 2.07 | 0.383 |
| 25711-2.4 | C | 0.021 | 0.021 | 0.016 | 0.011 | 0.024 | 0.200 | 0.044 |
| 25925-2.22 | C | 0.117 | 0.519 | 0.016 | 0.032 | 0.042 | >50 | 8.78 |
| 26191-2.48 | C | >50 | >50 | 0.018 | 0.091 | 0.010 | >50 | >50 |
| 3168.V4.C10 | C | 0.380 | 0.440 | >50 | 0.453 | 0.391 | 0.856 | 1.16 |
| 3637.V5.C3 | C | >50 | >50 | >50 | >25 | >50 | >50 | >50 |
| 3873.V1.C24 | C | 0.056 | 0.043 | 0.015 | 0.030 | 0.019 | 0.374 | 0.100 |

*Figure 14A cont.*

| | | | | | | | | |
|---|---|---|---|---|---|---|---|---|
| 426c | C | 0.104 | 0.197 | >50 | >25 | 0.068 | >50 | 0.916 |
| 6322.V4.C1 | C | >50 | >50 | >50 | >25 | >50 | >50 | >50 |
| 6471.V1.C16 | C | 0.148 | 0.429 | >50 | >25 | 0.827 | >50 | 3.43 |
| 6631.V3.C10 | C | >50 | >50 | 1.25 | >25 | 0.158 | >50 | >50 |
| 6644.V2.C33 | C | 0.034 | 0.033 | 0.066 | 0.012 | 0.002 | 0.128 | 0.095 |
| 6785.V5.C14 | C | 0.043 | 0.050 | 0.016 | 0.015 | 0.004 | 0.247 | 0.138 |
| 6838.V1.C35 | C | >50 | >50 | >50 | 0.093 | 0.611 | >50 | >50 |
| 96ZM651.02 | C | 0.025 | 0.027 | 0.026 | 0.001 | 0.002 | 0.660 | 0.103 |
| BR025.9 | C | 0.014 | 0.015 | 0.005 | 0.001 | 0.002 | 0.060 | 0.029 |
| CAP210.E8 | C | >50 | >50 | >50 | >25 | >50 | >50 | >50 |
| CAP244.D3 | C | 0.564 | 5.23 | >50 | >25 | 41.1 | >50 | >50 |
| CAP256.206.C9 | C | 0.063 | 0.043 | 0.018 | 0.003 | 0.030 | 0.128 | 0.084 |
| CAP45.G3 | C | >50 | >50 | >50 | 1.74 | >50 | >50 | >50 |
| Ce1176.A3 | C | 0.108 | 0.098 | 0.015 | 0.004 | 0.024 | 0.294 | 0.222 |
| CE703010217.B6 | C | 0.048 | 0.040 | 0.043 | 0.0007 | 0.004 | 0.457 | 0.078 |
| CNE30 | C | 0.959 | 0.742 | 0.269 | 0.068 | 0.222 | 3.02 | 1.84 |
| CNE31 | C | >50 | >50 | >50 | 0.947 | 0.348 | >50 | >50 |
| CNE53 | C | 0.184 | 0.143 | 0.030 | 0.003 | 0.002 | 0.406 | 0.272 |
| CNE58 | C | 0.175 | 0.250 | 0.988 | >25 | 0.097 | 2.20 | 0.325 |
| DU123.06 | C | 0.171 | 0.175 | 0.061 | 0.033 | 0.072 | 0.531 | 0.288 |
| DU151.02 | C | 0.219 | 0.820 | 0.010 | 0.002 | 0.015 | >50 | 24.6 |
| DU156.12 | C | 0.046 | 0.053 | 0.020 | 0.002 | 0.053 | 0.234 | 0.126 |
| DU172.17 | C | 0.118 | 0.300 | 0.041 | 0.030 | 0.016 | 13.8 | 1.39 |
| DU422.01 | C | 0.183 | 0.120 | 0.064 | 0.022 | 0.027 | 0.554 | 0.243 |
| MW965.26 | C | | 0.019 | 0.179 | 0.0008 | 0.015 | 0.135 | 0.091 |
| SO18.18 | C | 0.021 | 0.015 | 0.041 | 0.0005 | 0.0007 | 0.073 | 0.039 |
| TV1.29 | C | 0.368 | 0.670 | 0.122 | 0.035 | 0.410 | 8.94 | 1.62 |
| TZA125.17 | C | 11.4 | >50 | 0.511 | 5.55 | 1.77 | >50 | >50 |
| TZBD.02 | C | 0.064 | 0.057 | >50 | <0.0003 | 0.022 | 1.82 | 0.081 |
| ZA012.29 | C | 0.078 | 0.066 | 0.040 | 0.0008 | 0.010 | 9.33 | 0.125 |
| ZM106.9 | C | 0.034 | 0.031 | 0.025 | 0.0007 | 0.028 | 0.127 | 0.078 |
| ZM109.4 | C | >50 | >50 | >50 | 11.7 | >50 | >50 | >50 |
| ZM135.10a | C | 0.094 | 0.122 | >50 | 1.94 | 0.052 | 2.12 | 0.302 |
| ZM176.66 | C | 0.358 | 0.504 | 0.026 | 15.4 | 0.209 | >50 | 8.01 |
| ZM197.7 | C | >50 | >50 | >50 | >25 | >50 | >50 | >50 |
| ZM214.15 | C | 0.667 | 0.563 | 0.522 | 1.03 | 0.491 | 46.9 | 6.22 |
| ZM215.8 | C | 0.112 | 0.161 | 0.045 | 0.011 | 0.004 | 5.13 | 0.361 |
| ZM233.6 | C | >50 | >50 | >50 | 2.13 | 0.003 | >50 | >50 |
| ZM249.1 | C | >50 | >50 | 0.363 | >25 | >50 | >50 | >50 |
| ZM53.12 | C | >50 | >50 | >50 | <0.0003 | >50 | >50 | >50 |
| ZM55.28a | C | 0.032 | 0.052 | 0.024 | 0.046 | 0.002 | 0.145 | 0.074 |
| 3326.V4.C3 | CD | >50 | >50 | >50 | >25 | >50 | >50 | >50 |
| 3337.V2.C6 | CD | 0.112 | 0.305 | 0.004 | 8.10 | 0.008 | 34.0 | 6.88 |
| 3817.v2.c59 | CD | 0.234 | 0.332 | 0.017 | >25 | 0.308 | 0.736 | 0.856 |
| 191821.E6.1 | D | 4.79 | 6.91 | 0.035 | >25 | >50 | >50 | >50 |
| 231965.c1 | D | >50 | >50 | >50 | >25 | 10.0 | >50 | >50 |
| 247-23 | D | >50 | >50 | >50 | >25 | >50 | >50 | >50 |

*Figure 14A cont.*

| | | | | | | | |
|---|---|---|---|---|---|---|---|
| 3016.v5.c45 | D | >50 | >50 | >50 | >25 | >50 | >50 | >50 |
| 57128.vrc15 | D | 0.673 | 2.40 | 0.059 | 2.60 | 0.252 | 17.4 | 23.0 |
| 6405.v4.c34 | D | 1.12 | 2.88 | 1.63 | 0.009 | 0.007 | >50 | >50 |
| A03349M1.vrc4a | D | 6.57 | >50 | 0.019 | 0.025 | 0.010 | >50 | >50 |
| A07412M1.vrc12 | D | >50 | >50 | 24.7 | 0.013 | 0.021 | >50 | >50 |
| NKU3006.ec1 | D | >50 | >50 | >50 | >25 | >50 | >50 | >50 |
| UG021.16 | D | | >50 | >50 | 2.49 | 0.068 | >50 | >50 |
| UG024.2 | D | >50 | >50 | >50 | >25 | 0.111 | >50 | >50 |
| P0402.c2.11 | G | 0.042 | 0.107 | 0.007 | 0.0007 | 0.006 | 14.8 | 2.81 |
| P1981.C5.3 | G | 0.016 | 0.015 | 0.015 | <0.0003 | 0.007 | 0.047 | 0.038 |
| X1193.c1 | G | 0.170 | 0.213 | 0.020 | 0.019 | 0.036 | 31.3 | 1.19 |
| X1254.c3 | G | 0.043 | 0.070 | 0.023 | 0.008 | 0.037 | 0.259 | 0.174 |
| X1632.S2.B10 | G | >50 | >50 | >50 | >25 | >50 | >50 | >50 |
| X2088.c9 | G | 0.029 | 0.022 | >50 | 0.0006 | 0.005 | 0.158 | 0.083 |
| X2131.C1.B5 | G | 0.078 | 0.096 | 0.023 | 0.003 | 0.021 | 0.972 | 0.197 |
| SIVmac251.30.SG3 | NA | >50 | >50 | >50 | >25 | >50 | >50 | >50 |
| SVA.MLV | NA | >50 | >50 | >50 | >25 | >50 | >50 | >50 |

Figure 14A cont.

| | DH542 L4 | DH542 | PGT128 | PGT121 | 10-1074 | DH270 | DH471 |
|---|---|---|---|---|---|---|---|
| # Viruses | 203 | 208 | 208 | 208 | 208 | 208 | 208 |
| Total VS Neutralized | | | | | | | |
| IC50 <50ug/ml | 119 | 114 | 128 | 127 | 137 | 88 | 100 |
| IC50 <10ug/ml | 113 | 107 | 127 | 121 | 134 | 81 | 95 |
| IC50 <1.0ug/ml | 99 | 97 | 119 | 104 | 127 | 65 | 79 |
| IC50 <0.1ug/ml | 61 | 62 | 101 | 90 | 101 | 17 | 33 |
| IC50 <0.01ug/ml | 1 | 1 | 21 | 54 | 42 | 0 | 0 |
| % VS Neutralized | | | | | | | |
| IC50 <50ug/ml | 59 | 55 | 62 | 61 | 66 | 42 | 48 |
| IC50 <10ug/ml | 56 | 51 | 61 | 58 | 64 | 39 | 46 |
| IC50 <1.0ug/ml | 49 | 47 | 57 | 50 | 61 | 31 | 38 |
| IC50 <0.1ug/ml | 30 | 30 | 49 | 43 | 49 | 8 | 16 |
| IC50 <0.01ug/ml | 0 | 0 | 10 | 26 | 20 | 0 | 0 |
| | | | | | | | |
| Median IC50 | 0.095 | 0.076 | 0.021 | 0.014 | 0.021 | 0.390 | 0.151 |
| Geometric Mean | 0.142 | 0.136 | 0.034 | 0.027 | 0.033 | 0.482 | 0.268 |

Figure 14B

High Throughput Antibody Screen - CHAVI mAbs
Assay - Luc/TZM-bl
values represent IC80 in ug/ml                    IC80

| Virus ID | Clade | Panel R DH542 L4 | Panel P DH542 | Panel P PGT128 | Panel M PGT121 | Panel M 10-1074 | Panel M DH270 | Panel M DH471 |
|---|---|---|---|---|---|---|---|---|
| 0260.v5.c36 | A | 0.893 | 0.849 | 0.102 | 0.193 | 0.431 | 5.38 | 4.90 |
| 0330.v4.c3 | A | 3.55 | 10.4 | 1.30 | 0.241 | 0.062 | >50 | >50 |
| 0439.v5.c1 | A | >50 | >50 | 17.4 | >25 | >50 | >50 | >50 |
| 3365.v2.c20 | A | 12.8 | >50 | >50 | 0.734 | 0.057 | >50 | >50 |
| 3415.v1.c1 | A | >50 | >50 | 0.031 | >25 | >50 | >50 | >50 |
| 3718.v3.c11 | A | >50 | >50 | >50 | 14.0 | >50 | >50 | >50 |
| 398-F1_F6_20 | A | 0.044 | 0.047 | 0.011 | 0.007 | 0.060 | 0.101 | 0.106 |
| BB201.B42 | A | >50 | >50 | 0.009 | 0.010 | 0.093 | >50 | >50 |
| BB539.2B13 | A | >50 | >50 | >50 | >25 | >50 | >50 | >50 |
| BG505.W6M.C2 | A | >50 | >50 | 0.441 | 0.162 | >50 | >50 | >50 |
| BI369.9A | A | 0.319 | 0.292 | 0.084 | 0.040 | 0.015 | 1.01 | 0.866 |
| BS208.B1 | A | >50 | >50 | >50 | >25 | >50 | >50 | >50 |
| KER2008.12 | A | 0.251 | 0.215 | >50 | >25 | 1.25 | >50 | 0.754 |
| KER2018.11 | A | >50 | >50 | >50 | >25 | >50 | >50 | >50 |
| KNH1209.18 | A | 0.081 | 0.064 | 0.019 | 0.006 | 0.045 | 0.205 | 0.141 |
| MB201.A1 | A | >50 | >50 | 0.070 | 0.002 | >50 | >50 | >50 |
| MB539.2B7 | A | >50 | >50 | >50 | >25 | >50 | >50 | >50 |
| MI369.A5 | A | 0.330 | 0.458 | 0.067 | 0.054 | 0.070 | 1.32 | 1.02 |
| MS208.A1 | A | >50 | >50 | >50 | >25 | >50 | >50 | >50 |
| Q23.17 | A | 0.051 | 0.042 | 0.021 | 0.001 | 0.047 | 0.138 | 0.096 |
| Q259.17 | A | >50 | >50 | >50 | >25 | >50 | >50 | >50 |
| Q769.d22 | A | >50 | >50 | >50 | >25 | >50 | >50 | >50 |
| Q769.h5 | A | >50 | >50 | >50 | >25 | >50 | >50 | >50 |
| Q842.d12 | A | >50 | >50 | 0.139 | 0.030 | >50 | >50 | >50 |
| QH209.14M.A2 | A | >50 | >50 | >50 | >25 | >50 | >50 | >50 |
| RW020.2 | A | 0.030 | 0.028 | 0.011 | 0.002 | 0.009 | 0.116 | 0.122 |
| UG037.8 | A | 0.368 | 0.170 | 0.073 | 0.315 | 0.184 | 7.61 | 1.44 |
| 246-F3.C10.2 | AC | >50 | >50 | 0.008 | >25 | >50 | >50 | >50 |
| 3301.V1.C24 | AC | 0.423 | 0.307 | 0.386 | 0.030 | 0.065 | 1.50 | 0.817 |
| 3589.V1.C4 | AC | >50 | >50 | 0.041 | >25 | >50 | >50 | >50 |
| 6540.v4.c1 | AC | >50 | >50 | 5.54 | >25 | >50 | >50 | >50 |
| 6545.V4.C1 | AC | >50 | >50 | >50 | >25 | >50 | >50 | >50 |
| 0815.V3.C3 | ACD | 0.292 | 0.360 | 0.070 | 0.082 | 0.072 | 1.64 | 1.32 |
| 6095.V1.C10 | ACD | >50 | >50 | >50 | >25 | >50 | >50 | >50 |
| 3468.V1.C12 | AD | >50 | >50 | >50 | 0.635 | 0.031 | >50 | >50 |
| Q168.a2 | AD | >50 | >50 | >50 | >25 | >50 | >50 | >50 |
| Q461.e2 | AD | >50 | >50 | >50 | >25 | >50 | >50 | >50 |
| 620345.c1 | AE | >50 | >50 | >50 | >25 | >50 | >50 | >50 |
| BJOX009000.02.4 | AE | >50 | >50 | 0.020 | >25 | >50 | >50 | >50 |
| BJOX010000.06.2 | AE | >50 | >50 | >50 | >25 | >50 | >50 | >50 |
| BJOX025000.01.1 | AE | >50 | >50 | >50 | >25 | >50 | >50 | >50 |
| BJOX028000.10.3 | AE | >50 | >50 | 0.068 | >25 | >50 | >50 | >50 |
| C1080.c3 | AE | >50 | >50 | 0.437 | >25 | >50 | >50 | >50 |

Figure 15A

| | | | | | | | |
|---|---|---|---|---|---|---|---|
| C2101.c1 | AE | >50 | >50 | 0.036 | >25 | >50 | >50 | >50 |
| C3347.c11 | AE | >50 | >50 | 0.020 | >25 | >50 | >50 | >50 |
| C4118.09 | AE | >50 | >50 | >50 | >25 | >50 | >50 | >50 |
| CM244.ec1 | AE | >50 | >50 | 0.032 | >25 | >50 | >50 | >50 |
| CNE3 | AE | >50 | >50 | >50 | >25 | >50 | >50 | >50 |
| CNE5 | AE | >50 | >50 | 0.256 | >25 | >50 | >50 | >50 |
| CNE55 | AE | >50 | >50 | >50 | >25 | >50 | >50 | >50 |
| CNE56 | AE | >50 | >50 | >50 | >25 | >50 | >50 | >50 |
| CNE59 | AE | >50 | >50 | >50 | >25 | >50 | >50 | >50 |
| CNE8 | AE | >50 | >50 | 0.032 | >25 | >50 | >50 | >50 |
| M02138 | AE | >50 | >50 | >50 | >25 | >50 | >50 | >50 |
| R1166.c1 | AE | >50 | >50 | >50 | >25 | >50 | >50 | >50 |
| R2184.c4 | AE | >50 | >50 | 3.00 | >25 | >50 | >50 | >50 |
| R3265.c6 | AE | >50 | >50 | >50 | >25 | >50 | >50 | >50 |
| TH023.6 | AE | | >50 | 3.47 | >25 | >50 | >50 | >50 |
| TH966.8 | AE | >50 | >50 | 0.070 | >25 | >50 | >50 | >50 |
| TH976.17 | AE | >50 | >50 | >50 | >25 | >50 | >50 | >50 |
| 235-47 | AG | 0.505 | 0.736 | >50 | 1.10 | 0.058 | 12.1 | 1.55 |
| 242-14 | AG | >50 | >50 | >50 | >25 | >50 | >50 | >50 |
| 263-8 | AG | 0.441 | 1.10 | 0.870 | 4.22 | 1.76 | >50 | 30.4 |
| 269-12 | AG | 0.080 | 0.101 | 0.060 | 1.57 | 0.051 | 9.15 | 0.992 |
| 271-11 | AG | >50 | >50 | >50 | >25 | >50 | >50 | >50 |
| 928-28 | AG | 3.54 | 12.2 | >50 | >25 | 2.10 | >50 | >50 |
| DJ263.8 | AG | 0.194 | 0.226 | >50 | 0.187 | 0.143 | 0.865 | 0.537 |
| T250-4 | AG | >50 | >50 | 0.010 | 0.0009 | 0.008 | >50 | >50 |
| T251-18 | AG | 27.5 | >50 | >50 | >25 | 1.67 | >50 | >50 |
| T253-11 | AG | >50 | >50 | >50 | >25 | 34.6 | >50 | >50 |
| T255-34 | AG | >50 | >50 | >50 | >25 | >50 | >50 | >50 |
| T257-31 | AG | >50 | >50 | >50 | >25 | >50 | >50 | >50 |
| T266-60 | AG | 0.543 | 1.49 | 0.032 | 0.601 | 0.763 | 30.9 | 39.3 |
| T278-50 | AG | 19.5 | >50 | 0.117 | >25 | 2.40 | >50 | >50 |
| T280-5 | AG | 0.092 | 0.069 | 0.026 | 0.031 | 0.025 | 0.169 | 0.083 |
| T33-7 | AG | >50 | >50 | >50 | >25 | >50 | >50 | >50 |
| 3988.25 | B | 0.072 | 0.047 | 0.013 | 0.007 | 0.034 | 0.184 | 0.151 |
| 5768.04 | B | 0.117 | 0.688 | >50 | 3.06 | 2.40 | >50 | 31.3 |
| 6101.10 | B | 0.085 | 0.066 | 0.008 | 0.010 | 0.101 | 0.327 | 0.312 |
| 6535.3 | B | 0.107 | 0.079 | 0.025 | 0.007 | 0.068 | 0.276 | 0.163 |
| 7165.18 | B | 0.263 | 0.173 | 0.038 | 0.069 | 0.069 | 0.815 | 0.519 |
| 45_01dG5 | B | 0.098 | 0.086 | 0.027 | 0.010 | 0.057 | 0.301 | 0.255 |
| 89.6.DG | B | 0.139 | 0.118 | 0.027 | 0.062 | 0.014 | 0.628 | 0.980 |
| AC10.29 | B | 0.050 | 0.042 | 0.031 | 0.112 | 0.109 | 4.47 | 0.088 |
| ADA.DG | B | 0.347 | 0.100 | 0.070 | 0.131 | 0.042 | 1.97 | 1.17 |
| Bal.01 | B | 0.150 | 0.098 | >50 | 0.010 | 0.029 | 0.636 | 0.394 |
| BaL.26 | B | 0.156 | 0.200 | 0.300 | 0.059 | 0.032 | 0.541 | 0.349 |
| BG1168.01 | B | >50 | >50 | >50 | >25 | >50 | >50 | >50 |
| BL01.DG | B | | >50 | >50 | >25 | 32.6 | >50 | >50 |
| BR07.DG | B | >50 | >50 | >50 | 2.37 | 0.190 | >50 | >50 |
| BX08.16 | B | | 0.053 | 0.017 | 0.006 | 0.038 | 0.198 | 0.083 |
| CAAN.A2 | B | 0.111 | 0.091 | >50 | 0.020 | 0.056 | 0.267 | 0.226 |

Figure 15A cont.

| | | | | | | | | |
|---|---|---|---|---|---|---|---|---|
| CNE10 | B | 6.55 | >50 | 0.036 | 0.020 | 0.041 | >50 | >50 |
| CNE12 | B | 0.182 | 0.125 | 0.043 | 0.009 | 0.060 | 0.325 | 0.235 |
| CNE14 | B | 0.076 | 0.051 | 0.033 | 0.006 | 0.041 | 0.153 | 0.114 |
| CNE4 | B | 10.8 | 42.1 | >50 | >25 | 0.624 | >50 | >50 |
| CNE57 | B | 0.130 | 0.112 | 0.026 | 0.034 | 0.055 | 0.291 | 0.206 |
| HO86.8 | B | >50 | >50 | >50 | >25 | >50 | >50 | >50 |
| HT593.1 | B | >50 | >50 | >50 | >25 | 3.67 | >50 | >50 |
| HXB2.DG | B | >50 | >50 | >50 | >25 | 28.5 | >50 | >50 |
| JRCSF.JB | B | 0.129 | 0.113 | 0.022 | 0.095 | 0.059 | 4.55 | 0.463 |
| JRFL.JB | B | 0.080 | 0.057 | 0.060 | 0.043 | 0.096 | 0.202 | 0.100 |
| MN.3 | B | >50 | >50 | >50 | >25 | 17.9 | >50 | >50 |
| PVO.04 | B | 0.278 | 0.200 | 0.025 | 0.414 | 0.272 | 1.39 | 0.988 |
| QH0515.01 | B | 2.12 | 4.25 | >50 | >25 | 0.886 | >50 | >50 |
| QH0692.42 | B | 0.545 | 0.539 | 0.096 | 11.4 | 0.643 | 24.1 | 6.47 |
| REJO.67 | B | >50 | >50 | >50 | >25 | >50 | >50 | >50 |
| RHPA.7 | B | 0.168 | 0.168 | 0.117 | 0.052 | 0.066 | 1.20 | 0.540 |
| SC422.8 | B | 0.269 | 0.242 | 1.10 | 0.375 | 0.244 | 1.82 | 0.599 |
| SF162.LS | B | 0.027 | 0.024 | 0.017 | 0.002 | 0.014 | 0.096 | 0.060 |
| SS1196.01 | B | 0.079 | 0.063 | 0.024 | 0.007 | 0.033 | 0.214 | 0.191 |
| THRO.18 | B | >50 | >50 | >50 | >25 | >50 | >50 | >50 |
| TRJO.58 | B | 0.400 | 0.360 | 0.041 | >25 | 0.525 | >50 | 0.893 |
| TRO.11 | B | 0.159 | 0.117 | 0.044 | 0.012 | 0.075 | 0.510 | 0.323 |
| WITO.33 | B | >50 | >50 | >50 | 5.23 | 1.06 | >50 | >50 |
| X2278.C2.B6 | B | 0.095 | 0.104 | 0.033 | 0.027 | 0.074 | 4.58 | 0.292 |
| YU2.DG | B | 0.255 | 0.310 | 0.355 | 0.272 | 0.342 | 1.81 | 1.31 |
| BJOX002000.03.2 | BC | 0.066 | 0.052 | 0.049 | 0.047 | 0.045 | 0.236 | 0.119 |
| CH038.12 | BC | 0.099 | 0.091 | 0.015 | 0.010 | 0.078 | 0.674 | 0.206 |
| CH070.1 | BC | 0.308 | 0.245 | 0.077 | 0.056 | 0.204 | 1.70 | 0.863 |
| CH117.4 | BC | >50 | >50 | >50 | >25 | >50 | >50 | >50 |
| CH119.10 | BC | 0.145 | 0.113 | 0.052 | 0.073 | 0.077 | 0.412 | 0.194 |
| CH181.12 | BC | 0.366 | 0.266 | 0.054 | 0.062 | 0.107 | 2.52 | 0.855 |
| CNE15 | BC | >50 | >50 | >50 | >25 | >50 | >50 | >50 |
| CNE19 | BC | 0.300 | 0.297 | >50 | 0.020 | >50 | >50 | 1.99 |
| CNE20 | BC | 6.73 | >50 | 0.006 | 0.0007 | 0.008 | >50 | >50 |
| CNE21 | BC | 0.188 | 0.142 | 0.025 | 0.011 | 0.090 | 1.61 | 0.392 |
| CNE40 | BC | >50 | >50 | >50 | 1.70 | 12.3 | >50 | >50 |
| CNE7 | BC | >50 | >50 | 0.103 | 0.072 | 0.302 | >50 | >50 |
| 286.36 | C | 0.069 | 0.076 | 0.023 | 0.005 | 0.063 | 0.342 | 0.191 |
| 288.38 | C | 0.123 | 0.125 | 0.030 | 0.019 | 0.054 | 0.390 | 0.283 |
| 0013095-2.11 | C | >50 | >50 | >50 | >25 | >50 | >50 | >50 |
| 001428-2.42 | C | 15.9 | >50 | 0.084 | 0.066 | 0.082 | >50 | >50 |
| 0077_V1.C16 | C | >50 | >50 | >50 | >25 | >50 | >50 | >50 |
| 00836-2.5 | C | >50 | >50 | >50 | >25 | >50 | >50 | >50 |
| 0921.V2.C14 | C | 6.41 | 23.0 | >50 | >25 | >50 | >50 | >50 |
| 16055-2.3 | C | >50 | >50 | >50 | 11.1 | >50 | >50 | >50 |
| 16845-2.22 | C | 3.34 | 7.17 | 0.390 | >25 | 2.20 | >50 | >50 |
| 16936-2.21 | C | 0.098 | 0.136 | 0.075 | 0.004 | 0.019 | 2.05 | 0.807 |
| 25710-2.43 | C | 0.335 | 0.346 | 0.047 | 0.070 | 0.109 | 8.80 | 1.37 |
| 25711-2.4 | C | 0.068 | 0.060 | 0.047 | 0.052 | 0.096 | 1.50 | 0.119 |
| 25925-2.22 | C | 0.537 | 1.84 | 0.040 | 0.086 | 0.156 | >50 | >50 |
| 26191-2.48 | C | >50 | >50 | 0.047 | 0.338 | 0.070 | >50 | >50 |
| 3168.V4.C10 | C | 1.39 | 1.30 | >50 | 1.95 | 1.41 | 4.14 | 3.56 |
| 3637.V5.C3 | C | >50 | >50 | >50 | >25 | >50 | >50 | >50 |
| 3873.V1.C24 | C | 0.118 | 0.124 | 0.037 | 0.148 | 0.152 | 0.976 | 0.328 |

Figure 15A cont.

| | | | | | | | | |
|---:|---|---|---|---|---|---|---|---|
| 426c | C | 0.510 | 1.69 | >50 | >25 | 0.262 | >50 | 26.8 |
| 6322.V4.C1 | C | >50 | >50 | >50 | >25 | >50 | >50 | >50 |
| 6471.V1.C16 | C | 0.487 | 1.83 | >50 | >25 | 3.29 | >50 | 22.4 |
| 6631.V3.C10 | C | >50 | >50 | 12.5 | >25 | 0.800 | >50 | >50 |
| 6644.V2.C33 | C | 0.098 | 0.098 | 0.560 | 0.139 | 0.090 | 0.328 | 0.253 |
| 6785.V5.C14 | C | 0.111 | 0.124 | 0.035 | 0.068 | 0.033 | 0.525 | 0.397 |
| 6838.V1.C35 | C | >50 | >50 | >50 | 0.483 | 4.74 | >50 | >50 |
| 96ZM651.02 | C | 0.099 | 0.119 | >50 | 0.035 | 0.017 | >50 | 0.631 |
| BR025.9 | C | 0.040 | 0.034 | 0.013 | 0.004 | 0.014 | 0.127 | 0.076 |
| CAP210.E8 | C | >50 | >50 | >50 | >25 | >50 | >50 | >50 |
| CAP244.D3 | C | 5.18 | >50 | >50 | >25 | >50 | >50 | >50 |
| CAP256.206.C9 | C | 0.172 | 0.128 | 0.039 | 0.020 | 0.095 | 0.325 | 0.235 |
| CAP45.G3 | C | >50 | >50 | >50 | >25 | >50 | >50 | >50 |
| Ce1176.A3 | C | 0.266 | 0.221 | 0.036 | 0.024 | 0.131 | 0.755 | 0.568 |
| CE703010217.B6 | C | 0.130 | 0.101 | 0.137 | 0.006 | 0.025 | 1.81 | 0.228 |
| CNE30 | C | 2.19 | 1.85 | 0.979 | 0.236 | 0.773 | 6.49 | 4.91 |
| CNE31 | C | >50 | >50 | >50 | 3.23 | 1.30 | >50 | >50 |
| CNE53 | C | 0.397 | 0.408 | 0.075 | 0.021 | 0.021 | 1.14 | 0.824 |
| CNE58 | C | 0.426 | 0.584 | 4.93 | >25 | 0.387 | 10.3 | 0.882 |
| DU123.06 | C | 0.551 | 0.406 | 0.159 | 0.104 | 0.334 | 1.72 | 0.891 |
| DU151.02 | C | 0.953 | 3.78 | 0.023 | 0.006 | 0.078 | >50 | >50 |
| DU156.12 | C | 0.162 | 0.151 | 0.057 | 0.010 | 0.164 | 0.710 | 0.417 |
| DU172.17 | C | 0.414 | 1.49 | 0.098 | 0.452 | 0.217 | >50 | 9.69 |
| DU422.01 | C | 0.429 | 0.296 | 0.137 | 0.084 | 0.186 | 1.30 | 0.671 |
| MW965.26 | C | | 0.051 | >50 | 0.020 | 0.057 | 0.773 | 0.250 |
| SO18.18 | C | 0.059 | 0.038 | 0.180 | 0.001 | 0.002 | 0.167 | 0.106 |
| TV1.29 | C | 1.00 | 2.26 | 0.309 | 0.255 | 1.67 | 26.1 | 5.09 |
| TZA125.17 | C | >50 | >50 | 1.79 | >25 | 11.6 | >50 | >50 |
| TZBD.02 | C | 0.167 | 0.100 | >50 | 0.031 | 0.065 | 10.4 | 0.313 |
| ZA012.29 | C | 0.201 | 0.165 | 0.107 | 0.007 | 0.080 | >50 | 0.314 |
| ZM106.9 | C | 0.109 | 0.084 | 0.064 | 0.005 | 0.071 | 0.316 | 0.183 |
| ZM109.4 | C | >50 | >50 | >50 | >25 | >50 | >50 | >50 |
| ZM135.10a | C | 0.312 | 0.342 | >50 | 7.92 | 0.342 | 18.7 | 1.71 |
| ZM176.66 | C | 1.04 | 1.58 | 0.066 | >25 | 1.03 | >50 | 45.6 |
| ZM197.7 | C | >50 | >50 | >50 | >25 | >50 | >50 | >50 |
| ZM214.15 | C | 2.09 | 2.11 | 2.31 | 2.58 | 2.21 | >50 | 13.0 |
| ZM215.8 | C | 0.376 | 1.04 | 0.194 | 0.054 | 0.041 | 31.1 | 1.39 |
| ZM233.6 | C | >50 | >50 | >50 | 11.0 | 0.107 | >50 | >50 |
| ZM249.1 | C | >50 | >50 | >50 | >25 | >50 | >50 | >50 |
| ZM53.12 | C | >50 | >50 | >50 | 0.0006 | >50 | >50 | >50 |
| ZM55.28a | C | 0.113 | 0.124 | 0.057 | 0.216 | 0.018 | 0.329 | 0.187 |
| 3326.V4.C3 | CD | >50 | >50 | >50 | >25 | >50 | >50 | >50 |
| 3337.V2.C6 | CD | 0.478 | 1.23 | 0.011 | >25 | 0.070 | >50 | 31.2 |
| 3817.v2.c59 | CD | 0.647 | 0.855 | 0.048 | >25 | 3.17 | 2.76 | 4.71 |
| 191821.E6.1 | D | 22.3 | >50 | 0.102 | >25 | >50 | >50 | >50 |
| 231965.c1 | D | >50 | >50 | >50 | >25 | >50 | >50 | >50 |
| 247-23 | D | >50 | >50 | >50 | >25 | >50 | >50 | >50 |

Figure 15A cont.

| | | | | | | | | |
|---|---|---|---|---|---|---|---|---|
| 3016.v5.c45 | D | >50 | >50 | >50 | >25 | >50 | >50 | >50 |
| 57128.vrc15 | D | 7.05 | >50 | 0.486 | >25 | 1.36 | >50 | >50 |
| 6405.v4.c34 | D | 4.40 | 14.5 | 8.66 | 0.101 | 0.065 | >50 | >50 |
| A03349M1.vrc4a | D | >50 | >50 | 0.089 | 0.262 | 0.178 | >50 | >50 |
| A07412M1.vrc12 | D | >50 | >50 | >50 | 0.147 | 0.046 | >50 | >50 |
| NKU3006.ec1 | D | >50 | >50 | >50 | >25 | >50 | >50 | >50 |
| UG021.16 | D | | >50 | >50 | >25 | 0.461 | >50 | >50 |
| UG024.2 | D | >50 | >50 | >50 | >25 | 1.35 | >50 | >50 |
| P0402.c2.11 | G | 0.172 | 0.903 | 0.026 | 0.003 | 0.040 | >50 | 20.8 |
| P1981.C5.3 | G | 0.038 | 0.031 | 0.048 | 0.0006 | 0.018 | 0.108 | 0.084 |
| X1193.c1 | G | 0.392 | 0.650 | 0.050 | 0.116 | 0.231 | >50 | 4.83 |
| X1254.c3 | G | 0.149 | 0.176 | 0.057 | 0.060 | 0.163 | 0.727 | 0.470 |
| X1632.S2.B10 | G | >50 | >50 | >50 | >25 | >50 | >50 | >50 |
| X2088.c9 | G | 0.071 | 0.061 | >50 | 0.003 | 0.022 | 0.406 | 0.228 |
| X2131.C1.B5 | G | 0.196 | 0.236 | 0.062 | 0.014 | 0.102 | 5.13 | 0.766 |
| SIVmac251.30.SG3 | NA | >50 | >50 | >50 | >25 | >50 | >50 | >50 |
| SVA.MLV | NA | >50 | >50 | >50 | >25 | >50 | >50 | >50 |

Figure 15A cont.

| | DH542 L4 | DH542 | PGT128 | PGT121 | 10-1074 | DH270 | DH471 |
|---|---|---|---|---|---|---|---|
| # Viruses | 203 | 208 | 208 | 208 | 208 | 208 | 208 |
| Total VS Neutralized | | | | | | | |
| IC80 <50ug/ml | 110 | 103 | 116 | 113 | 130 | 79 | 94 |
| IC80 <10ug/ml | 104 | 98 | 114 | 109 | 124 | 71 | 85 |
| IC80 <1.0ug/ml | 89 | 82 | 105 | 98 | 105 | 42 | 67 |
| IC80 <0.1ug/ml | 26 | 28 | 81 | 72 | 69 | 1 | 7 |
| IC80 <0.01ug/ml | 0 | 0 | 4 | 26 | 4 | 0 | 0 |
| % VS Neutralized | | | | | | | |
| IC80 <50ug/ml | 54 | 50 | 56 | 54 | 63 | 38 | 45 |
| IC80 <10ug/ml | 51 | 47 | 55 | 52 | 60 | 34 | 41 |
| IC80 <1.0ug/ml | 44 | 39 | 50 | 47 | 50 | 20 | 32 |
| IC80 <0.1ug/ml | 13 | 13 | 39 | 35 | 33 | 0 | 3 |
| IC80 <0.01ug/ml | 0 | 0 | 2 | 13 | 2 | 0 | 0 |
| Median IC80 | 0.259 | 0.173 | 0.056 | 0.054 | 0.092 | 0.815 | 0.528 |
| Geometric Mean | 0.332 | 0.267 | 0.080 | 0.057 | 0.159 | 1.02 | 0.687 |

Figure 15B

>DH542_HC_nt (SEQ ID NO:113)
CAGGTGCAGCTGGTGCAGTCTGGGGCTCAAATGAAGAACCCTGGGGC
CTCAGTGAAGGTCTCCTGCGCGCCTTCTGGATATACCTTCACCGACT
TTTACATACATTGGTTGCGCCAGGCCCCTGGCCAGGGGCTTCAGTGG
ATGGGATGGATGAACCCTCAGACTGGTCGCACAAACACTGCACGAAA
CTTTCAGGGGAGGGTCACCATGACCAGGGACACGTCCATCGGCACAG
CCTACATGGAGTTGAGAAGCCTGACATCTGACGACACGGCCATATAT
TACTGTACGACAGGGGGATGGATCAGTCTTTACTATGATAGTAGTTA
TTACCCCAACTTTGACCACTGGGGTCAGGGAACCCTGCTCACCGTCT
CCTCAG

>DH542_HC_aa (SEQ ID NO:114)
QVQLVQSGAQMKNPGASVKVSCAPSGYTFTDFYIHWLRQAPGQGLQW
MGWMNPQTGRTNTARNFQGRVTMTRDTSIGTAYMELRSLTSDDTAIY
YCTTGGWISLYYDSSYYPNFDHWGQGTLLTVSS

>DH542_LC_nt_corrected (DH542_QSA) (SEQ ID NO:115)
CAGTCTGCCCTGACTCAGCCTGCCTCCGTGTCTGGGTCTCCTGGACA
GTCGATCACCATCTCCTGCACTGGAACCAAGTATGATGTTGGGAGTC
ATGACCTTGTCTCCTGGTACCAACAGTACCCAGGCAAAGTCCCCAAA
TACATGATTTATGAAGTCAATAAACGGCCCTCAGGAGTTTCTAATCG
CTTCTCTGGCTCCAAATCTGGCAACACGGCCTCCCTGACAATCTCTG
GGCTCCGGGCTGAGGACGAGGCTGACTATTATTGCTGTTCATTTGGA
GGGAGTGCCACCGTGGTCTGCGGCGGCGGGACCAAGGTGACCGTCCT
Ag >DH542_LC_aa_corrected (DH542_QSA) (SEQ ID NO:116)
QSALTQPASVSGSPGQSITISCTGTKYDVGSHDLVSWYQQYPGKVPK
YMIYEVNKRPSGVSNRFSGSKSGNTASLTISGLRAEDEADYYCCSFG
GSATVVCGGGTKVTVL

Figure 16

```
DH270 lineage - Heavy chain nucleotide sequences
            ....|....|  ....|....|  ....|....|  ....|....|  ....|....|
                    10          20          30          40          50
UCA         CAGGTGCAGC  TGGTGCAGTC  TGGGGCTGAG  GTGAAGAAGC  CTGGGGCCTC
I4          CAGGTGCAGC  TGGTGCAGTC  TGGGGCTGAG  GTGAAGAAGC  CTGGGGCCTC
I1          CAGGTGCAGC  TGGTGCAGTC  TGGGGCTGAG  BTGAAGAAGC  CTGGGGCCTC
DH473       GAGGTTCAGC  TGGTGGAGTC  TGGGCCTGAG  TTGAAGGAGC  CTGGGGCCTC
DH391       CAGGTGCAGC  TGGTGCAGTC  TGGGGCTGAA  CTGAAGAAGC  CTGGGGCCTC
I3          CAGGTGCAGC  TGGTGCAGTC  TGGGGCTGAG  RTGAAGAAGC  CTGGGGCCTC
I2          CAGGTGCAGC  TGGTGCAGTC  TGGGGCTGAA  RTGAAGAACC  CTGGGGCCTC
DH471       CAGGTGCAGC  TGGTGCAGTC  TGGGGCTGAA  GTGAAGAACC  CTGGGGCCTC
DH429       GAGGTGCAGC  TGGTGCAGTC  TGGGGCTGAA  ATGAAGAACC  CTGGGGCCTC
DH270       CAGGTGCAGC  TGGTGCAGTC  TGGGGCTGAG  ATGAAGAAGC  CTGGGGCCTC CDR1
            ....|....|  ....|....|  ....|....|  ....|....|  ....|....|
                    60          70          80          90         100
UCA         AGTGAAGGTC  TCCTGCAAGG  CTTCTGGATA  CACCTTCACC  GGCTACTATA
I4          AGTGAAGGTC  TCCTGCAAGG  CTTCTGGATA  CACCTTCACC  GACTACTATA
I1          AGTGAAGGTC  TCCTGCAAGG  CTTCTGGATA  CACCTTCACC  GACTACTATA
DH473       AGTGAAAGTC  TCCTGCAAGG  CTTCTGGATA  CACCTTCACC  GACTACTACA
DH391       AGTGAAGGTC  TCCTGCAAGG  CTTCTGGATA  CACCCTCAGC  GACTACTATG
I3          AGTGAAGGTC  TCCTGCAAGG  CTTCTGGATA  CACCTTCACC  GACTACTATA
I2          AGTGAAAGTC  TCCTGCGCGG  CTTCTGGATA  TACCTTCACC  GACTTCTACA
DH471       AGTGAAAGTC  TCCTGCGCGC  CTTCTGGATA  TACCTTCACT  GACTTCTACA
DH429       AGTGAAAGTC  TCCTGCGCGG  CTTCTGGATA  TGGTTTCACC  GACTTCTACA
DH270       AGTGAGGGTC  TCCTGCAAGG  CTTCTGGATA  CACCTTCACC  GACTACTATA ....|....|  ....|....|  ....|....|  ....|....|  ....|....|
                   110         120         130         140         150
UCA         TGCACTGGGT  GCGACAGGCC  CCTGGACAAG  GGCTTGAGTG  GATGGGATGG
I4          TACACTGGGT  GCGACAGGCC  CCTGGACAAG  GGCTTGAGTG  GATGGGATGG
I1          TACACTGGGT  GCGACAGGCC  CCTGGACAAG  GGCTTGAGTG  GATGGCATGG
DH473       TACACTGGGT  GCGACAGGCC  CCTGGACAAG  GTCTTGAGTG  GATGGCATGG
DH391       TACACTGGCT  GCGACAGGCC  CCTGGACAGG  GGCTTGAGTG  GGTGGCTTGG
I3          TACACTGGGT  GCGACAGGCC  CCTGGACAAG  GGCTTGAGTG  GATGGGATGG
I2          TACACTGGGT  GCGACTGGCC  CCTGGACAAG  GGCTTGAGTG  GATGGGATGG
DH471       TACACTGGGT  GCGACTGGCC  CCTGGACAAG  GGCTTGAGTG  GCTGGGGTGG
DH429       TACACTGGGT  GCGACTGGCC  CCTGGACACG  GGCTCCAGTG  GATGGGATGG
DH270       TACACTGGGT  GCGACAGGCC  CCTGGACAAG  GGCCTGAGTG  GATGGGATGG CDR2
            ....|....|  ....|....|  ....|....|  ....|....|  ....|....|
                   160         170         180         190         200
UCA         ATCAACCCTA  ACAGTGGTGG  CACAAACTAT  GCACAGAAGT  TTCAGGGCAG
I4          ATCAACCCTA  ACASTGGTCG  CACAAACTAT  GCACAGAAGT  TTCAGGGCAG
I1          ATCAACCCTA  CCASTGGTCG  CACAADCTHT  GCACGGAAGT  TTCAGGGCAG
DH473       ATCAACCCTA  CCACTGGTCG  CTCTAGCTTT  GCCCGGGGT   TTCAGGGCAG
DH391       ATCAACCCTA  CCAGTGGTCG  CACAATCTCT  CCACGGAAGT  TTCAGGGCAG
I3          ATCAACCCTA  ACACTGGTCG  CACAAACTAT  GCACAGAAGT  TTCAGGGCAG
I2          ATGAACCCTA  AGACTGGTCG  CACAAATHAT  GCACAAABT   TTCAGGGCAG
DH471       ATGAACCCTA  AGACTGGTCG  CACAAATCAA  GGACAAAACT  TTCAGGGCAG
DH429       ATGAACCCTA  AGACTGGTCG  CACAAATAAT  GCACAAGATT  TTCAGGGCAG
DH270       ATCAACCCTA  GCACTGGTCG  CACAAACTCT  CCACAGAAGT  TTCAGGGCAG
```

Figure 17A

```
              ....|....| ....|....| ....|....| ....|....| ....|....|
                  210        220        230        240        250
UCA      GGTCACCATG ACCAGGGACA CGTCCATCAG CACAGCCTAC ATGGAGCTGA
I4       GGTCACCATG ACCAGGGACA CGTCCATCAG CACAGCCTAC ATGGAGCTGA
I1       GGTCACCATG ACCAGGGACA CGTCCATCAG CACDGCCTAC ATGGAACTGA
DH473    GGTCACCATG ACCAGGGAAA CGTCCGTCAG CACGGCCTAT ATGGAACTGA
DH391    GGTCACGATG ACTACGGACA CGTCCATGAA TGTTGCCTAC ATGGAACTGA
I3       GGTCACCATG ACCAGGGACA CGTCCATCAG CACAGCCTAC ATGGAGCTGA
I2       GGTCACCATG ACCAGGGACA CGTCCATCGG CACAGCCTAC ATGGAGCTGA
DH471    GGTCACCATG ACCAGGGACA CGTCCATCGG CACAGCCTAC ATGGAGTTGA
DH429    GGTCACCCTG ACCAGGGACA CGTCCATCGG CACAGCCTAC ATGGAGCTGA
DH270    GGTCACCATG ACCAGGGACA CGTCCATCAG CACAGCCTAC ATGGACCTGA

CDR3
              ....|....| ....|....| ....|....| ....|....| ....|....|
                  260        270        280        290        300
UCA      GCAGGCTGAG ATCTGACGAC ACGGCCGTGT ATTACTGTGC GAGAGGGGGG
I4       GCAGGCTGAG ATCTGACGAC ACGGCCGTGT ATTACTGTGC GAGAGGGGGG
I1       GAAGVCTGAG ATCTGACGAC ACGGCCGTCT ATTACTGTGC GAGAGGGGGA
DH473    GAAGACTGAG ATCTGACGAC ACGGCCGTCT ATTACTGTGC GAAAGCGGGA
DH391    GAGGCTTGAG ATCTGACGAC ACGGCCGTCT ATTTCTGTGC GAGAGGGGGA
I3       GCAGGCTGAC ATCTGACGAC ACGGCCGTGT ATTACTGTGC GACAGGGGGG
I2       GGAGGCTGAC ATCTGACGAC ACGGCCGTCT ATTACTGTGT GACAGGGGGG
DH471    GGAGCCTCAC ATCTGACGAC ACGGCCGTCT ATTACTGTGT GACAGGGGCC
DH429    GGAGGCTGAC ATCTGACGAC ACGGCCGTCT ATTACTGTGT GACAGGGGGG
DH270    ACAGACTGAC GTCTGACGAC ACGGCCATGT ATTACTGTAC GACCGGGGGG

....|....| ....|....| ....|....| ....|....| ....|....|
                  310        320        330        340        350
UCA      TGGATCRGTC TTTACTATGA TAGTAGTGGT TACCCTAACT TTGACTACTG
I4       TGGATCRGTC TTTACTATGA TAGTAGTGGT TACCCTAACT TTGACTACTG
I1       TGGATCRGTC TTTACGTTGA TTATAGTGGT TACCCTAACT TTGACTCCTG
DH473    TACATCGCCC TTTACGTTGA CTATAGTGGT TACCCTAACT TTAATTCCTG
DH391    TGGATCAGTC TCTACGTTGA TTACAGTTAT TACCCTAACT TTGACTCGTG
I3       TGGATCRGTC TTTACTATGA TAGTAGTGGT TACCCTAACT TTGACTACTG
I2       TGGATCAGTC HTTATTATGA TAGTAGTTAT TACCCTAACT TTGACCACTG
DH471    TGGATCAGTG ATTATTATGA TAGTAGTTAT TATCCTAACT TTGACCACTG
DH429    TGGATCAGTC CTTATTATGA TAGTAGTTAT TACCCTAATT TTGACCACTG
DH270    TGGATCGGTC TTTACTCTGA TACTAGTGGT TACCCTAACT TTGACTACTG

....|....| ....|....| ....|....| ..
                  360        370        380
UCA      GGGCCAGGGA ACCCTGGTCA CCGTCTCCTC AG
I4       GGGCCAGGGA ACCCTGGTCA CCGTCTCCTC AG
I1       GGGCCAGGGA ACCCTGGTCA CCGTCTCCTC AG
DH473    GGGCCAGGGA ACCCTGGTCA CCGTCTCCTC AG
DH391    GGGCCAGGGA ACCCTGGTCT CCGTCTCTTC AG
I3       GGGCCAGGGA ACCCTGGTCA CCGTCTCCTC AG
I2       GGGTCAGGGA ACCCTGGTCA CCGTCTCCTC AG
DH471    GGGTCAGGGA ACCCTGGTCA CCGTCTCCTC AG
DH429    GGGTCAGGGA ACCCTGATCA CCGTCTCCTC AG
DH270    GGGCCAGGGA ACCCTGGTCA CCGTCTCCTC AG
```

Figure 17A cont.

DH270 lineage - Heavy chain amino acid sequences

```
                                          CDR1
            ....|....| ....|....| ....|....| ....|....| ....|....|
                    10         20         30         40         50
UCA         QVQLVQSGAE VKKPGASVKV SCKASGYTFT GYYMHWVRQA PGQGLEWMGW
I4          QVQLVQSGAE VKKPGASVKV SCKASGYTFT DYYIHWVRQA PGQGLEWMGW
I1          QVQLVQSGAE XKKPGASVKV SCKASGYTFT DYYIHWVRQA PGQGLEWMAW
DH473       EVQLVESGPE LKEPGASVKV SCKASGYTFT DYYIHWVRQA PGQGLEWMAW
DH391       QVQLVQSGAE LKKPGASVKV SCKASGYTLS DYYVHWLRQA PGQGLEWVAW
I3          QVQLVQSGAE XKKPGASVKV SCKASGYTFT DYYIHWVRQA PGQGLEWMGW
I2          QVQLVQSGAE XKNPGASVKV SCAASGYTFT DFYIHWVRLA PGQGLEWMGW
DH471       QVQLVQSGAE VKNPGASVKV SCAPSGYTFT DFYIHWVRLA PGQGLEWLGW
DH429       EVQLVQSGAE MKNPGASVKV SCAASGYGFT DFYIHWVRLA PGHGLQWMGW
DH270       QVQLVQSGAE MKKPGASVRV SCKASGYTFT DYYIHWVRQA PGQGPEWMGW

CDR2                                              CDR3
            ....|....| ....|....| ....|....| ....|....| ....|....|
                    60         70         80         90        100
UCA         INPNSGGTNY AQKFQGRVTM TRDTSISTAY MELSRLRSDD TAVYYCARGG
I4          INPNXGRTNY AQKFQGRVTM TRDTSISTAY MELSRLRSDD TAVYYCARGG
I1          INPTXGRTXX ARKFQGRVTM TRDTSISXAY MELRXLRSDD TAVYYCARGG
DH473       INPTTGRSSF ARGFQGRVTM TRETSVSTAY MELRRLRSDD TAVYYCAKAG
DH391       INPTSGRTIS PRKFQGRVTM TTDTSMNVAY MELRGLRSDD TAVYFCARGG
I3          INPNTGRTNY AQKFQGRVTM TRDTSISTAY MELSRLTSDD TAVYYCATGG
I2          MNPKTGRTNX AQXFQGRVTM TRDTSIGTAY MELRRLTSDD TAVYYCVTGG
DH471       MNPKTGRTNQ GQNFQGRVTM TRDTSIGTAY MELRSLTSDD TAVYYCVTGA
DH429       MNPKTGRTNN AQDFQGRVTL TRDTSIGTAY MELRRLTSDD TAVYYCVTGG
DH270       INPSTGRTNS PQKFQGRVTM TRDTSISTAY MDLNRLTSDD TAMYYCTTGG

....|....| ....|....| ....|..
                   110        120
UCA         WIXLYYDSSG YPNFDYWGQG TLVTVSS
I4          WIXLYYDSSG YPNFDYWGQG TLVTVSS
I1          WIXLYVDYSG YPNFDSWGQG TLVTVSS
DH473       YIALYVDYSG YPNFNSWGQG TLVTVSS
DH391       WISLYVDYSY YPNFDSWGQG TLVSVSS
I3          WIXLYYDSSG YPNFDYWGQG TLVTVSS
I2          WISXYYDSSY YPNFDHWGQG TLVTVSS
DH471       WISDYYDSSY YPNFDHWGQG TLVTVSS
DH429       WISPYYDSSY YPNFDHWGQG TLITVSS
DH270       WIGLYSDTSG YPNFDYWGQG TLVTVSS
```

Figure 17A cont.

```
DH270 lineage - Light chain nucleotide sequences

....|....| ....|....| ....|....| ....|....| ....|....|
                           10         20         30         40         50
UCA(SEQ ID NO:137)    CAGTCTGCCC TGACTCAGCC TGCCTCCGTG TCTGGGTCTC CTGGACAGTC
I4(SEQ ID NO:138)     CAGTCTGCCC TGACTCAGCC TGCCTCCGTG TCTGGGTCTC CTGGACAGTC
I1(SEQ ID NO:139)     CAGTCTGCCC TGACTCAGCC TGCCTCCGTG TCTGGGTCTC CTGGACAGTC
DH473(SEQ ID NO:140)  CAGTCTGCCC TGACTCAGCC TGCCTCCGTG TCTGGTCTC CTGGCCAGTC
DH391(SEQ ID NO:141)  CAGCCTGTGC TGACTCAGCC TGCCTCCGTG TCTGGGTCTC CTGGACAGTC
I3(SEQ ID NO:142)     CAGTCTGCCC TGACTCAGCC TGCCTCCGTG TCTGGGTCTC CTGGACAGTC
I2(SEQ ID NO:143)     CAGTCTGCCC TGACTCAGCC TGCCTCCGTG TCTGGGTCTC CTGGACAGTC
DH471(SEQ ID NO:144)  CTGCCTGTGC TGACTCAGCC TGCCTCCGTG TCTGGGTCTC CTGGGCAGTC
DH429(SEQ ID NO:145)  CAGTCTGCCC TGACTCAGCC TGCCTCCGTG TCTGGGTCTC CTGGACAGTC
DH270(SEQ ID NO:146)  CAGTCTGCCC TGACTCAGCC TGCCTCCGTG TCTGGGTCTC CTGGACAGTC

....|....| ....|....| ....|....| ....|....| ....|....|
                           60         70         80         90        100
UCA                   GATCACCATC TCCTGCACTG GAACC
I4                    GATCACCATC TCCTGCACTG GAACC
I1                    GATCACCATC TCCTGCACTG GAACC
DH473                 GATCACCATC TCCTGCACTG GAACC
DH391                 GATCACCATC TCCTGCACTG GAAGC
I3                    GATCACCATC TCCTGCACTG GAACC
I2                    GATCACCATC TCCTGCACTG GAACC
DH471                 GATCACCATC TCCTGCACTG GGACC
DH429                 GATCACCATC TCCTGCACTG GAACC
DH270                 GATCACCATC TCCTGCACTG GAACC

....|....| ....|....| ....|....| ....|....| ....|....|
                          110        120        130        140        150
UCA                   GTCTCCTG GTACCAACAG CACCCAGGCA AAGCCCCCAA ACTCATGATT
I4                    GTCTCCTG GTACCAACAG CACCCAGGCA AAGCCCCCAA ACTCATGATT
I1                    GTCTCCTG GTACCAACAG CACCCAGGCA AAGCCCCCAA ATACATGATT
DH473                 GTCTCCTG GTACCAACAG CACCCAGGCA AAGCCCCCAA ACTCATTATT
DH391                 GTGTCCTG GTACCAGCAG CACCCAGGCA AAGCCCCCAA ACTGATGATT
I3                    GTCTCCTG GTACCAACAG CACCCAGGCA AAGCCCCCAA ACTCATGATT
I2                    GTCTCCTG GTACCAACAG CACCCAGGCA AAGCCCCCAA ATACATGATT
DH471                 GTCTCCTG GTACCAGCAC CACCCAGGCA AAGCCCCCAA ATATTTGATT
DH429                 GTCTCCTG GTTCCAACAG CACCCAGGCA AAGCCCCCAA ATACATGATT
DH270                 GTCTCCTG GTATCAACAG CACCCAGGCA AAGTCCCCAA ATACATAATT

....|....| ....|....| ....|....| ....|....| ....|....|
                          160        170        180        190        200
UCA                   TAT                AAGCGGCC CTCAGGGGTT CTAATCGCT TCTCTGGCTC
I4                    TAT                AAGTGGCC CTCAGGGGTT CTAATCGCT TCTCTGGCTC
I1                    TAT                AAGTGGCC CTCAGGAGTT CTCATCGCT TCTCTGGCTC
DH473                 TAT                CAGTGGCC CTCAGGGGTT CTAAGCGCT TCTCTGGCTC
DH391                 TAT                AAGTGGGC CTCAGGGGTT CTGATCGCT TCGCTGGCTC
I3                    TAT                AAGTGGCC CTCAGGGGTT CTAATCGCT TCTCTGGCTC
I2                    TAT                AAGTGGCC CTCAGGGGTT CTAATCGCT TCTCTGGCTC
DH471                 TAT                AAGTGGCC CTCAGGAGTT CTCATCGCT TCTCTGGCTC
DH429                 TAT                AAGTGGCC CTCAGGAGTT CTCATCGCT TCTCTGGTTC
DH270                 TAT                AAGCGGCC CTCAGGGGTT CTAATCGCT TCTCTGGCTC
```

Figure 17B

|        | 210 | 220 | 230 | 240 | 250 |
|--------|-----|-----|-----|-----|-----|
| UCA    | CAAGTCTGGC | AACACGGCCT | CCCTGACAAT | CTCTGGGCTC | CAGGCTGAGG |
| I4     | CAAGTCTGGC | AACACGGCCT | CCCTGACAAT | CTCTGGGCTC | CAGGCTGAGG |
| I1     | CAAATCTGGC | AACACGGCCT | CCCTGACAAT | CTCTGGGCTC | CAGGCTGAGG |
| DH473  | CAAGTCTGGC | AACACGGCCT | CCCTGACAAT | CTCTGGGCTC | CAGGCTGAGG |
| DH391  | CAAGTCTGGC | AACACGGCCT | CCCTGACAAT | CTCTAGACTC | CAGGCTGAGG |
| I3     | CAAGTCTGGC | AACACGGCCT | CCCTGACAAT | CTCTGGGCTC | CAGGCTGAGG |
| I2     | CAAGTCTGGC | AACACGGCCT | CCCTGACAAT | CTCTGGGCTC | CAGGCTGAGG |
| DH471  | CAAATCTGGC | AACACGGCCT | CCCTGACAAT | CTCTGGGCTC | CAGGTTGAGG |
| DH429  | CAAATCTGGC | AACACGGCCT | CCCTGACAAT | CTCTGGGCTC | CAGGCTGAGG |
| DH270  | CAAGTCTGGC | AACACGGCCT | CCCTGACAAT | CTCTGGGCTC | CAGGCTGAGG |

CDR3

|        | 260 | 270 | 280 | 290 | 300 |
|--------|-----|-----|-----|-----|-----|
| UCA    | ACGAGGCTGA | TTATTACTGC | TGCTCATATG | CAGGTAGTAG | CACTGTAATA |
| I4     | ACGAGGCTGA | TTATTACTGT | TGCTCATATG | CAGGTAGTAG | CACTGTAATA |
| I1     | ACGAGGCTGA | CTATTATTGC | TGCTCATTCG | GAGGTAGTGC | CACTGTAGTC |
| DH473  | ACGAGGCTCA | TTATTACTGT | TGCTCATATG | CAGGCAGTAG | CACTGTAATA |
| DH391  | ACGAGGCTAA | TTACTTTTGT | TCCTCATCTA | CAAATAGTGC | CACTGTCATA |
| I3     | ACGAGGCTGA | TTATTACTGT | TGCTCATATG | CAGGTAGTAG | CACTGTAATA |
| I2     | ACGAGGCTGA | TTATTACTGT | TGCTCATATG | CAGGTAGTAG | CACTGTAWTW |
| DH471  | ACGAGGCTGA | CTATTATTGC | TGCTCATTCG | GAGGTAGTGC | CGCTGTGGTC |
| DH429  | ACGAGGCTGA | CTATTATTGC | TGCTCATTCG | GAGGTAGTGC | CACTGTAGTC |
| DH270  | ACGAGGCCAC | TTATTACTGT | TGTTCATATG | CAGGTAGTAG | CATTATATTT |

|        | 310 | 320 | 330 |   |
|--------|-----|-----|-----|---|
| UCA    | TTCGGCGGAG | GGACCAAGCT | GACCGTCCTA | G |
| I4     | TTCGGCGGAG | GGACCAAGCT | GACCGTCCTA | G |
| I1     | TGCGGCGGAG | GGACCAAGGT | GACCGTCCTA | G |
| DH473  | TTCGGCGGAG | GGACCTCGCT | GACCGTCCTA | G |
| DH391  | TTCGGCGGAG | GGACCAAGCT | GACCGTCCTA | G |
| I3     | TTCGGCGGAG | GGACCAAGCT | GACCGTCCTA | G |
| I2     | TTCGGCGGAG | GGACCAAGCT | GACCGTCCTA | G |
| DH471  | TGCGGCGGAG | GGACCAAGGT | GACCGTCCTA | G |
| DH429  | TGCGGCGGAG | GGACCAAGGT | GACCGTCCTA | G |
| DH270  | TTCGGCGGTG | GGACCAAGCT | GACCGTCATA | G |

Figure 17B cont.

DH270 lineage - Light chain amino acid sequences

```
                              ....|....| ....|....| ....|....| ....|....| ....|....|
                                       10         20         30         40         50
UCA   (SEQ ID NO:147)   QSALTQPASV SGSPGQSITI SCTGT          VSWYQQ HPGKAPKLMI
I4    (SEQ ID NO:148)   QSALTQPASV SGSPGQSITI SCTGT          VSWYQQ HPGKAPKLMI
I1    (SEQ ID NO:149)   QSALTQPASV SGSPGQSITI SCTGT          VSWYQQ HPGKAPKYMI
DH473 (SEQ ID NO:150)   QSALTQPASV SGSPGQSITI SCTGT          VSWYQQ HPGKAPKLII
DH391 (SEQ ID NO:151)   QPVLTQPASV SGSPGQSITI SCTGS          VSWYQQ HPGKAPKLMI
I3    (SEQ ID NO:152)   QSALTQPASV SGSPGQSITI SCTGT          VSWYQQ HPGKAPKLMI
I2    (SEQ ID NO:153)   QSALTQPASV SGSPGQSITI SCTGT          VSWYQQ HPGKAPKYMI
DH471 (SEQ ID NO:154)   LPVLTQPASV SGSPGQSITI SCTGT          VSWYQH HPGKAPKYLI
DH429 (SEQ ID NO:155)   QSALTQPASV SGSPGQSITI SCTGT          VSWFQQ HPGKAPKYMI
DH270 (SEQ ID NO:156)   QSALTQPASV SGSPGQSITI SCTGT          VSWYQQ HPGKVPKYII

CDR3
                ....|....| ....|....| ....|....| ....|....| ....|....|
                         60         70         80         90        100
UCA       Y    KRPSGV SNRFSGSKSG NTASLTISGL QAEDEADYYC CSYAGSSTVI
I4        Y    KWPSGV SNRFSGSKSG NTASLTISGL QAEDEADYYC CSYAGSSTVI
I1        Y    KWPSGV SHRFSGSKSG NTASLTISGL QAEDEADYYC CSFGGSATVV
DH473     Y    QWPSGV SKRFSGSKSG NTASLTISGL QAEDEAHYYC CSYAGSSTVI
DH391     Y    KWASGV SDRFAGSKSG NTASLTISRL QAEDEANYFC SSSTNSATVI
I3        Y    KWPSGV SNRFSGSKSG NTASLTISGL QAEDEADYYC CSYAGSSTVI
I2        Y    KWPSGV SNRFSGSKSG NTASLTISGL QAEDEADYYC CSYAGSSTVX
DH471     Y    KWPSGV SHRFSGSKSG NTASLTISGL QVEDEADYYC CSFGGSAAVV
DH429     Y    KWPSGV SHRFSGSKSG NTASLTISGL QAEDEADYYC CSFGGSATVV
DH270     Y    KRPSGV SNRFSGSKSG NTASLTISGL QAEDEATYYC CSYAGSSIIF

....|....|
                        110
UCA       FGGGTKLTVL
I4        FGGGTKLTVL
I1        CGGGTKVTVL
DH473     FGGGTSLTVL
DH391     FGGGTKLTVL
I3        FGGGTKLTVL
I2        FGGGTKLTVL
DH471     CGGGTKVTVL
DH429     CGGGTKVTVL
DH270     FGGGTKLTVI
```

Figure 17B cont.

| | | IC50 (ug/ml) in TZM-bl Cells1 | | | | | |
|---|---|---|---|---|---|---|---|
| | | DH272 (29-214-G4) | DH272UCA_4A | DH391_4A/293i | DH542/293i | DH563/293i | CH01-31 |
| | | CH0848 | CH0848 | CH0848 | CH0848 | CH0765 | |
| | | Lot#199SMI | Lot#79RKK | Lot#332HC | Lot#014RM | Lot#015RM | |
| | | Rec'd&Aliq 11/MAY/15 | Rec'd&Aliq 11/MAY/15 | Rec'd&Aliq 11/MAY/15 | Rec'd&Aliq 11/MAY/15 | Rec'd&Aliq 11/MAY/15 | prep. 26/MAR/15 |
| Virus Name | Virus Lot | | | | | | |
| SVA-MLV | 5545 | >50 | >50 | >50 | >50 | >50 | >25 |
| Q23.17 | 2435 | 6.0 | >50 | <0.023 | <0.023 | 4.5 | <0.011 |
| DJ263.8 | 2220 | >50 | >50 | >50 | 0.08 | >50 | 0.84 |
| C1080.c03 | 3757 | 42 | >50 | >50 | >50 | >50 | 0.05 |
| 6540.v4.c1 | 2746 | >50 | >50 | >50 | >50 | >50 | 0.58 |
| Q168.a2 | 1715 | >50 | >50 | >50 | >50 | >50 | 0.08 |
| 6101.10 | 737 | >50 | >50 | 0.18 | 0.03 | 11 | 0.57 |
| BG1168.1 | 530 | >50 | >50 | >50 | >50 | >50 | 2.1 |
| DU172.17 | 4168 | >50 | >50 | >50 | 0.27 | 27 | 0.73 |
| DU156.12 | 4166 | >50 | >50 | 0.50 | 0.07 | 8.5 | 0.30 |
| DU422.1 | 3803 | >50 | >50 | 5.5 | 0.19 | 23 | >25 |
| 57128.vrc15 | 1940 | >50 | >50 | >50 | 2.0 | 28 | >25 |
| X1632-S2-B10 | 2900 | >50 | >50 | >50 | >50 | >50 | 0.07 |

Figure 18

| | | IC50 (ug/ml) in TZM-bl Cells1 | | | | | |
|---|---|---|---|---|---|---|---|
| | | DH272 (29-214-G4) | DH272UCA_4A | DH391_4A/293i | DH542/293i | DH563/293i | CH01-31 |
| | | CH0848 | CH0848 | CH0848 | CH0848 | CH0765 | |
| | | Lot#199SMI | Lot#79RKK | Lot#332HC | Lot#014RM | Lot#015RM | |
| | | Rec'd&Aliq 11/MAY/15 | Rec'd&Aliq 11/MAY/15 | Rec'd&Aliq 11/MAY/15 | Rec'd&Aliq 11/MAY/15 | Rec'd&Aliq 11/MAY/15 | prep. 26/MAR/15 |
| Virus Name | Virus Lot | | | | | | |
| Q769.d22 | 4405 | >50 | >50 | >50 | >50 | 50 | 0.07 |
| ZM106F.PB9 | 824 | >50 | >50 | 0.26 | 0.05 | 7.1 | 9.2 |
| CNE58 | 6509 | >50 | >50 | >50 | 0.28 | >50 | 0.11 |
| 92RW020.2 | 1573 | >50 | >50 | 0.03 | <0.023 | 2.1 | 0.05 |
| CAAN5342.A2 | 995 | >50 | >50 | >50 | 0.03 | 7.2 | >25 |
| JR-FL | 730 | >50 | >50 | 1.0 | 0.04 | 8.0 | 0.03 |
| PVO.4 | 3801 | >50 | >50 | 39 | 0.14 | >50 | 0.86 |
| THRO4156.18 | 967 | >50 | >50 | >50 | >50 | >50 | 3.1 |
| TRJO4551.58 | 4159 | >50 | >50 | >50 | 0.16 | >50 | 0.42 |
| TRO.11 | 772 | >50 | >50 | 0.56 | 0.06 | 8.0 | 0.25 |
| YU2 | 4098 | >50 | >50 | 2.3 | 0.06 | 12 | 0.10 |
| ZM55F.PB28a | 819 | >50 | >50 | 0.59 | 0.05 | >50 | 3.1 |

*Figure 18 cont.*

| | |
|---|---|
| I0848_00001_L1_4A | M0321121000000000-AFR8K1111925631189371 |
| I0848_00004_L1_4A | M0321121000000000-AFR8K12115806388351 |
| I0848_00005_L1_4A | M03211_22_000000000-AGC44_1_1110_4877_72881 |
| I0848_00006_L1_4A | M03211_22_000000000-AGC44_1_1111_27759_176681 |
| I0848_00007_L1_4A | M03211_22_000000000-AGC44_1_1104_4244_82371 |

\>IH0848_00001 (SEQ ID NO: 157)

CAGGGGCACTTGGTGCAGTCTGGGGCTGAGGTGAAGAAACCTGGGGCCT
CAGTGAAGGTCTCCTGCACGGTCACCACATACAGTTTCACCGAGCACTAT
TTACACTGGCTGCGGCAGGCCCCTGGACAGGCGCCTGAGTGGATGGGTT
GGGTCAATCCTGCAAATGATCGCGCAAAATATGCATACAAATTTCAGGGC
AGAGTCACCATGACCACCGACATGTCCGCCTACACAGCCTACATGGAGTT
GAGAAGGCTGACATCCGACGACACGGCCATGTATTACTGTACGACAGGG
GCGTGGATTAGTCCCTACTATGACAGTAGTTATTACCCTAACTTTGACCAC
TGGGGTCAGGGAACCCTGGTCACCGTCTCCTCA

\>IH0848_00004 (SEQ ID NO:158)

CAGGCGCAACTGGCGCAGTCTGGGCCTGAGGTGGGCAAGCCTGGCTCCT
CAGTAAACGTCTCCTGCAAGGCTTCTGGATACGACTTCACTGGCCAATATT
TACATTGGTTTCGTCAGGCCCCTCGACAGGGACTTGAGTGGATGGGGTG
GCTCAATCCTGACACTGGTGAAGCAAAATATGTTGAGAAGTTTCAGGGCA
GAGTCATCATGACCAGGGACACGTCCATCGGCACAGCCTACATGGAGTTG
AAGAGGCTAACATCTGACGACACGGCCGTCTATTACTGTGTGACAGGGG
CCTGGATCAGTCAATACTATGACAGTAGTTATTACCCTAACTTTGACCACT
GGGGTCAGGGAACCCTGGTCACCGTCTCCTCA

\>IH0848_00005 (SEQ ID NO:159)

CAGGTGCAGCTGGTGCAATCTGGGGCTGAAGTGAGGAACCCTGGGGCCT
CAGTGAAAGTCTCCTGCGCGCCTTCTGGATATGCCTTCACTGACTTCTACA
TACACTGGGTGCGACTGGCCCCTGGACAAGGGCTTGAGTGGCTGGGGTG
GATGGACCCTAAGACTGGTCGCACAAATCAAGGACACAACTTTCAGGGC
AGGGTCACCATGACCAGGGACACGTCCATCGGCACAGCCTACATGGAGT
TGAGGAGCCTCACAGCTGACGACACGGCCGTCTATTACTGTGTGACAGG
GGCCTGGATCAGTGATTATTATGATAGTAGTTATTATCCTAATTTTGACCA
CTGGGGTCAGGGAACCCTGGTCACCGTCTCCTCA

Figure 20A

>IH0848_00006 (SEQ ID NO:160)
CAGGTGCGACTGGTGCAATCTGGGGCTGAATTGAAGAACCCTGGGGCCG
CAGTGAAGGTCTCCTGCGCGGCTTCCGGATATACCTTCACCGACTACTATC
TACACTGGGTGCGACTGGCCCCTGGGCAAGGGCTTCAGTGGATGGGATG
GATGAACCCTATTACTGGTCGCACAAACAATGCACAAAGGTTTCAGGGCA
GGGTCACCATGACCAGGGACACGTCCATCGGCACAGCCTACATGGAATT
GAAGAGGCTAACATCTGACGACACGGCCGTCTATTACTGTGTGACAGGG
GCCTGGATCAGTCAATACTATGACAGTAGTTATTACCCTAATTTTGACCAC
TGGGGTCAGGGAACCCTGGTCACCGTCTCCTCA

>IH0848_00007 (SEQ ID NO:161)
CAGGTGCAACTGGTGCAGTCTGGGCCTGAGATGAAGCAGCCTGGGGCCT
CAGTGAAAGTCTCCTGCAGGGCTTCTGGATACAAGTTCACCGACTACTAT
TTACACTGGGTGCGACAGGCCCCTGGACAAGGGCCTGAGTGGATGGCGT
GGATGAACCCTGCCAGTGGTCGCACAAACTTTGCACAGAAATTTCAGGGC
AGGGTCACCATGACCAGGGACACGTCCATCAACACAGGCTACATGGAGC
TGAGAAGACTGCGATCTGACGACACGGCCGTATACTACTGTGCGAAGGC
GGGGTGGATCAGTCTTTACAATGATTATAGTGCTTACCCTAACTTTAATTC
CTGGGGCCAGGGAACCCTGGTCACCGTCTCCTCA

>IH0848_00001 (SEQ ID NO:162)
QGHLVQSGAEVKKPGASVKVSCTVTTYSFTEHYLHWLRQAPGQAPEWMG
WVNPANDRAKYAYKFQGRVTMTTDMSAYTAYMELRRLTSDDTAMYYCTT
GAWISPYYDSSYYPNFDHWGQGTLVTVSS

*Figure 20A cont.*

>IH0848_00004 (SEQ ID NO:163)

QAQLAQSGPEVGKPGSSVNVSCKASGYDFTGQYLHWFRQA
PRQGLEWMGWLNPDTGEAKYVEKFQGRVIMTRDTSIGTAY
MELKRLTSDDTAVYYCVTGAWISQYYDSSYYPNFDHWGQG
TLVTVSS

>IH0848_00005 (SEQ ID NO:164)

QVQLVQSGAEVRNPGASVKVSCAPSGYAFTDFYIHWVRLAP
GQGLEWLGWMDPKTGRTNQGHNFQGRVTMTRDTSIGTA
YMELRSLTADDTAVYYCVTGAWISDYYDSSYYPNFDHWGQ
GTLVTVSS

>IH0848_00006 (SEQ ID NO:165)

QVRLVQSGAELKNPGAAVKVSCAASGYTFTDYYLHWVRLAP
GQGLQWMGWMNPITGRTNNAQRFQGRVTMTRDTSIGTA
YMELKRLTSDDTAVYYCVTGAWISQYYDSSYYPNFDHWGQ
GTLVTVSS

>IH0848_00007 (SEQ ID NO:166)

QVQLVQSGPEMKQPGASVKVSCRASGYKFTDYYLHWVRQ
APGQGPEWMAWMNPASGRTNFAQKFQGRVTMTRDTSIN
TGYMELRRLRSDDTAVYYCAKAGWISLYNDYSAYPNFNSW
GQGTLVTVSS

Figure 20A cont.

|  |  | HCDR1 | HCDR2 |
|---|---|---|---|
| SEQ ID NO:162 | IH0848_00001 | QGHLVQSGAEVKKPGASVKVSCTVTTYSFTEHYLHWLRQAPGQAPEWMGWVNPANDRA |  |
| SEQ ID NO:163 | IH0848_00004 | QAQLAQSGPEVGKPGSSVNVSCKASGYDFTGQYLHWERQAPRQGLEWMGWMLNPDTGEA |  |
| SEQ ID NO:164 | IH0848_00005 | QVQLVQSGAEVRNPGASVKVSCAPSGYAFTDFYIHWVRLAPGQGLEWLGWMDPKTGRT |  |
| SEQ ID NO:165 | IH0848_00006 | QVRLVQSGAELKNPGAAVKVSCAASGYTFTDYYLHWVRLAPGSQLQWMGWMPITGRT |  |
| SEQ ID NO:166 | IH0848_00007 | QVQLVQSGPEMKQPGASVKVSCRASGYKFTDYYLHWVRQAPGQGPEWMAWMNPASGRT |  | continued:

HCDR3

KVAYKFQGRVTMTTDMSAVTAYMELRRLTSDDTAMYYCVTTGAWISPYYDSSYYPNFDHWGQGTLVTVSS

KYVEKFQGRVIMTRDTSIGTAYMELKRLTSDDTAVYYCVTGAWISQYYDSSYYPNFDHWGQGTLVTVSS

NQGHNFQGRVIMTRDTSIGTAYMELRSITADDTAVYYCVTGAWISDYYDSSYYPNFDHWGQGTLVTVSS

NNAQRFQGRVIMTRDTSIGTAYMELKRLTSDDTAVYYCVTGAWISQYYDSSYYPNFDHWGQGTLVTVSS

NFAQKFQGRVTMTRDTSINTGYMELRRLRSDDTAVYYCAKAGWISLINDVSAYPNFNSWGQGTLVTVSS

*Figure 20B*

>CH557_aa_HC (SEQ ID NO:167)
QVRLAQYGGGVKRLGATMTLSCVASGYTFNDYYIHWVRQAPGQGFEL
LGYIDPANGRPDYAGALRERLSFYRDKSMETLYMDLRSLRYDDTAMY
YCVRNVGTAGSLLHYDHWGSGSPVIVSS
>CH557_aa_LC (SEQ ID NO:168)
EIVLTQSPATLSASPGERVTLTCRASRSVRNNVAWYQHKGGQSPRLL
IYDASTRAAGVPARFSGSASGTEFTLAISNLESEDFTVYF**CLQYNNW
WTF**GQGTRVDIK

>CH557_nt_HC (SEQ ID NO:169)
CAGGTCCGACTAGCCCAATATGGTGGTGGGGTGAAGAGGCTAGGGGC
ACAATGACCCTTTCCTGCGTGGCATCT**GGATACACCTTCAACGACT
ACTAC**ATACATTGGGTGCGGCAGGCCCCTGGACAAGGCTTTGAGTTG
TTGGGATACATCGACCCCGCTAATGGTCGCCCAGACTACGCAGGGGC
GTTGAGGGAGAGACTCTCCTTCTACAGGGACAAGTCCATGGAGACGC
TGTACATGGACCTGAGGAGCCTAAGATATGACGACACGGCCATGTAT
TATTGT**GTTAGAAATGTGGGGACCGCTGGCAGCTTGCTGCATTATGA
CCAC**TGGGGCTCGGGAAGCCCGGTCATCGTCTCCTCC
>CH557_nt_LC (SEQ ID NO:170)
GAAATTGTGTTGACGCAGTCTCCAGCCACCCTGTCCGCGTCTCCAGG
GGAAAGAGTCACCCTAACTTGCAGGGCCAGT**CGGAGTGTCCGAAACA
AC**GTGGCCTGGTATCAGCACAAGGGTGGCCAGAGTCCCAGGCTCCTC
ATTTATGATGCGTCCACGAGGGCCGCTGGTGTCCCAGCCAGGTTCAG
CGGCAGTGCATCTGGGACAGAGTTCACTCTCGCCATCAGCAACTTGG
AGTCTGAAGATTTTACAGTCTACTTCTGT**CTGCAGTATAATAACTGG
TGGACC**TTCGGCCAAGGGACCAGGGTGGACATCAAA

Figure 21

| IMGT | | | | |
|---|---|---|---|---|
| Heavy | | | | |
| | | FR1 | CDR1 | FR2 | CDR2 |
| SEQ ID NO:171 | 40.01 | QVQLIQSGPGQKTPGASVTVYSCKAS | GYIFTDYL | IHWVRLVPGKGLEWLGR | INTNAGLM |
| SEQ ID NO:172 | 40.02 | QVRLMQSGPGQLKTPGASVTVYSCKAS | GYIFTDYL | IHWVRLVPGKGLEWLGR | INTNGGLM |
| SEQ ID NO:173 | 40.03 | QVQLIQSGPGQLKTPGASVTVYSCKAS | GYYFADYL | IHWVRLVPGKGLEWLGR | INTNAGLM |
| SEQ ID NO:174 | 40.04 | QVRLMQSGTEKKTPGASVRVYSCKTS | GYIFSDYL | IHWVRLVPGKGLEWLGR | INTNAGLM |
| | | ---FR1--- | ---CDR1--- | ---FR2--- | ---CDR2--- | continued:

| | FR3 | CDR3 | FR4 |
|---|---|---|---|
| | YLSHKFEGRALLIRKVVDMRTPSLGTVYMELRNVRSDDSAIYFC | GRVVDGFMAAGPLEF | WGQQSPVIVSS |
| | YLSYKFEGRLLLIRADVLMRTPSLGTVYMELRNVKNLRSDDSAIYFC | GRVVDGFMAAGPLEF | WGQQSPVIVSS |
| | YLSHKFEGRLLLIRADADMRTPSLGTLVMELRNLRNLKSDDSAIYFC | GRVVDGFMAAGPLEF | WGQQSPVIVSS |
| | YLSPKFEGRVILAAESSTRTPSLGTVYMELRNLKFDDSAIYFC | GRVVDGFMAAGPLEF | WGQQSLIVSS |
| | ---FR3--- | ---CDR3--- | ---FR4--- |

Figure 22

IMGT

Light

| | | FR1 | CDR1 | FR2 |
|---|---|---|---|---|
| SEQ ID NO:175 | 40.01 | QVVMTQSPATLSLSPGETAAVSCRAS | QYVDRS | ISWYQLKTGRAPRLLVY |
| SEQ ID NO:176 | 40.02 | QVVMTQSPVTLSVSPGETAAVSCRAS | QYVDRS | ISWYQLKTGRAPRLLVY |
| SEQ ID NO:177 | 40.03 | QVLMTQSPATLSVSPGETAAVSCRAS | QYVDRS | ISWYQVKSGRAPRLLVY |
| SEQ ID NO:178 | 40.04 | EVVMTQSPATLSVSPGEEAALSCGAS | DYIDRS | VSWYQLKPGRAPRLLVY | continued:

| | CDR2 | FR3 | CDR3 | FR4 |
|---|---|---|---|---|
| | AAS | SRSIGVPDRFSGSGSGSGRADFTLTIRGVQSDDFALYYC | QQDYXMPVTF | GQGTRLDMK |
| | AAS | SRSIGVPDRFSGSGSGSGRDFTLTIRGVQSDDFAVYYC | QQDYXMPVTF | GQGTRLDMK |
| | AAS | SRSIGVPDRFSGSGSGSGTDFTLTIRGVQSDDFALYYC | QQDYGMPVTF | GQGTRLDMK |
| | AAS | SRSIGIPDRFSGSGSGSTAFTLTIRGVQSDDFALYYC | QQDYMPVTF | GQGTRLDMK |

Figure 22 cont.

KABAT
Heavy

```
              1               2              3                    4                  5         6
          1234567890123456789012345678901234567890    12345    6789012345678    901234567890123456
40.01     QVQLIQSGPQFKTPGASVTVSCKASGYIFT              DYLIH    WVRLVPGKGLEWLG    RINTNAGLMYLSKFEG
40.02     QVRLMQSGPQLKTPGASVTVSCKASGYIFT              DYLIH    WVRLVPGKGLEWLG    RINTNAGLMYLSKFEG
40.03     QVQLIQSGPQLKTPGASVKTGASGYVFA                DYLIH    WVRLVPGKGLEWLG    RINTNAGLMYLSKFEG
40.04     QVRLMQSGTEFTPGASVKVSCKTSGYIFS               DYLIH    WVRLVPGKGLEWLG    RINTNAGLMYLSPRFEG
          ------FR1-----------------------            --CDR1   ------FR2-----    -----CDR2-------
```

SEQ ID NO:171
SEQ ID NO:172
SEQ ID NO:173
SEQ ID NO:174 continued:

```
              7                 8                 9                1                     1          1
          6789012A----BC34567890123456789012345    67890ABCDE12   VVDGFWAGPLEF     345678901123        1
          RLILRRVVDMRFPSLGTVNMELRNVRSDDSAIYFCGR     VVDGFWAGPLEF                    WGQGSPVTVSS
          RLILRRDVDMRFPSLGTVNMELRNVRSDDSAIYFCGR     VVDGFWAGPLEF                    WGQGSPVTVSS
          RLILRRDRDMRFPSLGTLYMELRNLRSDDSAIYFCGR     VVDGFWAGPLEF                    WGQGSPVTVSS
          RVILRRESFRTPSLGTVYMELRNIRFDDSAVYFCGR      VVDGFWAGPLEF                    WGQGSPVTVSS
          -------------FR3--------------------     -----CDR3----                    -----FR4---
```

Figure 22 cont.

KABAT

Light

```
                    1                   2                   3                   4                   5
           1234567890123456789012345678901234567890123456789012345678901234567890123456
SEQ ID NO:175  40.01  QVVMTQSPATLSLSPGETAAVSC  RASQYVDRSIS  WYQLKTGRAPRLLVY  AASSRSI
SEQ ID NO:176  40.02  QVVMTQSPVTLSVSPGETAAVSC  RASQYVDRSIS  WYQLKTGRAPRLLVY  AASSRSI
SEQ ID NO:177  40.03  QVLMTQSPATLSVSPGETAAVSC  RASQYVDRSIS  WYQYVKSGRAPRLLVY  AASSRSI
SEQ ID NO:178  40.04  EVVMTQSPATLSVSPGEEAALSC  GASDYIDRSVS  WYQLKPGRAPRLLVY  AASSRSI
                      ---FR1---                ---CDR1---   ---FR2---        ---CDR2---
``` continued:

```
            6                   7                   8                   9                   0
    7890123456789012345678901234567890123456789012345678  901234567  890123456
    GVPDRFSGSGSGSGRDFTLTIRGVQSDDFALYYC                    QQDYYMPVT  FGQGTRLDMK
    GVPDRFSGSGSGSGRDFTLTIRGVQSDDFALYYC                    QQDYYMPVT  FGQGTRLDMK
    GVPDRFSGSGSGSGTDFTLTIRGVQSDDFALYYC                    QQDYGMPVT  FGQGTRLDMK
    GIPDRFSGSGSGSCTAFTLTIRGVQSDDFALYYC                    QQDYYMPVT  FGQGTRLDMK
    ---FR3---                                             ---CDR3---  ---FR4---
```

Figure 22 cont.

Amino acid alignment of CH235 lineage antibody heavy chains

|  |  | 10 | 20 | 30 | 40 |
|---|---|---|---|---|---|
| SEQ ID NO:179 | UCA_HC | QVQLVQSGAEVKKPGASVKVSCKASGYTFTSYYMHWVRQA |
| SEQ ID NO:180 | CH240_HC | ----------T--R--TI---------------WNF-V- |
| SEQ ID NO:181 | CH235_HC | -----------------T--Q---------------N-V |
| SEQ ID NO:182 | CH239_HC | ----------R--T--------------------WNF-V |
| SEQ ID NO:183 | CH236_HC | --------A--R--TI--R------------T--T---- |
| SEQ ID NO:184 | CH241_HC | --------A--R---------------------SHI--- |
| SEQ ID NO:185 | CH491_HC | --------A--R--TI--R------------T--I---- |
| SEQ ID NO:186 | CH493_HC | -R-L-Y-GG--R--MTI--V--M-MD-I--R-------- |
| SEQ ID NO:187 | CH555_HC | ---T--R--TL--RT--W-ID-FI--R------------ |
| SEQ ID NO:188 | CH558_HC | --GG--R--STTTI--V---S-MD-I------------- |
| SEQ ID NO:189 | CH556_HC | --GT-S--T-TL----T--W-ID-I--R----------- |
| SEQ ID NO:190 | CH557_HC | -R-A-Y-GG--RL-TMTI-V-----ND-I---------- |

Figure 23

Amino acid alignment of CH235 lineage antibody light chains

|  |  | | | 10 | 20 | 30 | 40 | |
|---|---|---|---|---|---|---|---|---|
| SEQ ID NO:191 | UCA LC   | EIVLTQSPATLSVSPGERATLSCRASQSVSSNLAWYQQKPGQAPRLLIY( |
| SEQ ID NO:192 | CH236 LC | .........................RN.....R..R. |
| SEQ ID NO:193 | CH240 LC | ..............V.........T..R.....R. |
| SEQ ID NO:194 | CH241 LC | ..............................R.I........H |
| SEQ ID NO:195 | CH235 LC | ...........A...................R.....R. |
| SEQ ID NO:196 | CH239 LC | ...........A........V.T....T...R.V. |
| SEQ ID NO:197 | CH558 LC | ...........A........V.T.....RG.RN.V...HNV..S |
| SEQ ID NO:198 | CH557 LC | ...D.......A........V......R..RN.V...H.G..S |
| SEQ ID NO:199 | CH555 LC | ...D...................A....GTKV...RHVR..P |
| SEQ ID NO:200 | CH556 LC | TT.....................A...G.QV..FRHIR..P......S |

Figure 24

```
         50         60         70         80         90
         |....|....|....|....|....|....|....|....|....|
UCA  LC  GASTRATGIPARFSGSGSGTEFTLTISSLQSEDFAVYYCQQ
CH236 LC ........................................
CH240 LC .S......................M...............
CH241 LC ..............G.................L.......
CH235 LC .T...........V........P..A...V..........
CH239 LC .S.............R........A...M...L.L.....
CH558 LC .D........P.........A.......A.M...L.....
CH557 LC .D.....A.V..........A....I..TL....H.....
CH556 LC .......A.V..........D....GM......E.F....
CH555 LC .......A........G...N....I.NNF...E.L....
```

Figure 24 cont.

```
                 .....|....|....|....|
                              100
UCA   LC    YNNWWTFGQGTKVEIK
CH236 LC    ...............
CH240 LC    ...............
CH241 LC    ..D............
CH235 LC    ...............
CH239 LC    .DD............
CH558 LC    ............R.D.N
CH557 LC    ............R.D.
CH555 LC    .KS.........DN.
CH556 LC    .HM.........R.DKN
```

*Figure 24 cont.*

|    | mAbs Name | Lot | VH | VL |
|----|-----------|-----|-----|-----|
| 1  | DH542 |  | DH542 | DH542 |
| 2  | DH542_L2_4A | 61TCB |  | DH270 UCA |
| 3  | DH542_L3_4A | 62TCB | DH542 | DH270 |
| 4  | DH542_L4_4A | 63TCB | DH542 | DH429 |
| 5  | I0848_00001_L2_4A/293i | 416JAH | I0848_00001_L1_4A | DH542 |
| 6  | I0848_00004_L2_4A/293i | 419JAH | I0848_00004_L1_4A | DH542 |
| 7  | I0848_00005_L1_4A/293i | 411HC | I0848_00005_L1_4A | DH471 |
| 8  | I0848_00006_L1_4A/293i | 417JAH | I0848_00006_L1_4A | DH542 |
| 9  | I0848_00007_L1_4A/293i | 413HC | I0848_00007_L1_4A | DH473 |
| 10 | DH542 |  |  | DH542 |
| 11 | DH542QSA | 024RM | DH542 | DH542_QSA |
| 12 | AbI0848_00001_L2_4A | 123RKK | I0848_00001_L1_4A | DH542_QSA |
| 13 | AbI0848_00004_L2_4A | 427HC | I0848_00004_L1_4A | DH542_QSA |
| 14 | AbI0848_00006_L2_4A | 429HC | I0848_00006_L1_4A | DH542_QSA |
| 15 | AbI0848_00007_L2_4A | 430HC | I0848_00007_L1_4A | DH542_QSA |

Figure 25

| | DH542 | DH542 QSA | DH542 _L2 | DH542 _L3 | DH542 _L4 | I0848_000 01_L1 | I0848_000 04_L1 | I0848_000 05_L1 | I0848_000 06_L1 | I0848_000 07_L1 |
|---|---|---|---|---|---|---|---|---|---|---|
| 57128.vrc15 | 3.59 | 0.879 | >50 | >50 | 1.105 | >50 | >50 | >50 | 4.119 | >50 |
| C1080.3 | >50 | >50 | >50 | >50 | >50 | >50 | >50 | >50 | >50 | >50 |
| CNE58 | 0.263 | 0.128 | >50 | 8.994 | 0.187 | >50 | >50 | >50 | 0.616 | 3.851 |
| DU172.17 | 0.315 | 0.539 | >50 | >50 | 0.203 | >50 | >50 | >50 | 1.11 | >50 |
| DU422.1 | 0.19 | 0.079 | >50 | 0.517 | 0.273 | 2.515 | >50 | >50 | 0.296 | 0.41 |
| Q23.17 | 0.01 | 0.01 | >50 | 0.01 | 0.01 | 0.087 | >50 | 2.279 | 0.01 | 0.01 |
| CAP244.2.0.3 | 8.976 | 9.161 | >50 | >50 | 0.328 | >50 | >50 | >50 | 11.299 | >50 |
| CH0848.d0 078.30.02 | 3.889 | 1.219 | >50 | >50 | 1.325 | >50 | >50 | >50 | 16.882 | >50 |
| CH0848.TF | 47.507 | 34.503 | >50 | >50 | 3.431 | >50 | >50 | >50 | >50 | >50 |
| CNE20 | 13.171 | >50 | >50 | >50 | 1.289 | >50 | >50 | 0.183 | >50 | >50 |
| DU151.02 | 1.449 | 3.457 | >50 | >50 | 0.109 | >50 | >50 | 0.01 | 1.365 | >50 |
| TV1.21 | 0.502 | 0.354 | >50 | 3.552 | 0.174 | >50 | >50 | >50 | 0.502 | 1.267 |

Figure 26A

| Ab I0848_00001_L2 | Ab I0848_00004_L2 | Ab I0848_00006_L2 | Ab I0848_00007_L2 | Ab I0848_00006_L3 | |
|---|---|---|---|---|---|
| >50 | >50 | 0.867 | >50 | 1.327 | 57128.vrc15 |
| >50 | >50 | >50 | >50 | >50 | C1080.3 |
| >50 | >50 | 0.27 | >50 | 0.206 | CNE58 |
| >50 | >50 | 0.731 | >50 | 0.402 | DU172.17 |
| 1.444 | >50 | 0.161 | >50 | 0.406 | DU422.1 |
| 0.083 | >50 | 0.01 | 0.45 | 0.01 | Q23.17 |
| >50 | >50 | >50 | >50 | 0.358 | CAP244.2.00.3 |
| >50 | >50 | 16.394 | >50 | 2.256 | CH0848.d007 8.30.02 |
| >50 | >50 | >50 | >50 | 5.451 | CH0848.TF |
| >50 | >50 | >50 | >50 | 0.425 | CNE20 |
| >50 | >50 | 6.291 | >50 | 0.192 | DU151.02 |
| >50 | >50 | 0.817 | >50 | 0.567 | TV1.21 |

Figure 26B

| Antibody ID | $V_H$ | D | $J_H$ | Mutation frequency | | | CDRH3 length |
|---|---|---|---|---|---|---|---|
| | | | | $V_H$ | $V_HDJ_H$ nt | $V_HDJ_H$ aa | |
| DH270.UCA | 1-2*02 | 3-22*01 | 4*02 | 0.0% | 0 (0%) | 0 (0%) | 20 |
| DH270.IA4 | 1-2*02 | 3-22*01 | 4*02 | 1.4% | 4/381 (1.0%) | 4/127 (3.1%) | 20 |
| DH270.IA2 | 1-2*02 | 3-22*01 | 4*02 | 2.1% | 7/381 (1.8%) | 7/127 (5.5%) | 20 |
| DH270.IA3 | 1-2*02 | 3-22*01 | 4*02 | 3.5% | 16/381 (4.2%) | 11/127 (8.7%) | 20 |
| DH270.1 | 1-2*02 | 3-22*01 | 4*02 | 5.6% | 21/381 (5.5%) | 18/127 (14.2%) | 20 |
| DH270.IA1 | 1-2*02 | 3-22*01 | 4*02 | 8.3% | 33/381 (8.7%) | 22/127 (17.3%) | 20 |
| DH270.2 | 1-2*02 | 3-22*01 | 4*02 | 10.8% | 46/381 (12.1%) | 27/127 (21.3%) | 20 |
| DH270.3 | 1-2*02 | 3-22*01 | 4*02 | 11.8% | 48/381 (12.6%) | 27/127 (21.3%) | 20 |
| DH270.4 | 1-2*02 | 3-22*01 | 4*02 | 11.5% | 44/381 (11.6%) | 28/127 (22.0%) | 20 |
| DH270.5 | 1-2*02 | 3-22*01 | 4*02 | 11.1% | 45/381 (11.8%) | 26/127 (20.5%) | 20 |
| DH270.6 | 1-2*02 | 3-22*01 | 4*02 | 12.9% | 47/381 (12.3%) | 28/127 (22.0%) | 20 |

Figure 29

| Antibody ID | VL | JL | Mutation frequency ||| CDRL3 length | Week of isolation | Insertions/ deletions |
|---|---|---|---|---|---|---|---|---|
| | | | V_L | V_LJ_L nt | V_LJ_L aa | | | |
| DH270.UCA | 2-23*02 | 2*01 | 0.0% | 0 (0%) | 0 (0%) | 10 | - | none |
| DH270.IA4 | 2-23*02 | 2*01 | 0.7% | 2/330 (0.6%) | 1/110 (0.9%) | 10 | - | none |
| DH270.IA2 | 2-23*02 | 2*01 | 2.1% | 6/330 (1.8%) | 3/110 (2.7%) | 10 | - | none |
| DH270.IA3 | 2-23*02 | 2*01 | 1.4% | 4/330 (1.2%) | 2/110 (1.8%) | 10 | - | none |
| DH270.1 | 2-23*02 | 2*01 | 5.2% | 21/330 (6.3%) | 11/110 (10.0%) | 10 | 205 | none |
| DH270.IA1 | 2-23*02 | 2*01 | 6.9% | 26/330 (7.9%) | 14/110 (12.7%) | 10 | - | none |
| DH270.2 | 2-23*02 | 2*01 | 3.8% | 13/330 (3.9%) | 7/110 (6.4%) | 10 | 232 | none |
| DH270.3 | 2-23*02 | 2*01 | 8.3% | 27/330 (8.2%) | 16/110 (14.5%) | 10 | 205 | none |
| DH270.4 | 2-23*02 | 2*01 | 8.0% | 29/330 (8.8%) | 16/110 (14.5%) | 10 | 232 | none |
| DH270.5 | 2-23*02 | 2*01 | 11.5% | 41/330 (12.4%) | 22/110 (20.0%) | 10 | 232 | none |
| DH270.6 | 2-23*02 | 2*01 | 7.6% | 39/330 (11.8%) | 17/110 (15.5%) | 10 | 234 | none |

Figure 29 cont.

|  | AC13.8 | | PVO.4 | | TRO.11 | | AC10.029 | | RHPA.4259 | |
|---|---|---|---|---|---|---|---|---|---|---|
|  | wt | N332A | wt | N332A | wt | N332A | wt | N332A | wt | N332A |
| DH270.UCA | >50 | >50 | >50 | >50 | >50 | >50 | >50 | >50 | >50 | >50 |
| DH270.IA4 | >50 | >50 | 42 | >50 | 43 | >50 | >50 | >50 | >50 | >50 |
| DH270.IA3 | >50 | >50 | >50 | >50 | 0.2 | >50 | >50 | >50 | 6.6 | >50 |
| DH270.IA2 | >50 | >50 | >50 | >50 | 0.1 | >50 | >50 | >50 | 6.4 | >50 |
| DH270.1 | >50 | >50 | 0.2 | >50 | 0.08 | >50 | 1.9 | >50 | 0.2 | >50 |
| DH270.IA1 | >50 | >50 | 0.07 | >50 | 0.05 | 32.4 | <0.02 | >50 | 0.04 | >50 |
| DH270.2 | 21 | >50 | 0.3 | >50 | 0.06 | >50 | 0.3 | >50 | 0.1 | >50 |
| DH270.3 | >50 | >50 | 23 | >50 | 0.3 | >50 | 43 | >50 | 42 | >50 |
| DH270.4 | 15 | >50 | 0.1 | >50 | 0.04 | 14 | <0.02 | >50 | 0.05 | >50 |
| DH270.5 | 41 | >50 | 0.1 | >50 | 0.07 | >50 | <0.02 | >50 | 0.04 | >50 |
| DH270.6 | 1.4 | >50 | 0.03 | >50 | 0.02 | >50 | <0.02 | >50 | <0.02 | >50 |

Figure 30

SEQUENCE LISTING

```
<160> NUMBER OF SEQ ID NOS: 296

<210> SEQ ID NO 1
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
caggtgcagc tggtgcagtc tggggctcaa atgaagaacc ctggggcctc agtgaaggtc      60
tcctgcgcgc cttctggata taccttcacc gactttaca tacattggtt gcgccaggcc     120
cctggccagg ggcttcagtg gatgggatgg atgaaccctc agactggtcg cacaaacact     180
gcacgaaact tcaggggag gtcaccatg accagggaca cgtccatcgg cacagcctac     240
atggagttga agcctgac atctgacgac acggccatat attactgtac gacaggggga     300
tggatcagtc tttactatga tagtagttat taccccaact ttgaccactg gggtcaggga     360
accctgctca ccgtctcctc ag                                             382

<210> SEQ ID NO 2
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
accagtctgc tgactcagcc tgcctccgtg tctgggtctc ctggacagtc gatcaccatc      60
tcctgcactg gaaccaagta tgatgttggg agtcatgacc ttgtctcctg gtaccaacag     120
tacccaggca aagtccccaa atacatgatt tatgaagtca ataaacggcc ctcaggagtt     180
tctaatcgct tctctggctc caaatctggc aacacggcct ccctgacaat ctctgggctc     240
cgggctgagg acgaggctga ctattattgc tgttcatttg gagggagtgc caccgtggtc     300
tgcggcggcg ggaccaaggt gaccgtccta g                                    331
```

<210> SEQ ID NO 3
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Gln Val Gln Leu Val Gln Ser Gly Ala Gln Met Lys Asn Pro Gly Ala
1               5                   10                  15

Ser Val Lys Val Ser Cys Ala Pro Ser Gly Tyr Thr Phe Thr Asp Phe
            20                  25                  30

Tyr Ile His Trp Leu Arg Gln Ala Pro Gly Gln Gly Leu Gln Trp Met
        35                  40                  45

Gly Trp Met Asn Pro Gln Thr Gly Arg Thr Asn Thr Ala Arg Asn Phe
    50                  55                  60

Gln Gly Arg Val Thr Met Thr Arg Asp Thr Ser Ile Gly Thr Ala Tyr
65                  70                  75                  80

Met Glu Leu Arg Ser Leu Thr Ser Asp Asp Thr Ala Ile Tyr Tyr Cys
                85                  90                  95

Thr Thr Gly Gly Trp Ile Ser Leu Tyr Tyr Asp Ser Ser Tyr Tyr Pro
            100                 105                 110

Asn Phe Asp His Trp Gly Gln Gly Thr Leu Leu Thr Val Ser Ser
        115                 120                 125
```

<210> SEQ ID NO 4
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Thr Ser Leu Leu Thr Gln Pro Ala Ser Val Ser Gly Ser Pro Gly Gln
1               5                   10                  15

Ser Ile Thr Ile Ser Cys Thr Gly Thr Lys Tyr Asp Val Gly Ser His
            20                  25                  30

Asp Leu Val Ser Trp Tyr Gln Gln Tyr Pro Gly Lys Val Pro Lys Tyr
        35                  40                  45

Met Ile Tyr Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Arg Ala Glu Asp Glu Ala Asp Tyr Tyr Cys Cys Ser Phe Gly Gly Ser
                85                  90                  95

Ala Thr Val Val Cys Gly Gly Gly Thr Lys Val Thr Val Leu
            100                 105                 110
```

<210> SEQ ID NO 5
<211> LENGTH: 382
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5
caggtgcagc tggtgcagtc tggggctgag gtgaagaagc ctggggcctc agtgaaggtc    60

```
tcctgcaagg cttctggata caccttcacc ggctactata tgcactgggt gcgacaggcc      120
cctggacaag gcttgagtg gatgggatgg atcaaccca acagtggtgg cacaaactat        180
gcacagaagt tcagggcag ggtcaccatg accagggaca cgtccatcag cacagcctac       240
atggagctga gcaggctgag atctgacgac acggccgtgt attactgtgc gagaggggr       300 tggatcrgtc tttactatga tagtagtggt taccctaact ttgactactg gggccaggga     360
accctggtca ccgtctcctc ag                                               382
```

<210> SEQ ID NO 6
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
caggtgcagc tggtgcagtc tggggctgag rtgaagaagc ctggggcctc agtgaaggtc      60
tcctgcaagg cttctggata caccttcacc gactactata tacactgggt gcgacaggcc     120
cctggacaag gcttgagtg gatgggatgg atcaaccta acastggtcg cacaaactmt       180
gcacagaagt tcagggcag ggtcaccatg accagggaca cgtccatcag cacagcctac       240
atggagctga gcagvctgag atctgacgac acggccgtgt attactgtgc gagaggggr      300 tggatcrgtc tttactatga tagtagtggt taccctaact ttgactactg gggccaggga     360
accctggtca ccgtctcctc ag                                               382
```

<210> SEQ ID NO 7
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
caggtgcagc tggtgcagtc tggggctgag dtgaagaagc ctggggcctc agtgaaggtc      60
tcctgcaagg cttctggata caccttcacc gactactata tacactgggt gcgacaggcc     120
cctggacaag gcttgagtg gatggcatgg atcaaccta ccastggtcg cacaarctmt       180
gcacggaagt tcagggcag ggtcaccatg accagggaca cgtccatcag cacrgcctac       240
atggaactga gaagmctgag atctgacgac acggccgtct attactgtgc gagaggggga    300
tggatcrgtc tttacgttga ttatagtggt taccctaact ttgactcctg gggccaggga    360
accctggtca ccgtctcctc ag                                               382
```

<210> SEQ ID NO 8
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
gaggttcagc tggtggagtc tgggcctgag ttgaaggagc ctggggcctc agtgaaagtc      60
tcctgcaagg cttctggata caccttcacc gactactaca tacactgggt gcgacaggcc     120
cctggacaag gtcttgagtg gatggcatgg atcaaccta ccactggtcg ctctagcttt      180
```

```
gcccgggggt tcagggcag ggtcaccatg accagggaaa cgtccgtcag cacggcctat    240
atggaactga aagactgag atctgacgac acggccgtct attactgtgc gaaagcggga    300
tacatcgccc tttacgttga ctatagtggt taccctaact ttaattcctg gggccaggga   360
accctggtca ccgtctcctc ag                                            382
```

<210> SEQ ID NO 9
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
caggtgcagc tggtgcagtc tggggctgaa ctgaagaagc ctggggcctc agtgaaggtc    60
tcctgcaagg cttctggata caccctcagc gactactatg tacactggct gcgacaggcc   120
cctggacagg gcttgagtg gtggcttggg atcaacccta ccagtggtcg cacaatctct   180
ccacggaagt tcagggcag ggtcacgatg actacggaca cgtccatgaa tgttgcctac    240
atggaactga aggcttgag atctgacgac acggccgtct atttctgtgc gagaggggga   300
tggatcagtc tctacgttga ttacagttat taccctaact ttgactcgtg gggccaggga  360
accctggtct ccgtctcttc ag                                            382
```

<210> SEQ ID NO 10
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
caggtgcagc tggtgcagtc tggggctgag atgaagaagc ctggggcctc agtgaaggtc    60
tcctgcaagg cttctggata caccttcacc gactactata tacactgggt gcgacaggcc   120
cctggacaag gcttgagtg gatgggatgg atcaacccta acactggtcg cacaaactmt   180
gcacagaagt tcagggcag ggtcaccatg accagggaca cgtccatcag cacagcctac    240
atggagctga gcagvctgac atctgacgac acggccgtgt attactgtgc gacagggggr  300
tggatcrgtc tttactatga tagtagtggt taccctaact ttgactactg gggccaggga  360
accctggtca ccgtctcctc ag                                            382
```

<210> SEQ ID NO 11
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
caggtgcagc tggtgcagtc tggggctgaa atgaagaacc ctggggcctc agtgaaggtc    60
tcctgcgcgs cttctggata tacettcacc gacttctaca tacactgggt gcgacaggcc  120
cctggacaag gcttsagtg gatgggatgg atgaaccta agactggtcg cacaaacamt   180
gcacaaaact ttcagggcag ggtcaccatg accagggaca cgtccatcgg cacagcctac   240
atggagytga gvagcctgac atctgacgac acggccgtvt attactgtgc gacaggggr    300
```

```
tggatcagtc tttactatga tagtagttat taccctaact ttgaccactg gggtcaggga    360
accctggtca ccgtctcctc ag                                             382
```

<210> SEQ ID NO 12
<211> LENGTH: 382
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
caggtgcagc tggtgcagtc tggggctcaa atgaagaacc ctggggcctc agtgaaggtc     60
tcctgcgcgc cttctggata taccttcacc gacttttaca tacattggtt gcgccaggcc    120
cctggccagg ggcttcagtg gatgggatgg atgaaccctc agactggtcg cacaaacact    180
gcacgaaact ttcaggggag ggtcaccatg accagggaca cgtccatcgg cacagcctac    240
atggagttga aagcctgac atctgacgac acggccatat attactgtac gacaggggga     300
tggatcagtc tttactatga tagtagttat taccccaact ttgaccactg gggtcaggga    360
accctgctca ccgtctcctc ag                                             382
```

<210> SEQ ID NO 13
<211> LENGTH: 382
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13

```
caggtgcagc tggtgcagtc tggggctgaa atgaagaacc ctggggcctc agtgaaagtc     60
tcctgcgcgs cttctggata taccttcacc gacttctaca tacactgggt gcgactggcc    120
cctggacaag ggcttsagtg gatgggatgg atgaaccccta agactggtcg cacaaataat    180
gcacaaaact ttcagggcag ggtcaccatg accagggaca cgtccatcgg cacagcctac    240
atggagytga ggagcctgac atctgacgac acggccgtct attactgtgt gacaggggggr   300 tggatcagtc httattatga tagtagttat taccctaact ttgaccactg gggtcaggga    360
accctggtca ccgtctcctc ag                                             382
```

<210> SEQ ID NO 14
<211> LENGTH: 382
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
caggtgcagc tggtgcagtc tggggctgaa gtgaagaacc ctggggcctc agtgaaagtc     60
tcctgcgcgc cttctggata taccttcact gacttctaca tacactgggt gcgactggcc    120
cctggacaag ggcttgagtg gctggggtgg atgaaccccta agactggtcg cacaaatcaa    180
ggacaaaact ttcagggcag ggtcaccatg accagggaca cgtccatcgg cacagcctac    240
atggagttga ggagcctcac atctgacgac acggccgtct attactgtgt gacaggggcc    300
tggatcagtg attattatga tagtagttat tatcctaact ttgaccactg gggtcaggga    360
accctggtca ccgtctcctc ag                                             382
```

<210> SEQ ID NO 15
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
gaggtgcagc tggtgcagtc tggggctgaa atgaagaacc ctggggcctc agtgaaagtc    60
tcctgcgcgg cttctggata tggtttcacc gacttctaca tacactgggt gcgactggcc   120
cctggacacg gctccagtg gatgggatgg atgaaccta agactggtcg cacaaataat    180
gcacaagatt ttcagggcag ggtcaccctg accagggaca cgtccatcgg cacagcctac   240
atggagctga ggaggctgac atctgacgac acggccgtct attactgtgt gacaggggggg   300 tggatcagtc cttattatga tagtagttat taccctaatt ttgaccactg gggtcaggga   360
accctgatca ccgtctcctc ag                                            382
```

<210> SEQ ID NO 16
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
caggtgcagc tggtgcagtc tggggctgag atgaagaagc tggggcctc agtgagggtc     60 tcctgcaagg cttctggata caccttcacc gactactata tacactgggt gcgacaggcc   120
cctggacaag gcctgagtg gatgggatgg atcaacccta gcactggtcg cacaaactct    180
ccacagaagt ttcagggcag ggtcaccatg accagggaca cgtccatcag cacagcctac   240
atggacctga acagactgac gtctgacgac acggccatgt attactgtac gaccggggggg   300 tggatcggtc tttactctga tactagtggt taccctaact ttgactactg gggccaggga   360
accctggtca ccgtctcctc ag                                            382
```

<210> SEQ ID NO 17
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (100)..(100)
<223> OTHER INFORMATION: Any amino acid
<220> FEATURE:
<221> NAME/KEY: MOD_RES
<222> LOCATION: (103)..(103)
<223> OTHER INFORMATION: Any amino acid

<400> SEQUENCE: 17

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
```

```
                    50                  55                  60
Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Gly Xaa Trp Ile Xaa Leu Tyr Tyr Asp Ser Ser Gly Tyr Pro
            100                 105                 110

Asn Phe Asp Tyr Trp Gly Gln Gly Thr Leu Val Thr Val Ser Ser
            115                 120                 125

<210> SEQ ID NO 18
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (55)..(55)
<223> OTHER INFORMATION: Any amino acid
<220> FEATURE:
<221> NAME/KEY: MOD_RES
<222> LOCATION: (60)..(60)
<223> OTHER INFORMATION: Any amino acid
<220> FEATURE:
<221> NAME/KEY: MOD_RES
<222> LOCATION: (85)..(85)
<223> OTHER INFORMATION: Any amino acid
<220> FEATURE:
<221> NAME/KEY: MOD_RES
<222> LOCATION: (100)..(100)
<223> OTHER INFORMATION: Any amino acid
<220> FEATURE:
<221> NAME/KEY: MOD_RES
<222> LOCATION: (103)..(103)
<223> OTHER INFORMATION: Any amino acid

<400> SEQUENCE: 18

Gln Val Gln Leu Val Gln Ser Gly Ala Glu Xaa Lys Lys Pro Gly Ala
  1               5                  10                  15

Ser Val Lys Val Ser Cys Lys Ala Ser Gly Tyr Thr Phe Thr Asp Tyr
                 20                  25                  30

Tyr Ile His Trp Val Arg Gln Ala Pro Gly Gln Gly Leu Glu Trp Met
             35                  40                  45

Gly Trp Ile Asn Pro Asn Xaa Gly Arg Thr Asn Xaa Ala Gln Lys Phe
         50                  55                  60

Gln Gly Arg Val Thr Met Thr Arg Asp Thr Ser Ile Ser Thr Ala Tyr
 65                  70                  75                  80

Met Glu Leu Ser Xaa Leu Arg Ser Asp Asp Thr Ala Val Tyr Tyr Cys
                 85                  90                  95

Ala Arg Gly Xaa Trp Ile Xaa Leu Tyr Tyr Asp Ser Ser Gly Tyr Pro
            100                 105                 110

Asn Phe Asp Tyr Trp Gly Gln Gly Thr Leu Val Thr Val Ser Ser
            115                 120                 125

<210> SEQ ID NO 19
<211> LENGTH: 127
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (55)..(55)
<223> OTHER INFORMATION: Any amino acid
<220> FEATURE:
<221> NAME/KEY: MOD_RES
<222> LOCATION: (59)..(60)
<223> OTHER INFORMATION: Any amino acid
<220> FEATURE:
<221> NAME/KEY: MOD_RES
<222> LOCATION: (78)..(78)
<223> OTHER INFORMATION: Any amino acid
<220> FEATURE:
<221> NAME/KEY: MOD_RES
<222> LOCATION: (85)..(85)
<223> OTHER INFORMATION: Any amino acid
<220> FEATURE:
<221> NAME/KEY: MOD_RES
<222> LOCATION: (103)..(103)
<223> OTHER INFORMATION: Any amino acid

<400> SEQUENCE: 19

Gln Val Gln Leu Val Gln Ser Gly Ala Glu Xaa Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Ala Trp Ile Asn Pro Thr Xaa Gly Arg Thr Xaa Xaa Ala Arg Lys Phe
    50                  55                  60

Gln Gly Arg Val Thr Met Thr Arg Asp Thr Ser Ile Ser Xaa Ala Tyr
65                  70                  75                  80

Met Glu Leu Arg Xaa Leu Arg Ser Asp Asp Thr Ala Val Tyr Tyr Cys
                85                  90                  95

Ala Arg Gly Gly Trp Ile Xaa Leu Tyr Val Asp Tyr Ser Gly Tyr Pro
            100                 105                 110

Asn Phe Asp Ser Trp Gly Gln Gly Thr Leu Val Thr Val Ser Ser
        115                 120                 125

<210> SEQ ID NO 20
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Val Gln Leu Val Glu Ser Gly Pro Glu Leu Lys Glu Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Ala Trp Ile Asn Pro Thr Thr Gly Arg Ser Ser Phe Ala Arg Gly Phe
    50                  55                  60

Gln Gly Arg Val Thr Met Thr Arg Glu Thr Ser Val Ser Thr Ala Tyr
65                  70                  75                  80
```

```
Met Glu Leu Arg Arg Leu Arg Ser Asp Asp Thr Ala Val Tyr Tyr Cys
             85                  90                  95

Ala Lys Ala Gly Tyr Ile Ala Leu Tyr Val Asp Tyr Ser Gly Tyr Pro
            100                 105                 110

Asn Phe Asn Ser Trp Gly Gln Gly Thr Leu Val Thr Val Ser Ser
        115                 120                 125
```

<210> SEQ ID NO 21
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Leu Ser Asp Tyr
            20                  25                  30

Tyr Val His Trp Leu Arg Gln Ala Pro Gly Gln Gly Leu Glu Trp Val
        35                  40                  45

Ala Trp Ile Asn Pro Thr Ser Gly Arg Thr Ile Ser Pro Arg Lys Phe
    50                  55                  60

Gln Gly Arg Val Thr Met Thr Thr Asp Thr Ser Met Asn Val Ala Tyr
65                  70                  75                  80

Met Glu Leu Arg Gly Leu Arg Ser Asp Asp Thr Ala Val Tyr Phe Cys
             85                  90                  95

Ala Arg Gly Gly Trp Ile Ser Leu Tyr Val Asp Tyr Ser Tyr Tyr Pro
            100                 105                 110

Asn Phe Asp Ser Trp Gly Gln Gly Thr Leu Val Ser Val Ser Ser
        115                 120                 125
```

<210> SEQ ID NO 22
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (60)..(60)
<223> OTHER INFORMATION: Any amino acid
<220> FEATURE:
<221> NAME/KEY: MOD_RES
<222> LOCATION: (85)..(85)
<223> OTHER INFORMATION: Any amino acid
<220> FEATURE:
<221> NAME/KEY: MOD_RES
<222> LOCATION: (100)..(100)
<223> OTHER INFORMATION: Any amino acid
<220> FEATURE:
<221> NAME/KEY: MOD_RES
<222> LOCATION: (103)..(103)
<223> OTHER INFORMATION: Any amino acid

<400> SEQUENCE: 22

```
Gln Val Gln Leu Val Gln Ser Gly Ala Glu Met Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45
```

```
Gly Trp Ile Asn Pro Asn Thr Gly Arg Thr Asn Xaa Ala Gln Lys Phe
            50                  55                  60

Gln Gly Arg Val Thr Met Thr Arg Asp Thr Ser Ile Ser Thr Ala Tyr
65                  70                  75                  80

Met Glu Leu Ser Xaa Leu Thr Ser Asp Asp Thr Ala Val Tyr Tyr Cys
                85                  90                  95

Ala Thr Gly Xaa Trp Ile Xaa Leu Tyr Tyr Asp Ser Ser Gly Tyr Pro
            100                 105                 110

Asn Phe Asp Tyr Trp Gly Gln Gly Thr Leu Val Thr Val Ser Ser
            115                 120                 125
```

```
<210> SEQ ID NO 23
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (46)..(46)
<223> OTHER INFORMATION: Any amino acid
<220> FEATURE:
<221> NAME/KEY: MOD_RES
<222> LOCATION: (60)..(60)
<223> OTHER INFORMATION: Any amino acid
<220> FEATURE:
<221> NAME/KEY: MOD_RES
<222> LOCATION: (83)..(84)
<223> OTHER INFORMATION: Any amino acid
<220> FEATURE:
<221> NAME/KEY: MOD_RES
<222> LOCATION: (93)..(93)
<223> OTHER INFORMATION: Any amino acid
<220> FEATURE:
<221> NAME/KEY: MOD_RES
<222> LOCATION: (100)..(100)
<223> OTHER INFORMATION: Any amino acid

<400> SEQUENCE: 23

Gln Val Gln Leu Val Gln Ser Gly Ala Glu Met Lys Asn Pro Gly Ala
1               5                   10                  15

Ser Val Lys Val Ser Cys Ala Xaa Ser Gly Tyr Thr Phe Thr Asp Phe
                20                  25                  30

Tyr Ile His Trp Val Arg Gln Ala Pro Gly Gln Gly Leu Xaa Trp Met
            35                  40                  45

Gly Trp Met Asn Pro Lys Thr Gly Arg Thr Asn Xaa Ala Gln Asn Phe
            50                  55                  60

Gln Gly Arg Val Thr Met Thr Arg Asp Thr Ser Ile Gly Thr Ala Tyr
65                  70                  75                  80

Met Glu Xaa Xaa Ser Leu Thr Ser Asp Asp Thr Ala Xaa Tyr Tyr Cys
                85                  90                  95

Ala Thr Gly Xaa Trp Ile Ser Leu Tyr Tyr Asp Ser Ser Tyr Tyr Pro
            100                 105                 110

Asn Phe Asp His Trp Gly Gln Gly Thr Leu Val Thr Val Ser Ser
            115                 120                 125
```

```
<210> SEQ ID NO 24
<211> LENGTH: 127
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Val Gln Ser Gly Ala Gln Met Lys Asn Pro Gly Ala
1               5                   10                  15

Ser Val Lys Val Ser Cys Ala Pro Ser Gly Tyr Thr Phe Thr Asp Phe
            20                  25                  30

Tyr Ile His Trp Leu Arg Gln Ala Pro Gly Gln Gly Leu Gln Trp Met
        35                  40                  45

Gly Trp Met Asn Pro Gln Thr Gly Arg Thr Asn Thr Ala Arg Asn Phe
    50                  55                  60

Gln Gly Arg Val Thr Met Thr Arg Asp Thr Ser Ile Gly Thr Ala Tyr
65                  70                  75                  80

Met Glu Leu Arg Ser Leu Thr Ser Asp Asp Thr Ala Ile Tyr Tyr Cys
                85                  90                  95

Thr Thr Gly Gly Trp Ile Ser Leu Tyr Tyr Asp Ser Ser Tyr Tyr Pro
            100                 105                 110

Asn Phe Asp His Trp Gly Gln Gly Thr Leu Leu Thr Val Ser Ser
        115                 120                 125

<210> SEQ ID NO 25
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (46)..(46)
<223> OTHER INFORMATION: Any amino acid
<220> FEATURE:
<221> NAME/KEY: MOD_RES
<222> LOCATION: (83)..(83)
<223> OTHER INFORMATION: Any amino acid
<220> FEATURE:
<221> NAME/KEY: MOD_RES
<222> LOCATION: (100)..(100)
<223> OTHER INFORMATION: Any amino acid
<220> FEATURE:
<221> NAME/KEY: MOD_RES
<222> LOCATION: (104)..(104)
<223> OTHER INFORMATION: Any amino acid

<400> SEQUENCE: 25

Gln Val Gln Leu Val Gln Ser Gly Ala Glu Met Lys Asn Pro Gly Ala
1               5                   10                  15

Ser Val Lys Val Ser Cys Ala Xaa Ser Gly Tyr Thr Phe Thr Asp Phe
            20                  25                  30

Tyr Ile His Trp Val Arg Leu Ala Pro Gly Gln Gly Leu Xaa Trp Met
        35                  40                  45

Gly Trp Met Asn Pro Lys Thr Gly Arg Thr Asn Asn Ala Gln Asn Phe
    50                  55                  60

Gln Gly Arg Val Thr Met Thr Arg Asp Thr Ser Ile Gly Thr Ala Tyr
65                  70                  75                  80

Met Glu Xaa Arg Ser Leu Thr Ser Asp Asp Thr Ala Val Tyr Tyr Cys
                85                  90                  95
```

```
Val Thr Gly Xaa Trp Ile Ser Xaa Tyr Tyr Asp Ser Ser Tyr Tyr Pro
            100                 105                 110

Asn Phe Asp His Trp Gly Gln Gly Thr Leu Val Thr Val Ser Ser
            115                 120                 125

<210> SEQ ID NO 26
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Val Gln Ser Gly Ala Glu Val Lys Asn Pro Gly Ala
1               5                   10                  15

Ser Val Lys Val Ser Cys Ala Pro Ser Gly Tyr Thr Phe Thr Asp Phe
            20                  25                  30

Tyr Ile His Trp Val Arg Leu Ala Pro Gly Gln Gly Leu Glu Trp Leu
        35                  40                  45

Gly Trp Met Asn Pro Lys Thr Gly Arg Thr Asn Gln Gly Gln Asn Phe
    50                  55                  60

Gln Gly Arg Val Thr Met Thr Arg Asp Thr Ser Ile Gly Thr Ala Tyr
65                  70                  75                  80

Met Glu Leu Arg Ser Leu Thr Ser Asp Asp Thr Ala Val Tyr Tyr Cys
                85                  90                  95

Val Thr Gly Ala Trp Ile Ser Asp Tyr Tyr Asp Ser Ser Tyr Tyr Pro
            100                 105                 110

Asn Phe Asp His Trp Gly Gln Gly Thr Leu Val Thr Val Ser Ser
            115                 120                 125

<210> SEQ ID NO 27
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Gln Ser Gly Ala Glu Met Lys Asn Pro Gly Ala
1               5                   10                  15

Ser Val Lys Val Ser Cys Ala Ala Ser Gly Tyr Gly Phe Thr Asp Phe
            20                  25                  30

Tyr Ile His Trp Val Arg Leu Ala Pro Gly His Gly Leu Gln Trp Met
        35                  40                  45

Gly Trp Met Asn Pro Lys Thr Gly Arg Thr Asn Asn Ala Gln Asp Phe
    50                  55                  60

Gln Gly Arg Val Thr Leu Thr Arg Asp Thr Ser Ile Gly Thr Ala Tyr
65                  70                  75                  80

Met Glu Leu Arg Arg Leu Thr Ser Asp Asp Thr Ala Val Tyr Tyr Cys
                85                  90                  95

Val Thr Gly Gly Trp Ile Ser Pro Tyr Tyr Asp Ser Ser Tyr Tyr Pro
            100                 105                 110

Asn Phe Asp His Trp Gly Gln Gly Thr Leu Ile Thr Val Ser Ser
            115                 120                 125

<210> SEQ ID NO 28
```

<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Gln Val Gln Leu Val Gln Ser Gly Ala Glu Met Lys Pro Gly Ala
1               5                   10                  15

Ser Val Arg Val Ser Cys Lys Ala Ser Gly Tyr Thr Phe Thr Asp Tyr
            20                  25                  30

Tyr Ile His Trp Val Arg Gln Ala Pro Gly Gln Gly Pro Glu Trp Met
        35                  40                  45

Gly Trp Ile Asn Pro Ser Thr Gly Arg Thr Asn Ser Pro Gln Lys Phe
    50                  55                  60

Gln Gly Arg Val Thr Met Thr Arg Asp Thr Ser Ile Ser Thr Ala Tyr
65                  70                  75                  80

Met Asp Leu Asn Arg Leu Thr Ser Asp Thr Ala Met Tyr Tyr Cys
                85                  90                  95

Thr Thr Gly Gly Trp Ile Gly Leu Tyr Ser Asp Thr Ser Gly Tyr Pro
            100                 105                 110

Asn Phe Asp Tyr Trp Gly Gln Gly Thr Leu Val Thr Val Ser Ser
        115                 120                 125
```

<210> SEQ ID NO 29
<211> LENGTH: 331
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29

```
cagtctgccc tgactcagcc tgcctccgtg tctgggtctc ctggacagtc gatcaccatc      60
tcctgcactg gaaccagcag tgatgttggg agttataacc ttgtctcctg gtaccaacag     120
cacccaggca agcccccaa actcatgatt tatgaggtca gtaagcggcc ctcagggatt      180
tctaatcgct tctctggctc caagtctggc aacacggcct ccctgacaat ctctgggctc     240
caggctgagg acgaggctga ttattactgc tgctcatatg caggtagtag cactgtawta     300
ttcggcggag ggaccaagct gaccgtccta g                                    331
```

<210> SEQ ID NO 30
<211> LENGTH: 331
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

```
cagtctgccc tgactcagcc tgcctccgtg tctgggtctc ctggacagtc gatcaccatc      60
tcctgcactg gaaccagcwr tgatgttggg agttataacc ttgtctcctg gtaccaacag     120
cacccaggca agcccccaa actcatgatt tatgaggtca rtaagcggcc ctcagggatt      180
tctaatcgct tctctggctc caagtctggc aacacggcct ccctgacaat ctctgggctc     240
caggctgagg acgaggctga ttattactgy tgctcatatg caggtagtag cactgtawta     300
ttcggcggag ggaccaagct gaccgtccta g                                    331
```

<210> SEQ ID NO 31
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
cagtctgccc tgactcagcc tgcctccgtg tctgggtctc ctggacagtc gatcaccatc      60
tcctgcactg gaaccagcwr tgatgttggg agttataacc ttgtctcctg gtaccaacag     120
cacccaggca aagcccccaa actcatgatt tatgaggtca rtaagtggcc ctcagggggtt    180 tctaatcgct ctctctggctc caagtctggc aacacggcct ccctgacaat ctctgggctc    240
caggctgagg acgaggctva ttattactgt tgctcatatg caggtagtag cactgtaata    300
ttcggcggag ggaccaagct gaccgtccta g                                    331

<210> SEQ ID NO 32
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
cagtctgccc tgactcagcc tgcctccgtg tctgggtctc ctggccagtc gatcaccatc      60
tcctgcactg gaaccagcta tgatgttggg agttataatc ttgtctcctg gtaccaacag     120
cacccaggca aagcccccaa actcattatt tatgaggtca gtcagtggcc ctcagggggtt    180 tctaagcgct ctctctggctc caagtctggc aacacggcct ccctgacaat ctctgggctc    240
caggctgagg acgaggctca ttattactgt tgctcatatg caggcagtag cactgtaata    300
ttcggcggag ggacctcgct gaccgtccta g                                    331

<210> SEQ ID NO 33
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
cagcctgtgc tgactcagcc tgcctccgtg tctgggtctc ctggacagtc gatcaccatc      60
tcctgcactg gaagcagcag tgatgttggg agttataacc ttgtgtcctg gtaccagcag     120
cacccaggca aagcccccaa actgatgatt tatgaggtca ataagtgggc ctcagggggtt    180 tctgatcgct tcgctggctc caagtctggc aacacggcct ccctgacaat ctctagactc    240
caggctgagg acgaggctaa ttacttttgt tcctcatcta caaatagtgc cactgtcata    300
ttcggcggag ggaccaagct gaccgtccta g                                    331

<210> SEQ ID NO 34
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

```
cagtctgccc tgactcagcc tgcctccgtg tctgggtctc ctggacagtc gatcaccatc    60
tcctgcactg gaaccagtta tgatgttggg agttataacc ttgtctcctg gtaccaacag   120
cacccaggca agccccccaa atacatgatt tatgaggtca ataagcggcc ctcagggggtt   180 tctaatcgct tctctggctc caagtctggc aacacggcct ccctgacaat ctctgggctc   240
caggctgagg acgaggctga ttattactgy tgctcatatg caggtagtag cactgtadtw   300
ttcggcggag ggaccaagct gaccgtccta g                                  331
```

<210> SEQ ID NO 35
<211> LENGTH: 331
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 35

```
cagtctgysc tgactcagcc tgcctccgtg tctgggtctc ctggacagtc gatcaccatc    60
tcctgcactg gaaccagtta tgatgttggg agttatgacc ttgtctcctg gtaccaacag   120
cacccaggca agccccccaa atacatgatt tatgaagtca ataagcggcc ctcaggagtt   180
tctaatcgct tctctggctc caaatctggc aacacggcct ccctgacaat ctctgggctc   240
caggctgagg acgaggctga ctattattgc tgctcatttg gaggtagtgc cactgtrgtc   300
tgcggcggag ggaccaaggt gaccgtccta g                                  331
```

<210> SEQ ID NO 36
<211> LENGTH: 331
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 36

```
accagtctgc tgactcagcc tgcctccgtg tctgggtctc ctggacagtc gatcaccatc    60
tcctgcactg gaaccaagta tgatgttggg agtcatgacc ttgtctcctg gtaccaacag   120
tacccaggca agtcccccaa atacatgatt tatgaagtca ataaacggcc ctcaggagtt   180
tctaatcgct tctctggctc caaatctggc aacacggcct ccctgacaat ctctgggctc   240
cgggctgagg acgaggctga ctattattgc tgttcatttg gagggagtgc caccgtggtc   300
tgcggcggcg ggaccaaggt gaccgtccta g                                  331
```

<210> SEQ ID NO 37
<211> LENGTH: 331
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 37

```
cagtctgysc tgactcagcc tgcctccgtg tctgggtctc ctggacagtc gatcaccatc    60
tcctgcactg gaaccagtta tgatgttggg aagtttgacc ttgtctcctg gtaccaacag   120
cacccaggca agccccccaa atacatgatt tatgaagtca ataagtggcc ctcaggagtt   180
tctcatcgct tctctggctc caaatctggc aacacggcct ccctgacaat ctctgggctc   240
caggctgagg acgaggctga ctattattgc tgctcattcg gaggtagtgc cactgtrgtc   300
```
tgcggcggag ggaccaaggt gaccgtccta g         331

<210> SEQ ID NO 38
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
ctgcctgtgc tgactcagcc tgcctccgtg tctgggtctc ctgggcagtc gatcaccatc         60
tcctgcactg ggaccattta tgatgttggg aagtttgacc ttgtctcctg gtaccagcac        120
cacccaggca agccccccaa atatttgatt tatgaagtca aaaagtggcc ctcaggagtt        180
tctcatcgct tctctggctc caaatctggc aacacggcct ccctgacaat ctctgggctc        240
caggttgagg acgaggctga ctattattgc tgctcattcg gaggtagtgc cgctgtggtc        300
tgcggcggag ggaccaaggt gaccgtccta g         331

<210> SEQ ID NO 39
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
cagtctgccc tgactcagcc tgcctccgtg tctgggtctc ctggacagtc gatcaccatc         60
tcctgcactg gaaccagtta tgatgttgcg aagtttgacc ttgtctcctg gttccaacag        120
cacccaggca agccccccaa atacatgatt tatgaagtca ataagtggcc ctcaggagtt        180
tctcatcgct tctctggttc caaatctggc aacacggcct ccctgacaat ctctgggctc        240
caggctgagg acgaggctga ctattattgc tgctcattcg gaggtagtgc cactgtagtc        300
tgcggcggag ggaccaaggt gaccgtccta g         331

<210> SEQ ID NO 40
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
cagtctgccc tgactcagcc tgcctccgtg tctgggtctc ctggacagtc gatcaccatc         60
tcctgcactg gaaccaatta tgatgttggg agttataacc ttgtctcctg gtatcaacag        120
cacccaggca agtcccccaa atacataatt tatgaggtca ataagcggcc ctcaggggtt        180
tctaatcgct tctctggctc caagtctggc aacacggcct ccctgacaat ctctgggctc        240
caggctgagg acgaggccac ttattactgt tgttcatatg caggtagtag cattatattt        300
ttcggcggtg ggaccaagct gaccgtcata g         331

<210> SEQ ID NO 41
<211> LENGTH: 100
<212> TYPE: PRT
<213> ORGANISM: Artificial Sequence
<220> FEATURE:
<223> OTHER INFORMATION: Description of Artificial Sequence: Synthetic

```
      polypeptide
<220> FEATURE:
<221> NAME/KEY: MOD_RES
<222> LOCATION: (100)..(100)
<223> OTHER INFORMATION: Any amino acid

<400> SEQUENCE: 41

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Val Xaa
            100

<210> SEQ ID NO 42
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (54)..(54)
<223> OTHER INFORMATION: Any amino acid
<220> FEATURE:
<221> NAME/KEY: MOD_RES
<222> LOCATION: (90)..(90)
<223> OTHER INFORMATION: Any amino acid
<220> FEATURE:
<221> NAME/KEY: MOD_RES
<222> LOCATION: (100)..(100)
<223> OTHER INFORMATION: Any amino acid

<400> SEQUENCE: 42

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Xaa Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Xaa Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Xaa Cys Ser Tyr Ala Gly Ser
                85                  90                  95

Ser Thr Val Xaa
            100

<210> SEQ ID NO 43
```

```
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (54)..(54)
<223> OTHER INFORMATION: Any amino acid
<220> FEATURE:
<221> NAME/KEY: MOD_RES
<222> LOCATION: (87)..(87)
<223> OTHER INFORMATION: Any amino acid

<400> SEQUENCE: 43

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Xaa Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Xaa Lys Trp Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Xaa Tyr Tyr Cys Cys Ser Tyr Ala Gly Ser
                85                  90                  95

Ser Thr Val Ile
            100

<210> SEQ ID NO 44
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Tyr Asp Val Gly Ser Tyr
            20                  25                  30

Asn Leu Val Ser Trp Tyr Gln Gln His Pro Gly Lys Ala Pro Lys Leu
        35                  40                  45

Ile Ile Tyr Glu Val Ser Gln Trp Pro Ser Gly Val Ser Lys Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala His Tyr Tyr Cys Cys Ser Tyr Ala Gly Ser
                85                  90                  95

Ser Thr Val Ile
            100

<210> SEQ ID NO 45
<211> LENGTH: 100
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 45

Gln Pro Val Leu Thr Gln Pro Ala Ser Val Ser Gly Ser Pro Gly Gln
1               5                   10                  15

Ser Ile Thr Ile Ser Cys Thr Gly Ser Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Asn Lys Trp Ala Ser Gly Val Ser Asp Arg Phe
    50                  55                  60

Ala Gly Ser Lys Ser Gly Asn Thr Ala Ser Leu Thr Ile Ser Arg Leu
65                  70                  75                  80

Gln Ala Glu Asp Glu Ala Asn Tyr Phe Cys Ser Ser Ser Thr Asn Ser
                85                  90                  95

Ala Thr Val Ile
            100

<210> SEQ ID NO 46
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (90)..(90)
<223> OTHER INFORMATION: Any amino acid
<220> FEATURE:
<221> NAME/KEY: MOD_RES
<222> LOCATION: (100)..(100)
<223> OTHER INFORMATION: Any amino acid

<400> SEQUENCE: 46

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Tyr Asp Val Gly Ser Tyr
            20                  25                  30

Asn Leu Val Ser Trp Tyr Gln Gln His Pro Gly Lys Ala Pro Lys Tyr
        35                  40                  45

Met Ile Tyr Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Xaa Cys Ser Tyr Ala Gly Ser
                85                  90                  95

Ser Thr Val Xaa
            100

<210> SEQ ID NO 47
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid

```
<220> FEATURE:
<221> NAME/KEY: MOD_RES
<222> LOCATION: (99)..(99)
<223> OTHER INFORMATION: Any amino acid

<400> SEQUENCE: 47

Gln Ser Xaa Leu Thr Gln Pro Ala Ser Val Ser Gly Ser Pro Gly Gln
1               5                   10                  15

Ser Ile Thr Ile Ser Cys Thr Gly Thr Ser Tyr Asp Val Gly Ser Tyr
            20                  25                  30

Asp Leu Val Ser Trp Tyr Gln Gln His Pro Gly Lys Ala Pro Lys Tyr
        35                  40                  45

Met Ile Tyr Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Phe Gly Gly Ser
                85                  90                  95

Ala Thr Xaa Val
            100

<210> SEQ ID NO 48
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Thr Ser Leu Leu Thr Gln Pro Ala Ser Val Ser Gly Ser Pro Gly Gln
1               5                   10                  15

Ser Ile Thr Ile Ser Cys Thr Gly Thr Lys Tyr Asp Val Gly Ser His
            20                  25                  30

Asp Leu Val Ser Trp Tyr Gln Gln Tyr Pro Gly Lys Val Pro Lys Tyr
        35                  40                  45

Met Ile Tyr Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Arg Ala Glu Asp Glu Ala Asp Tyr Tyr Cys Cys Ser Phe Gly Gly Ser
                85                  90                  95

Ala Thr Val Val
            100

<210> SEQ ID NO 49
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (99)..(99)
<223> OTHER INFORMATION: Any amino acid

<400> SEQUENCE: 49
```

```
Gln Ser Xaa Leu Thr Gln Pro Ala Ser Val Ser Gly Ser Pro Gly Gln
1               5                   10                  15

Ser Ile Thr Ile Ser Cys Thr Gly Thr Ser Tyr Asp Val Gly Lys Phe
                20                  25                  30

Asp Leu Val Ser Trp Tyr Gln Gln His Pro Gly Lys Ala Pro Lys Tyr
            35                  40                  45

Met Ile Tyr Glu Val Asn Lys Trp Pro Ser Gly Val Ser His Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Phe Gly Gly Ser
                85                  90                  95

Ala Thr Xaa Val
            100
```

```
<210> SEQ ID NO 50
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50
```

```
Leu Pro Val Leu Thr Gln Pro Ala Ser Val Ser Gly Ser Pro Gly Gln
1               5                   10                  15

Ser Ile Thr Ile Ser Cys Thr Gly Thr Ile Tyr Asp Val Gly Lys Phe
                20                  25                  30

Asp Leu Val Ser Trp Tyr Gln His Pro Gly Lys Ala Pro Lys Tyr
            35                  40                  45

Leu Ile Tyr Glu Val Lys Lys Trp Pro Ser Gly Val Ser His Arg Phe
        50                  55                  60

Ser Gly Ser Lys Ser Gly Asn Thr Ala Ser Leu Thr Ile Ser Gly Leu
65                  70                  75                  80

Gln Val Glu Asp Glu Ala Asp Tyr Tyr Cys Cys Ser Phe Gly Gly Ser
                85                  90                  95

Ala Ala Val Val
            100
```

```
<210> SEQ ID NO 51
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51
```

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Tyr Asp Val Ala Lys Phe
                20                  25                  30

Asp Leu Val Ser Trp Phe Gln Gln His Pro Gly Lys Ala Pro Lys Tyr
            35                  40                  45

Met Ile Tyr Glu Val Asn Lys Trp Pro Ser Gly Val Ser His Arg Phe
        50                  55                  60

Ser Gly Ser Lys Ser Gly Asn Thr Ala Ser Leu Thr Ile Ser Gly Leu
65                  70                  75                  80
```

Gln Ala Glu Asp Glu Ala Asp Tyr Tyr Cys Cys Ser Phe Gly Gly Ser
            85                  90                  95

Ala Thr Val Val
        100

<210> SEQ ID NO 52
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Ser Ala Leu Thr Gln Pro Ala Ser Val Ser Gly Ser Pro Gly Gln
1               5                   10                  15

Ser Ile Thr Ile Ser Cys Thr Gly Thr Asn Tyr Asp Val Gly Ser Tyr
            20                  25                  30

Asn Leu Val Ser Trp Tyr Gln Gln His Pro Gly Lys Val Pro Lys Tyr
        35                  40                  45

Ile Ile Tyr Glu Val Asn Lys Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Thr Tyr Tyr Cys Cys Ser Tyr Ala Gly Ser
            85                  90                  95

Ser Ile Ile Phe
        100

<210> SEQ ID NO 53
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
gaggttcagc tggtggagtc tgggggaggc ttggtgaagc cggggggggtc tcttagactc      60 cccggtgcag cctctggttt cactttcacc aacacgtgga tgagttgggt ccgtcaggcg     120
ccagggaagg gactggagtg ggtcggtcgg attagccgga acaaagatgg cgcgaaaaca     180
gagtacgccg cacccgtgag aggcagattc accatctcaa gagatgactc cagagacaca     240
ttgtatctgc agatgaccag cctgaaaata gaggattcag gccggtattt ttgcaccgca     300
gatcttgggg agcccgtggt gtcacgatcc atttttgagt gggggtctta ttattattat     360
atggacctct ggggcaaggg gaccacggtc accgtctctt ca                        402

<210> SEQ ID NO 54
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
gacatccagt tgacccagtc tccatctccc ctgtctgcgt ctgtgggaga cacagtcact      60
atcacttgtc gggccagcca agagattagc gactatttga actggtacca acagaagccg     120
gggagagccc ccaaaatact catttacgct gcgtccaagt tggggagtgg cgtcccatca     180

```
aggttcagtg gcagtggata tggcagagat ttcactctca ccatcaccgg tctgcagcct    240
gaagattttg caacctatta ttgtcaggag gcttacagtt ctactcccac gttaactttt    300
ggccagggga ccaggctgga tctcaaac                                       328
```

<210> SEQ ID NO 55
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

```
caggtgcagc tggtacagtc tgggggaggt ctggtgaagc cggggggggtc cctcacactc    60 tcctgttcag cctctggatt ctttttcgat aattcatgga tgggtggggt ccgtcaggcg    120
ccagggaagg gactggagtg ggttggccgc attagaaggc tcaaagacgg tgcgacagga    180
gaatatggtg cagccgtgaa ggacagattc accatttcaa gagatgacag tagaaatatg    240
ctgtacctgc acatgaggac cctgaaaacc gaggactcag gcacttatta ttgtaccatg    300
gatgagggga ccccagtaac acgcttctta gaatggggct acttctatta ttatatggcc    360
gtttggggca gagggaccac ggtcatcgtc tcttca                              396
```

<210> SEQ ID NO 56
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

```
gacatcgtga tgacccagtc tccgtcctcc gtgtctgcat ctgtgggaga cagagtcacc    60
atcacttgcc gggcaagtca gaatattaga gactatttaa attggtatca acataaaccc    120
gggggatccc ctagactcct aatttatgct gcgtcaactt tgcaaactgg ggtcccgtcc    180
agattcagcg gcagtggatc tgggaacctt ttcactctca ccattaccaa tctgcaacct    240
gaagattttg caacttatta ttgtcaagag aattataata ctatcccctc gctcagcttt    300
ggtcagggga ccaaggtgga catcaggc                                       328
```

<210> SEQ ID NO 57
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
gaggttcagc tggtggagtc tgggggaggc ttggtgaagc cggggggggtc tcttagactc    60 tcctgtgtag cctctggctt cactttcagc aacacgtgga tgagttgggt ccgtcaggcg    120
ccagggaagg gactggagtg ggtcggtcgg attagccgga acaaagatgg cgcgaaaaca    180
gagtacgccg cacccgtgag aggcagattc accatctcaa gagatgactc cagagacaca    240
ttgtatctgc agatgagcag cctgaaaata gaggattcag ccggtatttt tgcaccgca    300 gatcttgggg aggccgttgt gtcacgattt tttgagtggg ggtcctatta ttactacatg    360
gacttctggg gcaagggggac cacggtcacc gtctcttca                          399
```

<210> SEQ ID NO 58
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
gacattcaga tgacccaatc tccatctccc ctgtctgcgt ctgtgggaga cacagtcact      60
atcacttgcc gggccagcca gaagattagc gactatttga actggtacca acagaggccg     120
gggagagccc ccaagatcct catttacgct gcgtccaagt tggcaagcga cgtcccatca     180
agatttagtg gcagtggata tgcagagat ttcactctca ccataaccgg tctgcagcct      240
gaagattttg caacctatta ttgtcaggag gcttacagtt ctacccccac gttaactttt     300
ggccagggga ccaggctgga tctcaaac                                        328

<210> SEQ ID NO 59
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
gaggtgcagc tggtggagtc tgggggcggc ttgataaagc cgggacagtc actcacacta      60
ttctgtgtgg gctttggatt caacttcgct aacgactgga tgggctgggt ccgccaggct     120
ccagggaagg gactgaatg ggttgggcgt ataaggagac tgaaagatgg tgcgaaagct      180
gaatatggat cttccgtgaa gggtagattc accatctcaa gggatgattc caaaaacacc     240
ctatacttgc acatgagcag cctcaaggtc gaagacacag ccgtctacta ttgcacccga     300
gacgaggggg ccccagttac ccggtttctg gagtggggct cctattacta ctacatggcc     360
gtctggggca aagggaccac ggtcaccgtc tcttca                               396

<210> SEQ ID NO 60
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
gacatccagt tgacccagtc tccagcctct ctgtctgcat ctgtaggaga cacagtgact      60
atcacttgcc gggcaagtca gagtataaaa gattacataa attggtatca acacaaatcc     120
gggagcgccc ctagactcct gatttatgct gcgtcaacct acaaagtgg aatctcgtca      180 aggttcactg gcagtgggtc tgggacacag ttcactctca ccattaacag tctgcaacct     240
gaagattttg cgacttatta ttgtcaagag gcttataaca ccaaccccac actctccttt     300
ggtcagggga ccagggtgga caagaagc                                        328

<210> SEQ ID NO 61
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 61

```
gaggttcagc tggtggagtc tgggggcggc ttggtgaagc cgggacagtc actcacactt      60
tcctgtgtgg gctttggatt caatttcgct aacgactgga tgggctgggt ccgccaggct     120
ccagggaagg gactggaatg ggttggtcga ataaggagac taaaagacgg tgcgacaaca     180
gaatattctt catccgtgaa ggggagattc agtgtctcaa gagatgattc aaggaacaca     240
gtatacttac acatgagtag cctcaaagtc caggacattg gcgtctatta ttgtactcga     300
gacgaggggg ccccggttac tcgatttctg gagtggggct cctattacta ctatatggcc     360
gtctggggca gagggaccac ggtcaccgtc tcttca                               396
```

<210> SEQ ID NO 62
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

```
gacatccaga tgacccagtc tccaacctct ctgtctgcat ctgtaggaga cacagttgct      60
atcacttgcc gggcaagtca gagtgttaaa gattatgtga attggtatca acacaaatcc     120
gggagcgccc ctcgactcct gatttatgct gcctcagtct tacatactgg agtctcgtca     180
aggttcactg gcagtgggtc tgggacacag ttcactctca ccattagcag tctacaacct     240
gaagattttg ctacttatta ttgtcaagag gcttataaca cctatcccac actctccttt     300
ggtcagggga ccagggtgga caggaaac                                       328
```

<210> SEQ ID NO 63
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
gaggttcagc tggtggagtc tgggggaggc ttggtgaagc cggggggggtc tcttagactc      60
tcctgtgtag cctctggctt cactttcagc aacacgtgga tgagttgggt ccgtcaggcg     120
ccagggaagg gactggagtg ggtcggtcgg attagccgga acaaagatgg cgcgaaaaca     180
gactacgccg cacccgtgag aggcagattc accatctcca gagatgactc cagagacaca     240
ttgtatctgc agatgagcag cctgaaaata gaggattcag gccggtattt ttgcaccgca     300
gatcttgggg aggccgtggt gtcacgattt tttgagtggg ggtcctatta ttactacatg     360
gacttctggg gcaagggac cacggtcacc gtctcttca                             399
```

<210> SEQ ID NO 64
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64

```
gatattgtga tgacccagtc tccacctccc ctgtctgcgt ctgtgggaga cacagtcact      60
```

```
atcacttgcc gggccagcca aagattagc gactatttga actggtacca acagaggccg    120
gggagagccc ccaaaatact catttacgct gcgtccaagt tgggaagcga cgtcccatca    180
aggttcagtg gcagtggata tggcagagat ttcactctca ccatcaccgg tctgcagcct    240
gaagattttg caacctatta ttgtcaggag gcttacagtt ctactcccac gttaagtttt    300
ggccagggga ccaggctgga tctcaaac                                      328
```

<210> SEQ ID NO 65
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

```
gaaaggcagg tggtggaata tgggggaggc ttggtgaagc cggggggggtc tcttagactc    60 tcttgtttac cgtttgcctt tgggttcagg gccccctgga ggagttctgt ccgtcacgcg    120
cctgggggcg gagcggagtg ggtcggtcgg attagccgga acaaagatgg cgcgaaaaca    180
gagtacgccg cacccgtgag aggcagattc accatctcaa gagatgactc cagagacaca    240
ttgtatctgc agatgaccag cctgaaaata gaggattcag gccggtattt ttgcaccgca    300
gatcttgggg agcccgtggt gtcacgattt tttgagtggg ggtcttatta ttattatatg    360
gacctctggg gcaaggggac cacggtcacc gtctcttca                          399
```

<210> SEQ ID NO 66
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

```
tcttctgagc tgactcagga ccccactgtg tctgtggcct tgggccagac agtcaagatc    60
agatgccaag agccagcct cagagactgt tatgcgacct ggtaccggca gaagccagga    120
caggccccaa cacttctcat ttatgatata aataagaggc cctcaggtat cccagaccga    180
ttctctgcct cctactcagg gagcacttct tccttgacca ttattgggc tcagccggaa    240 gatgaggctg actattttg tgcttcgcgg gacaggagtg gtgaccgtct ggcgtcttc    300 ggcggtggga ccaaactgac cgtcctg                                       327
```

<210> SEQ ID NO 67
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

```
cagctgcagg agtcgggtcc cagactggtg aggccttcgg agaccctgtc cctcacctgc    60
actgtatctg gctctggtgt ctccgtcagt cgtgggagtt attattgggg ctggatacgc    120
cagtccccag aaaagggact cgaatggatt ggaagtgtct attccactac tagtggaaaa    180
acctactaca acccgtccct caagagtcga gtcaccttttt cgaaggacac gtcccagaac    240
gccttctccc tgactctgac gtctattacc gccgcggaca cggccgtcta ttactgtgca    300
```
agacaatttg gcttcatggg gggcttttg gagtggtatc cgcactattt tgacttctgg    360
ggcccgggaa tccaggtcgt cgtgtcttct                                    390

<210> SEQ ID NO 68
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
gacattgtga tgacccagtc tccatcctac ctgtctacat ctgtcggtga cagcatcacc    60
atcacttgcc gggcaagtca gagtattaaa acatatgtaa attggtatca acaaagacca   120
gggagagccc ctaaactcct catctattct tcatccactt tgcaacctgg ggtcccgtca   180
agattcagcg ccagtggatc tgggacagat ttcgttctct ccatcaccaa tttgcagtct   240
gaagattttg caacttacta ctgtcaacag acctactaca cccctctac ttttggccag   300 gggaccacac tggacatcaa g                                             321

<210> SEQ ID NO 69
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
caggtgcagc tggtacagtc tggggctgag gtgaagaagc ctgggtcctc ggtcaaggtc    60
tcctgcaagg cctctggagg ctccttctac acctatacta tcaactgggt gcgacaggcc   120
cctggacaag gcttgagtg gatgggcagg gtcaccacta tgtttggtgt aacactttac   180
gcacagaaat tccagggcag agtcacactt accgcggaca atccacgag cacagcctac   240 atggaactga gcagtctaag atctgaggac acggccgtct attattgtgc gacagatggg   300
cctgacaatt tttggagtgg cttgtctcat gctttcgatc tctggggcca ggggacaatg   360
gtcaccgtct cttca                                                    375

<210> SEQ ID NO 70
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
cagtctgccc tgactcagcc tgcctccgtg gctgggtctc ctggacagtc gatcaccatc    60
tcctgcactg gaaccagcag tgacattggt gattctaagt atgtctcctg gtaccaacag   120
ttcccaggca aagcccccaa agtcatgatt tatgaggtca gttatcggcc ctcaggagtc   180
tctagccgct tctctggctc caagtctggc aacacggcct ccctgaccat ctctggactc   240
cagactgagg acgaggctga ttattattgc atggcatata caggcacctt cactgctatt   300
ttcggcggag ggaccaagct gaccgtcctg                                    330

<210> SEQ ID NO 71
<211> LENGTH: 372
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 71

```
caggtgcagc tggtgcagtc tggggctgag gtgaggaagg ctgggtcgtc ggtgaaggtc    60
tcctgcaagg cttctggagg caccttcacc agctatggct tcagctggat acggcaggcc   120
cctggccaag gcttgagtg gatgggaaac gtcatccctg tctttggttc aacaaactac    180
gcacagaaat ttcagggcag agtcagtatt accgcggacg aagccacggg cacagtccac   240
atggacctca ccagcctgac atctgacgac acggccgttt attactgtgt gaggtcgagt   300
agagaactgc aacgtcaat ggaacggtgg ttcgacccct ggggccaggg aacccaggtc    360
attgtctcct cg                                                       372
```

<210> SEQ ID NO 72
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72

```
gacatccaga tgacccagtc tccatcctcc ctgtctgcat ctgtgggaga cagcgtcacc    60
attacttgcc gggcaagtca gagcattaac acctatttaa attggtatca gcagaaacca   120
gggaaggccc ctaaactcct gatctattct gcatccaatt tacacaatgg ggtcccatcg   180
aggttcagtg gcagtggatc tgggacatct ttcactctca ccatcaacaa tctacaacct   240
gaagattttg caacttacta ctgtcaacag agttacagtg ccccttacac ttttggccag   300
gggaccaagt cagacaccaa a                                             321
```

<210> SEQ ID NO 73
<211> LENGTH: 134
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 73

```
Glu Val Gln Leu Val Glu Ser Gly Gly Gly Leu Val Lys Pro Gly Gly
1               5                   10                  15

Ser Leu Arg Leu Pro Gly Ala Ala Ser Gly Phe Thr Phe Thr Asn Thr
            20                  25                  30

Trp Met Ser Trp Val Arg Gln Ala Pro Gly Lys Gly Leu Glu Trp Val
        35                  40                  45

Gly Arg Ile Ser Arg Asn Lys Asp Gly Ala Lys Thr Glu Tyr Ala Ala
    50                  55                  60

Pro Val Arg Gly Arg Phe Thr Ile Ser Arg Asp Asp Ser Arg Asp Thr
65                  70                  75                  80

Leu Tyr Leu Gln Met Thr Ser Leu Lys Ile Glu Asp Ser Gly Arg Tyr
                85                  90                  95

Phe Cys Thr Ala Asp Leu Gly Glu Pro Val Val Ser Arg Ser Ile Phe
            100                 105                 110

Glu Trp Gly Ser Tyr Tyr Tyr Met Asp Leu Trp Gly Lys Gly Thr
        115                 120                 125
```

Thr Val Thr Val Ser Ser
    130

<210> SEQ ID NO 74
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Asp Ile Gln Leu Thr Gln Ser Pro Ser Leu Ser Ala Ser Val Gly
1               5                   10                  15

Asp Thr Val Thr Ile Thr Cys Arg Ala Ser Gln Lys Ile Ser Asp Tyr
            20                  25                  30

Leu Asn Trp Tyr Gln Gln Lys Pro Gly Arg Ala Pro Lys Ile Leu Ile
        35                  40                  45

Tyr Ala Ala Ser Lys Leu Gly Ser Gly Val Pro Ser Arg Phe Ser Gly
    50                  55                  60

Ser Gly Tyr Gly Arg Asp Phe Thr Leu Thr Ile Thr Gly Leu Gln Pro
65                  70                  75                  80

Glu Asp Phe Ala Thr Tyr Tyr Cys Gln Glu Ala Tyr Ser Ser Thr Pro
                85                  90                  95

Thr Leu Thr Phe Gly Gln Gly Thr Arg Leu Asp Leu Lys
            100                 105

<210> SEQ ID NO 75
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
    130

<210> SEQ ID NO 76
<211> LENGTH: 109
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 76

Asp Ile Val Met Thr Gln Ser Pro Ser Ser Val Ser Ala Ser Val Gly
1               5                   10                  15

Asp Arg Val Thr Ile Thr Cys Arg Ala Ser Gln Asn Ile Arg Asp Tyr
            20                  25                  30

Leu Asn Trp Tyr Gln His Lys Pro Gly Gly Ser Pro Arg Leu Leu Ile
        35                  40                  45

Tyr Ala Ala Ser Thr Leu Gln Thr Gly Val Pro Ser Arg Phe Ser Gly
50                  55                  60

Ser Gly Ser Gly Asn Leu Phe Thr Leu Thr Ile Thr Asn Leu Gln Pro
65                  70                  75                  80

Glu Asp Phe Ala Thr Tyr Tyr Cys Gln Glu Asn Tyr Asn Thr Ile Pro
                85                  90                  95

Ser Leu Ser Phe Gly Gln Gly Thr Lys Val Asp Ile Arg
            100                 105

<210> SEQ ID NO 77
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Gln Leu Val Glu Ser Gly Gly Gly Leu Val Lys Pro Gly Gly
1               5                   10                  15

Ser Leu Arg Leu Ser Cys Val Ala Ser Gly Phe Thr Phe Ser Asn Thr
            20                  25                  30

Trp Met Ser Trp Val Arg Gln Ala Pro Gly Lys Gly Leu Glu Trp Val
        35                  40                  45

Gly Arg Ile Ser Arg Asn Lys Asp Gly Ala Lys Thr Glu Tyr Ala Ala
50                  55                  60

Pro Val Arg Gly Arg Phe Thr Ile Ser Arg Asp Asp Ser Arg Asp Thr
65                  70                  75                  80

Leu Tyr Leu Gln Met Ser Ser Leu Lys Ile Glu Asp Ser Gly Arg Tyr
                85                  90                  95

Phe Cys Thr Ala Asp Leu Gly Glu Ala Val Val Ser Arg Phe Phe Glu
            100                 105                 110

Trp Gly Ser Tyr Tyr Tyr Tyr Met Asp Phe Trp Gly Lys Gly Thr Thr
        115                 120                 125

Val Thr Val Ser Ser
    130

<210> SEQ ID NO 78
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Val Lys Asp Ile Gln Met Thr Gln Ser Pro Ser Pro Leu Ser Ala Ser
1               5                   10                  15

Val Gly Asp Thr Val Thr Ile Thr Cys Arg Ala Ser Gln Lys Ile Ser

```
                        20                  25                  30

Asp Tyr Leu Asn Trp Tyr Gln Gln Arg Pro Gly Arg Ala Pro Lys Ile
                35                  40                  45

Leu Ile Tyr Ala Ala Ser Lys Leu Ala Ser Asp Val Pro Ser Arg Phe
         50                  55                  60

Ser Gly Ser Gly Tyr Gly Arg Asp Phe Thr Leu Thr Ile Thr Gly Leu
 65                  70                  75                  80

Gln Pro Glu Asp Phe Ala Thr Tyr Tyr Cys Gln Glu Ala Tyr Ser Ser
                 85                  90                  95

Thr Pro Thr Leu Thr Phe Gly Gln Gly Thr Arg Leu Asp Leu Lys
                100                 105                 110

<210> SEQ ID NO 79
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Val Gln Leu Val Glu Ser Gly Gly Gly Leu Ile Lys Pro Gly Gln
 1               5                  10                  15

Ser Leu Thr Leu Phe Cys Val Gly Phe Gly Phe Asn Phe Ala Asn Asp
                20                  25                  30

Trp Met Gly Trp Val Arg Gln Ala Pro Gly Lys Gly Leu Glu Trp Val
            35                  40                  45

Gly Arg Ile Arg Arg Leu Lys Asp Gly Ala Lys Ala Glu Tyr Gly Ser
         50                  55                  60

Ser Val Lys Gly Arg Phe Thr Ile Ser Arg Asp Asp Ser Lys Asn Thr
 65                  70                  75                  80

Leu Tyr Leu His Met Ser Ser Leu Lys Val Glu Asp Thr Ala Val Tyr
                 85                  90                  95

Tyr Cys Thr Arg Asp Glu Gly Ala Pro Val Thr Arg Phe Leu Glu Trp
                100                 105                 110

Gly Ser Tyr Tyr Tyr Met Ala Val Trp Gly Lys Gly Thr Thr Val
            115                 120                 125

Thr Val Ser Ser
        130

<210> SEQ ID NO 80
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Asp Ile Gln Leu Thr Gln Ser Pro Ala Ser Leu Ser Ala Ser Val Gly
 1               5                  10                  15

Asp Thr Val Thr Ile Thr Cys Arg Ala Ser Gln Ser Ile Lys Asp Tyr
                20                  25                  30

Ile Asn Trp Tyr Gln His Lys Ser Gly Ser Ala Pro Arg Leu Leu Ile
            35                  40                  45

Tyr Ala Ala Ser Thr Leu Gln Ser Gly Ile Ser Ser Arg Phe Thr Gly
         50                  55                  60

Ser Gly Ser Gly Thr Gln Phe Thr Leu Thr Ile Asn Ser Leu Gln Pro
```

```
                65                  70                  75                  80
Glu Asp Phe Ala Thr Tyr Tyr Cys Gln Glu Ala Tyr Asn Thr Asn Pro
                    85                  90                  95

Thr Leu Ser Phe Gly Gln Gly Thr Arg Val Asp Lys Lys
                100                 105

<210> SEQ ID NO 81
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Glu Val Gln Leu Val Glu Ser Gly Gly Gly Leu Val Lys Pro Gly Gln
1               5                   10                  15

Ser Leu Thr Leu Ser Cys Val Gly Phe Gly Phe Asn Phe Ala Asn Asp
                20                  25                  30

Trp Met Gly Trp Val Arg Gln Ala Pro Gly Lys Gly Leu Glu Trp Val
            35                  40                  45

Gly Arg Ile Arg Arg Leu Lys Asp Gly Ala Thr Thr Glu Tyr Ser Ser
        50                  55                  60

Ser Val Lys Gly Arg Phe Ser Val Ser Arg Asp Asp Ser Arg Asn Thr
65                  70                  75                  80

Val Tyr Leu His Met Ser Ser Leu Lys Val Gln Asp Ile Gly Val Tyr
                85                  90                  95

Tyr Cys Thr Arg Asp Glu Gly Ala Pro Val Thr Arg Phe Leu Glu Trp
                100                 105                 110

Gly Ser Tyr Tyr Tyr Tyr Met Ala Val Trp Gly Arg Gly Thr Thr Val
            115                 120                 125

Thr Val Ser Ser
        130

<210> SEQ ID NO 82
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Asp Ile Gln Met Thr Gln Ser Pro Thr Ser Leu Ser Ala Ser Val Gly
1               5                   10                  15

Asp Thr Val Ala Ile Thr Cys Arg Ala Ser Gln Ser Val Lys Asp Tyr
                20                  25                  30

Val Asn Trp Tyr Gln His Lys Ser Gly Ser Ala Pro Arg Leu Leu Ile
            35                  40                  45

Tyr Ala Ala Ser Val Leu His Thr Gly Val Ser Ser Arg Phe Thr Gly
        50                  55                  60

Ser Gly Ser Gly Thr Gln Phe Thr Leu Thr Ile Ser Ser Leu Gln Pro
65                  70                  75                  80

Glu Asp Phe Ala Thr Tyr Tyr Cys Gln Glu Ala Tyr Asn Thr Tyr Pro
                85                  90                  95

Thr Leu Ser Phe Gly Gln Gly Thr Arg Val Asp Arg Lys
                100                 105
```

```
<210> SEQ ID NO 83
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Glu Val Gln Leu Val Glu Ser Gly Gly Leu Val Lys Pro Gly Gly
1               5                   10                  15

Ser Leu Arg Leu Ser Cys Val Ala Ser Gly Phe Thr Phe Ser Asn Thr
            20                  25                  30

Trp Met Ser Trp Val Arg Gln Ala Pro Gly Lys Gly Leu Glu Trp Val
        35                  40                  45

Gly Arg Ile Ser Arg Asn Lys Asp Gly Ala Lys Thr Asp Tyr Ala Ala
    50                  55                  60

Pro Val Arg Gly Arg Phe Thr Ile Ser Arg Asp Asp Ser Arg Asp Thr
65                  70                  75                  80

Leu Tyr Leu Gln Met Ser Ser Leu Lys Ile Glu Asp Ser Gly Arg Tyr
                85                  90                  95

Phe Cys Thr Ala Asp Leu Gly Glu Ala Val Val Ser Arg Phe Phe Glu
            100                 105                 110

Trp Gly Ser Tyr Tyr Tyr Tyr Met Asp Phe Trp Gly Lys Gly Thr Thr
        115                 120                 125

Val Thr Val Ser Ser
    130

<210> SEQ ID NO 84
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Asp Ile Val Met Thr Gln Ser Pro Pro Leu Ser Ala Ser Val Gly
1               5                   10                  15

Asp Thr Val Thr Ile Thr Cys Arg Ala Ser Gln Lys Ile Ser Asp Tyr
            20                  25                  30

Leu Asn Trp Tyr Gln Gln Arg Pro Gly Arg Ala Pro Lys Ile Leu Ile
        35                  40                  45

Tyr Ala Ala Ser Lys Leu Gly Ser Asp Val Pro Ser Arg Phe Ser Gly
    50                  55                  60

Ser Gly Tyr Gly Arg Asp Phe Thr Leu Thr Ile Thr Gly Leu Gln Pro
65                  70                  75                  80

Glu Asp Phe Ala Thr Tyr Tyr Cys Gln Glu Ala Tyr Ser Ser Thr Pro
                85                  90                  95

Thr Leu Ser Phe Gly Gln Gly Thr Arg Leu Asp Leu Lys
            100                 105

<210> SEQ ID NO 85
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85
```

```
Glu Arg Gln Val Val Glu Tyr Gly Gly Gly Leu Val Lys Pro Gly Gly
1               5                   10                  15

Ser Leu Arg Leu Ser Cys Leu Pro Phe Ala Phe Gly Phe Arg Ala Pro
            20                  25                  30

Trp Arg Ser Val Arg His Ala Pro Gly Gly Gly Ala Glu Trp Val
        35                  40                  45

Gly Arg Ile Ser Arg Asn Lys Asp Gly Ala Lys Thr Glu Tyr Ala Ala
    50                  55                  60

Pro Val Arg Gly Arg Phe Thr Ile Ser Arg Asp Asp Ser Arg Asp Thr
65                  70                  75                  80

Leu Tyr Leu Gln Met Thr Ser Leu Lys Ile Glu Asp Ser Gly Arg Tyr
                85                  90                  95

Phe Cys Thr Ala Asp Leu Gly Glu Pro Val Val Ser Arg Phe Phe Glu
            100                 105                 110

Trp Gly Ser Tyr Tyr Tyr Tyr Met Asp Leu Trp Gly Lys Gly Thr Thr
        115                 120                 125

Val Thr Val Ser Ser
    130
```

<210> SEQ ID NO 86
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 86

```
Ser Ser Glu Leu Thr Gln Asp Pro Thr Val Ser Val Ala Leu Gly Gln
1               5                   10                  15

Thr Val Lys Ile Arg Cys Gln Gly Ala Ser Leu Arg Asp Cys Tyr Ala
            20                  25                  30

Thr Trp Tyr Arg Gln Lys Pro Gly Gln Ala Pro Thr Leu Leu Ile Tyr
        35                  40                  45

Asp Ile Asn Lys Arg Pro Ser Gly Ile Pro Asp Arg Phe Ser Ala Ser
    50                  55                  60

Tyr Ser Gly Ser Thr Ser Ser Leu Thr Ile Ile Gly Ala Gln Pro Glu
65                  70                  75                  80

Asp Glu Ala Asp Tyr Phe Cys Ala Ser Arg Asp Arg Ser Gly Asp Arg
                85                  90                  95

Leu Gly Val Phe Gly Gly Gly Thr Lys Leu Thr Val Leu
            100                 105
```

<210> SEQ ID NO 87
<211> LENGTH: 130
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 87

```
Gln Leu Gln Glu Ser Gly Pro Arg Leu Val Arg Pro Ser Glu Thr Leu
1               5                   10                  15

Ser Leu Thr Cys Thr Val Ser Gly Ser Gly Val Ser Val Ser Arg Gly
            20                  25                  30

Ser Tyr Tyr Trp Gly Trp Ile Arg Gln Ser Pro Glu Lys Gly Leu Glu
        35                  40                  45
```

```
Trp Ile Gly Ser Val Tyr Ser Thr Thr Ser Gly Lys Thr Tyr Tyr Asn
    50                  55                  60

Pro Ser Leu Lys Ser Arg Val Thr Phe Ser Lys Asp Thr Ser Gln Asn
65                  70                  75                  80

Ala Phe Ser Leu Thr Leu Thr Ser Ile Thr Ala Ala Asp Thr Ala Val
                85                  90                  95

Tyr Tyr Cys Ala Arg Gln Phe Gly Phe Met Gly Gly Phe Leu Glu Trp
            100                 105                 110

Tyr Pro His Tyr Phe Asp Phe Trp Gly Pro Gly Ile Gln Val Val Val
        115                 120                 125

Ser Ser
    130

<210> SEQ ID NO 88
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ser Phe Tyr Thr Tyr
                20                  25                  30

Thr Ile Asn Trp Val Arg Gln Ala Pro Gly Gln Gly Leu Glu Trp Met
            35                  40                  45

Gly Arg Val Thr Thr Met Phe Gly Val Thr Leu Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Gly Pro Asp Asn Phe Trp Ser Gly Leu Ser His Ala Phe
            100                 105                 110

Asp Leu Trp Gly Gln Gly Thr Met Val Thr Val Ser Ser
        115                 120                 125

<210> SEQ ID NO 89
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Ile Val Met Thr Gln Ser Pro Ser Tyr Leu Ser Thr Ser Val Gly
1               5                   10                  15

Asp Ser Ile Thr Ile Thr Cys Arg Ala Ser Gln Ser Ile Lys Thr Tyr
                20                  25                  30

Val Asn Trp Tyr Gln Gln Arg Pro Gly Arg Ala Pro Lys Leu Leu Ile
            35                  40                  45

Tyr Ser Ser Ser Thr Leu Gln Pro Gly Val Pro Ser Arg Phe Ser Ala
    50                  55                  60

Ser Gly Ser Gly Thr Asp Phe Val Leu Ser Ile Thr Asn Leu Gln Ser
65                  70                  75                  80
```

Glu Asp Phe Ala Thr Tyr Tyr Cys Gln Gln Thr Tyr Thr Pro Ser
                85                  90                  95

Thr Phe Gly Gln Gly Thr Leu Asp Ile Lys
            100                 105

<210> SEQ ID NO 90
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ser Phe Tyr Thr Tyr
                20                  25                  30

Thr Ile Asn Trp Val Arg Gln Ala Pro Gly Gln Gly Leu Glu Trp Met
            35                  40                  45

Gly Arg Val Thr Thr Met Phe Gly Val Thr Leu Tyr Ala Gln Lys Phe
        50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Gly Pro Asp Asn Phe Trp Ser Gly Leu Ser His Ala Phe
            100                 105                 110

Asp Leu Trp Gly Gln Gly Thr Met Val Thr Val Ser Ser
        115                 120                 125

<210> SEQ ID NO 91
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gln Ser Ala Leu Thr Gln Pro Ala Ser Val Ala Gly Ser Pro Gly Gln
1               5                   10                  15

Ser Ile Thr Ile Ser Cys Thr Gly Thr Ser Ser Asp Ile Gly Asp Ser
                20                  25                  30

Lys Tyr Val Ser Trp Tyr Gln Gln Phe Pro Gly Lys Ala Pro Lys Val
            35                  40                  45

Met Ile Tyr Glu Val Ser Tyr Arg Pro Ser Gly Val Ser Ser Arg Phe
        50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Met Ala Tyr Thr Gly Thr
                85                  90                  95

Phe Thr Ala Ile Phe Gly Gly Gly Thr Lys Leu Thr Val Leu
            100                 105                 110

<210> SEQ ID NO 92
<211> LENGTH: 124
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 92

Gln Val Gln Leu Val Gln Ser Gly Ala Glu Val Arg Lys Ala Gly Ser
1               5                   10                  15

Ser Val Lys Val Ser Cys Lys Ala Ser Gly Gly Thr Phe Thr Ser Tyr
            20                  25                  30

Gly Phe Ser Trp Ile Arg Gln Ala Pro Gly Gln Gly Leu Glu Trp Met
        35                  40                  45

Gly Asn Val Ile Pro Val Phe Gly Ser Thr Asn Tyr Ala Gln Lys Phe
    50                  55                  60

Gln Gly Arg Val Ser Ile Thr Ala Asp Glu Ala Thr Gly Thr Val His
65                  70                  75                  80

Met Asp Leu Thr Ser Leu Thr Ser Asp Thr Ala Val Tyr Tyr Cys
                85                  90                  95

Val Arg Ser Ser Arg Glu Leu Pro Thr Ser Met Glu Arg Trp Phe Asp
            100                 105                 110

Pro Trp Gly Gln Gly Thr Gln Val Ile Val Ser Ser
        115                 120

<210> SEQ ID NO 93
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Asp Ile Gln Met Thr Gln Ser Pro Ser Ser Leu Ser Ala Ser Val Gly
1               5                   10                  15

Asp Ser Val Thr Ile Thr Cys Arg Ala Ser Gln Ser Ile Asn Thr Tyr
            20                  25                  30

Leu Asn Trp Tyr Gln Gln Lys Pro Gly Lys Ala Pro Lys Leu Leu Ile
        35                  40                  45

Tyr Ser Ala Ser Asn Leu His Asn Gly Val Pro Ser Arg Phe Ser Gly
    50                  55                  60

Ser Gly Ser Gly Thr Ser Phe Thr Leu Thr Ile Asn Asn Leu Gln Pro
65                  70                  75                  80

Glu Asp Phe Ala Thr Tyr Tyr Cys Gln Gln Ser Tyr Ser Ala Pro Tyr
                85                  90                  95

Thr Phe Gly Gln Gly Thr Lys Ser Asp Thr Lys
            100                 105

<210> SEQ ID NO 94
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30
```

```
Trp Met Gly Trp Val Arg Gln Ala Pro Gly Lys Gly Leu Glu Trp Val
            35                  40                  45

Gly Arg Ile Arg Arg Leu Lys Asp Gly Ala Thr Gly Glu Tyr Gly Ala
 50                  55                  60

Ala Val Lys Asp Arg Phe Thr Ile Ser Arg Asp Asp Ser Arg Asn Met
 65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Glu Trp
            100                 105                 110

Gly Tyr Phe Tyr Tyr Tyr Met Ala Val Trp Gly Arg Gly Thr Thr Val
            115                 120                 125

Ile Val Ser Ser
    130

<210> SEQ ID NO 95
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
caggtgcagc tggtacagtc tgggggaggt ctggtgaagc cggggggggtc cctcacactc      60 tcctgttcag cctctggatt cttttttcgat aattcatgga tggggtgggt ccgtcaggcg     120
ccagggaagg gactggagtg ggttggccgc attagaaggc tcaaagacgg tgcgacagga     180
gaatatggtg cagccgtgaa ggacagattc accatttcaa gagatgacag tagaaatatg     240
ctgtacctgc acatgaggac cctgaaaacc gaggactcag gcacttatta ttgtaccatg     300
gatgagggga cccccagtaac acgcttctta gaatggggct acttctatta ttatatggcc     360
gtttggggca gagggaccac ggtcatcgtc tcttca                                 396

<210> SEQ ID NO 96
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gln Val Gln Leu Val Gln Ser Gly Gly Gly Leu Val Lys Pro Gly Gly
 1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
            35                  40                  45

Gly Arg Ile Arg Arg Leu Lys Asp Gly Ala Thr Gly Glu Tyr Gly Ala
 50                  55                  60

Ala Val Lys Asp Arg Phe Thr Ile Ser Arg Asp Asp Ser Arg Asn Met
 65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Glu Trp
            100                 105                 110

Gly Tyr Phe Tyr Tyr Tyr Met Ala Val Trp Gly Arg Gly Thr Thr Val
```

Ile Val Ser Ser
    130

<210> SEQ ID NO 97
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Trp Gly Thr Pro Val Thr Arg Phe Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
    130

<210> SEQ ID NO 98
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Trp Thr Pro Val Thr Arg Phe Leu Glu Trp
            100                 105                 110

Gly Tyr Phe Tyr Tyr Tyr Met Ala Val Trp Gly Arg Gly Thr Thr Val
        115                 120                 125

Ile Val Ser Ser

<210> SEQ ID NO 99
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 99

```
Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Trp Pro Val Thr Arg Phe Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
    130
```

<210> SEQ ID NO 100
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 100

```
Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Trp Val Thr Arg Phe Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
    130
```

<210> SEQ ID NO 101
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Phe Thr Arg Phe Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
    130

<210> SEQ ID NO 102
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Ile Thr Arg Phe Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
    130

<210> SEQ ID NO 103
<211> LENGTH: 132
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 103

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Trp Arg Phe Leu Glu Trp
            100                 105                 110

Gly Tyr Phe Tyr Tyr Met Ala Val Trp Gly Arg Gly Thr Thr Val
        115                 120                 125

Ile Val Ser Ser
    130

<210> SEQ ID NO 104
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 104

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Ser Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Trp Phe Leu Glu Trp
            100                 105                 110

Gly Tyr Phe Tyr Tyr Met Ala Val Trp Gly Arg Gly Thr Thr Val
        115                 120                 125

Ile Val Ser Ser
    130

<210> SEQ ID NO 105
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 105

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Trp Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
    130

<210> SEQ ID NO 106
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Trp Glu Trp
            100                 105                 110

Gly Tyr Phe Tyr Tyr Tyr Met Ala Val Trp Gly Arg Gly Thr Thr Val
        115                 120                 125

Ile Val Ser Ser
    130

<210> SEQ ID NO 107
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Phe Glu Trp
            100                 105                 110

Gly Tyr Phe Tyr Tyr Tyr Met Ala Val Trp Gly Arg Gly Thr Thr Val
        115                 120                 125

Ile Val Ser Ser
    130

<210> SEQ ID NO 108
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Trp Trp
            100                 105                 110

Gly Tyr Phe Tyr Tyr Tyr Met Ala Val Trp Gly Arg Gly Thr Thr Val
        115                 120                 125

Ile Val Ser Ser
    130

<210> SEQ ID NO 109
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Asp Asn Ser
            20                  25                  30

Trp Met Gly Trp Val Arg Gln Ala Pro Gly Lys Gly Leu Glu Trp Val
            35                  40                  45

Gly Arg Ile Arg Arg Leu Lys Asp Gly Ala Thr Gly Glu Tyr Gly Ala
 50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Glu Trp
            100                 105                 110

Trp Tyr Phe Tyr Tyr Tyr Met Ala Val Trp Gly Arg Gly Thr Thr Val
            115                 120                 125

Ile Val Ser Ser
    130

<210> SEQ ID NO 110
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
            35                  40                  45

Gly Arg Ile Arg Arg Leu Lys Asp Gly Ala Thr Gly Glu Tyr Gly Ala
 50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Glu Trp
            100                 105                 110

Gly Trp Phe Tyr Tyr Tyr Met Ala Val Trp Gly Arg Gly Thr Thr Val
            115                 120                 125

Ile Val Ser Ser
    130

<210> SEQ ID NO 111
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
            35                  40                  45

Gly Arg Ile Arg Arg Leu Lys Asp Gly Ala Thr Gly Glu Tyr Gly Ala
        50                  55                  60

Ala Val Lys Asp Arg Phe Thr Ile Ser Arg Asp Asp Ser Arg Asn Met
 65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Glu Trp
                    100                 105                 110

Gly Tyr Trp Tyr Tyr Tyr Met Ala Val Trp Gly Arg Gly Thr Thr Val
            115                 120                 125

Ile Val Ser Ser
    130

<210> SEQ ID NO 112
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Gln Val Gln Leu Val Gln Ser Gly Gly Gly Leu Val Lys Pro Gly Gly
 1               5                  10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
            35                  40                  45

Gly Arg Ile Arg Arg Leu Lys Asp Gly Ala Thr Gly Glu Tyr Gly Ala
        50                  55                  60

Ala Val Lys Asp Arg Phe Thr Ile Ser Arg Asp Asp Ser Arg Asn Met
 65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Glu Trp
                    100                 105                 110

Gly Tyr Phe Tyr Trp Tyr Met Ala Val Trp Gly Arg Gly Thr Thr Val
            115                 120                 125

Ile Val Ser Ser
    130

<210> SEQ ID NO 113
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113
caggtgcagc tggtgcagtc tggggctcaa atgaagaacc tggggcctc agtgaaggtc      60 tcctgcgcgc cttctggata taccttcacc gactttaca tacattggtt gcgccaggcc    120
cctggccagg ggcttcagtg gatgggatgg atgaaccctc agactggtcg cacaaacact    180
gcacgaaact ttcaggggag ggtcaccatg accagggaca cgtccatcgg cacagcctac    240

```
atggagttga agcctgac atctgacgac acggccatat attactgtac gacaggggga      300
tggatcagtc tttactatga tagtagttat taccccaact ttgaccactg gggtcaggga    360
accctgctca ccgtctcctc ag                                             382
```

<210> SEQ ID NO 114
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

```
Gln Val Gln Leu Val Gln Ser Gly Ala Gln Met Lys Asn Pro Gly Ala
1               5                   10                  15

Ser Val Lys Val Ser Cys Ala Pro Ser Gly Tyr Thr Phe Thr Asp Phe
            20                  25                  30

Tyr Ile His Trp Leu Arg Gln Ala Pro Gly Gln Gly Leu Gln Trp Met
        35                  40                  45

Gly Trp Met Asn Pro Gln Thr Gly Arg Thr Asn Thr Ala Arg Asn Phe
    50                  55                  60

Gln Gly Arg Val Thr Met Thr Arg Asp Thr Ser Ile Gly Thr Ala Tyr
65                  70                  75                  80

Met Glu Leu Arg Ser Leu Thr Ser Asp Asp Thr Ala Ile Tyr Tyr Cys
                85                  90                  95

Thr Thr Gly Gly Trp Ile Ser Leu Tyr Tyr Asp Ser Ser Tyr Tyr Pro
            100                 105                 110

Asn Phe Asp His Trp Gly Gln Gly Thr Leu Leu Thr Val Ser Ser
        115                 120                 125
```

<210> SEQ ID NO 115
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115

```
cagtctgccc tgactcagcc tgcctccgtg tctgggtctc ctggacagtc gatcaccatc     60
tcctgcactg gaaccaagta tgatgttggg agtcatgacc ttgtctcctg gtaccaacag    120
tacccaggca agtcccccaa atacatgatt tatgaagtca ataaacggcc ctcaggagtt    180
tctaatcgct tctctggctc caaatctggc aacacggcct ccctgacaat ctctgggctc    240
cgggctgagg acgaggctga ctattattgc tgttcatttg gagggagtgc caccgtggtc    300
tgcggcggcg ggaccaaggt gaccgtccta g                                   331
```

<210> SEQ ID NO 116
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

```
Gln Ser Ala Leu Thr Gln Pro Ala Ser Val Ser Gly Ser Pro Gly Gln
1               5                   10                  15

Ser Ile Thr Ile Ser Cys Thr Gly Thr Lys Tyr Asp Val Gly Ser His
```

```
                    20                  25                  30
Asp Leu Val Ser Trp Tyr Gln Gln Tyr Pro Gly Lys Val Pro Lys Tyr
                35                  40                  45

Met Ile Tyr Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Arg Ala Glu Asp Glu Ala Asp Tyr Tyr Cys Cys Ser Phe Gly Gly Ser
                85                  90                  95

Ala Thr Val Val Cys Gly Gly Gly Thr Lys Val Thr Val Leu
                100                 105                 110
```

<210> SEQ ID NO 117
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117

```
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccctc acagtggtgg cacaaactat      180
gcacagaagt ttcagggcag ggtcaccatg accagggaca cgtccatcag cacagcctac     240
atggagctga gcaggctgag atctgacgac acggccgtgt attactgtgc gagagggggg     300
tggatcrgtc tttactatga tagtagtggt tacccctaact ttgactactg gggccaggga   360
accctggtca ccgtctcctc ag                                               382
```

<210> SEQ ID NO 118
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118

```
caggtgcagc tggtgcagtc tggggctgag gtgaagaagc ctggggcctc agtgaaggtc      60
tcctgcaagg cttctggata caccttcacc gactactata tacactgggt gcgacaggcc    120
cctggacaag gcttgagtg gatgggatgg atcaaccctc acastggtcg cacaaactat      180
gcacagaagt ttcagggcag ggtcaccatg accagggaca cgtccatcag cacagcctac     240
atggagctga gcaggctgag atctgacgac acggccgtgt attactgtgc gagagggggg     300
tggatcrgtc tttactatga tagtagtggt tacccctaact ttgactactg gggccaggga   360
accctggtca ccgtctcctc ag                                               382
```

<210> SEQ ID NO 119
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119

```
caggtgcagc tggtgcagtc tggggctgag btgaagaagc ctggggcctc agtgaaggtc      60
```

```
tcctgcaagg cttctggata caccttcacc gactactata tacactgggt gcgacaggcc    120
cctggacaag ggcttgagtg gatggcatgg atcaaccta ccastggtcg cacaadctht    180
gcacggaagt ttcagggcag ggtcaccatg accagggaca cgtccatcag cacdgcctac    240
atggaactga aagvctgag atctgacgac acggccgtct attactgtgc gagagggga    300 tggatcrgtc tttacgttga ttatagtggt taccctaact ttgactcctg gggccaggga    360
accctggtca ccgtctcctc ag                                             382
```

<210> SEQ ID NO 120
<211> LENGTH: 382
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 120

```
gaggttcagc tggtggagtc tgggcctgag ttgaaggagc ctggggcctc agtgaaagtc    60
tcctgcaagg cttctggata caccttcacc gactactaca tacactgggt gcgacaggcc    120
cctggacaag gtcttgagtg gatggcatgg atcaaccta ccactggtcg ctctagcttt    180
gcccgggggt ttcagggcag ggtcaccatg accagggaaa cgtccgtcag cacggcctat    240
atggaactga aagactgag atctgacgac acggccgtct attactgtgc gaaagcggga    300
tacatcgccc tttacgttga ctatagtggt taccctaact ttaattcctg gggccaggga    360
accctggtca ccgtctcctc ag                                             382
```

<210> SEQ ID NO 121
<211> LENGTH: 382
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 121

```
caggtgcagc tggtgcagtc tggggctgaa ctgaagaagc ctggggcctc agtgaaggtc    60
tcctgcaagg cttctggata caccctcagc gactactatg tacactggct gcgacaggcc    120
cctggacagg ggcttgagtg gtggcttgg atcaaccta ccagtggtcg cacaatctct    180
ccacggaagt ttcagggcag ggtcacgatg actacggaca cgtccatgaa tgttgcctac    240
atggaactga gaggcttgag atctgacgac acggccgtct atttctgtgc gagagggga    300 tggatcagtc tctacgttga ttacagttat taccctaact ttgactcgtg gggccaggga    360
accctggtct ccgtctcttc ag                                             382
```

<210> SEQ ID NO 122
<211> LENGTH: 382
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 122

```
caggtgcagc tggtgcagtc tggggctgag rtgaagaagc ctggggcctc agtgaaggtc    60
tcctgcaagg cttctggata caccttcacc gactactata tacactgggt gcgacaggcc    120
cctggacaag ggcttgagtg gatgggatgg atcaaccta acactggtcg cacaaactat    180
```

```
gcacagaagt tcagggcag ggtcaccatg accagggaca cgtccatcag cacagcctac    240
atggagctga gcaggctgac atctgacgac acggccgtgt attactgtgc gacagggggg    300
tggatcrgtc tttactatga tagtagtggt taccctaact ttgactactg gggccaggga    360
accctggtca ccgtctcctc ag                                            382
```

<210> SEQ ID NO 123
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123

```
caggtgcagc tggtgcagtc tggggctgaa rtgaagaacc ctggggcctc agtgaaagtc    60
tcctgcgcgg cttctggata taccttcacc gacttctaca tacactgggt gcgactggcc    120
cctggacaag gcttgagtg gatgggatgg atgaacccta agactggtcg cacaaathat    180
gcacaaaabt ttcagggcag ggtcaccatg accagggaca cgtccatcgg cacagcctac    240
atggagctga ggaggctgac atctgacgac acggccgtct attactgtgt gacaggggggg   300 tggatcagtc httattatga tagtagttat taccctaact ttgaccactg gggtcaggga    360
accctggtca ccgtctcctc ag                                            382
```

<210> SEQ ID NO 124
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124

```
caggtgcagc tggtgcagtc tggggctgaa gtgaagaacc ctggggcctc agtgaaagtc    60
tcctgcgcgc cttctggata taccttcact gacttctaca tacactgggt gcgactggcc    120
cctggacaag gcttgagtg gctggggtgg atgaacccta agactggtcg cacaaatcaa    180
ggacaaaact ttcagggcag ggtcaccatg accagggaca cgtccatcgg cacagcctac    240
atggagttga ggagcctcac atctgacgac acggccgtct attactgtgt gacaggggcc    300
tggatcagtg attattatga tagtagttat tatcctaact ttgaccactg gggtcaggga    360
accctggtca ccgtctcctc ag                                            382
```

<210> SEQ ID NO 125
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125

```
gaggtgcagc tggtgcagtc tggggctgaa atgaagaacc ctggggcctc agtgaaagtc    60
tcctgcgcgg cttctggata tggtttcacc gacttctaca tacactgggt gcgactggcc    120
cctggacacg ggctccagtg gatgggatgg atgaacccta agactggtcg cacaaataat    180
gcacaagatt ttcagggcag ggtcaccctg accagggaca cgtccatcgg cacagcctac    240
atggagctga ggaggctgac atctgacgac acggccgtct attactgtgt gacagggggg    300
```

```
tggatcagtc cttattatga tagtagttat taccctaatt ttgaccactg gggtcaggga      360
accctgatca ccgtctcctc ag                                              382

<210> SEQ ID NO 126
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126
caggtgcagc tggtgcagtc tggggctgag atgaagaagc ctggggcctc agtgagggtc      60
tcctgcaagg cttctggata caccttcacc gactactata tacactgggt gcgacaggcc     120
cctggacaag ggcctgagtg gatgggatgg atcaacccta gcactggtcg cacaaactct     180
ccacagaagt ttcagggcag ggtcaccatg accagggaca cgtccatcag cacagcctac     240
atggacctga acagactgac gtctgacgac acggccatgt attactgtac gaccgggggg     300
tggatcggtc tttactctga tactagtggt taccctaact ttgactactg gggccaggga     360
accctggtca ccgtctcctc ag                                              382

<210> SEQ ID NO 127
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (103)..(103)
<223> OTHER INFORMATION: Any amino acid

<400> SEQUENCE: 127

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Trp Ile Xaa Leu Tyr Tyr Asp Ser Ser Gly Tyr Pro
            100                 105                 110

Asn Phe Asp Tyr Trp Gly Gln Gly Thr Leu Val Thr Val Ser Ser
        115                 120                 125

<210> SEQ ID NO 128
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

<222> LOCATION: (55)..(55)
<223> OTHER INFORMATION: Any amino acid
<220> FEATURE:
<221> NAME/KEY: MOD_RES
<222> LOCATION: (103)..(103)
<223> OTHER INFORMATION: Any amino acid

<400> SEQUENCE: 128

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile Asn Pro Asn Xaa Gly Arg Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Trp Ile Xaa Leu Tyr Tyr Asp Ser Ser Gly Tyr Pro
            100                 105                 110

Asn Phe Asp Tyr Trp Gly Gln Gly Thr Leu Val Thr Val Ser Ser
        115                 120                 125

<210> SEQ ID NO 129
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (55)..(55)
<223> OTHER INFORMATION: Any amino acid
<220> FEATURE:
<221> NAME/KEY: MOD_RES
<222> LOCATION: (59)..(60)
<223> OTHER INFORMATION: Any amino acid
<220> FEATURE:
<221> NAME/KEY: MOD_RES
<222> LOCATION: (78)..(78)
<223> OTHER INFORMATION: Any amino acid
<220> FEATURE:
<221> NAME/KEY: MOD_RES
<222> LOCATION: (85)..(85)
<223> OTHER INFORMATION: Any amino acid
<220> FEATURE:
<221> NAME/KEY: MOD_RES
<222> LOCATION: (103)..(103)
<223> OTHER INFORMATION: Any amino acid

<400> SEQUENCE: 129

Gln Val Gln Leu Val Gln Ser Gly Ala Glu Xaa Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Ala Trp Ile Asn Pro Thr Xaa Gly Arg Thr Xaa Xaa Ala Arg Lys Phe
    50                  55                  60

Gln Gly Arg Val Thr Met Thr Arg Asp Thr Ser Ile Ser Xaa Ala Tyr
65                  70                  75                  80

Met Glu Leu Arg Xaa Leu Arg Ser Asp Asp Thr Ala Val Tyr Tyr Cys
                85                  90                  95

Ala Arg Gly Gly Trp Ile Xaa Leu Tyr Val Asp Tyr Ser Gly Tyr Pro
            100                 105                 110

Asn Phe Asp Ser Trp Gly Gln Gly Thr Leu Val Thr Val Ser Ser
        115                 120                 125

<210> SEQ ID NO 130
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Glu Val Gln Leu Val Glu Ser Gly Pro Glu Leu Lys Glu Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Ala Trp Ile Asn Pro Thr Thr Gly Arg Ser Ser Phe Ala Arg Gly Phe
    50                  55                  60

Gln Gly Arg Val Thr Met Thr Arg Glu Thr Ser Val Ser Thr Ala Tyr
65                  70                  75                  80

Met Glu Leu Arg Arg Leu Arg Ser Asp Asp Thr Ala Val Tyr Tyr Cys
                85                  90                  95

Ala Lys Ala Gly Tyr Ile Ala Leu Tyr Val Asp Tyr Ser Gly Tyr Pro
            100                 105                 110

Asn Phe Asn Ser Trp Gly Gln Gly Thr Leu Val Thr Val Ser Ser
        115                 120                 125

<210> SEQ ID NO 131
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Leu Ser Asp Tyr
            20                  25                  30

Tyr Val His Trp Leu Arg Gln Ala Pro Gly Gln Gly Leu Glu Trp Val
        35                  40                  45

Ala Trp Ile Asn Pro Thr Ser Gly Arg Thr Ile Ser Pro Arg Lys Phe
    50                  55                  60

Gln Gly Arg Val Thr Met Thr Asp Thr Ser Met Asn Val Ala Tyr
65                  70                  75                  80

Met Glu Leu Arg Gly Leu Arg Ser Asp Asp Thr Ala Val Tyr Phe Cys
                85                  90                  95

Ala Arg Gly Gly Trp Ile Ser Leu Tyr Val Asp Tyr Ser Tyr Tyr Pro
            100                 105                 110

```
Asn Phe Asp Ser Trp Gly Gln Gly Thr Leu Val Ser Val Ser Ser
            115                 120                 125
```

```
<210> SEQ ID NO 132
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (103)..(103)
<223> OTHER INFORMATION: Any amino acid

<400> SEQUENCE: 132

Gln Val Gln Leu Val Gln Ser Gly Ala Glu Xaa Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile Asn Pro Asn Thr Gly Arg Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Ala Thr Gly Gly Trp Ile Xaa Leu Tyr Tyr Asp Ser Ser Gly Tyr Pro
            100                 105                 110

Asn Phe Asp Tyr Trp Gly Gln Gly Thr Leu Val Thr Val Ser Ser
            115                 120                 125
```

```
<210> SEQ ID NO 133
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (60)..(60)
<223> OTHER INFORMATION: Any amino acid
<220> FEATURE:
<221> NAME/KEY: MOD_RES
<222> LOCATION: (63)..(63)
<223> OTHER INFORMATION: Any amino acid
<220> FEATURE:
<221> NAME/KEY: MOD_RES
<222> LOCATION: (104)..(104)
<223> OTHER INFORMATION: Any amino acid

<400> SEQUENCE: 133

Gln Val Gln Leu Val Gln Ser Gly Ala Glu Xaa Lys Asn Pro Gly Ala
1               5                   10                  15

Ser Val Lys Val Ser Cys Ala Ala Ser Gly Tyr Thr Phe Thr Asp Phe
            20                  25                  30
```

Tyr Ile His Trp Val Arg Leu Ala Pro Gly Gln Gly Leu Glu Trp Met
            35                  40                  45

Gly Trp Met Asn Pro Lys Thr Gly Arg Thr Asn Xaa Ala Gln Xaa Phe
    50                  55                  60

Gln Gly Arg Val Thr Met Thr Arg Asp Thr Ser Ile Gly Thr Ala Tyr
65                  70                  75                  80

Met Glu Leu Arg Arg Leu Thr Ser Asp Thr Ala Val Tyr Tyr Cys
                85                  90                  95

Val Thr Gly Gly Trp Ile Ser Xaa Tyr Tyr Asp Ser Ser Tyr Tyr Pro
            100                 105                 110

Asn Phe Asp His Trp Gly Gln Gly Thr Leu Val Thr Val Ser Ser
            115                 120                 125

<210> SEQ ID NO 134
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gln Val Gln Leu Val Gln Ser Gly Ala Glu Val Lys Asn Pro Gly Ala
1               5                   10                  15

Ser Val Lys Val Ser Cys Ala Pro Ser Gly Tyr Thr Phe Thr Asp Phe
            20                  25                  30

Tyr Ile His Trp Val Arg Leu Ala Pro Gly Gln Gly Leu Glu Trp Leu
            35                  40                  45

Gly Trp Met Asn Pro Lys Thr Gly Arg Thr Asn Gln Gly Gln Asn Phe
    50                  55                  60

Gln Gly Arg Val Thr Met Thr Arg Asp Thr Ser Ile Gly Thr Ala Tyr
65                  70                  75                  80

Met Glu Leu Arg Ser Leu Thr Ser Asp Asp Thr Ala Val Tyr Tyr Cys
                85                  90                  95

Val Thr Gly Ala Trp Ile Ser Asp Tyr Tyr Asp Ser Ser Tyr Tyr Pro
            100                 105                 110

Asn Phe Asp His Trp Gly Gln Gly Thr Leu Val Thr Val Ser Ser
            115                 120                 125

<210> SEQ ID NO 135
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Glu Val Gln Leu Val Gln Ser Gly Ala Glu Met Lys Asn Pro Gly Ala
1               5                   10                  15

Ser Val Lys Val Ser Cys Ala Ala Ser Gly Tyr Gly Phe Thr Asp Phe
            20                  25                  30

Tyr Ile His Trp Val Arg Leu Ala Pro Gly His Gly Leu Gln Trp Met
            35                  40                  45

Gly Trp Met Asn Pro Lys Thr Gly Arg Thr Asn Asn Ala Gln Asp Phe
    50                  55                  60

Gln Gly Arg Val Thr Leu Thr Arg Asp Thr Ser Ile Gly Thr Ala Tyr
65                  70                  75                  80

Met Glu Leu Arg Arg Leu Thr Ser Asp Asp Thr Ala Val Tyr Tyr Cys
                85                  90                  95

Val Thr Gly Gly Trp Ile Ser Pro Tyr Tyr Asp Ser Tyr Tyr Pro
            100                 105                 110

Asn Phe Asp His Trp Gly Gln Gly Thr Leu Ile Thr Val Ser Ser
            115                 120                 125

<210> SEQ ID NO 136
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Gln Val Gln Leu Val Gln Ser Gly Ala Glu Met Lys Lys Pro Gly Ala
1               5                   10                  15

Ser Val Arg Val Ser Cys Lys Ala Ser Gly Tyr Thr Phe Thr Asp Tyr
            20                  25                  30

Tyr Ile His Trp Val Arg Gln Ala Pro Gly Gln Gly Pro Glu Trp Met
        35                  40                  45

Gly Trp Ile Asn Pro Ser Thr Gly Arg Thr Asn Ser Pro Gln Lys Phe
    50                  55                  60

Gln Gly Arg Val Thr Met Thr Arg Asp Thr Ser Ile Ser Thr Ala Tyr
65                  70                  75                  80

Met Asp Leu Asn Arg Leu Thr Ser Asp Asp Thr Ala Met Tyr Tyr Cys
                85                  90                  95

Thr Thr Gly Gly Trp Ile Gly Leu Tyr Ser Asp Thr Ser Gly Tyr Pro
            100                 105                 110

Asn Phe Asp Tyr Trp Gly Gln Gly Thr Leu Val Thr Val Ser Ser
            115                 120                 125

<210> SEQ ID NO 137
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137
cagtctgccc tgactcagcc tgcctccgtg tctgggtctc ctggacagtc gatcaccatc      60
tcctgcactg gaaccagcag tgatgttggg agttataacc ttgtctcctg gtaccaacag     120
cacccaggca agcccccaa actcatgatt tatgaggtca gtaagcggcc ctcagggggtt     180 tctaatcgct tctctggctc caagtctggc aacacggcct ccctgacaat ctctgggctc     240
caggctgagg acgaggctga ttattactgc tgctcatatg caggtagtag cactgtaata     300
ttcggcggag ggaccaagct gaccgtccta g                                    331

<210> SEQ ID NO 138
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138

```
cagtctgccc tgactcagcc tgcctccgtg tctgggtctc ctggacagtc gatcaccatc      60
tcctgcactg gaaccagcag tgatgttggg agttataacc ttgtctcctg gtaccaacag     120
cacccaggca agccccaa actcatgatt tatgaggtca gtaagtggcc ctcaggggtt      180
tctaatcgct tctctggctc caagtctggc aacacggcct ccctgacaat ctctgggctc     240
caggctgagg acgaggctga ttattactgt tgctcatatg caggtagtag cactgtaata     300
ttcggcggag ggaccaagct gaccgtccta g                                    331
```

<210> SEQ ID NO 139
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139

```
cagtctgccc tgactcagcc tgcctccgtg tctgggtctc ctggacagtc gatcaccatc      60
tcctgcactg gaaccagtta tgatgttggg aagtttgacc ttgtctcctg gtaccaacag     120
cacccaggca agccccaa atacatgatt tatgaagtca ataagtggcc ctcaggagtt      180
tctcatcgct tctctggctc caaatctggc aacacggcct ccctgacaat ctctgggctc     240
caggctgagg acgaggctga ctattattgc tgctcattcg gaggtagtgc cactgtagtc     300
tgcggcggag ggaccaaggt gaccgtccta g                                    331
```

<210> SEQ ID NO 140
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140

```
cagtctgccc tgactcagcc tgcctccgtg tctgggtctc ctggccagtc gatcaccatc      60
tcctgcactg gaaccagcta tgatgttggg agttataatc ttgtctcctg gtaccaacag     120
cacccaggca agccccaa actcattatt tatgaggtca gtcagtggcc ctcaggggtt      180
tctaagcgct tctctggctc caagtctggc aacacggcct ccctgacaat ctctgggctc     240
caggctgagg acgaggctca ttattactgt tgctcatatg caggcagtag cactgtaata     300
ttcggcggag ggacctcgct gaccgtccta g                                    331
```

<210> SEQ ID NO 141
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 141

```
cagcctgtgc tgactcagcc tgcctccgtg tctgggtctc ctggacagtc gatcaccatc      60
tcctgcactg gaagcagcag tgatgttggg agttataacc ttgtgtcctg gtaccagcag     120
cacccaggca agccccaa actgatgatt tatgaggtca ataagtgggc ctcaggggtt      180
tctgatcgct tctctggctc caagtctggc aacacggcct ccctgacaat ctctagactc     240
caggctgagg acgaggctaa ttacttttgt tcctcatcta caaatagtgc cactgtcata     300
```

-continued ttcggcggag ggaccaagct gaccgtccta g    331

<210> SEQ ID NO 142
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 142
cagtctgccc tgactcagcc tgcctccgtg tctgggtctc ctggacagtc gatcaccatc    60
tcctgcactg gaaccagcta tgatgttggg agttataacc ttgtctcctg gtaccaacag    120
cacccaggca agccccccaa actcatgatt tatgaggtca gtaagtggcc ctcaggggtt    180
tctaatcgct tctctggctc caagtctggc aacacggcct ccctgacaat ctctgggctc    240
caggctgagg acgaggctga ttattactgt tgctcatatg caggtagtag cactgtaata    300
ttcggcggag ggaccaagct gaccgtccta g    331

<210> SEQ ID NO 143
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 143
cagtctgccc tgactcagcc tgcctccgtg tctgggtctc ctggacagtc gatcaccatc    60
tcctgcactg gaaccagtta tgatgttggg agttataacc ttgtctcctg gtaccaacag    120
cacccaggca agccccccaa atacatgatt tatgaggtca ataagtggcc ctcaggggtt    180
tctaatcgct tctctggctc caagtctggc aacacggcct ccctgacaat ctctgggctc    240
caggctgagg acgaggctga ttattactgt tgctcatatg caggtagtag cactgtawtw    300
ttcggcggag ggaccaagct gaccgtccta g    331

<210> SEQ ID NO 144
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 144
ctgcctgtgc tgactcagcc tgcctccgtg tctgggtctc ctgggcagtc gatcaccatc    60
tcctgcactg ggaccattta tgatgttggg aagtttgacc ttgtctcctg gtaccagcac    120
cacccaggca agccccccaa atatttgatt tatgaagtca aaaagtggcc ctcaggagtt    180
tctcatcgct tctctggctc caaatctggc aacacggcct ccctgacaat ctctgggctc    240
caggttgagg acgaggctga ctattattgc tgctcattcg gaggtagtgc cgctgtggtc    300
tgcggcggag ggaccaaggt gaccgtccta g    331

<210> SEQ ID NO 145
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145

```
cagtctgccc tgactcagcc tgcctccgtg tctgggtctc ctggacagtc gatcaccatc      60
tcctgcactg gaaccagtta tgatgttgcg aagtttgacc ttgtctcctg gttccaacag     120
cacccaggca agccccccaa atacatgatt tatgaagtca ataagtggcc ctcaggagtt     180
tctcatcgct ctctggttc caaatctggc aacacggcct ccctgacaat ctctgggctc      240
caggctgagg acgaggctga ctattattgc tgctcattcg gaggtagtgc cactgtagtc     300
tgcggcggag ggaccaaggt gaccgtccta g                                    331
```

<210> SEQ ID NO 146
<211> LENGTH: 331
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 146

```
cagtctgccc tgactcagcc tgcctccgtg tctgggtctc ctggacagtc gatcaccatc      60
tcctgcactg gaaccaatta tgatgttggg agttataacc ttgtctcctg gtatcaacag     120
cacccaggca agtccccaa atacataatt tatgaggtca ataagcggcc ctcaggggtt      180
tctaatcgct ctctggctc caagtctggc aacacggcct ccctgacaat ctctgggctc      240
caggctgagg acgaggccac ttattactgt tgttcatatg caggtagtag cattatattt     300
ttcggcggtg ggaccaagct gaccgtcata g                                    331
```

<210> SEQ ID NO 147
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 147

```
Gln Ser Ala Leu Thr Gln Pro Ala Ser Val Ser Gly Ser Pro Gly Gln
1               5                   10                  15
Ser Ile Thr Ile Ser Cys Thr Gly Thr Ser Ser Asp Val Gly Ser Tyr
            20                  25                  30
Asn Leu Val Ser Trp Tyr Gln Gln His Pro Gly Lys Ala Pro Lys Leu
        35                  40                  45
Met Ile Tyr Glu Val Ser Lys Arg Pro Ser Gly Val Ser Asn Arg Phe
    50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Cys Ser Tyr Ala Gly Ser
                85                  90                  95
Ser Thr Val Ile Phe Gly Gly Gly Thr Lys Leu Thr Val Leu
            100                 105                 110
```

<210> SEQ ID NO 148
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 148

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Ser Lys Trp Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Val Ile Phe Gly Gly Gly Thr Lys Leu Thr Val Leu
            100                 105                 110

<210> SEQ ID NO 149
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Tyr Asp Val Gly Lys Phe
            20                  25                  30

Asp Leu Val Ser Trp Tyr Gln Gln His Pro Gly Lys Ala Pro Lys Tyr
        35                  40                  45

Met Ile Tyr Glu Val Asn Lys Trp Pro Ser Gly Val Ser His Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Phe Gly Gly Ser
                85                  90                  95

Ala Thr Val Val Cys Gly Gly Gly Thr Lys Val Thr Val Leu
            100                 105                 110

<210> SEQ ID NO 150
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Tyr Asp Val Gly Ser Tyr
            20                  25                  30

Asn Leu Val Ser Trp Tyr Gln Gln His Pro Gly Lys Ala Pro Lys Leu
        35                  40                  45

Ile Ile Tyr Glu Val Ser Gln Trp Pro Ser Gly Val Ser Lys Arg Phe
50                  55                  60

Ser Gly Ser Lys Ser Gly Asn Thr Ala Ser Leu Thr Ile Ser Gly Leu

```
                65                  70                  75                  80
Gln Ala Glu Asp Glu Ala His Tyr Tyr Cys Cys Ser Tyr Ala Gly Ser
                    85                  90                  95

Ser Thr Val Ile Phe Gly Gly Gly Thr Ser Leu Thr Val Leu
                100                 105                 110

<210> SEQ ID NO 151
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Gln Pro Val Leu Thr Gln Pro Ala Ser Val Ser Gly Ser Pro Gly Gln
1               5                   10                  15

Ser Ile Thr Ile Ser Cys Thr Gly Ser Ser Asp Val Gly Ser Tyr
                20                  25                  30

Asn Leu Val Ser Trp Tyr Gln Gln His Pro Gly Lys Ala Pro Lys Leu
            35                  40                  45

Met Ile Tyr Glu Val Asn Lys Trp Ala Ser Gly Val Ser Asp Arg Phe
        50                  55                  60

Ala Gly Ser Lys Ser Gly Asn Thr Ala Ser Leu Thr Ile Ser Arg Leu
65                  70                  75                  80

Gln Ala Glu Asp Glu Ala Asn Tyr Phe Cys Ser Ser Thr Asn Ser
                    85                  90                  95

Ala Thr Val Ile Phe Gly Gly Gly Thr Lys Leu Thr Val Leu
                100                 105                 110

<210> SEQ ID NO 152
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Tyr Asp Val Gly Ser Tyr
                20                  25                  30

Asn Leu Val Ser Trp Tyr Gln Gln His Pro Gly Lys Ala Pro Lys Leu
            35                  40                  45

Met Ile Tyr Glu Val Ser Lys Trp Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                    85                  90                  95

Ser Thr Val Ile Phe Gly Gly Gly Thr Lys Leu Thr Val Leu
                100                 105                 110

<210> SEQ ID NO 153
<211> LENGTH: 110
<212> TYPE: PRT
<213> ORGANISM: Artificial Sequence
<220> FEATURE:
<223> OTHER INFORMATION: Description of Artificial Sequence: Synthetic
```

```
                    polypeptide
<220> FEATURE:
<221> NAME/KEY: MOD_RES
<222> LOCATION: (100)..(100)
<223> OTHER INFORMATION: Any amino acid

<400> SEQUENCE: 153

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Tyr Asp Val Gly Ser Tyr
            20                  25                  30

Asn Leu Val Ser Trp Tyr Gln Gln His Pro Gly Lys Ala Pro Lys Tyr
        35                  40                  45

Met Ile Tyr Glu Val Asn Lys Trp Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Val Xaa Phe Gly Gly Gly Thr Lys Leu Thr Val Leu
            100                 105                 110

<210> SEQ ID NO 154
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Leu Pro Val Leu Thr Gln Pro Ala Ser Val Ser Gly Ser Pro Gly Gln
1               5                   10                  15

Ser Ile Thr Ile Ser Cys Thr Gly Thr Ile Tyr Asp Val Gly Lys Phe
            20                  25                  30

Asp Leu Val Ser Trp Tyr Gln His His Pro Gly Lys Ala Pro Lys Tyr
        35                  40                  45

Leu Ile Tyr Glu Val Lys Lys Trp Pro Ser Gly Val Ser His Arg Phe
    50                  55                  60

Ser Gly Ser Lys Ser Gly Asn Thr Ala Ser Leu Thr Ile Ser Gly Leu
65                  70                  75                  80

Gln Val Glu Asp Glu Ala Asp Tyr Tyr Cys Cys Ser Phe Gly Gly Ser
                85                  90                  95

Ala Ala Val Val Cys Gly Gly Gly Thr Lys Val Thr Val Leu
            100                 105                 110

<210> SEQ ID NO 155
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Tyr Asp Val Ala Lys Phe
            20                  25                  30

Asp Leu Val Ser Trp Phe Gln Gln His Pro Gly Lys Ala Pro Lys Tyr
```

```
                    35                  40                  45
Met Ile Tyr Glu Val Asn Lys Trp Pro Ser Gly Val Ser His Arg Phe
             50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Phe Gly Gly Ser
                 85                  90                  95

Ala Thr Val Val Cys Gly Gly Thr Lys Val Thr Val Leu
            100                 105                 110

<210> SEQ ID NO 156
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Gln Ser Ala Leu Thr Gln Pro Ala Ser Val Ser Gly Ser Pro Gly Gln
 1               5                  10                  15

Ser Ile Thr Ile Ser Cys Thr Gly Thr Asn Tyr Asp Val Gly Ser Tyr
             20                  25                  30

Asn Leu Val Ser Trp Tyr Gln Gln His Pro Gly Lys Val Pro Lys Tyr
                 35                  40                  45

Ile Ile Tyr Glu Val Asn Lys Arg Pro Ser Gly Val Ser Asn Arg Phe
             50                  55                  60

Ser Gly Ser Lys Ser Gly Asn Thr Ala Ser Leu Thr Ile Ser Gly Leu
 65                  70                  75                  80

Gln Ala Glu Asp Glu Ala Thr Tyr Tyr Cys Cys Ser Tyr Ala Gly Ser
                 85                  90                  95

Ser Ile Ile Phe Phe Gly Gly Gly Thr Lys Leu Thr Val Ile
            100                 105                 110

<210> SEQ ID NO 157
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 157 cagggcact tggtgcagtc tggggctgag gtgaagaaac ctggggcctc agtgaaggtc      60
tcctgcacgg tcaccacata cagtttcacc gagcactatt tacactggct gcggcaggcc    120
cctggacagg cgcctgagtg gatgggttgg gtcaatcctg caaatgatcg cgcaaaatat    180
gcatacaaat ttcagggcag agtcaccatg accaccgaca tgtccgccta cacagcctac    240
atggagttga aaggctgac atccgacgac acgccatgt attactgtac gacaggggcg      300
tggattagtc cctactatga cagtagttat taccctaact tgaccactg gggtcaggga     360 accctggtca ccgtctcctc a                                              381

<210> SEQ ID NO 158
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 158

```
caggcgcaac tggcgcagtc tgggcctgag gtgggcaagc ctggctcctc agtaaacgtc      60
tcctgcaagg cttctggata cgacttcact ggccaatatt tacattggtt tcgtcaggcc     120
cctcgacagg gacttgagtg gatggggtgg ctcaatcctg acactggtga agcaaaatat     180
gttgagaagt ttcagggcag agtcatcatg accagggaca cgtccatcgg cacagcctac     240
atggagttga agaggctaac atctgacgac acggccgtct attactgtgt gacaggggcc     300
tggatcagtc aatactatga cagtagttat taccctaact ttgaccactg gggtcaggga     360
accctggtca ccgtctcctc a                                               381
```

<210> SEQ ID NO 159
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 159

```
caggtgcagc tggtgcaatc tggggctgaa gtgaggaacc ctggggcctc agtgaaagtc      60
tcctgcgcgc cttctggata tgccttcact gacttctaca tacactgggt gcgactggcc     120
cctggacaag gcttgagtg gctggggtgg atggacccta agactggtcg cacaaatcaa     180
ggacacaact ttcagggcag ggtcaccatg accagggaca cgtccatcgg cacagcctac     240
atggagttga ggagcctcac agctgacgac acggccgtct attactgtgt gacaggggcc     300
tggatcagtg attattatga tagtagttat tatcctaatt ttgaccactg gggtcaggga     360
accctggtca ccgtctcctc a                                               381
```

<210> SEQ ID NO 160
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 160

```
caggtgcgac tggtgcaatc tggggctgaa ttgaagaacc ctggggccgc agtgaaggtc      60
tcctgcgcgg cttccggata taccttcacc gactactatc tacactgggt gcgactggcc     120
cctgggcaag gcttcagtg gatgggatgg atgaaccta ttactggtcg cacaaacaat     180
gcacaaaggt ttcagggcag ggtcaccatg accagggaca cgtccatcgg cacagcctac     240
atggaattga agaggctaac atctgacgac acggccgtct attactgtgt gacaggggcc     300
tggatcagtc aatactatga cagtagttat taccctaatt ttgaccactg gggtcaggga     360
accctggtca ccgtctcctc a                                               381
```

<210> SEQ ID NO 161
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 161

```
caggtgcaac tggtgcagtc tgggcctgag atgaagcagc ctggggcctc agtgaaagtc      60
```

```
tcctgcaggg cttctggata caagttcacc gactactatt tacactgggt gcgacaggcc    120
cctggacaag ggcctgagtg gatggcgtgg atgaaccctg ccagtggtcg cacaaacttt    180
gcacagaaat ttcagggcag ggtcaccatg accagggaca cgtccatcaa cacaggctac    240
atggagctga aagactgcg atctgacgac acggccgtat actactgtgc gaaggcgggg    300
tggatcagtc tttacaatga ttatagtgct taccctaact ttaattcctg gggccaggga    360
accctggtca ccgtctcctc a                                              381
```

<210> SEQ ID NO 162
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

```
Gln Gly His Leu Val Gln Ser Gly Ala Glu Val Lys Lys Pro Gly Ala
1               5                   10                  15

Ser Val Lys Val Ser Cys Thr Val Thr Thr Tyr Ser Phe Thr Glu His
            20                  25                  30

Tyr Leu His Trp Leu Arg Gln Ala Pro Gly Gln Ala Pro Glu Trp Met
        35                  40                  45

Gly Trp Val Asn Pro Ala Asn Asp Arg Ala Lys Tyr Ala Tyr Lys Phe
    50                  55                  60

Gln Gly Arg Val Thr Met Thr Thr Asp Met Ser Ala Tyr Thr Ala Tyr
65                  70                  75                  80

Met Glu Leu Arg Arg Leu Thr Ser Asp Asp Thr Ala Met Tyr Tyr Cys
                85                  90                  95

Thr Thr Gly Ala Trp Ile Ser Pro Tyr Tyr Asp Ser Ser Tyr Tyr Pro
            100                 105                 110

Asn Phe Asp His Trp Gly Gln Gly Thr Leu Val Thr Val Ser Ser
        115                 120                 125
```

<210> SEQ ID NO 163
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

```
Gln Ala Gln Leu Ala Gln Ser Gly Pro Glu Val Gly Lys Pro Gly Ser
1               5                   10                  15

Ser Val Asn Val Ser Cys Lys Ala Ser Gly Tyr Asp Phe Thr Gly Gln
            20                  25                  30

Tyr Leu His Trp Phe Arg Gln Ala Pro Arg Gln Gly Leu Glu Trp Met
        35                  40                  45

Gly Trp Leu Asn Pro Asp Thr Gly Glu Ala Lys Tyr Val Glu Lys Phe
    50                  55                  60

Gln Gly Arg Val Ile Met Thr Arg Asp Thr Ser Ile Gly Thr Ala Tyr
65                  70                  75                  80

Met Glu Leu Lys Arg Leu Thr Ser Asp Asp Thr Ala Val Tyr Tyr Cys
                85                  90                  95

Val Thr Gly Ala Trp Ile Ser Gln Tyr Tyr Asp Ser Ser Tyr Tyr Pro
            100                 105                 110
```

Asn Phe Asp His Trp Gly Gln Gly Thr Leu Val Thr Val Ser Ser
        115                 120                 125

<210> SEQ ID NO 164
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Gln Val Gln Leu Val Gln Ser Gly Ala Glu Val Arg Asn Pro Gly Ala
1               5                   10                  15

Ser Val Lys Val Ser Cys Ala Pro Ser Gly Tyr Ala Phe Thr Asp Phe
                20                  25                  30

Tyr Ile His Trp Val Arg Leu Ala Pro Gly Gln Gly Leu Glu Trp Leu
            35                  40                  45

Gly Trp Met Asp Pro Lys Thr Gly Arg Thr Asn Gln Gly His Asn Phe
        50                  55                  60

Gln Gly Arg Val Thr Met Thr Arg Asp Thr Ser Ile Gly Thr Ala Tyr
65                  70                  75                  80

Met Glu Leu Arg Ser Leu Thr Ala Asp Thr Ala Val Tyr Tyr Cys
                85                  90                  95

Val Thr Gly Ala Trp Ile Ser Asp Tyr Tyr Asp Ser Ser Tyr Tyr Pro
            100                 105                 110

Asn Phe Asp His Trp Gly Gln Gly Thr Leu Val Thr Val Ser Ser
        115                 120                 125

<210> SEQ ID NO 165
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Gln Val Arg Leu Val Gln Ser Gly Ala Glu Leu Lys Asn Pro Gly Ala
1               5                   10                  15

Ala Val Lys Val Ser Cys Ala Ala Ser Gly Tyr Thr Phe Thr Asp Tyr
                20                  25                  30

Tyr Leu His Trp Val Arg Leu Ala Pro Gly Gln Gly Leu Gln Trp Met
            35                  40                  45

Gly Trp Met Asn Pro Ile Thr Gly Arg Thr Asn Asn Ala Gln Arg Phe
        50                  55                  60

Gln Gly Arg Val Thr Met Thr Arg Asp Thr Ser Ile Gly Thr Ala Tyr
65                  70                  75                  80

Met Glu Leu Lys Arg Leu Thr Ser Asp Thr Ala Val Tyr Tyr Cys
                85                  90                  95

Val Thr Gly Ala Trp Ile Ser Gln Tyr Tyr Asp Ser Ser Tyr Tyr Pro
            100                 105                 110

Asn Phe Asp His Trp Gly Gln Gly Thr Leu Val Thr Val Ser Ser
        115                 120                 125

<210> SEQ ID NO 166
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Gln Val Gln Leu Val Gln Ser Gly Pro Glu Met Lys Gln Pro Gly Ala
1               5                   10                  15

Ser Val Lys Val Ser Cys Arg Ala Ser Gly Tyr Lys Phe Thr Asp Tyr
            20                  25                  30

Tyr Leu His Trp Val Arg Gln Ala Pro Gly Gln Gly Pro Glu Trp Met
        35                  40                  45

Ala Trp Met Asn Pro Ala Ser Gly Arg Thr Asn Phe Ala Gln Lys Phe
    50                  55                  60

Gln Gly Arg Val Thr Met Thr Arg Asp Thr Ser Ile Asn Thr Gly Tyr
65                  70                  75                  80

Met Glu Leu Arg Arg Leu Arg Ser Asp Asp Thr Ala Val Tyr Tyr Cys
                85                  90                  95

Ala Lys Ala Gly Trp Ile Ser Leu Tyr Asn Asp Tyr Ser Ala Tyr Pro
            100                 105                 110

Asn Phe Asn Ser Trp Gly Gln Gly Thr Leu Val Thr Val Ser Ser
        115                 120                 125

<210> SEQ ID NO 167
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Gln Val Arg Leu Ala Gln Tyr Gly Gly Gly Val Lys Arg Leu Gly Ala
1               5                   10                  15

Thr Met Thr Leu Ser Cys Val Ala Ser Gly Tyr Thr Phe Asn Asp Tyr
            20                  25                  30

Tyr Ile His Trp Val Arg Gln Ala Pro Gly Gln Gly Phe Glu Leu Leu
        35                  40                  45

Gly Tyr Ile Asp Pro Ala Asn Gly Arg Pro Asp Tyr Ala Gly Ala Leu
    50                  55                  60

Arg Glu Arg Leu Ser Phe Tyr Arg Asp Lys Ser Met Glu Thr Leu Tyr
65                  70                  75                  80

Met Asp Leu Arg Ser Leu Arg Tyr Asp Asp Thr Ala Met Tyr Tyr Cys
                85                  90                  95

Val Arg Asn Val Gly Thr Ala Gly Ser Leu Leu His Tyr Asp His Trp
            100                 105                 110

Gly Ser Gly Ser Pro Val Ile Val Ser Ser
        115                 120

<210> SEQ ID NO 168
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Glu Ile Val Leu Thr Gln Ser Pro Ala Thr Leu Ser Ala Ser Pro Gly
1               5                   10                  15

```
Glu Arg Val Thr Leu Thr Cys Arg Ala Ser Arg Ser Val Arg Asn Asn
            20                  25                  30

Val Ala Trp Tyr Gln His Lys Gly Gly Gln Ser Pro Arg Leu Leu Ile
        35                  40                  45

Tyr Asp Ala Ser Thr Arg Ala Ala Gly Val Pro Ala Arg Phe Ser Gly
    50                  55                  60

Ser Ala Ser Gly Thr Glu Phe Thr Leu Ala Ile Ser Asn Leu Glu Ser
65                  70                  75                  80

Glu Asp Phe Thr Val Tyr Phe Cys Leu Gln Tyr Asn Asn Trp Trp Thr
                85                  90                  95

Phe Gly Gln Gly Thr Arg Val Asp Ile Lys
            100                 105
```

<210> SEQ ID NO 169
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 169

```
caggtccgac tagcccaata tggtggtggg gtgaagaggc taggggccac aatgacccct     60
tcctgcgtgg catctggata cacctttcaac gactactaca tcattgggt gcggcaggcc   120 cctggacaag gctttgagtt gttgggatac atcgaccccg ctaatggtcg cccagactac   180 gcagggggcgt tgagggagag actctccttc tacagggaca gtccatgga gacgctgtac   240 atggacctga ggagcctaag atatgacgac acggccatgt attattgtgt tagaaatgtg   300
gggaccgctg gcagcttgct gcattatgac cactggggct cgggaagccc ggtcatcgtc   360
tcctcc                                                              366
```

<210> SEQ ID NO 170
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 170

```
gaaattgtgt tgacgcagtc tccagccacc ctgtccgcgt ctccagggga aagagtcacc     60
ctaacttgca gggccagtcg gagtgtccga acaacgtgg cctggtatca gcacaagggt   120
ggccagagtc ccaggctcct catttatgat gcgtccacga gggccgctgg tgtcccagcc   180
aggttcagcg gcagtgcatc tgggacagag ttcactctcg ccatcagcaa cttggagtct   240
gaagatttta cagtctactt ctgtctgcag tataataact ggtggacctt cggccaaggg   300
accagggtgg acatcaaa                                                 318
```

<210> SEQ ID NO 171
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

```
Gln Val Gln Leu Ile Gln Ser Gly Pro Gln Phe Lys Thr Pro Gly Ala
1               5                   10                  15
```

-continued

Ser Val Thr Val Ser Cys Lys Ala Ser Gly Tyr Ile Phe Thr Asp Tyr
            20                  25                  30

Leu Ile His Trp Val Arg Leu Val Pro Gly Lys Gly Leu Glu Trp Leu
            35                  40                  45

Gly Arg Ile Asn Thr Asn Ala Gly Leu Met Tyr Leu Ser His Lys Phe
50                  55                  60

Glu Gly Arg Leu Ile Leu Arg Arg Val Val Asp Trp Arg Thr Pro Ser
65                  70                  75                  80

Leu Gly Thr Val Asn Met Glu Leu Arg Asn Val Arg Ser Asp Asp Ser
                85                  90                  95

Ala Ile Tyr Phe Cys Gly Arg Val Val Asp Gly Phe Asn Ala Ala Gly
            100                 105                 110

Pro Leu Glu Phe Trp Gly Gln Gly Ser Pro Val Ile Val Ser Ser
            115                 120                 125

<210> SEQ ID NO 172
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Gln Val Arg Leu Met Gln Ser Gly Pro Gln Leu Lys Thr Pro Gly Ala
1               5                   10                  15

Ser Val Thr Val Ser Cys Lys Ala Ser Gly Tyr Ile Phe Thr Asp Tyr
            20                  25                  30

Leu Ile His Trp Val Arg Leu Val Pro Gly Lys Gly Leu Glu Trp Leu
            35                  40                  45

Gly Arg Ile Asn Thr Asn Gly Gly Leu Met Tyr Leu Ser Tyr Lys Phe
50                  55                  60

Glu Gly Arg Leu Ile Leu Arg Arg Asp Val Asp Trp Arg Thr Pro Ser
65                  70                  75                  80

Leu Gly Thr Val Tyr Met Glu Leu Lys Asn Leu Arg Ser Asp Asp Ser
                85                  90                  95

Ala Ile Tyr Phe Cys Gly Arg Val Val Asp Gly Phe Asn Ala Ala Gly
            100                 105                 110

Pro Leu Glu Phe Trp Gly Gln Gly Ser Pro Val Ile Val Ser Ser
            115                 120                 125

<210> SEQ ID NO 173
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Gln Val Gln Leu Ile Gln Ser Gly Pro Gln Leu Lys Thr Pro Gly Ala
1               5                   10                  15

Ser Val Thr Val Ser Cys Lys Ala Ser Gly Tyr Val Phe Ala Asp Tyr
            20                  25                  30

Leu Ile His Trp Val Arg Leu Val Pro Gly Lys Gly Leu Glu Trp Leu
            35                  40                  45

Gly Arg Ile Asn Thr Asn Ala Gly Leu Met Tyr Leu Ser His Lys Phe
50                  55                  60

Glu Gly Arg Leu Ile Leu Arg Arg Asp Arg Asp Trp Arg Thr Pro Ser
65                  70                  75                  80

Leu Gly Thr Leu Tyr Met Glu Leu Arg Asn Leu Lys Ser Asp Asp Ser
                85                  90                  95

Ala Ile Tyr Phe Cys Gly Arg Val Val Asp Gly Phe Asn Ala Ala Gly
                100                 105                 110

Pro Leu Glu Phe Trp Gly Gln Gly Ser Pro Val Ile Val Ser Ser
            115                 120                 125

<210> SEQ ID NO 174
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Gln Val Arg Leu Met Gln Ser Gly Thr Glu Phe Lys Thr Pro Gly Ala
1               5                   10                  15

Ser Val Lys Val Ser Cys Lys Thr Ser Gly Tyr Ile Phe Ser Asp Tyr
                20                  25                  30

Leu Ile His Trp Val Arg Leu Val Pro Gly Lys Gly Leu Glu Trp Leu
            35                  40                  45

Gly Arg Ile Asn Thr Asn Ala Gly Leu Met Tyr Leu Ser Pro Arg Phe
        50                  55                  60

Glu Gly Arg Val Ile Leu Arg Glu Ser Ser Phe Arg Thr Pro Ser
65                  70                  75                  80

Leu Gly Thr Val Tyr Met Glu Leu Arg Asn Leu Lys Phe Asp Asp Ser
                85                  90                  95

Ala Val Tyr Phe Cys Gly Arg Val Val Asp Gly Phe Asn Ala Ala Gly
                100                 105                 110

Pro Leu Glu Phe Trp Gly Gln Gly Ser Leu Val Ile Val Ser Ser
            115                 120                 125

<210> SEQ ID NO 175
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Gln Val Val Met Thr Gln Ser Pro Ala Thr Leu Ser Leu Ser Pro Gly
1               5                   10                  15

Glu Thr Ala Ala Val Ser Cys Arg Ala Ser Gln Tyr Val Asp Arg Ser
                20                  25                  30

Ile Ser Trp Tyr Gln Leu Lys Thr Gly Arg Ala Pro Arg Leu Leu Val
            35                  40                  45

Tyr Ala Ala Ser Ser Arg Ser Ile Gly Val Pro Asp Arg Phe Ser Gly
        50                  55                  60

Ser Gly Ser Gly Arg Asp Phe Thr Leu Thr Ile Arg Gly Val Gln Ser
65                  70                  75                  80

Asp Asp Phe Ala Leu Tyr Tyr Cys Gln Gln Asp Tyr Tyr Trp Pro Val
                85                  90                  95

Thr Phe Gly Gln Gly Thr Arg Leu Asp Met Lys
            100                 105

<210> SEQ ID NO 176
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Gln Val Val Met Thr Gln Ser Pro Val Thr Leu Ser Val Ser Pro Gly
1               5                   10                  15

Glu Thr Ala Ala Val Ser Cys Arg Ala Ser Gln Tyr Val Asp Arg Ser
            20                  25                  30

Ile Ser Trp Tyr Gln Leu Lys Thr Gly Arg Ala Pro Arg Leu Leu Val
        35                  40                  45

Tyr Ala Ala Ser Ser Arg Ser Ile Gly Val Pro Asp Arg Phe Ser Gly
    50                  55                  60

Ser Gly Ser Gly Arg Asp Phe Thr Leu Thr Ile Arg Gly Val Gln Ser
65                  70                  75                  80

Asp Asp Phe Ala Val Tyr Tyr Cys Gln Gln Asp Tyr Tyr Trp Pro Val
                85                  90                  95

Thr Phe Gly Gln Gly Thr Arg Leu Asp Met Lys
                100                 105

<210> SEQ ID NO 177
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Gln Val Leu Met Thr Gln Ser Pro Ala Thr Leu Ser Val Ser Pro Gly
1               5                   10                  15

Glu Thr Ala Ala Val Ser Cys Arg Ala Ser Gln Tyr Val Asp Arg Ser
            20                  25                  30

Ile Ser Trp Tyr Gln Val Lys Ser Gly Arg Ala Pro Arg Leu Leu Val
        35                  40                  45

Tyr Ala Ala Ser Ser Arg Ser Ile Gly Val Pro Asp Arg Phe Ser Gly
    50                  55                  60

Ser Gly Ser Gly Thr Asp Phe Thr Leu Thr Ile Arg Gly Val Gln Ser
65                  70                  75                  80

Asp Asp Phe Ala Leu Tyr Tyr Cys Gln Gln Asp Tyr Gly Trp Pro Val
                85                  90                  95

Thr Phe Gly Gln Gly Thr Arg Leu Asp Met Lys
                100                 105

<210> SEQ ID NO 178
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Glu Val Val Met Thr Gln Ser Pro Ala Thr Leu Ser Val Ser Pro Gly
1               5                   10                  15

```
Glu Glu Ala Ala Leu Ser Cys Gly Ala Ser Asp Tyr Ile Asp Arg Ser
            20                  25                  30

Val Ser Trp Tyr Gln Leu Lys Pro Gly Arg Ala Pro Arg Leu Leu Val
        35                  40                  45

Tyr Ala Ala Ser Ser Arg Ser Ile Gly Ile Pro Asp Arg Phe Ser Gly
    50                  55                  60

Ser Gly Ser Gly Thr Ala Phe Thr Leu Thr Ile Arg Gly Val Gln Ser
65                  70                  75                  80

Asp Asp Phe Ala Leu Tyr Tyr Cys Gln Gln Asp Lys Tyr Trp Pro Val
                85                  90                  95

Thr Phe Gly Gln Gly Thr Arg Leu Asp Met Lys
            100                 105

<210> SEQ ID NO 179
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Val Gly Thr Glu Gly Ser Leu Leu His Phe Asp Tyr Trp
            100                 105                 110

Gly Gln Gly Thr Leu Val Thr Val Ser Ser
        115                 120

<210> SEQ ID NO 180
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Gln Val Gln Leu Val Gln Ser Gly Thr Glu Val Arg Lys Pro Gly Ala
1               5                   10                  15

Ser Val Thr Ile Ser Cys Lys Ala Ser Gly Tyr Thr Phe Asn Asn Phe
            20                  25                  30

Tyr Val His Trp Val Arg Gln Ala Pro Gly Gln Gly Leu Glu Cys Met
        35                  40                  45

Gly Trp Ile Asp Pro Ser Val Gly Arg Ile Ser Tyr Gly Gln Lys Phe
    50                  55                  60

Gln Gly Arg Val Thr Met Thr Arg Asp Arg Ser Thr Ser Thr Val Tyr
65                  70                  75                  80
```

Met Gly Leu Ser Ser Leu Arg Ser Glu Asp Thr Ala Met Tyr Tyr Cys
            85                  90                  95

Val Arg Asp Val Gly Thr Glu Gly Ser Leu Leu His Phe Asp His Trp
            100                 105                 110

Gly Gln Gly Thr Leu Val Ile Val Ser Ala
        115                 120

<210> SEQ ID NO 181
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Gln Val Gln Leu Val Gln Ser Gly Ala Glu Val Lys Lys Pro Gly Ala
1               5                   10                  15

Ser Val Thr Val Ser Cys Gln Ala Ser Gly Tyr Thr Phe Thr Asn Tyr
            20                  25                  30

Tyr Val His Trp Val Arg Gln Ala Pro Gly Gln Gly Leu Gln Leu Met
        35                  40                  45

Gly Trp Ile Asp Pro Ser Trp Gly Arg Thr Asn Tyr Ala Gln Asn Phe
    50                  55                  60

Gln Gly Arg Ile Thr Met Thr Arg Asp Thr Ser Thr Ser Thr Val Tyr
65                  70                  75                  80

Met Glu Met Arg Ser Leu Arg Ser Glu Asp Thr Ala Val Tyr Tyr Cys
            85                  90                  95

Ala Arg Asn Val Ala Thr Glu Gly Ser Leu Leu His Tyr Asp Tyr Trp
            100                 105                 110

Gly Gln Gly Thr Leu Val Thr Val Ser Ala
        115                 120

<210> SEQ ID NO 182
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Gln Val Gln Leu Val Gln Ser Gly Ala Glu Val Arg Lys Pro Gly Ala
1               5                   10                  15

Ser Val Thr Val Ser Cys Lys Ala Ser Gly Tyr Thr Phe Asn Asn Phe
            20                  25                  30

Tyr Val His Trp Val Arg Gln Ala Pro Gly Gln Gly Leu Glu Cys Met
        35                  40                  45

Gly Trp Ile Asp Pro Ser Val Gly Arg Ile Asn Tyr Ala Gln Lys Phe
    50                  55                  60

Gln Gly Arg Val Thr Met Thr Arg Asp Arg Ser Thr Ser Thr Val Tyr
65                  70                  75                  80

Met Gly Leu Ser Ser Leu Arg Ser Glu Asp Thr Ala Ile Tyr Tyr Cys
            85                  90                  95

Val Arg Asp Val Gly Thr Glu Gly Ser Leu Leu His Phe Asp His Trp
            100                 105                 110

Gly Gln Gly Thr Leu Val Ile Val Ser Ala
        115                 120

<210> SEQ ID NO 183
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Gln Val Gln Leu Val Gln Ser Gly Ala Ala Val Lys Arg Pro Gly Ala
1               5                   10                  15

Ser Val Thr Ile Ser Cys Arg Ala Ser Gly Tyr Thr Phe Thr Thr Tyr
                20                  25                  30

Tyr Ile His Trp Val Arg Gln Ala Pro Gly Gln Arg Leu Glu Leu Met
            35                  40                  45

Gly Met Ile Asp Pro Ser Arg Gly Arg Thr Asp Tyr Ala Gln Lys Phe
    50                  55                  60

Gln Gly Arg Val Thr Met Ser Arg Asp Thr Ser Thr Ser Thr Leu Tyr
65                  70                  75                  80

Met Glu Leu Arg Ser Leu Arg Pro Asp Thr Ala Leu Tyr Tyr Cys
                85                  90                  95

Val Arg Asn Val Gly Thr Glu Gly Ser Leu Leu His Tyr Asp Tyr Trp
                100                 105                 110

Gly Gln Gly Thr Leu Val Thr Val Ser Ser
            115                 120

<210> SEQ ID NO 184
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Gln Val Gln Leu Val Gln Ser Gly Ala Ala Val Lys Lys Pro Gly Ala
1               5                   10                  15

Ser Val Arg Val Ser Cys Lys Ala Ser Gly Tyr Thr Phe Thr Ser Ser
                20                  25                  30

His Ile His Trp Val Arg Gln Ala Pro Gly Gln Gly Pro Glu Trp Met
            35                  40                  45

Gly Met Ile Asp Pro Ser Val Gly Arg Pro Thr Thr Ala Gly Lys Phe
    50                  55                  60

Gln Gly Arg Val Thr Met Thr Arg Asp Arg Tyr Thr Ser Thr Ala Tyr
65                  70                  75                  80

Met Asp Leu Ser Ser Leu Arg Ser Glu Asp Thr Ala Val Tyr Tyr Cys
                85                  90                  95

Ala Arg Ser Val Glu Thr Thr Gly Ser Leu Leu Tyr Phe Asp Tyr Trp
                100                 105                 110

Gly Gln Gly Thr Leu Ile Thr Val Ser Ser
            115                 120

<210> SEQ ID NO 185
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Gln Val Gln Leu Val Gln Ser Gly Ala Ala Val Lys Arg Pro Gly Ala
1               5                   10                  15

Ser Val Thr Ile Ser Cys Arg Ala Ser Gly Tyr Thr Phe Thr Thr Tyr
            20                  25                  30

Tyr Ile His Trp Val Arg Gln Ala Pro Gly Gln Gly Leu Glu Leu Met
        35                  40                  45

Gly Trp Ile Asn Pro Arg Gly Gly Arg Thr Asp Tyr Ser Tyr Arg Phe
    50                  55                  60

Glu Asp Arg Val Ser Met Tyr Arg Asp Thr Ser Met Ser Ile Val Tyr
65                  70                  75                  80

Met Asp Leu Arg Asn Leu Lys Ser Ala Asp Thr Ala Val Tyr Tyr Cys
                85                  90                  95

Val Arg Asn Val Gly Thr Ser Gly Ser Leu Leu His Tyr Asp Phe Trp
            100                 105                 110

Gly Gln Gly Ser Leu Val Thr Val Ser Ser
        115                 120

<210> SEQ ID NO 186
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Gln Val Arg Leu Leu Gln Tyr Gly Gly Gly Val Lys Arg Pro Gly Ala
1               5                   10                  15

Ser Met Thr Ile Ser Cys Val Ala Ser Gly Tyr Asn Phe Asn Asp Tyr
            20                  25                  30

Tyr Ile His Trp Val Arg Gln Ala Pro Gly Gln Gly Leu Glu Leu Met
        35                  40                  45

Gly Trp Ile Asp Pro Ser Gly Gly Arg Thr Asp Tyr Ala Gly Ala Phe
    50                  55                  60

Gly Asp Arg Val Ser Met Tyr Arg Asp Lys Ser Met Asn Thr Leu Tyr
65                  70                  75                  80

Met Asp Leu Arg Ser Leu Arg Ser Gly Asp Thr Ala Met Tyr Tyr Cys
                85                  90                  95

Val Arg Asn Val Gly Thr Ala Gly Ser Leu Leu His Tyr Asp His Trp
            100                 105                 110

Gly Leu Gly Val Met Val Thr Val Ser Ser
        115                 120

<210> SEQ ID NO 187
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Gln Val Gln Leu Val Gln Ser Gly Ala Thr Val Lys Lys Pro Arg Ala
1               5                   10                  15

Ser Val Thr Leu Ser Cys Arg Thr Ser Gly Tyr Asn Phe Ile Asp Tyr
            20                  25                  30

Phe Ile His Trp Val Arg Arg Ala Pro Gly Gln Arg Leu Glu Val Met

```
            35                  40                  45
Gly Tyr Ile Asp Pro Ser Arg Gly Arg Pro Asp Tyr Ala Pro Asn Phe
        50                  55                  60

Arg Asp Arg Val Ser Leu Tyr Arg Asp Thr Ser Met Ser Ile Val Tyr
 65                  70                  75                  80

Leu Asp Leu Arg Asp Leu Thr Pro Asp Thr Ala Ile Tyr Tyr Cys
                85                  90                  95

Val Arg Ser Glu Gly Thr Glu Gly Thr Val Leu His Tyr Asp His Trp
                100                 105                 110

Gly Pro Gly Thr Arg Val Thr Val Ser Pro
                115                 120

<210> SEQ ID NO 188
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Gln Val Gln Leu Val Gln Ser Gly Gly Gly Val Lys Arg Pro Gly Ser
  1               5                  10                  15

Thr Thr Thr Ile Ser Cys Val Ala Ser Gly Tyr Ser Phe Asn Asp Tyr
                 20                  25                  30

Tyr Ile His Trp Val Arg Gln Ala Pro Gly Gln Gly Leu Glu Val Leu
            35                  40                  45

Gly Phe Ile Asp Pro Ser Asn Gly Arg Thr Asn Tyr Ala Gly Ala Phe
        50                  55                  60

Gly Asp Arg Phe Ser Met Tyr Arg Asp Lys Ser Met Glu Thr Leu Tyr
 65                  70                  75                  80

Met Asp Leu Arg Asn Leu Arg Ser Asp Thr Ala Met Tyr Tyr Cys
                85                  90                  95

Val Arg Asn Val Gly Thr Ala Gly Ser Leu Leu His Tyr Asp His Trp
                100                 105                 110

Gly Thr Gly Ser Lys Ile Ile Val Ser Ser
                115                 120

<210> SEQ ID NO 189
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Gln Val Gln Leu Val Gln Ser Gly Gly Thr Val Lys Ser Pro Gly Thr
  1               5                  10                  15

Ser Val Thr Leu Ser Cys Lys Thr Ser Gly Tyr Asn Phe Ile Asp Tyr
                 20                  25                  30

Tyr Ile His Trp Val Arg Arg Ala Pro Gly Gln Arg Pro Glu Leu Met
            35                  40                  45

Gly Tyr Ile Asp Pro Ser His Gly Arg Pro Asp Tyr Glu Gly Lys Phe
        50                  55                  60

Arg Asp Arg Ile Ser Leu Tyr Arg Asp Thr Ser Thr Ser Val Val Tyr
 65                  70                  75                  80

Met Asp Val Arg Gly Leu Arg Leu Asp Asp Thr Ala Leu Tyr Tyr Cys
```

85                  90                  95

Val Arg Gly Gly Gly Val Glu Val Ser Ser Asn His Tyr Asp His Trp
            100                 105                 110

Gly Pro Gly Thr Met Val Phe Val Ser Pro
        115                 120

<210> SEQ ID NO 190
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Gln Val Arg Leu Ala Gln Tyr Gly Gly Val Lys Arg Leu Gly Ala
1               5                   10                  15

Thr Met Thr Leu Ser Cys Val Ala Ser Gly Tyr Thr Phe Asn Asp Tyr
            20                  25                  30

Tyr Ile His Trp Val Arg Gln Ala Pro Gly Gln Gly Phe Glu Leu Leu
        35                  40                  45

Gly Tyr Ile Asp Pro Ala Asn Gly Arg Pro Tyr Ala Gly Ala Leu
    50                  55                  60

Arg Glu Arg Leu Ser Phe Tyr Arg Asp Lys Ser Met Glu Thr Leu Tyr
65                  70                  75                  80

Met Asp Leu Arg Ser Leu Arg Tyr Asp Thr Ala Met Tyr Tyr Cys
                85                  90                  95

Val Arg Asn Val Gly Thr Ala Gly Ser Leu Leu His Tyr Asp His Trp
            100                 105                 110

Gly Ser Gly Ser Pro Val Ile Val Ser Ser
        115                 120

<210> SEQ ID NO 191
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Trp Thr
                85                  90                  95

Phe Gly Gln Gly Thr Lys Val Glu Ile Lys
            100                 105

<210> SEQ ID NO 192
<211> LENGTH: 106
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 192

```
Glu Ile Val Leu Thr Gln Ser Pro Ala Thr Leu Ser Val Ser Pro Gly
1               5                   10                  15

Glu Arg Val Thr Leu Ser Cys Arg Ala Ser Gln Ser Val Arg Asn Asn
            20                  25                  30

Leu Ala Trp Tyr Arg Gln Lys Arg Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Met Gln Ser
65                  70                  75                  80

Glu Asp Phe Ala Val Tyr Tyr Cys Gln Gln Tyr Asn Asn Trp Trp Thr
                85                  90                  95

Phe Gly Gln Gly Thr Lys Val Glu Ile Lys
            100                 105
```

<210> SEQ ID NO 193
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

```
Glu Ile Val Leu Thr Gln Ser Pro Ala Thr Leu Ser Val Ser Pro Gly
1               5                   10                  15

Glu Arg Ala Thr Leu Ser Cys Arg Ala Thr Gln Ser Val Arg Ser Asn
            20                  25                  30

Leu Ala Trp Tyr Gln Gln Lys Arg Gly Gln Ala Pro Arg Leu Leu Ile
        35                  40                  45

Tyr Ser Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Val Gln Ser
65                  70                  75                  80

Glu Asp Phe Ala Val Tyr Tyr Cys Leu Gln Tyr Asn Asn Trp Trp Thr
                85                  90                  95

Phe Gly Gln Gly Thr Lys Val Glu Ile Lys
            100                 105
```

<210> SEQ ID NO 194
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Asn
            20                  25                  30

Ile Ala Trp Tyr Gln Gln Lys Pro Gly Gln Ala Pro Arg Leu Leu Ile
        35                  40                  45
```

His Gly Ala Ser Thr Arg Ala Thr Gly Ile Pro Arg Phe Ser Gly
            50                  55                  60

Ser Gly Ser Gly Pro Glu Phe Thr Leu Ala Ile Ser Ser Val Gln Ser
 65                  70                  75                  80

Glu Asp Phe Ala Val Tyr Tyr Cys Gln Gln Tyr Asn Asp Trp Trp Thr
                 85                  90                  95

Phe Gly Gln Gly Thr Lys Val Glu Ile Lys
            100                 105

<210> SEQ ID NO 195
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Glu Ile Val Leu Thr Gln Ser Pro Ala Thr Leu Ser Val Ser Pro Gly
 1               5                  10                  15

Glu Arg Ala Thr Leu Ser Cys Arg Ala Ser Gln Ser Val Arg Ser Asn
             20                  25                  30

Leu Ala Trp Tyr Gln Gln Arg Pro Gly Gln Ala Pro Arg Leu Leu Ile
         35                  40                  45

Tyr Gly Thr Ser Thr Arg Ala Thr Gly Val Pro Ala Arg Phe Ser Gly
     50                  55                  60

Arg Gly Ser Gly Thr Glu Phe Thr Leu Ala Ile Ser Ser Met Gln Ser
 65                  70                  75                  80

Glu Asp Phe Ala Val Tyr Leu Cys Leu Gln Tyr Asn Asn Trp Trp Thr
                 85                  90                  95

Phe Gly Gln Gly Thr Lys Val Glu Ile Lys
            100                 105

<210> SEQ ID NO 196
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Glu Ile Val Leu Thr Gln Ser Pro Ala Thr Leu Ser Val Ser Pro Gly
 1               5                  10                  15

Glu Arg Ala Thr Leu Ser Cys Arg Ala Thr Gln Ser Val Arg Ser Asn
             20                  25                  30

Val Ala Trp Tyr Gln Gln Lys Pro Gly Gln Ala Pro Arg Leu Leu Ile
         35                  40                  45

Tyr Ser Ala Ser Thr Arg Ala Thr Gly Ile Pro Ala Arg Phe Ser Gly
     50                  55                  60

Ser Gly Ser Gly Thr Glu Phe Thr Leu Thr Ile Ala Ser Met Gln Ser
 65                  70                  75                  80

Glu Asp Phe Ala Val Tyr Tyr Cys Leu Gln Tyr Asp Asp Trp Trp Thr
                 85                  90                  95

Phe Gly Gln Gly Thr Lys Val Glu Ile Lys
            100                 105

<210> SEQ ID NO 197

```
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Glu Ile Val Leu Thr Gln Ser Pro Ala Thr Leu Ser Ala Ser Pro Gly
1               5                   10                  15

Glu Arg Val Thr Leu Thr Cys Arg Ala Ser Arg Gly Val Arg Asn Asn
                20                  25                  30

Val Ala Trp Tyr Gln His Asn Val Gly Gln Ser Pro Arg Leu Leu Ile
            35                  40                  45

Tyr Asp Ala Ser Thr Arg Ala Pro Gly Ile Pro Ala Arg Phe Ser Gly
50                  55                  60

Ser Ala Ser Gly Thr Glu Phe Thr Leu Ala Ile Ser Ser Ile Gln Ser
65                  70                  75                  80

Glu Asp Phe Thr Leu Tyr Tyr Cys His Gln Tyr Asn Asn Trp Trp Thr
                85                  90                  95

Phe Gly Gln Gly Thr Arg Val Asp Ile Asn
                100                 105

<210> SEQ ID NO 198
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Glu Ile Val Leu Thr Gln Ser Pro Ala Thr Leu Ser Ala Ser Pro Gly
1               5                   10                  15

Glu Arg Val Thr Leu Thr Cys Arg Ala Ser Arg Ser Val Arg Asn Asn
                20                  25                  30

Val Ala Trp Tyr Gln His Lys Gly Gly Gln Ser Pro Arg Leu Leu Ile
            35                  40                  45

Tyr Asp Ala Ser Thr Arg Ala Ala Gly Val Pro Ala Arg Phe Ser Gly
50                  55                  60

Ser Ala Ser Gly Thr Glu Phe Thr Leu Ala Ile Ser Asn Leu Glu Ser
65                  70                  75                  80

Glu Asp Phe Thr Val Tyr Phe Cys Leu Gln Tyr Asn Asn Trp Trp Thr
                85                  90                  95

Phe Gly Gln Gly Thr Arg Val Asp Ile Lys
                100                 105

<210> SEQ ID NO 199
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Glu Ile Val Leu Thr Gln Ser Pro Asp Thr Leu Ser Ala Ser Pro Gly
1               5                   10                  15

Glu Arg Val Thr Leu Ser Cys Arg Ala Ser Gln Ser Val Gly Thr Lys
                20                  25                  30
```

Val Ala Trp Tyr Arg His Val Arg Gly Gln Pro Pro Arg Leu Leu Ile
 35                  40                  45

Tyr Gly Ala Ser Thr Arg Ala Ala Gly Ile Pro Ala Arg Phe Ser Gly
 50                  55                  60

Gly Gly Ser Gly Thr Asn Phe Thr Leu Ile Ile Asn Asn Phe Gln Ser
65                  70                  75                  80

Glu Asp Phe Ala Glu Tyr Leu Cys Gln Gln Tyr Lys Ser Trp Trp Thr
                 85                  90                  95

Phe Gly Gln Gly Thr Lys Val Asp Asn Lys
            100                 105

<210> SEQ ID NO 200
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Glu Thr Thr Leu Thr Gln Ser Pro Asp Thr Leu Ser Ala Ser Pro Gly
1               5                   10                  15

Glu Arg Val Thr Leu Ser Cys Arg Ala Ala Gln Ser Val Gly Ser Gln
                 20                  25                  30

Val Ala Trp Phe Arg His Ile Arg Gly Gln Pro Pro Arg Leu Leu Ile
 35                  40                  45

Ser Gly Ala Ser Thr Arg Ala Ala Gly Val Pro Ala Arg Phe Ser Gly
 50                  55                  60

Ser Gly Ser Gly Thr Asp Phe Thr Leu Thr Ile Ser Gly Met Gln Ser
65                  70                  75                  80

Glu Asp Phe Ala Glu Tyr Phe Cys Gln Gln Tyr His Met Trp Trp Thr
                 85                  90                  95

Phe Gly Gln Gly Thr Arg Val Asp Lys Asn
            100                 105

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
atggactgga cctggaggat                                            20

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
atggactgga cctggagcat                                            20

<210> SEQ ID NO 203
<211> LENGTH: 20
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 203
atggactgga cctggagaat                                                 20

<210> SEQ ID NO 204
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
ggttcctctt tgtggtggc                                                  19

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
atggactgga cctggagggt                                                 20

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
atggactgga tttggaggat                                                 20

<210> SEQ ID NO 207
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
aggttcctct tgtggtggc ag                                               22

<210> SEQ ID NO 208
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
atggacatac tttgttccac gctc                                            24

<210> SEQ ID NO 209
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
      primer

<400> SEQUENCE: 209
atggacacac tttgctccac gct                                            23

<210> SEQ ID NO 210
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
atggacacac tttgctacac actc                                           24

<210> SEQ ID NO 211
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
ggaaggtgtg cacgccgctg gtc                                            23

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
atggactgga cctggaggat                                                20

<210> SEQ ID NO 213
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
atggactgga cctggagcat                                                20

<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
atggactgga cctggagaat                                                20

<210> SEQ ID NO 215
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 215
ggttcctctt tgtggtggc                                           19

<210> SEQ ID NO 216
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
atggactgga cctggagggt                                          20

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
atggactgga tttggaggat                                          20

<210> SEQ ID NO 218
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
aggttcctct ttgtggtggc ag                                       22

<210> SEQ ID NO 219
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
atggacatac tttgttccac gctc                                     24

<210> SEQ ID NO 220
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
atggacacac tttgctccac gct                                      23

<210> SEQ ID NO 221
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 221
atggacacac tttgctacac actc                                          24

<210> SEQ ID NO 222
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
ggaaggtgtg cacgccgctg gtc                                           23

<210> SEQ ID NO 223
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
taaaaggtgt ccagtgt                                                  17

<210> SEQ ID NO 224
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
taagaggtgt ccagtgt                                                  17

<210> SEQ ID NO 225
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
tagaaggtgt ccagtgt                                                  17

<210> SEQ ID NO 226
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
tacaaggtgt ccagtgt                                                  17

<210> SEQ ID NO 227
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
```

```
ttaaaggtgt ccagtgt                                                   17

<210> SEQ ID NO 228
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
atgaaacatc tgtggttctt                                                20

<210> SEQ ID NO 229
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
ttctccaagg agtctgt                                                   17

<210> SEQ ID NO 230
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
ggaaggtgtg cacgccgctg gtc                                            23

<210> SEQ ID NO 231
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231 gctatttta aaggtgtcca gtgt                                            24

<210> SEQ ID NO 232
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
atgaaacacc tgtggttctt cc                                             22

<210> SEQ ID NO 233
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
```
atgaaacacc tgtggttctt                                                    20

<210> SEQ ID NO 234
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
atgaagcacc tgtggttctt                                                    20

<210> SEQ ID NO 235
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
cctccacagt gagagtctg                                                     19

<210> SEQ ID NO 236
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
atgtctgtct ccttcctcat c                                                  21

<210> SEQ ID NO 237
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
ggcagcagca acaggtgccc a                                                  21

<210> SEQ ID NO 238
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
ggaaggtgtg cacgccgctg gtc                                                23

<210> SEQ ID NO 239
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
gctcagctcc tggggct                                                       17

<210> SEQ ID NO 240
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
ggaarcccca gcdcagc                                                  17

<210> SEQ ID NO 241
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
ctsttsctyt ggatctctg                                                19

<210> SEQ ID NO 242
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
ctsctgctct gggytgc                                                  17

<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
gaggcagttc cagatttcaa                                               20

<210> SEQ ID NO 244
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
cctgggccca gtctgtg                                                  17

<210> SEQ ID NO 245
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
ctcctcasyc tcctcact                                                 18

<210> SEQ ID NO 246
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
ggcctcctat gwgctgac                                                 18

<210> SEQ ID NO 247
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
gttctgtggt ttcttctgag ctg                                           23

<210> SEQ ID NO 248
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
acagggtctc tctcccag                                                 18

<210> SEQ ID NO 249
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
acaggtctct gtgctctgc                                                19

<210> SEQ ID NO 250
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
ccctctcsca gsctgtg                                                  17

<210> SEQ ID NO 251
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
tcttgggcca attttatgc                                                19

```
<210> SEQ ID NO 252
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
attcycagrc tgtggtgac                                                   19

<210> SEQ ID NO 253
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
cagtggtcca ggcaggg                                                     17

<210> SEQ ID NO 254
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
aggccactgt cacagct                                                     17

<210> SEQ ID NO 255
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
ctgggttcca ggttccactg gtgaccaggt gcagctggtr cagtctggg                  49

<210> SEQ ID NO 256
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
ctgggttcca ggttccactg gtgaccagrg caccttgarg gagtctggtc c               51

<210> SEQ ID NO 257
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
ctgggttcca ggttccactg gtgacgaggt kcagctggtg gagtctggg                  49

<210> SEQ ID NO 258
```

-continued

```
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
ctgggttcca ggttccactg gtgaccaggt gcagctgcag gagtcgg                 47

<210> SEQ ID NO 259
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
ctgggttcca ggttccactg gtgacgargt gcagctggtg cagtctggag              50

<210> SEQ ID NO 260
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
ctgggttcca ggttccactg gtgaccaggt acagctgcag cagtcaggtc c            51

<210> SEQ ID NO 261
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
gggccgctgt gcccccagag gtgctctygg a                                  31

<210> SEQ ID NO 262
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
ctgggttcca ggttccactg gtgacgacat ccagwtgacc cagtctc                 47

<210> SEQ ID NO 263
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
ctgggttcca ggttccactg gtgacgatat tgtgatgacc cagwctccac              50

<210> SEQ ID NO 264
<211> LENGTH: 49
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
ctgggttcca ggttccactg gtgacgaaat tgtgttgacr cagtctcca                    49

<210> SEQ ID NO 265
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
ctgggttcca ggttccactg gtgacgacat cgtgatgacc cagtctc                      47

<210> SEQ ID NO 266
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
ctgggttcca ggttccactg gtgacgaaac gacactcacg cagtctc                      47

<210> SEQ ID NO 267
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
ctgggttcca ggttccactg gtgacgaaat tgtgctgacw cagtctcca                    49

<210> SEQ ID NO 268
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
ctgggttcca ggttccactg gtgacgacat tgtgctgacc cagtct                       46

<210> SEQ ID NO 269
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
gggaagatga agacagatgg t                                                  21

<210> SEQ ID NO 270
<211> LENGTH: 45
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 270
ctgggttcca ggttccactg gtgaccagtc tgtgytgack cagcc           45

<210> SEQ ID NO 271
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
ctgggttcca ggttccactg gtgaccagtc tgccctgact cagcc           45

<210> SEQ ID NO 272
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
ctgggttcca ggttccactg gtgactcyta tgagctgacw cagccac         47

<210> SEQ ID NO 273
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
ctgggttcca ggttccactg gtgactcttc tgagctgact caggaccc        48

<210> SEQ ID NO 274
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
ctgggttcca ggttccactg gtgaccagcy tgtgctgact caatc           45

<210> SEQ ID NO 275
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
ctgggttcca ggttccactg gtgacctgcc tgtgctgact cagc            44

<210> SEQ ID NO 276
<211> LENGTH: 45
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 276
ctgggttcca ggttccactg gtgaccagsc tgtgctgact cagcc                    45

<210> SEQ ID NO 277
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
ctgggttcca ggttccactg gtgacaattt tatgctgact cagccccact              50

<210> SEQ ID NO 278
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
ctgggttcca ggttccactg gtgaccagrc tgtggtgacy caggag                   46

<210> SEQ ID NO 279
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
ctgggttcca ggttccactg gtgaccaggc agggcwgact cag                      43

<210> SEQ ID NO 280
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
gggygggaac agagtgacc                                                 19

<210> SEQ ID NO 281
<211> LENGTH: 328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 281
gacatccaga tgacccagtc tccgtctttc ctgtacggct ctgtaggcga tagagtcacc    60
atcacttgcc gggcaagtca gaatattaag gactatttaa attggtatca gcagagacca   120
gggagagccc ctagactcct gatctatgct gcatccaatt tgcaaagtgg ggtcccgtca   180
aggttcagtg gcagtggata tgggacagac tttactctca tcatcagcag tctgcaacct   240

```
gaggactttg cgacttattt ctgtcaagag agttatagtt ctacgcccac acacattttt      300
ggcctgggga ccaaattgga gaagaaac                                          328
```

<210> SEQ ID NO 282
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (110)..(110)
<223> OTHER INFORMATION: Any amino acid

<400> SEQUENCE: 282

Asp Ile Gln Met Thr Gln Ser Pro Ser Phe Leu Tyr Gly Ser Val Gly
1               5                   10                  15

Asp Arg Val Thr Ile Thr Cys Arg Ala Ser Gln Asn Ile Lys Asp Tyr
            20                  25                  30

Leu Asn Trp Tyr Gln Gln Arg Pro Gly Arg Ala Pro Arg Leu Leu Ile
        35                  40                  45

Tyr Ala Ala Ser Asn Leu Gln Ser Gly Val Pro Ser Arg Phe Ser Gly
    50                  55                  60

Ser Gly Tyr Gly Thr Asp Phe Thr Leu Ile Ile Ser Ser Leu Gln Pro
65                  70                  75                  80

Glu Asp Phe Ala Thr Tyr Phe Cys Gln Glu Ser Tyr Ser Ser Thr Pro
                85                  90                  95

Thr His Ile Phe Gly Leu Gly Thr Lys Leu Glu Lys Lys Xaa
            100                 105                 110

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283

```
aggtgtgcac gccgctggtc                                                   20
```

<210> SEQ ID NO 284
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284

```
tcgtcggcag cgtcagatgt gtataagaga cagccatgga ctggacctgg agg              53
```

<210> SEQ ID NO 285
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285

```
gtctcgtggg ctcggagatg tgtataagag acagcgatgg gcccttggtg ga              52
```

```
<210> SEQ ID NO 286
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Glu Ile Asn Cys Thr Arg Pro Asn Asn Asn Thr Arg Pro Gly Glu Ile
1               5                   10                  15

Ile Gly Asp Ile Arg Gln Ala His Cys Asn Ile Ser Arg Ala
            20                  25                  30

<210> SEQ ID NO 287
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Cys Thr Thr Gly Gly Trp Ile Ser Leu Tyr Tyr Asp Ser Ser Tyr Tyr
1               5                   10                  15

Pro Asn Phe Asp His Trp
            20

<210> SEQ ID NO 288
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Cys Thr Ala Asp Leu Gly Glu Pro Val Val Ser Arg Phe Phe Glu Trp
1               5                   10                  15

Gly Ser Tyr Tyr Tyr Tyr Met Asp Leu Trp Gly
            20                  25

<210> SEQ ID NO 289
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Cys Thr Met Asp Glu Gly Thr Pro Val Thr Arg Phe Leu Glu Trp Gly
1               5                   10                  15

Tyr Phe Tyr Tyr Tyr Met Ala Val Trp Gly
            20                  25

<210> SEQ ID NO 290
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 290

Gly Phe Thr Phe Ser Asn Thr Trp
1               5

<210> SEQ ID NO 291
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Gly Phe Phe Phe Asp Asn Ser Trp
1               5

<210> SEQ ID NO 292
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Ile Ser Arg Asn Lys Asp Gly Ala Lys Thr
1               5                   10

<210> SEQ ID NO 293
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Ile Arg Arg Leu Lys Asp Gly Ala Thr Gly
1               5                   10

<210> SEQ ID NO 294
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Asp Asp Ser Arg
1

<210> SEQ ID NO 295
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Asp Asp Ser Arg
1
```

```
<210> SEQ ID NO 296
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Gly Gly Gly Gly Ser Gly Gly Gly Gly Ser Gly Gly Gly Gly Ser
1               5                   10                  15
```

HIV-1 NEUTRALIZING ANTIBODIES AND USES THEREOF (V3 ANTIBODIES)

This application is a U.S. National Stage application under 35 U.S.C. § 371 of International Patent Application No. PCT/US2016/023380, filed, Mar. 21, 2016, which claims the benefit of and priority to U.S. Application Ser. No. 62/191,054 filed Jul. 10, 2015, U.S. Application Ser. No. 62/222,175 filed Sep. 22, 2015, U.S. Application Ser. No. 62/261,233 filed Nov. 30, 2015, U.S. Application Ser. No. 62/135,309 filed Mar. 19, 2015, and U.S. Application 62/260,100 filed Nov. 25, 2015 the entire content of each application is herein incorporated by reference in its entirety.

GOVERNMENT SUPPORT

This invention was made with government support under Center for HIV/AIDS Vaccine Immunology-Immunogen Design grant UM1-AI100645 from the NIH, NIAID, Division of AIDS. The government has certain rights in the invention.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

All patents, patent applications and publications cited herein are hereby incorporated by reference in their entirety. The disclosure of these publications in their entireties are hereby incorporated by reference into this application in order to more fully describe the state of the art as known to those skilled therein as of the date of the invention described herein.

SEQUENCE LISTING

The instant application contains a Sequence Listing which has been filed electronically in ASCII format and is hereby incorporated by reference in its entirety. Said ASCII copy, created on Oct. 11, 2018, is named 1234300_00280US1_SL.txt and is 223,914 bytes in size.

FIELD OF THE INVENTION

The invention relates to the identification of monoclonal HIV-1 neutralizing antibodies, such as, but not limited to, antibodies that bind to the V3 region of HIV-1 Env glycoprotein, their recombinant expression and purification and uses.

BACKGROUND

It is well documented that essentially all HIV-1 infected individuals develop antibodies capable of binding HIV-1 envelope, but that only a small subset of these antibodies are neutralizing and capable of blocking viral entry in target cells. See e.g. Doria-Rose N. "HIV Neutralizing Antibodies: Clinical Correlates and Implications for Vaccines" The Journal of Infectious Diseases (2010) Volume 201, Issue 7 Pp. 981-983. Over the time of an infection, some individuals develop neutralizing antibodies, and with some of these neutralizing antibodies having activity against diverse primary HIV-1 isolates. A number of broad neutralizing monoclonal antibodies (mAbs) have been identified from HIV-1 infected individuals and these define specific regions on the virus envelope, e.g. CD4 binding site, V3 loop, membrane proximal region (MPER) of gp41, that are vulnerable to neutralizing Abs.

Broadly neutralizing HIV-1 antibodies have been identified only from natural HIV-1 infection. See e.g. Mascola and Haynes, Immunological Reviews (2013) Vol. 254:225-244. Some examples of broadly neutralizing antibodies (bnAbs) targeting CD4 binding site or V3 loop are VRC01, CH103, CH31, CH98, 8ANC131, PGT121, PGT128. Unfortunately, so far none of these antibodies have been developed for HIV prevention or treatment. Thus, the need exists for monoclonal broadly neutralizing antibodies that can be developed and used for prevention and treatment for an infectious agent, such as HIV.

SUMMARY OF THE INVENTION

In certain aspects the invention provides an antibody or fragment thereof with the binding specificity of V3 glycan binding antibody DH542 (e.g. FIG. 2B).

In certain aspects the invention provides an antibody or fragment thereof with the binding specificity of V3 glycan binding antibody DH542_QSA (e.g. FIG. 16).

In certain aspects the invention provides an antibody or fragment thereof with the binding specificity of V3 glycan binding antibody of Example 10. In a non-limiting example the antibody is DH542_L4 (e.g. FIG. 25).

In certain aspects the invention provides a V3 binding antibody wherein the antibody or fragment thereof comprises a VH chain that is 90%, 91%, 92%, 93%, 94%, 95%, 96%, 97%, 98%, 99% or 100% identical to the VH chain of an antibody from DH270 lineage (FIGS. 8, 20B) and a VL chain that is 90%, 91%, 92%, 93%, 94%, 95%, 96%, 97%, 98%, 99% or 100% identical to the VL chain of an antibody from DH270 lineage (FIGS. 8, 16).

In certain aspects the invention provides a V3 binding antibody wherein the antibody or fragment thereof comprises the VH chain of an antibody from DH270 lineage (FIGS. 8, 20B) and the VL chain of an antibody from DH270 lineage (FIGS. 8, 16).

In certain embodiments, the antibody or fragment thereof is fully human and recombinantly produced. In certain embodiments, some of the VH and VL chains are isolated from a human subject who have been naturally infected with HIV-1. In certain embodiments the antibody is not naturally occurring. In certain embodiments the antibody comprises the amino acids of naturally occurring pair of VH and VL chains. In certain embodiments the antibody comprises amino acids of naturally occurring pair of VH and VL chains wherein the Fc portion of the antibody is not the natural isotype or portion of the naturally occurring pair of VH and VL chains. In certain embodiments the antibody is computationally designed, for example based on some naturally isolated VH and VL sequences. In certain embodiments the antibody is computationally designed, e.g. UCA, Intermediates in the antibody lineages. In certain embodiments the antibody comprises a non-naturally occurring pairing of VH and VL chains, wherein the VH or VL individually could be isolated from a subject. In some embodiments, the antibody comprises VH chain or HCDRs of a VH chain of one clonal member, and VL or LCDRs of another clonal member, i.e., a non-naturally occurring antibody comprising sequences derived from natural pairs. In certain embodiments the antibody comprises naturally occurring VH and VL chains modified by substituting one or more amino acids.

In certain embodiments the antibody or fragment thereof is fully human.

In certain embodiments, the antibody or fragment thereof comprises a VH chain that is 90%, 91%, 92%, 93%, 94%, 95%, 96%, 97%, 98%, 99% or 100% identical to the VH chain of antibody DH542 or DH542_QSA, or any of the other lineage members. In certain embodiments, the antibody or fragment thereof comprises a VL chain that is 90%, 91%, 92%, 93%, 94%, 95%, 96%, 97%, 98%, 99% or 100% identical to the VL chain of antibody DH542, DH429 or DH542_QSA, or any of the other lineage members.

In certain embodiments, the antibody or fragment thereof comprises a VH which comprises the HCDR1, HCDR2, and HCDR3 of antibody DH542 or DH542_QSA. In certain embodiments, the antibody or fragment thereof comprises a VL which comprises the CDR1, CDR2, and CDR3 of antibody DH542 or DH542_QSA.

In certain embodiments, the antibody or fragment thereof comprises a VH which comprises the HCDR1, HCDR2, and HCDR3 of any of the V3 antibodies of the invention, including but not limited to antibody DH542, DH542_QSA, DH542-L4, or any of the antibodies listed in FIG. 25 and further comprises the complementary VL which comprises the LCDR1, LCDR2, LCDR3 of antibody DH542, DH542_QSA, DH542-L4, or any of the antibodies listed in FIG. 25. In certain embodiments, the antibody or fragment thereof comprises VH and VL of antibody DH542, DH429 or DH542_QSA.

In certain embodiments, the antibody is DH542. In other embodiments the antibody is DH542_L4. In other embodiments the antibody is DH542-QSA. Thus in certain embodiments, the invention provides at least three V3 antibodies wherein each antibody comprises VH sequence from DH542 (e.g. FIG. 8) and VL sequence which can be VL sequence from DH542, VL sequence which is a VL from 542-QSA, or VL sequence from DH429.

In certain aspects, the invention provides a pharmaceutical composition comprising anyone of the antibodies of the invention or fragments thereof or any combination thereof.

In certain aspects, the invention provides a pharmaceutical composition comprising anyone of the antibodies of the invention, or a combination thereof.

In certain embodiments, the composition comprises an antibody or a fragment thereof which is recombinantly produced in CHO cells.

In certain aspects, the invention provides a pharmaceutical composition comprising a vector comprising a nucleic acid encoding anyone of inventive antibodies or fragments. In certain embodiments, the nucleic acids are optimized for expression in human host cells. In other embodiments, the nucleic acids are optimized for recombinant expression in a suitable host cell. In certain embodiments, the vector is suitable for gene delivery and expression. Non-limiting examples of such vectors include adenoviral vectors (Ads), adeno associated virus based vectors (AAVs), or a combination thereof. In certain aspects, the invention provides isolated cells comprising vectors and/or nucleic acids for expression of the inventive antibodies and fragments thereof. In certain aspects, the invention provides compositions of cells comprising vectors and/or nucleic acids for expression of the inventive antibodies and fragments thereof.

In certain embodiments, the compositions further comprise an additional antibody or fragment thereof. In certain embodiments, the compositions further comprise an antibody or a fragment thereof comprising CDR1, 2, and/or 3 of the VH and VL chains, or the VH and VL chains of antibody DH540. In certain embodiments, the compositions further comprise an antibody or a fragment thereof comprising CDR1, 2, and/or 3 of the VH and VL chains, or the VH and VL chains of antibody DH512.

In certain embodiments, the compositions further comprise an antibody or a fragment thereof comprising VH and VL chain of antibody DH429 or DH270IA1.

In certain embodiments the invention provides a composition which further comprises another therapeutic antibody with a different binding specificity. In certain embodiments, the invention provides an antibody or fragment thereof with the binding specificity of CD4 binding site antibody DH491 or CH493, or CH558, or CH557. In certain embodiments, the invention provides an antibody or fragment with the binding specificity of an MPER antibody.

In certain embodiments, the antibody or fragment thereof comprises a VH chain that is 90%, 91%, 92%, 93%, 94%, 95%, 96%, 97%, 98%, 99% or 100% identical to the VH chain of antibody CH557, or any of the other lineage members. In certain embodiments, the antibody or fragment thereof comprises a VL chain that is 90%, 91%, 92%, 93%, 94%, 95%, 96%, 97%, 98%, 99% or 100% identical to the VL chain of antibody CH557, or any of the other lineage members.

In certain embodiments, the antibody or fragment thereof comprises a VH chain that is 90%, 91%, 92%, 93%, 94%, 95%, 96%, 97%, 98%, 99% or 100% identical to the VH chain of antibody DH511, DH512, DH513, DH514, DH515, DH516, DH517, DH518, DH536, DH537, CH491 or CH493 and further comprises a VL chain that is 90%, 91%, 92%, 93%, 94%, 95%, 96%, 97%, 98%, 99% or 100% identical to the VL chain of antibody DH511, DH512, DH513, DH514, DH515, DH516, DH517, DH518, DH536, DH537, CH491 or CH493.

In certain embodiments, the antibody or fragment thereof comprises VH and VL of antibody CH557. In certain embodiments, the antibody or fragment thereof comprises a VH which comprises the HCDR1, HCDR2, and HCDR3 of antibody CH557. In certain embodiments, the antibody or fragment thereof comprises a VL which comprises the LCDR1, LCDR2, and LCDR3 of antibody CH557. In certain embodiments, the antibody or fragment thereof comprises a VH which comprises the HCDR3 of CH557 and further comprises a VL which comprises the LCDR3 of CH557.

In certain embodiments, the antibody or fragment thereof comprises a VH which comprises the HCDR1, HCDR2, and HCDR3 of antibody DH512, DH512-K3, or a modified variant of DH512 VH. In certain embodiments, the antibody or fragment thereof comprises a VL which comprises the LCDR1, LCDR2, and LCDR3 of antibody DH512 or DH512-K3. See U.S. Application 62/260,100 filed Nov. 25, 2015 incorporating by reference the sequences of the various NITER antibodies.

In certain embodiments, the antibody or antigen binding fragment can include an Fc domain that has been modified compared to a native Fc domain. In non-limiting embodiments, the Fc domain can be modified by amino acid substitution to increase binding to the neonatal Fc receptor and therefore the half-life of the antibody when administered to a subject.

In certain embodiments, the invention provides antibodies or fragments comprising a CDR(s) of the VH and/or VL chains, or VH and/or VL chains of the inventive antibodies, as the HIV-1 binding arm(s) of a bispecific molecules, e.g. but not limited to DARTS, diabodies, toxin labeled HIV-1 binding molecules.

In certain aspects the invention provides methods to treat or prevent HIV-1 infection in a subject comprising administering to the subject a pharmaceutical composition comprising any one of the inventive antibodies or fragments thereof in a therapeutically effective amount. The methods of the invention contemplate combination therapeutic methods, including but not limited to administering combinations of various antibodies or fragments thereof.

In certain embodiments of the methods, the pharmaceutical compositions are administered in a therapeutically effective dose and regimen.

BRIEF DESCRIPTION OF THE DRAWINGS

To conform to the requirements for PCT patent applications, many of the figures presented herein are black and white representations of images originally created in color.

FIG. 2A shows the gene information of DH542 and FIG. 2B shows DH542 sequences (CDRs are bolded and underlined) (SEQ ID NOs: 1-4). FIG. 2A discloses SEQ ID NO: 287.

FIGS. 4A-4D show DH542 neutralization data. FIG. 4A shows that DH542 neutralizes 71% of HIV-1 pseudoviruses tested in the TZM-bl assay. FIG. 4B shows neutralization of a panel of 24 viruses. FIGS. 4C and 4D show summary of neutralization data from TZM-bl assay.

FIG. 6 is summarized data showing that DH542 is not autoreactive by Athena ANA panel. Results are expressed as relative luminescence units. Readings <100 are considered negative, results between 100 and 120 are considered "indeterminate" and results >120 are considered positive.

FIG. 7 shows that DH542 binds HEp2 cells as demonstrated by intracellular fluorescence staining—left panel shows DH542/293i 50 ug/mL 40× obj 8 sec (2+), right panel shows DH542/293i 25 ug/mL 40× obj 8 sec (1+).

FIG. 9 shows Neutralizing Breadth and Potency of various HIV-1 BnAbs that are candidates for being combined with the inventive antibodies or other antibodies in FIG. 4 for a potent mixture of bnAbs. DH270IA1 is I1 in the DH270 lineage (See FIG. 8).

FIG. 10 shows Neutralizing Breadth and Potency of some candidate bnAbs for single or combination use.

FIG. 11 shows a clonal tree that was estimated using both the heavy and light chains of the listed lineage members.

FIG. 12A shows nucleic acid sequences of antibodies DH511-518, DH537 and 538 (SEQ ID NOs:53-72). FIG. 12B shows amino acid sequences of antibodies DH511-518, DH537 and 538 (SEQ ID NOs:73-93).

FIGS. 13A-13D show non-limiting examples of mutations in the VH chain of DH511 and DH512, and non-limiting examples of sequences including mutations in DH512 VH chain. FIG. 13A shows positions in the VHCDR3 chain of DH511 (SEQ ID NO: 288) which could be mutated. Amino acid positions refer to Kabat numbering. Most mutations are to changes to W, but F, L, or possibly other substitutions can also be tried. FIG. 13B shows positions in the VHCDR3 chain of DH512 (SEQ ID NO: 289) which could be mutated. Amino acid positions refer to Kabat numbering for the DH512VH chain: QVQLVQSGGGLVK-PGGSLTLSCSASGFFFDNSWMGWVRQAPGKGLEWV-GRIRRLKDGATGEYGAAVKDRFTISRDDSRNMLYLH-MRTLKTEDSGTYYCTMDEGTPVTRFLEWGYFYYY-MAVWGRGTTVIVSS(SEQ ID NO: 94). Most mutations are to changes to W, but F, L, or possibly other substitutions can also be tried. For both DH511 and DH512 position V100 can be changed to I. Position L100d can be changed to F. For both DH511 and DH512 combination mutations in the DH512 or DH511 VHCDR3 could include VH_L100dF together with T100aW; VH_L100dW together with T100aW. FIG. 13C shows positions outside of VHCDR3 which could be mutated. Most mutations are to changes to W, but F, L or possibly other substitutions can also be tried. FIG. 13C discloses SEQ ID NOS 290-295, respectively, in order of appearance. FIG. 13D shows amino acid sequences of some of the DH512 mutants from FIG. 31 (SEQ ID NOs: 95-112).

FIG. 14A shows summary results of neutralization data of DH542_L4, DH542, PGT128, PGT 121, 10-1074, DH270 and DH471 against a panel of HIV-1 isolates in the Luc/TZM-bl neutralization assay. Values represent IC50 in µg/ml. FIG. 14B shows the mean IC50 and percent of isolates neutralized at different IC50 values. Median and Geometric Mean titers are calculated only for samples with IC50 <50 ug/ml. Values less than the lowest concentration assayed were assigned a value 2-fold less for calculation purposes. Indicated in italics.

FIG. 15A shows summary results of neutralization data of DH542_L4, DH542, PGT128, PGT 121, 10-1074, DH270 and DH471 against a panel of HIV-1 isolates in the Luc/TZM-bl neutralization assay. Values represent IC80 in µg/ml. FIG. 15B shows the mean IC80 and percent of isolates neutralized at different IC80 <50 ug/ml values. Median and Geometric Mean titers are calculated only for samples with IC80 <50 ug/ml. Values less than the lowest concentration assayed were assigned a value 2-fold less for calculation purposes. Indicated in italics.

FIG. 16 shows DH542_QSA sequences (SEQ ID NO:113-116). DH542_QSA is a variant of DH542. The heavy chain is identical to that of DH542. The light chain has some variation in the N-terminus.

FIG. 17A shows an alignment of amino acid and FIG. 17B shows an alignment of nucleic acid sequences of VH and VL chains for antibodies from the DH270 lineage. CDRs are highlighted and underlined in the UCA. The FIG. 17A shows SEQ ID NOs:117-126 (Heavy chain nucleotide sequences in order of appearance from UCA-DH270), SEQ ID NOs:127-136 (Heavy chain amino acid sequences in order of appearance from UCA-DH270). FIG. 17B shows SEQ ID NOs: 137-146 (Light chain nucleotide sequences in order of appearance from UCA-DH270), SEQ ID NOs:147-156 (Light chain amino acid sequences in order of appearance from UCA-DH270H)

FIG. 18 shows neutralization by antibodies DH272, DH272_UCA, DH391 and DH542 identified from subject CH848 and DH563 identified from subject CH0765 measured in TZM-bl cells. Pseudoviruses were produced by transfection in 293T cells. Values are the antibody concentration (µg/ml) at which relative luminescence units (RLUs) were reduced 50% compared to virus control wells (no test sample). Values in bold are considered positive for neutralizing antibody activity. DH542 IC50 neutralization summary:mean IC50=0.21 µg/ml; geometric mean =0.08 µg/ml; median IC50=0.06 µg/ml.

FIG. 20A shows sequences of VH chains identified from CH0848 donor by Illumina deep sequencing (SEQ ID NOs: 157-166). No natural VL sequence pairing was identified for these VH sequences. FIG. 20B shows an alignment of the sequences in FIG. 20A (SEQ ID NOS 162-166, respectively, in order of appearance).

FIG. 21 shows sequences of CH557 (SEQ ID NOs:167-170). CDRs are bolded and underlined.

FIG. 22 shows a sequence alignment of the CD540-VRC40 antibodies, listing the heavy and light chain variable region sequences, Kabat and IMGT CDR and framework regions, and Kabat numbering. The heavy (SEQ ID NOs: 171-174) and light (SEQ ID NOs:175-178) chain variable region sequences of the CH540-VRC40.01, CH540-VRC40.02, CH540-VRC40.03, CH540-VRC40.04 are shown.

FIG. 24 shows amino acid alignment of CH235 lineage antibody light chain (SEQ ID NOs:191-200, in order of appearance from UCA LC to CH556_LC). Antibodies are listed in ascending order of somatic mutations and compared to the inferred unmutated common ancestor previously published (Gao, Bonsignori, Liao et al. Cell 2014)

FIG. 25 shows the names and VH:VLcomposition of chimeric antibodies of Example 10. Sequences for these antibodies are shown in FIGS. 8, 16 and 17.

FIGS. 26A and 26B show a summary of neutralization data for the chimeric antibodies of Example 10. Viruses used in this TZMB1 assay are described in the side line of the table in FIGS. 26A and 26B. Antibodies are shown in the top line of the table.

FIG. 29 shows $V_H$ and VL mutation frequencies of the isolated antibodies.

FIG. 30 shows Neutralization of wild-type and N332 mutated HIV-1 strains AC13.8, PVO4, TRO.11, AC10.0.29 and RHPA confirmed DH270 lineage N332 sensitivity of neutralization.

DETAILED DESCRIPTION

Figure 1A:
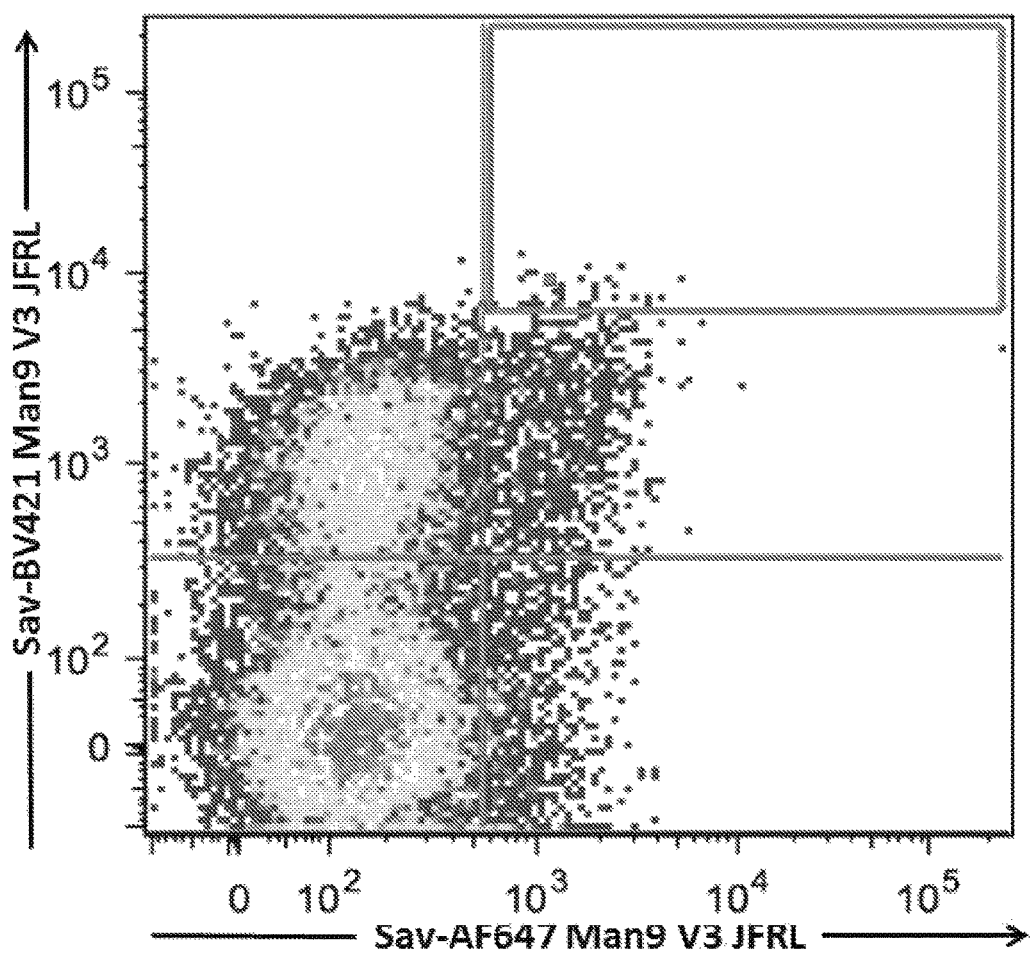
FIG. 1A shows index sorting of B cell that produced DH542 antibody.

Broadly neutralizing and potent HIV-1 envelope glycoprotein (Env) antibodies are now being developed for both prevention of HIV-1 (Rudicell R S et al. J. Virol 88:12669,-82, 2014) and for treatment of HIV-1 infected individuals (Barouch D H, et al. Nature 503:224-8, 2013; Shingai M et al. Nature 503:277-80, 2013). Thus, human recombinant antibodies either alone or in combinations have great prophylactic and therapeutic potential for the prevention and treatment of HIV-1 infection. Moreover, antibodies that bind with high affinity to Env may be useful in eliminating the latent pool of HIV-1 —infected CD4 T cells and curing HIV-1 infection, when either used to sensitize HIV-1 expressing target cells with bispecific bnAbs for NK or CD8 T cell killing or when bnAbs are conjugated with toxins or radionucleotides.

In certain aspects the invention provides fully human antibodies and fragments that specifically bind to and potently neutralize various isolates of HIV-1. In some embodiments, the antibodies bind to HIV-1 env V3 glycan. In some embodiments, the antibodies of the invention are combined in compositions with antibodies to HIV-1 gp120 Env CD4 binding site and/or MPER antibodies.

In certain aspects the invention provides pharmaceutical compositions including these human antibodies and a pharmaceutically acceptable carrier. In certain aspects the invention provides antibodies for passive immunization against HIV/AIDS. Nucleic acids encoding these antibodies, expression cassettes and vectors including these nucleic acids, and isolated cells that express the nucleic acids which encode the antibodies of the invention are also provided.

In some embodiments, the invention provides antibodies which are clonal variants. In some embodiments, clonal variants are sequences that differ by one or more nucleotides or amino acids, and have a V region with shared mutations compared to the germline, identical VHDJH or VJH gene usage, identical or similar HCDR3 length, and the same VL and JL usage. The germline sequence (unmutated common ancestor "UCA") is intended to be the sequence coding for the antibody/immunoglobulin (or of any fragment thereof) deprived of mutations, for example somatic mutations. Antibodies in a clone that are designated as UCA and/or I (for "Intermediate") are typically not identified from a biological sample, but are derived computationally based on VH and/or VL sequences isolated from subjects infected with HIV-1.

Compositions including the human antibodies of the invention, including V3 glycan and CD4 binding site antibodies, can be used for any purpose including but not limited to research, diagnostic and therapeutic purposes. In non-limiting embodiments, the human monoclonal antibodies disclosed herein can be used to detect HIV-1 in a biological sample or interfere with the HIV-1 activity, for example to diagnose or treat a subject having an HIV-1 infection and/or AIDS. For example, the antibodies can be used to determine HIV-1 titer in a subject. The antibodies disclosed herein also can be used to study the biology of the human immunodeficiency virus. The antibodies of the invention can be used for therapeutic purposes for treatment or prevention of HIV-1 infection, alone or in combination with other therapeutic modalities, including ART and/or combination with other HIV-1 targeting antibodies, neutralizing antibodies and/or ADCC inducing antibodies.

In some embodiments, the antibodies of the invention are expected not to exhibit self-reactivity—they do not bind or bind very weakly to self-antigens, such as human protein. For example, the antibodies of clone DH511 are not self-reactive although their UCA and some IAs are polyreactive. For use as preventive or therapeutic agents, what matters is whether the mature antibody will be polyreactive or not, and for example DH542 is not. DH270IA1 does not show self-reactivity, while DH491 and DH493 antibodies are polyreactive to varying degrees. Broadly neutralizing antibody CH557 displays exceptional neutralization breadth and high potency and it is not autoreactive nor polyreactive as determined by lack of binding to known human antigens associated with autoimmune disorders), negativity in Hep-2 cells IF staining and lack of binding to an array of 9,400 human antigens, including UBE3A and STUB-1 proteins, known to be bound by previously described broadly neutralizing antibodies targeting the CD4bs of gp120 Env (Liu et al J Virol 2014, Bonsignori et al JCI 2014).

The neutralization breadth of the inventive antibodies is demonstrated by the diversity of viruses which are neutralized in the TZMbl Env pseudovirus inhibition assay. In certain embodiments, the neutralization breadth and/or binding of the antibodies of the invention can be maintained in the presence of tolerate changes to the epitope. Comparing the sequences of the neutralized viruses, versus viruses that are not neutralized, a skilled artisan can readily determine the % virus changes, including changes in the epitope, which can be tolerated while neutralization and/or binding is maintained.

Comparing the sequences of the antibodies and their neutralization properties, a skilled artisan can readily determine sequence identity, compare sequence length and determine the % sequence identity and/or changes, including % sequence identity and/or changes in the VH and VL sequences, including % sequence identity and/or changes in the CDRs, as well as the specific positions and types of substitutions which can be tolerated while neutralization potency and breadth is maintained.

Various algorithms for sequence alignment are known in the art. The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in:Smith and Waterman, Adv. Appl. Math. 2:482, 1981; Needleman and Wunsch, J. Mol. Biol. 48:443, 1970; Pearson and Lipman, Proc. Natl. Acad. Sci. U.S.A. 85:2444, 1988; Higgins and Sharp, Gene 73:237, 1988; Higgins and Sharp, CABIOS 5:151, 1989; Corpet et al., Nucleic Acids Research 16:10881, 1988; and Pearson and Lipman, Proc. Natl. Acad. Sci. U.S.A. 85:2444, 1988. Altschul et al., Nature Genet. 6:119, 1994, presents a detailed consideration of sequence alignment methods and homology calculations.

The NCBI Basic Local Alignment Search Tool (BLAST) (Altschul et al., J. Mol. Biol. 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a VL or a VH of an antibody that specifically binds a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

In certain embodiments, the invention provides antibodies which are 99%, 98%, 97%, 96%, 95%, 94%, 93%, 92%, 91%, 90%, 89%, 88%, 87%, 86%, 85%, 84%, 83%, 82%, 81%, 80% identical to the VH and VL amino acid sequences of the antibodies described herein and still maintain the neutralization breadth, biding and/or potency. In certain embodiments, the invention provides antibodies which are 99%, 98%, 97%, 96%, 95%, 94%, 93%, 92%, 91%, 90%, 89%, 88%, 87%, 86%, 85%, 84%, 83%, 82%, 81%, 80% identical to the CDR1, 2, and/or 3 of VH and CDR1, 2, and/or 3 VL amino acid sequences of the antibodies described herein and still maintain the neutralization breadth, biding and/or potency.

In certain embodiments, the invention provides antibodies which can tolerate a larger percent variation in the sequences outside of the VH and/VL sequences of the antibodies. In certain embodiments, the invention provides antibodies which are 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65% identical, wherein the identity is outside of the VH or VL regions, or the CDRs of the VH or VL chains of the antibodies described herein.

Antibodies of the invention are expected to have the same binding specificity, for example as intact immunoglobulins and antigen binding variants or fragments e.g. as a number of well characterized fragments produced by digestion with various peptidases. For instance and without limitation, Fabs, Fvs, scFvs are fragments which are expected to have the same binding specificities as intact antibodies. Binding specificity can be determined by any suitable assay in the art, for example but not limited competition binding assays, epitope mapping, etc. Assays to determine glycan dependence and glycan specificity binding are also known in the art. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. Provided are also genetically engineered forms such as chimeric antibodies and heteroconjugate antibodies such as bispecific antibodies. See also, Pierce Catalog and Handbook, 1994-1995 (Pierce Chemical Co., Rockford, Ill.); Kuby, Immunology, 3. sup.rd Ed., W.H. Freeman & Co., New York, 1997.

In certain embodiments the invention provides antibody fragments, which have the binding specificity and/or properties of the inventive antibodies. Non-limiting examples include:(1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab').sub.2, the fragment of the antibody obtained by treating whole antibody with the enzyme pepsin without subsequent reduction; (4) F(ab').sub.2, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. In certain embodiments, the antibody fragments can be produces recombinantly.

In certain embodiments, VH refers to the variable region of an immunoglobulin heavy chain, including but not limited to that of an antibody fragment, such as Fv, scFv, dsFv or Fab. In certain embodiments, VL refers to the variable region of an immunoglobulin light chain, including but not limited to that of an Fv, scFv, dsFv or Fab.

Any of the nucleic acids encoding any of the antibodies, or fragment thereof can be expressed in a recombinantly engineered cell such as bacteria, plant, yeast, insect and mammalian cells. The nucleic acid sequences include any sequence necessary for expression, including but not limited to a promoter, a leader sequence. These antibodies can be expressed as individual VH and/or VL chain, or can be expressed as a fusion protein. In certain embodiments, the antibodies can be expressed by viral vector mediated delivery of genes encoding the antibodies of the invention (See e.g. Yang et al. Viruses 2014, 6, 428-447).

To create a single chain antibody, (scFv) the VH- and VL-encoding DNA fragments are operatively linked to another fragment encoding a flexible linker, e.g., encoding the amino acid sequence $(GLY_4-Ser)_3$ (SEQ ID NO: 296), such that the VH and VL sequences can be expressed as a contiguous single-chain protein, with the VH and VL domains joined by the flexible linker (see, e.g., Bird et al., Science 242:423-426, 1988; Huston et al., Proc. Natl. Acad. Sci. USA 85:5879-5883, 1988; McCafferty et al., Nature 348:552-554, 1990). Optionally, a cleavage site can be included in a linker, such as a furin cleavage site.

In some embodiments, a single chain antibody may be monovalent, if only a single VH and VL are used, bivalent, if two VH and VL are used, or polyvalent, if more than two VH and VL are used. Bispecific or polyvalent antibodies may be generated that bind specifically to different epitopes within the envelope. Bispecific or polyvalent antibodies may be generated that bind specifically to different epitopes within the envelope, and/or to another molecule.

There are numerous expression systems available for expression of proteins including *E. coli*, other bacterial hosts, yeast, and various higher eukaryotic cells such as the COS, CHO, HeLa and myeloma cell lines.

In certain embodiments, the invention provides monoclonal antibodies. In certain embodiments the monoclonal antibodies are produced by a clone of B-lymphocytes. In certain embodiments the monoclonal antibody is a recombinant antibody or fragment thereof and is produced by a host cell into which the light and heavy chain genes of a single antibody have been transfected. Any suitable cell could be used for transfection and expression of the antibodies of the invention. Suitable cell lines include without limitation 293T cells or CHO cells.

Monoclonal antibodies are produced by any suitable method known to those of skill in the art. In some embodiments, monoclonal antibodies are produced by immortalizing B-cell expressing an antibody. Methods for immortalizing B-cells are known in the art, for example but not limited to using EBV transformation, treatment with various stimulants, and/or apoptotic inhibitors (Bonsignori et al. J. Virol. 85:9998-10009, 2011). In some embodiments, monoclonal antibodies are produced by making hybrid antibody-forming cells from a fusion of myeloma cells with immune spleen cells to make hybridomas. In some embodiments monoclonal antibodies are identified from a subject, for example but not limited as described in Example 1 (Liao HX et al. J Virol Methods. 2009 June; 158(1-2):171-9). The amino acid and nucleic acid sequences of such monoclonal antibodies can be determined.

The antibodies described herein, or fragments thereof, may be recombinantly produced in prokaryotic or eukaryotic expression systems. These systems are well described in the art. In general, protein therapeutics are produced from mammalian cells. The most widely used host mammalian cells are Chinese hamster ovary (CHO) cells and mouse myeloma cells, including NSO and Sp2/0 cells. Two derivatives of the CHO cell line, CHO-K1 and CHO pro-3, gave rise to the two most commonly used cell lines in large scale production, DUKX-X11 and DG44. (See, e.g., Kim, J., et al., "CHO cells in biotechnology for production of recombinant proteins:current state and further potential," *Appl. Microbiol. Biotechnol.*, 2012, 93:917-30, which is hereby incorporated-by-reference.) Other mammalian cell lines for recombinant antibody expression include, but are not limited to, COS, HeLa, HEK293T, U2OS, A549, HT1080, CAD, P19, NIH 3T3, L929, N2a, HEK 293, MCF-7, Y79, SO-Rb50, HepG2, J558L, and BHK. If the aim is large-scale production, the most currently used cells for this application are CHO cells. Guidelines to cell engineering for mAbs production were also reported. (Costa et al., "Guidelines to cell engineering for monoclonal antibody production," *Eur J Pharm Biopharm*, 2010, 74:127-38, which is hereby incorporated-by-reference.) Using heterologous promoters, enhancers and amplifiable genetic markers, the yields of antibody and antibody fragments can be increased. Thus, in certain embodiments, the invention provides an antibody, or antibody fragment, that is recombinantly produced from a mammalian cell-line, including a CHO cell-line. In certain embodiments, the invention provides a composition comprising an antibody, or antibody fragment, wherein the antibody or antibody fragment was recombinantly produced in a mammalian cell-line, and wherein the antibody or antibody fragment is present in the composition at a concentration of at least 1, 10, 100, 1000 micrograms/mL, or at a concentration of at least 1, 2, 3, 4, 5, 6, 7, 8, 9, 10, 20, 50, or 100 milligrams/mL.

Furthermore, large-scale production of therapeutic-grade antibodies are much different than those for laboratory scale. There are extreme purity requirements for therapeutic-grade. Large-scale production of therapeutic-grade antibodies requires multiples steps, including product recovery for cell-culture harvest (removal of cells and cell debris), one or more chromatography steps for antibody purification, and formulation (often by tangential filtration). Because mammalian cell culture and purification steps can introduce antibody variants that are unique to the recombinant production process (i.e., antibody aggregates, N- and C-terminal variants, acidic variants, basic variants, different glycosylation profiles), there are recognized approaches in the art for analyzing and controlling these variants. (See, Fahrner, et al., Industrial purification of pharmaceutical antibodies: Development, operation, and validation of chromatography processes, *Biotech. Gen. Eng. Rev.*, 2001, 18:301-327, which is hereby incorporated-by-reference.) In certain embodiments of the invention, the antibody composition comprises less than 1, 2, 3, 4, 5, 10, 15, 20, 25, 30, 35, 50, or 100 nanograms of host cell protein (i.e., proteins from the cell-line used to recombinantly produce the antibody)). In other embodiments, the antibody composition comprises less than 1, 2, 3, 4, 5, 6, 7, 8, 9, 10, 15, 20, or 25 ng of protein A per milligram of antibody or antibody fragment (i.e., protein A is a standard approach for purifying antibodies from recombinant cell culture, but steps should be done to limit the amount of protein A in the composition, as it may be immunogenic). (See, e.g., U.S. Pat. No. 7,458,704, Reduced protein A leaching during protein A affinity chromatography; which is hereby incorporated-by-reference.)

The antibodies of the invention can be of any isotype. In certain embodiments, the antibodies of the invention can be used as IgG1, IgG2, IgG3, IgG4, whole IgG1 or IgG3s, whole monomeric IgAs, dimeric IgAs, secretory IgAs, IgMs as monomeric, pentameric or other polymer forms of IgM. The class of an antibody comprising the VH and VL chains described herein can be specifically switched to a different class of antibody by methods known in the art.

In some embodiments, the nucleic acid encoding the VH and VL can encode an Fc domain (immunoadhesin). The Fc domain can be an IgA, IgM or IgG Fc domain. The Fc domain can be an optimized Fc domain, as described in U.S. Published Patent Application No. 20100093979, incorporated herein by reference. In one example, the immunoadhesin is an IgG1 Fc. In one example, the immunoadhesin is an IgG3 Fc.

In certain embodiments the antibodies comprise amino acid alterations, or combinations thereof, for example in the Fc region outside of epitope binding, which alterations can improve their properties. Various Fc modifications are known in the art. Amino acid numbering is according to the EU Index in Kabat. In some embodiments, the invention contemplates antibodies comprising mutations that affect neonatal Fc receptor (FcRn) binding, antibody half-life, and localization and persistence of antibodies at mucosal sites. See e.g. Ko SY et al., Nature 514:642-45, 2014, at FIG. 1a and citations therein; Kuo, T. and and Averson, V., mAbs 3(5):422-430, 2011, at Table 1, US Pub 20110081347 (an aspartic acid at Kabat residue 288 and/or a lysine at Kabat residue 435), US Pub 20150152183 for various Fc region mutation, incorporated by reference in their entirety. In certain embodiments, the antibodies comprise AAAA substitution in and around the Fc region of the antibody that has been reported to enhance ADCC via NK cells (AAA mutations) containing the Fc region aa of S298A as well as E333A and K334A (Shields R I et al JBC , 276:6591-6604, 2001) and the $4^{th}$ A (N434A) is to enhance FcR neonatal mediated transport of the IgG to mucosal sites (Shields R I et al. ibid). Other antibody mutations have been reported to improve antibody half-life or function or both and can be incorporated in sequences of the antibodies. These include the DLE set of mutations (Romain G, et al. Blood 124:3241, 2014), the LS mutations M428L/N434S, alone or in a combination with other Fc region mutations, (Ko S Y et al. Nature 514:642-45, 2014, at FIG. 1a and citations therein; Zlevsky et al., Nature Biotechnology, 28(2):157-159, 2010; US Pub 20150152183); the YTE Fc mutations (Robbie G et al Antimicrobial Agents and Chemotherapy 12:6147-53, 2013) as well as other engineered mutations to the antibody such as QL mutations, IHH mutations (Ko S Y et al. Nature 514:642-45, 2014, at FIG. 1a and relevant citations; See also Rudicell R et al. J. Virol 88:12669-82, 201). In some embodiments, modifications, such as but not limited to antibody fucosylation, may affect interaction with Fc receptors (See e.g. Moldt, et al. JVI 86(11):66189-6196, 2012). In some embodiments, the antibodies can comprise modifications, for example but not limited to glycosylation, which reduce or eliminate polyreactivity of an antibody. See e.g. Chuang, et al. Protein Science 24:1019-1030, 2015. In some embodiments the antibodies can comprise modifications in the Fc domain such that the Fc domain exhibits, as compared to an unmodified Fc domain enhanced antibody dependent cell mediated cytotoxicity (ADCC); increased binding to Fc.gamma.RIIA or to Fc.gamma.RIIIA; decreased binding to Fc.gamma RIM; or increased binding to Fc.gamma.RIIB See e.g. US Pub 20140328836.

In certain embodiments, antibodies of the invention including but not limited to antibodies comprising a CDR(s) of VH and/or VL chains, or antibody fragments of the inventive antibodies can be used as the HIV-1 binding arm(s) of a bispecific molecule, e.g. DARTS, diabodies, toxin labeled HIV-1 binding molecules.

In accordance with the methods of the present invention, either the intact antibody or a fragment thereof can be used. Either single chain Fv, bispecific antibody for T cell engagement, or chimeric antigen receptors can be used (Chow et al, Adv. Exp. Biol. Med. 746:121-41 (2012)). That is, in non-limiting embodiments, intact antibody, a Fab fragment, a diabody, or a bispecific whole antibody can be used to inhibit HIV-1 infection in a subject (e.g., a human). A bispecific $F(ab)_2$ can also be used with one arm a targeting molecule like CD3 to deliver it to T cells and the other arm the arm of the native antibody (Chow et al, Adv. Exp. Biol. Med. 746:121-41 (2012)). Toxins that can be bound to the antibodies or antibody fragments described herein include unbound antibody, radioisotopes, biological toxins, boronated dendrimers, and immunoliposomes (Chow et al, Adv. Exp. Biol. Med. 746:121-41 (2012)). Toxins (e.g., radionucleotides or other radioactive species) can be conjugated to the antibody or antibody fragment using methods well known in the art (Chow et al, Adv. Exp. Biol. Med. 746: 121-41 (2012)). The invention also includes variants of the antibodies (and fragments) disclosed herein, including variants that retain the ability to bind to recombinant Env protein, the ability to bind to the surface of virus-infected cells and/or ADCC-mediating properties of the antibodies specifically disclosed, and methods of using same to, for example, reduce HIV-1 infection risk. Combinations of the antibodies, or fragments thereof, disclosed herein can also be used in the methods of the invention.

Antibodies of the invention and fragments thereof can be produced recombinantly using nucleic acids comprising nucleotide sequences encoding VH and VL sequences selected from those shown in the figures and examples.

In certain embodiments the invention provides intact/whole antibodies. In certain embodiments the invention provides antigen binding fragments thereof. Typically, fragments compete with the intact antibody from which they were derived for specific binding to the target including separate heavy chains, light chains Fab, Fab', F(ab').sub.2, F(ab)c, diabodies, Dabs, nanobodies, and Fv. Fragments can be produced by recombinant DNA techniques, or by enzymatic or chemical separation of intact immunoglobulins.

In certain embodiments the invention provides a bispecific antibody. A bispecific or bifunctional/dual targeting antibody is an artificial hybrid antibody having two different heavy/light chain pairs and two different binding sites (see, e.g., Romain Rouet & Daniel Christ "Bispecific antibodies with native chain structure" Nature Biotechnology 32,136-137 (2014); Garber "Bispecific antibodies rise again" Nature Reviews Drug Discovery 13,799-801 (2014), FIG. 1a; Byrne et al. "A tale of two specificities:bispecific antibodies for therapeutic and diagnostic applications" Trends in Biotechnology, Volume 31, Issue 11, November 2013, Pages 621-632 Songsivilai and Lachmann, Clin. Exp. Immunol., 79:315-321 (1990); Kostelny et al., J. Immunol. 148:1547-53 (1992) (and references therein)). In certain embodiments the bispecific antibody is a whole antibody of any isotype. In other embodiments it is a bispecific fragment, for example but not limited to $F(ab)_2$ fragment. In some embodiments, the bispecific antibodies do not include Fc portion, which makes these diabodies relatively small in size and easy to penetrate tissues.

In certain embodiments, the bispecific antibodies could include Fc region. Fc bearing diabodies, for example but not limited to Fc bearing DARTs are heavier, and could bind neonatal Fc receptor, increasing their circulating half-life. See Garber "Bispecific antibodies rise again" Nature Reviews Drug Discovery 13,799-801 (2014), FIG. 1a; See US Pub 20130295121, incorporated by reference in their entirety. In certain embodiments, the invention encompasses diabody molecules comprising an Fc domain or portion thereof (e.g. a CH2 domain, or CH3 domain). The Fc domain or portion thereof may be derived from any immunoglobulin isotype or allotype including, but not limited to, IgA, IgD, IgG, IgE and IgM. In some embodiments, the Fc domain (or portion thereof) is derived from IgG. In some embodiments, the IgG isotype is IgG1, IgG2, IgG3 or IgG4 or an allotype thereof. In some embodiments, the diabody molecule comprises an Fc domain, which Fc domain comprises a CH2 domain and CH3 domain independently selected from any immunoglobulin isotype (i.e. an Fc domain comprising the CH2 domain derived from IgG and the CH3 domain derived from IgE, or the CH2 domain derived from IgG1 and the CH3 domain derived from IgG2, etc.). In some embodiments, the Fc domain may be engineered into a polypeptide chain comprising the diabody molecule of the invention in any position relative to other domains or portions of the polypeptide chain (e.g., the Fc domain, or portion thereof, may be c-terminal to both the VL and VH domains of the polypeptide of the chain; may be n-terminal to both the VL and VH domains; or may be N-terminal to one domain and c-terminal to another (i.e., between two domains of the polypeptide chain)).

The present invention also encompasses molecules comprising a hinge domain. The hinge domain be derived from any immunoglobulin isotype or allotype including IgA, IgD, IgG, IgE and IgM. In preferred embodiments, the hinge domain is derived from IgG, wherein the IgG isotype is IgG1, IgG2, IgG3 or IgG4, or an allotype thereof. The hinge domain may be engineered into a polypeptide chain comprising the diabody molecule together with an Fc domain such that the diabody molecule comprises a hinge-Fc domain. In certain embodiments, the hinge and Fc domain are independently selected from any immunoglobulin isotype known in the art or exemplified herein. In other embodiments the hinge and Fc domain are separated by at least one other domain of the polypeptide chain, e.g., the VL domain. The hinge domain, or optionally the hinge-Fc domain, may be engineered in to a polypeptide of the invention in any position relative to other domains or portions of the polypeptide chain. In certain embodiments, a polypeptide chain of the invention comprises a hinge domain, which hinge domain is at the C-terminus of the polypeptide chain, wherein the polypeptide chain does not comprise an Fc domain. In yet other embodiments, a polypeptide chain of the invention comprises a hinge-Fc domain, which hinge-Fc domain is at the C-terminus of the polypeptide chain. In further embodiments, a polypeptide chain of the invention comprises a hinge-Fc domain, which hinge-Fc domain is at the N-terminus of the polypeptide chain.

In some embodiments, the invention encompasses multimers of polypeptide chains, each of which polypeptide chains comprise a VH and VL domain, comprising CDRs as described herein. In certain embodiments, the VL and VH domains comprising each polypeptide chain have the same specificity, and the multimer molecule is bivalent and monospecific. In other embodiments, the VL and VH domains comprising each polypeptide chain have differing specificity and the multimer is bivalent and bispecific. In some embodiments, the polypeptide chains in multimers further comprise an Fc domain. Dimerization of the Fc domains leads to formation of a diabody molecule that exhibits immunoglobulin-like functionality, i.e., Fc mediated function (e.g., Fc-Fc.gamma.R interaction, complement binding, etc.).

In yet other embodiments, diabody molecules of the invention encompass tetramers of polypeptide chains, each of which polypeptide chain comprises a VH and VL domain. In certain embodiments, two polypeptide chains of the tetramer further comprise an Fc domain. The tetramer is therefore comprised of two 'heavier' polypeptide chains, each comprising a VL, VH and Fc domain, and two 'lighter' polypeptide chains, comprising a VL and VH domain. Interaction of a heavier and lighter chain into a bivalent monomer coupled with dimerization of the monomers via the Fc domains of the heavier chains will lead to formation of a tetravalent immunoglobulin-like molecule. In certain aspects the monomers are the same, and the tetravalent diabody molecule is monospecific or bispecific. In other aspects the monomers are different, and the tetra valent molecule is bispecific or tetraspecific.

Formation of a tetraspecific diabody molecule as described supra requires the interaction of four differing polypeptide chains. Such interactions are difficult to achieve with efficiency within a single cell recombinant production system, due to the many variants of potential chain mispairings. One solution to increase the probability of mispairings, is to engineer "knobs-into-holes" type mutations into the desired polypeptide chain pairs. Such mutations favor heterodimerization over homodimerization. For example, with respect to Fc-Fc-interactions, an amino acid substitution (preferably a substitution with an amino acid comprising a bulky side group forming a 'knob', e.g., tryptophan) can be introduced into the CH2 or CH3 domain such that steric interference will prevent interaction with a similarly mutated domain and will obligate the mutated domain to pair with a domain into which a complementary, or accommodating mutation has been engineered, i.e., 'the hole' (e.g., a substitution with glycine). Such sets of mutations can be engineered into any pair of polypeptides comprising the diabody molecule, and further, engineered into any portion of the polypeptides chains of the pair. Methods of protein engineering to favor heterodimerization over homodimerization are well known in the art, in particular with respect to the engineering of immunoglobulin-like molecules, and are encompassed herein (see e.g., Ridgway et al. (1996) "'Knobs-Into-Holes' Engineering Of Antibody CH3 Domains For Heavy Chain Heterodimerization," Protein Engr. 9:617-621, Atwell et al. (1997) "Stable Heterodimers From Remodeling The Domain Interface Of A Homodimer Using A Phage Display Library," J. Mol. Biol. 270:26-35, and Xie et al. (2005) "A New Format Of Bispecific Antibody:Highly Efficient Heterodimerization, Expression And Tumor Cell Lysis," J. Immunol. Methods 296:95-101; each of which is hereby incorporated herein by reference in its entirety).

The invention also encompasses diabody molecules comprising variant Fc or variant hinge-Fc domains (or portion thereof), which variant Fc domain comprises at least one amino acid modification (e.g. substitution, insertion deletion) relative to a comparable wild-type Fc domain or hinge-Fc domain (or portion thereof). Molecules comprising variant Fc domains or hinge-Fc domains (or portion thereof) (e.g., antibodies) normally have altered phenotypes relative to molecules comprising wild-type Fc domains or hinge-Fc domains or portions thereof. The variant phenotype may be expressed as altered serum half-life, altered stability, altered susceptibility to cellular enzymes or altered effector function as assayed in an NK dependent or macrophage dependent assay. Fc domain variants identified as altering effector function are known in the art. For example International Application WO04/063351, U.S. Patent Application Publications 2005/0037000 and 2005/0064514.

The bispecific diabodies of the invention can simultaneously bind two separate and distinct epitopes. In certain embodiments the epitopes are from the same antigen. In other embodiments, the epitopes are from different antigens. In preferred embodiments, at least one epitope binding site is specific for a determinant expressed on an immune effector cell (e.g. CD3, CD16, CD32, CD64, etc.) which are expressed on T lymphocytes, natural killer (NK) cells or other mononuclear cells. In one embodiment, the diabody molecule binds to the effector cell determinant and also activates the effector cell. In this regard, diabody molecules of the invention may exhibit Ig-like functionality independent of whether they further comprise an Fc domain (e.g., as assayed in any effector function assay known in the art or exemplified herein (e.g., ADCC assay).

Non-limiting examples of bispecific antibodies can also be (1) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In:Antibody Engineering, Springer Berlin Heidelberg (2010)); (2) a Tandab, which is a fusion of two single chain diabodies resulting in a tetravalent bispecific antibody that has two binding sites for each of the target antigens; (3) a flexibody, which is a combination of scFvs with a diabody resulting in a multivalent molecule; (4) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (5) a so-called Scorpion molecule, comprising, e.g., two scFvs fused to both termini of a human Fc-region. Examples of platforms useful for preparing bispecific antibodies include but are not limited to BiTE (Micromet), DART (MacroGenics) (e,g, U.S. Pat. No. 8,795,667; No. 2014-0099318; 2013-0295121; 2010-0174053 and 2009-0060910; European Patent Publication No. EP 2714079; EP 2601216; EP 2376109; EP 2158221 and PCT Publications No. WO 2015/026894; WO 2015/026892; WO 2015/021089; WO 2014/159940; WO 2012/162068; WO 2012/018687; WO 2010/080538), the content of each of these publications in herein incorporated by reference in its entirety), Fcab and Mab2 (F-star), Fc-engineered IgG1 (Xencor) or DuoBody (based on Fab arm exchange, Genmab).

In certain embodiments, the bispecific antibody comprises an HIV envelope binding fragment, for example but not limited to an HIV envelope binding fragment from any of the antibodies described herein. In other embodiments, the bispecific antibody further comprises a second antigen-interaction-site/fragment. In other embodiments, the bispecific antibody further comprises at least one effector domain.

In certain embodiments the bispecific antibodies engage cells for Antibody-Dependent Cell-mediated Cytotoxicity (ADCC). In certain embodiments the bispecific antibodies engage natural killer cells, neutrophil polymorphonuclear leukocytes, monocytes and macrophages. In certain embodiments the bispecific antibodies are T-cell engagers. In certain embodiments, the bispecific antibody comprises an HIV envelope binding fragment and CD3 binding fragment. Various CD3 antibodies are known in the art. See for example U.S. Pat. No. 8,784,821. In certain embodiments, the bispecific antibody comprises an HIV envelope binding fragment and CD16 binding fragment.

In certain embodiments the invention provides antibodies with dual targeting specificity. In certain aspects the invention provides bi-specific molecules that are capable of localizing an immune effector cell to an HIV-1 envelope expressing cell, so as facilitate the killing of the HIV-1 envelope expressing cell. In this regard, bispecific antibodies bind with one "arm" to a surface antigen on target cells, and with the second "arm" to an activating, invariant component of the T cell receptor (TCR) complex. The simultaneous binding of such an antibody to both of its targets will force a temporary interaction between target cell and T cell, causing activation of any cytotoxic T cell and subsequent lysis of the target cell. Hence, the immune response is re-directed to the target cells and is independent of peptide antigen presentation by the target cell or the specificity of the T cell as would be relevant for normal MHC-restricted activation of CTLs. In this context it is crucial that CTLs are only activated when a target cell is presenting the bispecific antibody to them, i.e. the immunological synapse is mimicked. Particularly desirable are bispecific antibodies that do not require lymphocyte preconditioning or co-stimulation in order to elicit efficient lysis of target cells.

Several bispecific antibody formats have been developed and their suitability for T cell mediated immunotherapy investigated. Out of these, the so-called BiTE (bispecific T cell engager) molecules have been very well characterized and already shown some promise in the clinic (reviewed in Nagorsen and Bauerle, Exp Cell Res 317, 1255-1260 (2011)). BiTEs are tandem scFv molecules wherein two scFv molecules are fused by a flexible linker. Further bispecific formats being evaluated for T cell engagement include diabodies (Holliger et al., Prot Eng 9, 299-305 (1996)) and derivatives thereof, such as tandem diabodies (Kipriyanov et al., J Mol Biol 293, 41-66 (1999)). DART (dual affinity retargeting) molecules are based on the diabody format that separates cognate variable domains of heavy and light chains of the two antigen binding specificities on two separate polypeptide chains but feature a C-terminal disulfide bridge for additional stabilization (Moore et al., Blood 117, 4542-51 (2011)). The invention also contemplates Fc-bearing DARTs. The so-called triomabs, which are whole hybrid mouse/rat IgG molecules and also currently being evaluated in clinical trials, represent a larger sized format (reviewed in Seimetz et al., Cancer Treat Rev 36, 458-467 (2010)).

The invention also contemplates bispecific molecules with enhanced pharmacokinetic properties. In some embodiments, such molecules are expected to have increased serum half-life. In some embodiments, these are Fc-bearing DARTs (see supra).

In certain embodiments, such bispecific molecules comprise one portion which targets HIV-1 envelope and a second portion which binds a second target. In certain embodiments, the first portion comprises VH and VL sequences, or CDRs from the antibodies described herein. In certain embodiments, the second target could be, for example but not limited to an effector cell. In certain embodiments the second portion is a T-cell engager. In certain embodiments, the second portion comprises a sequence/paratope which targets CD3, CD16, or another suitable target. In certain embodiments, the second portion is an antigen-binding region derived from a CD3 antibody, optionally a known CD3 antibody. In certain embodiments, the anti-CD antibody induce T cell-mediated killing. In certain embodiments, the bispecific antibodies are whole antibodies. In other embodiments, the dual targeting antibodies consist essentially of Fab fragments. In other embodiments, the dual targeting antibodies comprise a heavy chain constant region (CH1). In certain embodiments, the bispecific antibody does not comprise Fc region. In certain embodiments, the bispecific antibodies have improved effector function. In certain embodiments, the bispecific antibodies have improved cell killing activity. Various methods and platforms for design of bispecific antibodies are known in the art. See for example US Pub. 20140206846, US Pub. 20140170149, US Pub. 20090060910, US Pub 20130295121, US Pub. 20140099318, US Pub. 20140088295 which contents are herein incorporated by reference in their entirety.

In certain embodiments the invention provides human, humanized and/or chimeric antibodies.

Pharmaceutical Compositions

In certain aspects the invention provides a pharmaceutical composition comprising an antibody of the invention wherein the composition is used for therapeutic purposes such as but not limited to prophylaxis, treatments, prevention, and/or cure. In certain aspects the invention provides a pharmaceutical composition comprising an antibody of the invention in combination with any other suitable antibody. In certain embodiments, the pharmaceutical compositions comprise nucleic acids which encode the antibodies of the invention. In certain embodiments, these nucleic acids can be expressed by any suitable vector for expression of antibodies. Non-limiting examples include attenuated viral hosts or vectors or bacterial vectors, recombinant vaccinia virus, adenovirus, adeno-associated virus (AAV), herpes virus, retrovirus, cytomegalovirus or other viral vectors can be used to express the antibody.

Various methods to make pharmaceutical compositions are known in the art and are contemplated by the invention. In some embodiments, the compositions include excipient suitable for a biologic molecule such as the antibodies of the invention. In some embodiments, the antibodies could be produced in specific cell lines and conditions so as to control glycosylation of the antibody. In some embodiments, the antibody framework for example, could comprise specific modification so as to increase stability of the antibody.

In certain aspects, the invention provides that the antibodies, and fragments thereof, described herein can be formulated as a composition (e.g., a pharmaceutical composition). Suitable compositions can comprise an inventive antibody (or antibody fragment) dissolved or dispersed in a pharmaceutically acceptable carrier (e.g., an aqueous medium). The compositions can be sterile and can be in an injectable form (e.g. but not limited to a form suitable for intravenous injection, intramascular injection). The antibodies (and fragments thereof) can also be formulated as a composition appropriate for topical administration to the skin or mucosa. Such compositions can take the form of liquids, ointments, creams, gels and pastes. The antibodies (and fragments thereof) can also be formulated as a composition appropriate for intranasal administration. The antibodies (and fragments thereof) can be formulated so as to be administered as a post-coital douche or with a condom. Standard formulation techniques can be used in preparing suitable compositions.

The antibody (and fragments thereof), described herein have utility, for example, in settings including but not limited to the following:

i) in the setting of anticipated known exposure to HIV-1 infection, the antibodies described herein (or fragments thereof) and be administered prophylactically (e.g., IV, topically or intranasally) as a microbiocide, ii) in the setting of known or suspected exposure, such as occurs in the setting of rape victims, or commercial sex workers, or in any homosexual or heterosexual transmission without condom protection, the antibodies described herein (or fragments thereof) can be administered as post-exposure prophylaxis, e.g., IV or topically, and iii) in the setting of Acute HIV infection (AHI), the antibodies described herein (or fragments thereof) can be administered as a treatment for AHI to control the initial viral load or for the elimination of virus-infected CD4 T cells.

In accordance with the invention, the antibodies (or antibody fragments) described herein can be administered prior to contact of the subject or the subject's immune system/cells with HIV-1 or within about 48 hours of such contact. Administration within this time frame can maximize inhibition of infection of vulnerable cells of the subject with HIV-1.

In addition, various forms of the antibodies described herein can be administered to chronically or acutely infected HIV patients and used to kill remaining virus infected cells by virtue of these antibodies binding to the surface of virus infected cells and being able to deliver a toxin to these reservoir cells.

Suitable dose ranges can depend on the antibody (or fragment) and on the nature of the formulation and route of administration. Optimum doses can be determined by one skilled in the art without undue experimentation. For example but not limited, doses of antibodies in the range of 0.1-50 mg/kg, 1-50 mg/kg, 1-10 mg/kg, 1, 1.25, 1.5, 2, 2.5, 3, 3.5, 4, 4.5, 5, 5.5, 6, 6.5, 7, 7.5, 8, 8.5, 9, 9.5 or 10 mg/kg of unlabeled or labeled antibody (with toxins or radioactive moieties) can be used. If antibody fragments, with or without toxins are used or antibodies are used that can be targeted to specific CD4 infected T cells, then less antibody can be used (e.g., from 5 mg/kg to 0.01 mg/kg). In other embodiments, the antibodies of the invention can be administered at a suitable fixed dose, regardless of body size or weight. See Bai et al. Clinical Pharmacokinetics February 2012, Volume 51, Issue 2, pp 119-135.

In certain aspects the invention provides use of the antibodies of the invention, including bispecific antibodies, in methods of treating and preventing HIV-1 infection in an individual, comprising administering to the individual a therapeutically effective amount of a composition comprising the antibodies of the invention in a pharmaceutically acceptable form. In certain embodiment, the methods include a composition which includes more than one HIV-1 targeting antibody. In certain embodiments, the HIV-1 targeting antibodies in such combination bind different epitopes on the HIV-1 envelope. In certain embodiments, such combinations of bispecific antibodies targeting more than one HIV-1 epitope provide increased killing of HIV-1 infected cells. In other embodiments, such combinations of bispecific antibodies targeting more than one HIV-1 epitope provide increased breadth in recognition of different HIV-1 subtypes.

In certain embodiments, the composition comprising the antibodies of the invention alone or in any combination can be administered via IM, subcutaneous, or IV delivery, or could be deposited at mucosal sites, such as the oral cavity to prevent maternal to child transmission, the rectal space or the vagina as a microbicide. In certain embodiments, the antibodies can be administered locally in the rectum, vagina, or in the oral cavity, and can be formulated as a microbiocide (Hladik F et al ELIFE Elife. 2015 Feb. 3; 4. doi:10.7554/eLife.04525.; Multipurpose prevention technologies for reproductive and sexual health. Stone A. Reprod Health Matters. 2014 November; 22(44):213-7. doi:10.1016/S0968-8080(14)44801-8). In other embodiments, antibodies can be formulated such that the therapeutic antibody or combination thereof is impregnated on a vaginal ring (Chen Y et al. Drug Des. Devel. Ther 8:1801-15, 2014; Malcolm R K et al BJOG 121 Suppl 5:62-9, 2014). Antibodies can be administered alone or with anti-retroviral drugs for a combination microbicide (Hladik F et al ELIFE Elife. 2015 Feb. 3; 4. doi:10.7554/eLife.04525).

Alternatively they can be administered in complex with a form of HIV Env, optimally gp120, but also an Env trimer, to enhance Env immunogenicity. In certain embodiments, the antibodies can be delivered by viral vector mediated delivery of genes encoding the antibodies of the invention (See e.g. Yang et al. Viruses 2014, 6, 428-447). In certain embodiments, the antibodies can be administered in viral vector, for example but not limited to adenoassociated viral vector, for expression in muscle and plasma.

Figure 8:
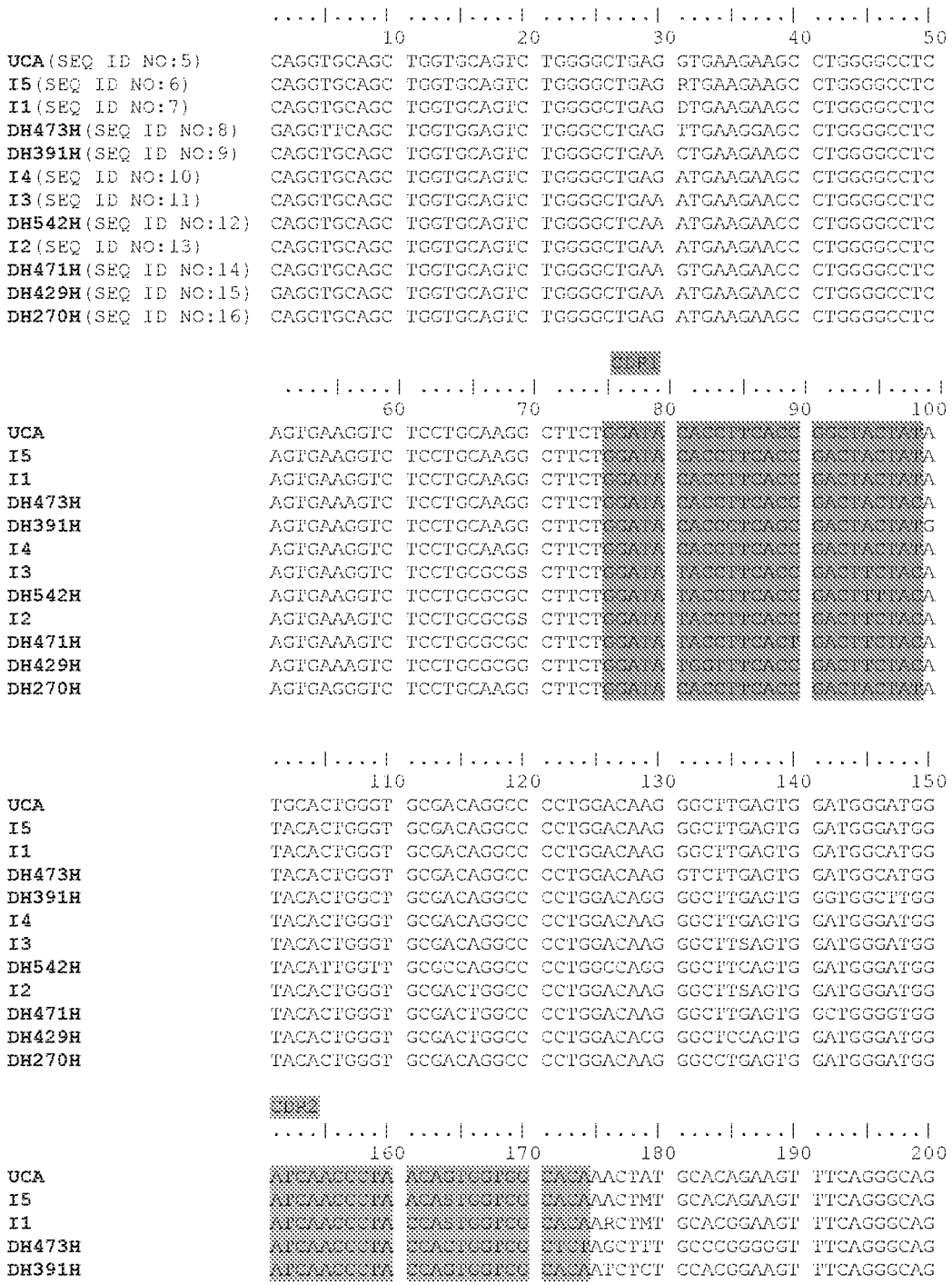
FIG. 8 shows the amino acids sequences of VH and VL chains of antibodies of the DH270 lineage, and nucleic acid sequences encoding these amino acids. CDRs are highlighted in each antibody. DH270IA1 as listed in FIG. 9 is the same antibody referred to as I1 in the sequence of FIG. 8. The figure shows SEQ ID NOs:5-16 (Heavy chain nucleotide sequences in order of appearance from UCA-DH270H), SEQ ID NOs:17-28 (Heavy chain amino acid sequences in order of appearance from UCA-DH270H), SEQ ID NOs: 29-40 (Light chain nucleotide sequences in order of appearance from UCA-DH270H), SEQ ID NOs:41-52 (Light chain amino acid sequences in order of appearance from UCA-DH270H).
Figure 19A:
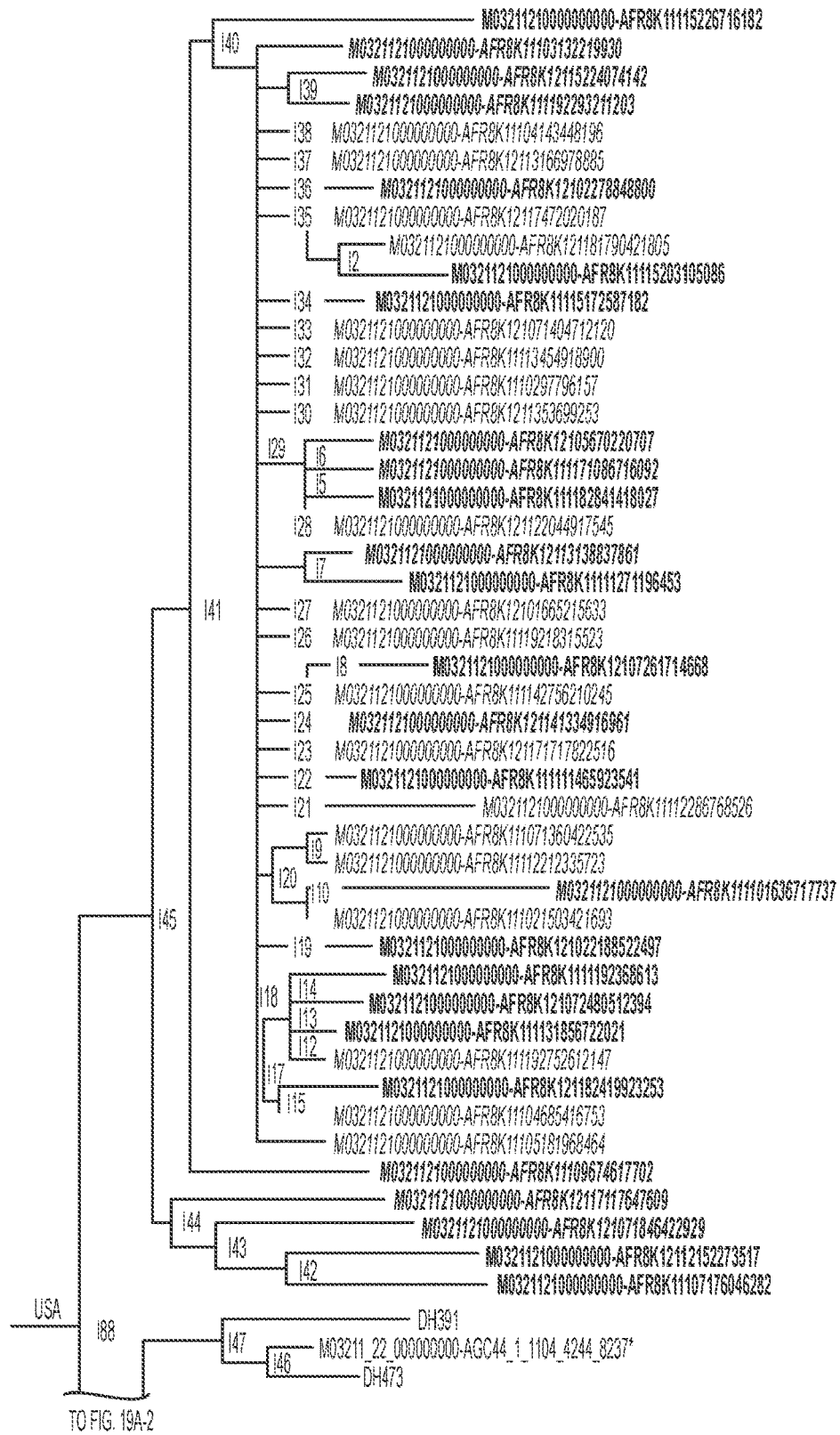
FIG. 19A shows a phylogenetic tree of VH sequences from CH0848 donor. The tree includes VH chains from natural VH:VL pairs (identified by single cell sorts) and VH chains identified by Illumina sequencing.
Figure 19A:
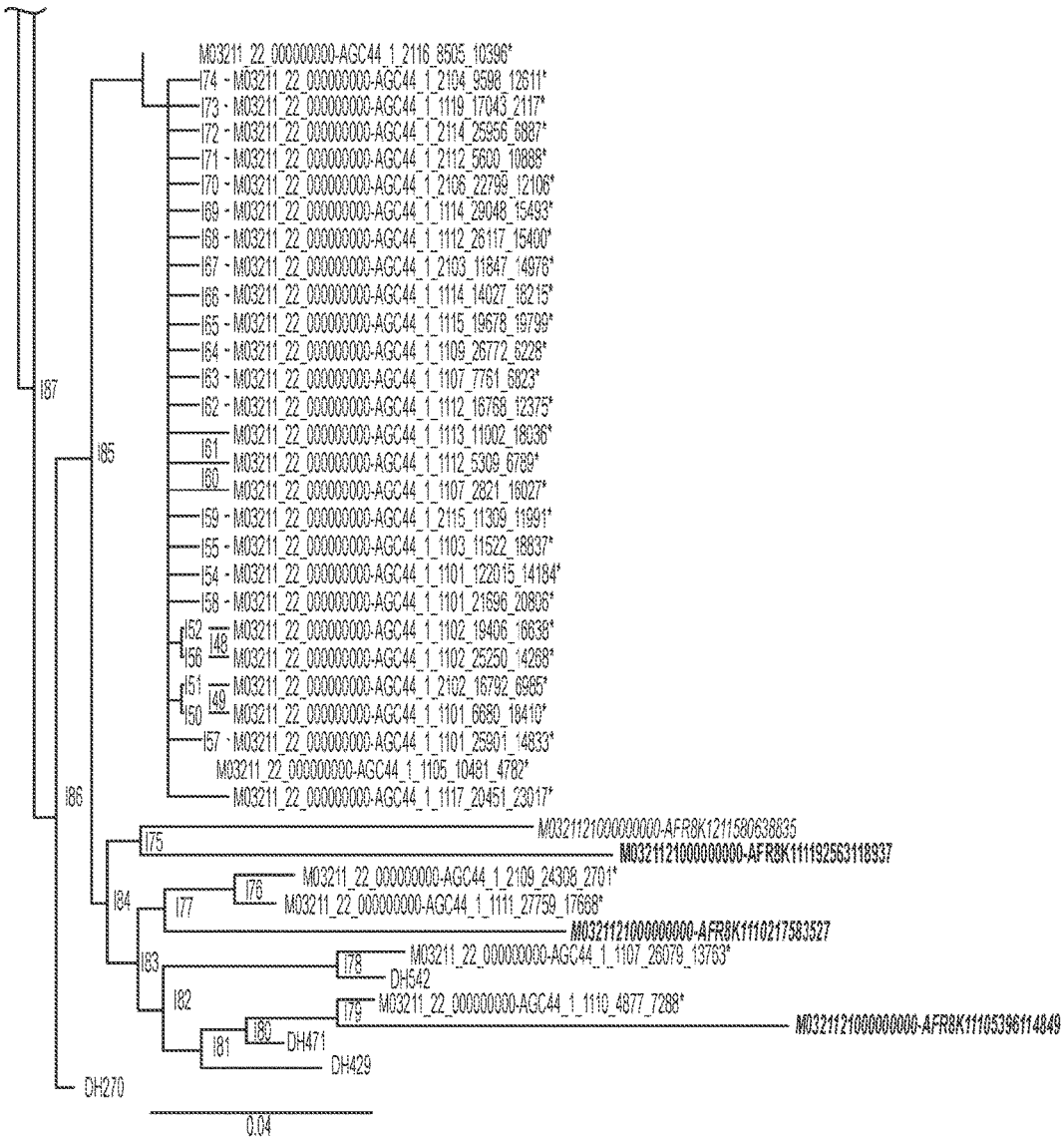
Figures 19B, 19C:
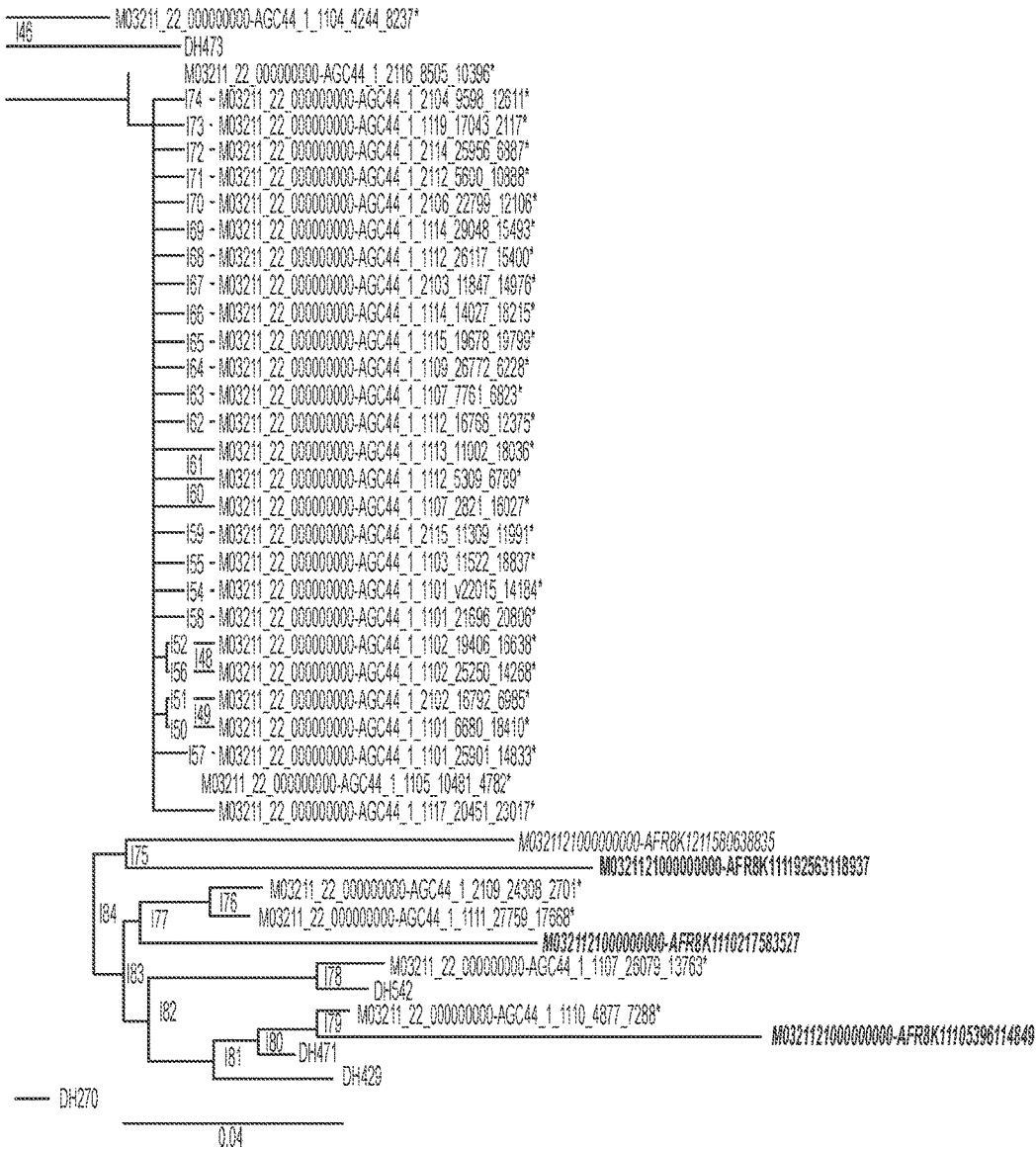
FIG. 19B shows a detailed view of the bottom portion of the tree in 19A.
FIG. 19C shows the IDs of the VH chains.

In certain embodiments, antibodies with different binding specificities are combined for use in pharmaceutical compositions and therapeutic methods. For example:CD4 binding site antibodies are combined with V3 antibodies, MPER antibodies and so forth. FIGS. 8, 9 and 10 show a selection of potent HIV-1 neutralizing antibodies which can be used in pharmaceutical compositions, and therapeutic methods. Non-limiting examples of selections of combinations of certain antibodies include:DH542, DH542_L4, DH542_QSA, DH429 and DH512 (or any of the DH512 variants); DH512 and CH31 (See US Publication 20140205607); DH512 (or any of the other DH512 variants) and DH540 (See Example 8, and this antibody will be described elsewhere); DH542, DH542_L4, DH542_QSA, DH429, DH512 and DH540; DH542, DH542_L4, DH542_QSA, DH429 and CH557; CH557 and DH512 (or any of the DH512 variants). These combinations are expected to give a greater overall potency and breadth. A polyclonal mixture of Abs is expected reduce or eliminate viral escape. It is readily understood by skilled artisans that in some embodiments a combination therapy envisions a composition which combines various antibodies. In other embodiments a combination therapy is provided wherein antibodies are administered as individual compositions, for example at different times, by different means, or at administered at different locations. In other embodiments, a combination therapy is provides wherein a therapeutic antibody or antibodies is combined with other therapeutic means, for example anti-retroviral drug cocktails, or drugs which activate latently infected HIV-1 cells.

In some embodiments, the disclosed antibodies or antigen binding fragments thereof are used to determine whether HIV-1 envelope(s) is a suitable antigen for inclusion in a vaccine composition. For example the antibodies can be used to determine whether an antigen in a vaccine composition including gp120 assumes a conformation including an epitope bound by the inventive antibodies or fragments thereof. This can be readily determined by a method which includes contacting a sample containing the vaccine, such as a gp120 antigen, with a disclosed antibody or antigen binding fragment under conditions sufficient for formation of an immune complex, and detecting the immune complex, to detect an HIV-1 antigen including an epitope of an inventive antibody in the sample. In one example, the detection of the immune complex in the sample indicates that vaccine component, such as a HIV-1 Env antigen assumes a conformation capable of binding the antibody or antigen binding fragment.

Antibody nomenclature and names:UCA4=DH270. UCA; IA4=DH270. IA4; IA3=DH270. IA3; IA2=DH270. IA2; IA1=DH270. IA1; DH270=DH270.1; DH473 =DH270.2; DH391 =DH270.3; DH429 =DH270.4; DH471 =DH270.5; DH542=DH270.6; DH542-L4 (comprising VH from DH542 and VL from DH429), DH542_QSA.

The following examples are provided to illustrate particular features of certain embodiments, but the scope of the claims should not be limited to those features exemplified.

EXAMPLES

Example 1

Isolating Antibodies from Natural HIV-1 Infected Individuals

Methods to identify and isolate antigen specific reactive antibodies were carried out essentially as described in Liao H X et al. J. Virol. Methods 158:171-9, 2009, incorporated by reference in its entirety. Specific hooks are designed to identify memory B cells which express antibodies that bind to specific HIV-1 envelope targets/antigens. Using such hooks, with fluorophore labeled streptavidin in two colors, cells are sorted by flow cytometry, into single wells, and the diagonally (that reacted with both colors hooks) reactive memory B cells are picked. B cells enriched from PBMC are sorted, and plated at limiting dilution (as single cell per well). Optionally, these cultures are grown and supernatants are functionally characterized.

PCR on these cells is carried out according to the protocol in Liao H X et al. J. Virol. Methods 158:171-9, 2009. PCR amplifications are carried out to amplify rearranged VH and VL fragment pairs from the diagonally sorted memory B cells (Liao et al JVM 158:171-9, 2009). Overlapping PCR is used to construct full length Ig heavy and Ig light linear genes comprising the rearranged VH and VL fragment pairs. RT-PCR and PCR reactions is carried out essentially as described in Liao H X et al. J. Virol. Methods 158:171-9, 2009, see for example FIG. 1, Section 3.3. Sequence analysis of the VH and VL genes was carried out to determine the VH and VL gene usage, CDR lengths, the % mutation of HCDR3 and LCDR3. Based on this sequence analysis, one to two pairs of linear VH and VL genes are selected and made in linear cassettes (essentially as described in Liao H X et al. J. Virol. Methods 158:171-9, 2009, see for example FIG. 1, Section 3.3) to produce recombinant monoclonal antibodies by transient transfection, e.g. in 293T cells.

Recombinant antibodies are grown and supernatants and/or purified antibodies are functionally characterized.

Pairs of VH and VL genes as selected above can also be used to produce plasmids for stable expression of recombinant antibodies.

In certain embodiments, the plasmids or linear constructs for recombinant antibody expression also comprise AAAA substitution in and around the Fc region of the antibody that has been reported to enhance ADCC via NK cells (AAA mutations) containing the Fc region aa of S298A as well as E333A and K334A (Shields R I et al JBC , 276:6591-6604, 2001) and the $4^{th}$ A (N434A) is to enhance FcR neonatal mediated transport of the IgG to mucosal sites (Shields R I et al. ibid).

The antibodies of the invention were selected based on a combination of criteria including sequence analyses, and functional analyses including but not limited as neutralization breadth, and potency.

In certain embodiments, the antibodies of the invention comprise naturally rearranged VH and VL gene pairs isolated as nucleic acids, wherein the rest of the Ig gene is not naturally occurring with the isolated rearranged VH and VL fragments. In certain embodiments, the antibodies of the invention are recombinantly produced.

Example 2

Antibodies from DH270 Lineage

Antibodies I1 (DH270IA1), I2, I4, I3 and UCA in FIG. 8 are not isolated from human subjects but are derived computationally based on VH and VL sequences of other clonal antibodies identified from memory B cells:DH471, DH429, DH473, DH391 and DH270. The VH and VL sequences of DH471, DH429, DH473, DH391 and DH270 are derived from a human subject infected with HIV-1.

The VH and VL sequences of DH471, DH429 and DH473are derived essentially as described in Example 1, using Consensus C gp120 Env and Consensus C gp120 N332A Env glycopeptides and by sorting cells that bound to Consensus C gp120 Env but not to Consensus C gp120 N332A Env. DH270 and DH391 were recombinantly produced from VH and VL chains isolated from clonal memory B cell cultures that bound to Consensus C gp120 Env but not to Consensus C gp120 N332A Env using the method previously described (Bonsignori et al J Virol 2011, Gao Bonsignori Liao et al Cell 2014).

Neutralization data for antibodies I1 (DH270IA1) and DH429 is summarized in FIG. 9, and FIG. 10.

DH542 Antibody Isolation

Biotinylated $Man_9GlcNac_2$ V3 peptides were tetramerized via streptavidin and conjugated with either AF647 or BV421 (Invitrogen) dyes. Peptide tetramer quality following conjugation was assessed by flow cytometry to a panel of well-characterized HIV-1 V3 glycan antibodies (PGT128, and 2G12) and linear V3 antibodies (F39F). The sequence of Man9V3 glycopeptide is EINCTRPNNNTRPGEI-IGDIRQAHCNISRA. This is a synthetic glycopeptide which has N-linked glycans (Man9GlcNac2) placed at the Asparagine residues in bold/underlined. The cysteine residues at the N and C terminal form a disulfide linkage under oxidative conditions creating a very stable cyclical conformation that expresses the epitope bound by V3 glycan bnAbs such as PGT128, 125, and 2G12, and now DH542 and other DH270 lineage members.

Roughly 10 million peripheral blood mononuclear cells (PBMCs) from the HIV-1-infected donor 703-01-084-8 (CH848) collected 234 weeks post infection were stained with AquaVital dye, anti-human IgM (FITC), anti-human IgD (PE), anti-human CD10 (ECD), anti-human CD3 (PE-Cy5), anti-human CD235a (PE-Cy5), anti-human CD27 (PE-Cy7), anti-human CD38 (APC-AF700), anti-human CD19 (APC-Cy7), anti-human CD16 (BV570), anti-human CD14 (BV605), and $Man_9GlcNac_2$ V3 tetramer in both AF647 and BV421. PBMCs that were AquaVital dye$^-$, CD14$^-$, CD16$^-$, CD3$^-$, CD235a$^-$, IgD$^-$, CD19$^+$, CD38$^+$, and $Man_9GlcNac_2$ V3$^+$were single-cell sorted using a BD FACS Aria II into 96-well plates containing 20 µl of reverse transcriptase buffer (RT). cDNA synthesis was performed as previously described (1). Immunoglobulin (Ig) heavy (VH) chains were PCR amplified using a nested approach. VH genes were amplified in the first round of amplification with primers grouped in Table 1a-1e as previously described (2). Nested amplification of VH genes was performed as in (Liao et al., 2009) with primers grouped in Table 2a. Kappa and lambda were amplified as in (Liao et al., 2009), with primers grouped in Table 2b-2c. PCR products were analyzed on 2% SYBR Safe E-Gels (Invitrogen). PCR-amplified VH and VL genes were purified and sequenced. Sequences were analyzed and VDJ arrangements were inferred using computational methods as previously described (3, 4).

TABLE 1a (SEQ ID NOs: 201-211, in order of appearance)

| Forward Primer | Sequence |
| --- | --- |
| VH1 Leader A | ATGGACTGGACCTGGAGGAT |
| VH1 Leader B | ATGGACTGGACCTGGAGCAT |
| VH1 Leader C | ATGGACTGGACCTGGAGAAT |
| VH1 Leader D | GGTTCCTCTTTGTGGTGGC |
| VH1 Leader E | ATGGACTGGACCTGGAGGGT |
| VH1 Leader F | ATGGACTGGATTTGGAGGAT |
| VH1 Leader G | AGGTTCCTCTTTGTGGTGGCAG |
| VH2 Leader A | ATGGACATACTTTGTTCCACGCTC |
| VH2 Leader B | ATGGACACACTTTGCTCCACGCT |
| VH2 Leader C | ATGGACACACTTTGCTACACACTC |
| Reverse Primer | |
| 3' Cγ CH1 | GGAAGGTGTGCACGCCGCTGGTC |

SEQ ID NOs:212-222, in order of appearance:

| Forward Primer | Sequence |
| --- | --- |
| VH1 Leader A | ATGGACTGGACCTGGAGGAT |
| VH1 Leader B | ATGGACTGGACCTGGAGCAT |
| VH1 Leader C | ATGGACTGGACCTGGAGAAT |
| VH1 Leader D | GGTTCCTCTTTGTGGTGGC |
| VH1 Leader E | ATGGACTGGACCTGGAGGGT |
| VH1 Leader F | ATGGACTGGATTTGGAGGAT |
| VH1 Leader G | AGGTTCCTCTTTGTGGTGGCAG |
| VH2 Leader A | ATGGACATACTTTGTTCCACGCTC |
| VH2 Leader B | ATGGACACACTTTGCTCCACGCT |
| VH2 Leader C | ATGGACACACTTTGCTACACACTC |
| Reverse Primer | |
| 3' Cγ CH1 | GGAAGGTGTGCACGCCGCTGGTC |

TABLE 1b (SEQ ID NOs: 223-230, in order of appearance)

| Forward Primer | Sequence |
| --- | --- |
| VH3 Leader A | TAAAAGGTGTCCAGTGT |
| VH3 Leader B | TAAGAGGTGTCCAGTGT |

TABLE 1b-continued (SEQ ID NOs: 223-230, in order of appearance)

| VH3 Leader C | TAGAAGGTGTCCAGTGT |
| --- | --- |
| VH3 Leader E | TACAAGGTGTCCAGTGT |
| VH3 Leader F | TTAAAGGTGTCCAGTGT |
| VH4 Leader D | ATGAAACATCTGTGGTTCTT |
| VH5 Leader A | TTCTCCAAGGAGTCTGT |
| Reverse Primer | |
| 3' Cγ CH1 | GGAAGGTGTGCACGCCGCTGGTC |

TABLE 1c (SEQ ID NOs: 231-238, in order of appearance)

| Forward Primer | Sequence |
| --- | --- |
| VH3 Leader D | GCTATTTTAAAGGTGTCCAGTGT |
| VH4 Leader A | ATGAAACACCTGTGGTTCTTCC |
| VH4 Leader B | ATGAAACACCTGTGGTTCTT |
| VH4 Leader C | ATGAAGCACCTGTGGTTCTT |
| VH5 Leader B | CCTCCACAGTGAGAGTCTG |
| VH6 Leader A | ATGTCTGTCTCCTTCCTCATC |
| VH7 Leader A | GGCAGCAGCAACAGGTGCCCA |
| Reverse Primer | |
| 3' Cγ CH1 | GGAAGGTGTGCACGCCGCTGGTC |

TABLE 1d (SEQ ID NOs: 239-243, in order of appearance)

| Forward Primer | Sequence |
| --- | --- |
| Vκ1,2 Ext | GCTCAGCTCCTGGGGCT |
| Vκ3 Ext | GGAARCCCCAGCDCAGC |
| Vκ4/5 Ext | CTSTTSCTYTGGATCTCTG |
| Vκ6/7 Ext | CTSCTGCTCTGGGYTGC |
| Reverse Primer | |
| CK Ext | GAGGCAGTTCCAGATTTCAA |

TABLE 1e (SEQ ID NOs: 244-254, in order of appearance)

| Forward Primer | Sequence |
| --- | --- |
| VL1 Ext | CCTGGGCCCAGTCTGTG |
| VL2 Ext | CTCCTCASYCTCCTCACT |
| VL3 Ext | GGCCTCCTATGWGCTGAC |
| VL31 Ext | GTTCTGTGGTTTCTTCTGAGCTG |

TABLE 1e-continued (SEQ ID NOs: 244-254, in order of appearance)

| | |
|---|---|
| VL4ab Ext | ACAGGGTCTCTCTCCCAG |
| VL4c Ext | ACAGGTCTCTGTGCTCTGC |
| VL5,9 Ext | CCCTCTCSCAGSCTGTG |
| VL6 Ext | TCTTGGGCCAATTTTATGC |
| VL7,8 Ext | ATTCYCAGRCTGTGGTGAC |
| VL 10 | CAGTGGTCCAGGCAGGG |
| Reverse Primer | |
| CL Ext | AGGCCACTGTCACAGCT |

TABLE 2a (SEQ ID NOs: 255-261, in order of appearance)

| Forward Primer | Sequence |
|---|---|
| VH1 Int | CTGGGTTCCAGGTTCCACTGGTGACCAGGTGCAGCTGGTRCAGTCTGGG |
| VH2 Int | CTGGGTTCCAGGTTCCACTGGTGACCAGRGCACCTTGARGGAGTCTGGTCC |
| VH3 Int | CTGGGTTCCAGGTTCCACTGGTGACGAGGTKCAGCTGGTGGAGTCTGGG |
| VH4 Int | CTGGGTTCCAGGTTCCACTGGTGACCAGGTGCAGCTGCAGGAGTCGG |
| VH5 Int | CTGGGTTCCAGGTTCCACTGGTGACGARGTGCAGCTGGTGCAGTCTGGAG |
| VH6 Int | CTGGGTTCCAGGTTCCACTGGTGACCAGGTACAGCTGCAGCAGTCAGGTCC |
| Reverse Primer | |
| IgG Int | GGGCCGCTGTGCCCCCAGAGGTGCTCTYGGA |

TABLE 2b (SEQ ID NOs: 262-269, in order of appearance)

| Forward | PrimerSequence |
|---|---|
| VK1 Int | CTGGGTTCCAGGTTCCACTGGTGACGACATCCAGWTGACCCAGTCTC |
| VK2 Int | CTGGGTTCCAGGTTCCACTGGTGACGATATTGTGATGACCCAGWCTCCAC |
| VK3 Int | CTGGGTTCCAGGTTCCACTGGTGACGAAATTGTGTTGACRCAGTCTCCA |
| VK4 Int | CTGGGTTCCAGGTTCCACTGGTGACGACATCGTGATGACCCAGTCTC |
| VK5 Int | CTGGGTTCCAGGTTCCACTGGTGACGAAACGACACTCACGCAGTCTC |
| VK6 Int | CTGGGTTCCAGGTTCCACTGGTGACGAAATTGTGCTGACWCAGTCTCCA |
| VK7 Int | CTGGGTTCCAGGTTCCACTGGTGACGACATTGTGCTGACCCAGTCT |
| Reverse Primer | |
| CK Int | GGGAAGATGAAGACAGATGGT |

TABLE 2c (SEQ ID NOs: 270-280, in order of appearance)

| Forward Primer | Sequence |
|---|---|
| VL1 Int | CTGGGTTCCAGGTTCCACTGGTGACCAGTCTGTGYTGACKCAGCC |
| VL2 Int | CTGGGTTCCAGGTTCCACTGGTGACCAGTCTGCCCTGACTCAGCC |
| VL3 Int | CTGGGTTCCAGGTTCCACTGGTGACTCYTATGAGCTGACWCAGCCAC |
| VL3l Int | CTGGGTTCCAGGTTCCACTGGTGACTCTTCTGAGCTGACTCAGGACCC |
| VL4ab Int | CTGGGTTCCAGGTTCCACTGGTGACCAGCYTGTGCTGACTCAATC |
| VL4c Int | CTGGGTTCCAGGTTCCACTGGTGACCTGCCTGTGCTGACTCAGC |

TABLE 2c-continued (SEQ ID NOs: 270-280, in order of appearance)

| | |
|---|---|
| VL5,9 Int | CTGGGTTCCAGGTTCCACTGGTGACCAGSCTGTGCTGACTCAGCC |
| VL6 Int | CTGGGTTCCAGGTTCCACTGGTGACAATTTTATGCTGACTCAGCCCCACT |
| VL7,8 Int | CTGGGTTCCAGGTTCCACTGGTGACCAGRCTGTGGTGACYCAGGAG |
| VL10 Int | CTGGGTTCCAGGTTCCACTGGTGACCAGGCAGGGCWGACTCAG |
| Reverse Primer | |
| CL Int | GGGYGGGAACAGAGTGACC |

Antibody Expression

Transient and recombinant monoclonal antibody production was performed as previously described (5, 6).

DH270 N332 Dependent V3 Glycan bnAb Lineage.

We describe here the co-evolution of a founder virus and a memory B cell lineage of gp120 V3-glycan directed bnAbs (DH270). We sequenced 1400 HIV quasispecies, isolated natural heavy- and light-chain pairs of 6 lineage DH270 antibodies, and analyzed this lineage by next generation sequencing (NGS) and structural studies. We found two additional TF-induced cooperating B-cell lineages that selected virus escape mutants that stimulated the DH270 lineage to potent neutralization breadth. Within the DH270 lineage we found a single early antibody CDR H2 mutation that was necessary for bnAb B cell lineage initiation. The combination for multiple cooperating lineages plus a rare antibody mutation thus explains the long period of antigenic stimulation required for bnAb induction.

Figure 28A:
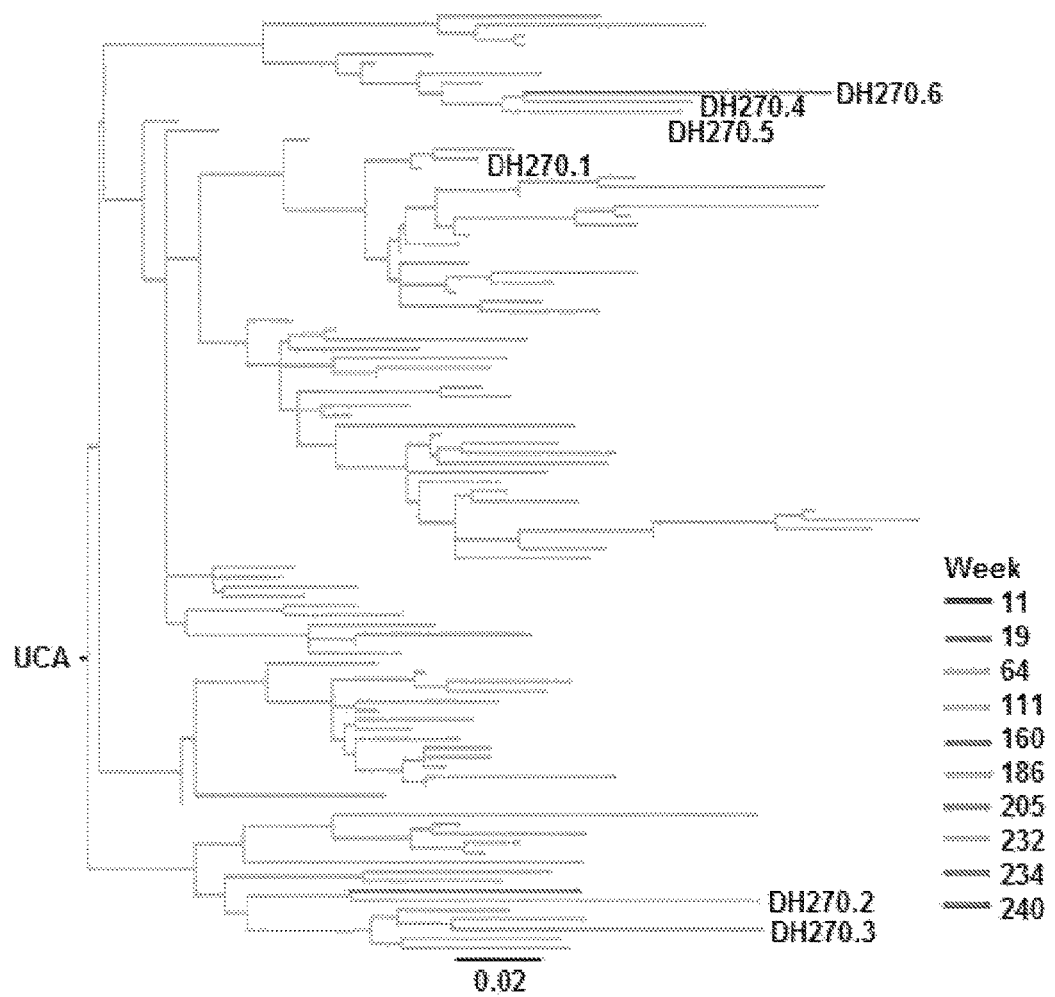
FIG. 28A shows Phylogram of DH270 lineage. Sequences shown were isolated by NGS in longitudinal analysis that overlapped in two separate runs. The phylogeny was computed by collapsing on a radius of 8 base pairs and the 90 sequences shown are representative of a total of 1500 sequences. VH sequences of isolated DH270 lineage antibodies were added and the lineage was inferred using Cloanalyst.

We studied an African individual (CH848) followed from time of infection to development of plasma neutralization breadth. Abrogation of the N332 glycan near the Env V3 loop by introducing a N332A mutation into consensus C, TRO.11, Q23.17 and DU156 HIV-1 pseudoviruses reduced CH848 plasma neutralization of these viruses, and demonstrated the presence of plasma N332-sensitive bnAbs (reference Georgiev paper). To isolate them, we probed memory B cells from weeks 205, 232 and 234 post-transmission using clonal memory B cell cultures and antigen-specific memory B cell sorting and isolated 6 naturally paired VH+VL N332-sensitive antibodies, designated DH270.1-6. Neutralization studies demonstrated that DH270 though containing only 5.5% VH mutations, mediated potent heterologous neutralization breadth (65.2% breadth and median IC50=0.17 ug/ml) (FIG. 28A-C).

We interrogated the depth of the DH270 clonal lineage by sequencing the DH270 variable heavy ($V_H$) gene using next generation sequencing (NGS) of memory B cell cDNA isolated at 11, 19, 64, 111, 160, 186 and 240 weeks post-transmission. A total of 767 unique DH270 lineage $V_H$ sequences from duplicated NGS experiments were found, with the earliest $V_H$ detected 186 weeks post-transmission (FIG. 28A). The DH270 lineage used VH1-2*02 paired with Vλ2-23 and had a 20 amino acid-long CDR H3. Clonal lineage intermediate and ancestor antibodies were computed from the naturally-paired sequences (Kepler refs) (FIG. 29). $V_H$ mutation frequencies of the isolated antibodies ranged from 5.6% (DH270.1) to 12.9% (DH270.6) (FIG. 29). Neutralization of wild-type and N332 mutated HIV-1 strains AC13.8, PVO4, TRO.11, AC10.0.29 and RHPA confirmed DH270 lineage N332 sensitivity of neutralization (FIG. 30). In competition binding assays, DH270.1 blocked binding of both V3-glycan bnAbs PGT125 and PGT128 to JRFL gp120 with IC50=0.4 ug/ml and DH270.1 binding to gp120 Env was dependent on N332 glycans.

Ontogeny of DH270 Neutralizing B Cell Lineage

Figure 28B:
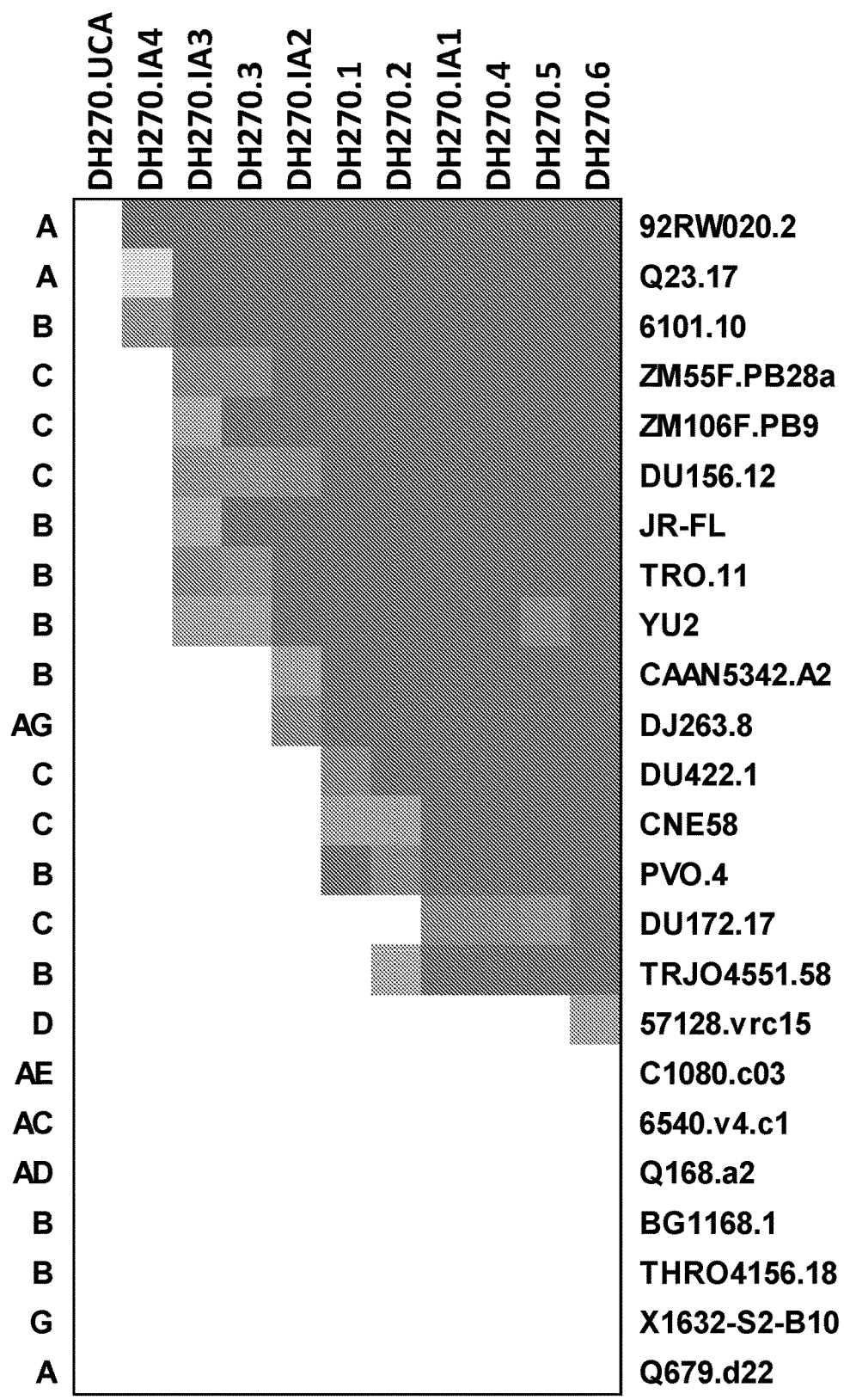
FIG. 28B shows Heatmap analysis of neutralization of 24 pseudoviruses (row) by 11 DH270 lineage mAbs.
Figure 28C:
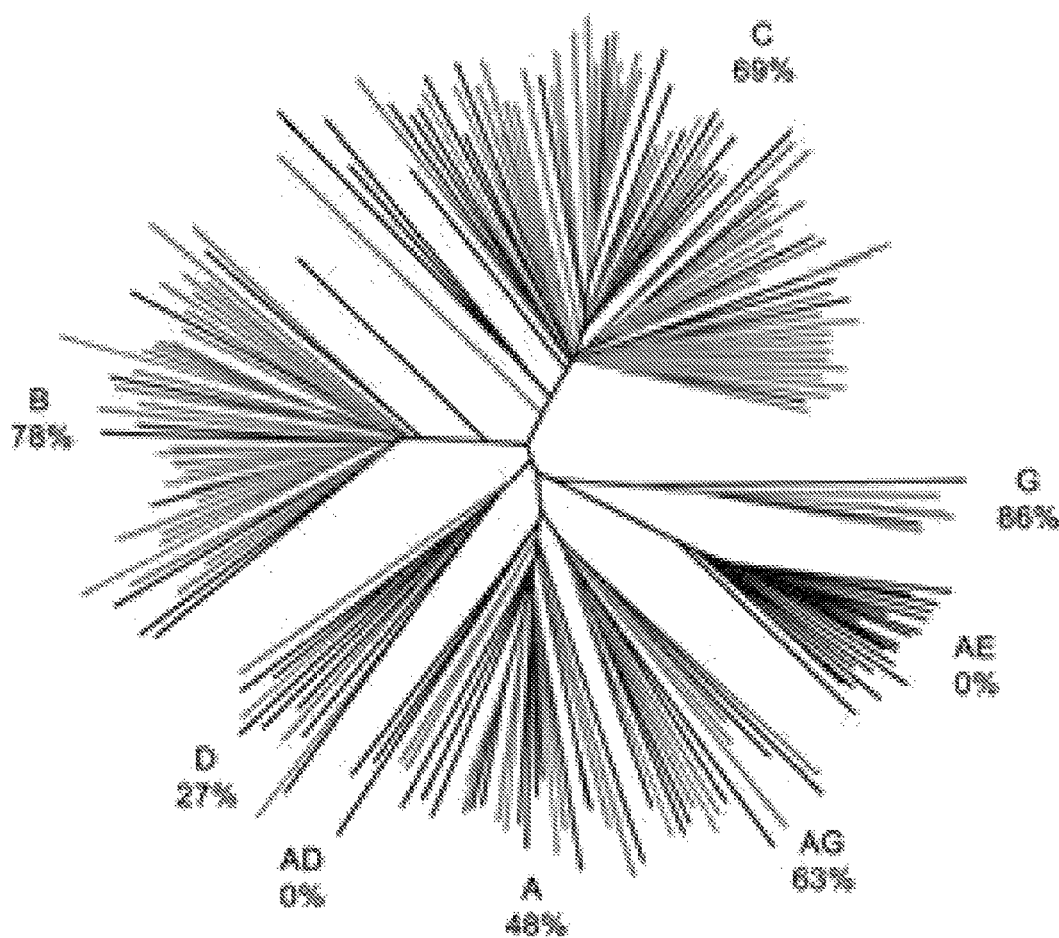
FIG. 28C shows Neutralization dendrograms display of DH270.6 (right) neutralization of a genetically diverse panel of 200 HIV-1 isolates. Coloration is by IC50 (red:<1 ug/ml; green:1-50 ug/ml; black:>50 ug/ml).

DH270 lineage antibodies displayed bnAb activity in a panel of 24 heterologous HIV-1 isolates, with DH270.6 the most broad (17 of 24) and potent (IC50=0.21 ug/ml) (FIG. 28B). The DH270 unmutated common ancestor antibody (DH270.UCA) did not neutralize heterologous HIV-1, but intermediate antibody 4 (DH270.IA4), which differed from UCA by 4 amino acids in the VH gene segment and one amino acid in VL neutralized 4/24 strains (16.7%) (FIG. 28B). Notably, DH270.IA4 acquired neutralizing activity while retaining the unmutated CDR H3 of the UCA.

As $V_H$ mutations accumulated in the DH270 B cell lineage, neutralization broadend only modestly while potency increased by 2 orders of magnitude. Thus, DH270-lineage heterologous neutralization evolved in two phases: first, early mutations conferred neutralization breadth, and second, further mutations enhanced neutralization potency.

DH270.1, DH270.5 and DH270.6 neutralization breadth was further evaluated in a large multi-clade panel of 201 HIV-1 heterologous strains (FIG. 28C). DH270.1 neutralized 88/201 (43.8%) HIV-1 isolates (median IC50=0.39 ug/ml), DH270.5 neutralized 99/201 (49.3%) HIV-1 isolates (median IC50=0.14 ug/ml), while DH270.6 was the most broad and potent antibody and neutralized 111/199 viruses (56%) (median IC50=0.07 ug/ml).

Figure 31:
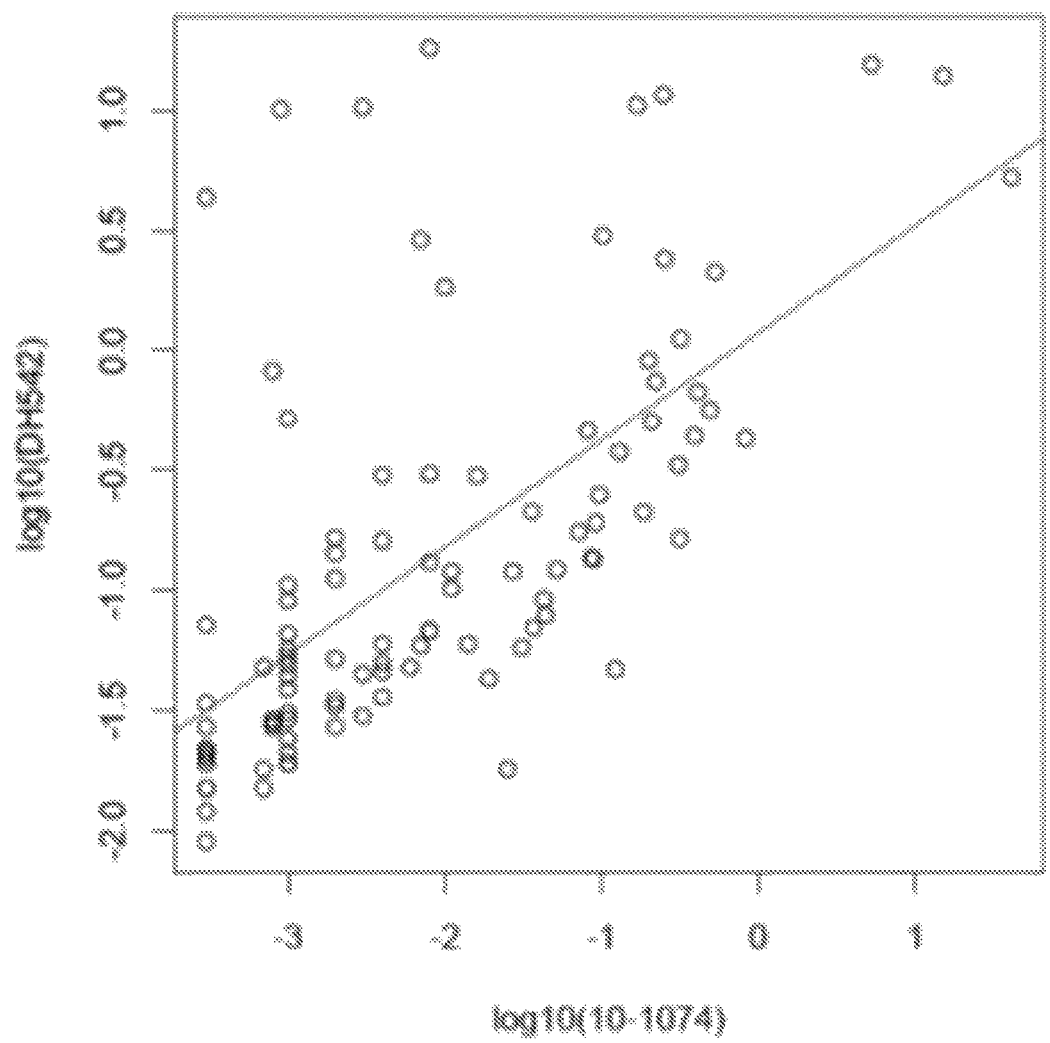
FIG. 31 shows the neutralization profile of DH270.6 most closely paralleled that of 10-1074.
Figure 31:
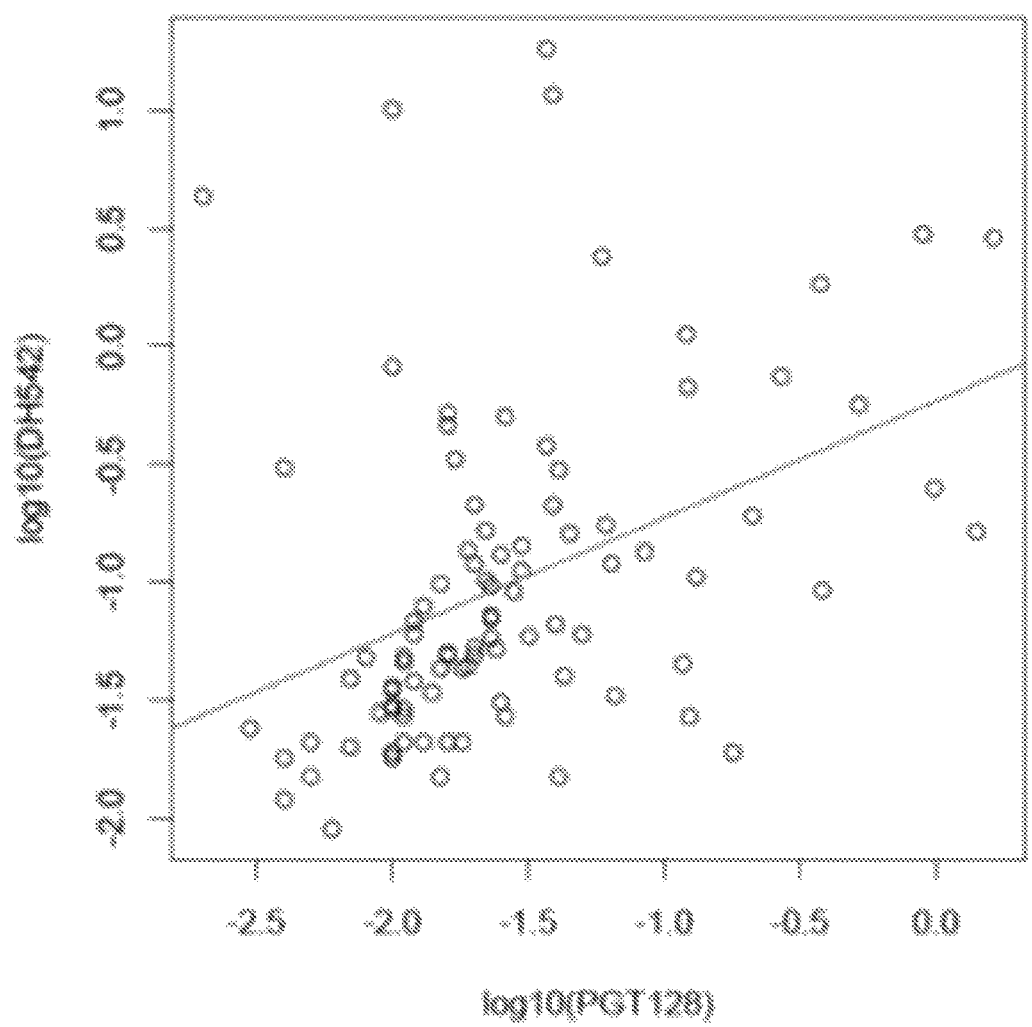

Antibody DH270.6 displayed strong clade preference for clade B (78%, n=41, p=0.0043) and sensitivity for clade C viruses (68%, n=55, p=0.029). It also neutralized 46% of clade A viruses and did not neutralize CRFO1 AE viruses. Presence for a glycosylation site in position N332 explained 75% of resistance of heterologous viruses to DH270.6. None of the viruses that shifted N332 glycan to N334 were neutralized by DH270.6 and, within each clade, N332 glycan tracked well with virus sensitivity to DH270.6 (p=0.03, Kendall's rank correlation). When compared to PGT128 and 10-1074, the neutralization profile of DH270.6 most closely paralleled that of 10-1074 (FIG. 31).

References for Example 2

1. Wardemann H, Yurasov S, Schaefer A, Young J W, Meffre E, Nussenzweig M C. Predominant autoantibody production by early human B cell precursors. Science (New York, N.Y.). 2003; 301(5638):1374-7. Epub 2003/08/16. doi:10.1126/science.1086907. PubMed PMID: 12920303.
2. Scheid J F, Mouquet H, Ueberheide B, Diskin R, Klein F, Oliveira T Y, Pietzsch J, Fenyo D, Abadir A, Velinzon K, Hurley A, Myung S, Boulad F, Poignard P, Burton D R, Pereyra F, Ho D D, Walker B D, Seaman M S, Bjorkman P J, Chait B T, Nussenzweig M C. Sequence and structural convergence of broad and potent HIV antibodies that mimic CD4 binding. Science (New York, N.Y.). 2011; 333(6049):1633-7. Epub 2011/07/19. doi:10.1126/science.1207227. PubMed PMID: 21764753; PubMed Central PMCID:PMCPmc3351836.
3. Kepler T B. Reconstructing a B-cell clonal lineage. I. Statistical inference of unobserved ancestors. F1000Research. 2013; 2:103. Epub 2014/02/21. doi: 10.12688/f1000research.2-103.v1. PubMed PMID: 24555054; PubMed Central PMCID:PMCPmc3901458.
4. Kepler T B, Munshaw S, Wiehe K, Zhang R, Yu J S, Woods C W, Denny T N, Tomaras G D, Alam S M, Moody M A, Kelsoe G, Liao H X, Haynes B F. Reconstructing a B-Cell Clonal Lineage. II. Mutation, Selection, and Affinity Maturation. Frontiers in immunology. 2014; 5:170. Epub 2014/05/06. doi:10.3389/fimmu.2014.00170. PubMed PMID:24795717; PubMed Central PMCID:PMCPmc4001017.
5. Liao H X, Chen X, Munshaw S, Zhang R, Marshall D J, Vandergrift N, Whitesides J F, Lu X, Yu J S, Hwang K K, Gao F, Markowitz M, Heath S L, Bar K J, Goepfert P A, Montefiori D C, Shaw G C, Alam S M, Margolis D M, Denny T N, Boyd S D, Marshal E, Egholm M, Simen B B, Hanczaruk B, Fire A Z, Voss G, Kelsoe G, Tomaras G D, Moody M A, Kepler T B, Haynes B F. Initial antibodies binding to HIV-1 gp41 in acutely infected subjects are polyreactive and highly mutated. The Journal of experimental medicine. 2011; 208(11):2237-49. Epub 2011/10/12. doi: 10.1084/jem.20110363. PubMed PMID: 21987658; PubMed Central PMCID:PMCPmc3201211.
6. Liao H X, Levesque M C, Nagel A, Dixon A, Zhang R, Walter E, Parks R, Whitesides J, Marshall D J, Hwang K K, Yang Y, Chen X, Gao F, Munshaw S, Kepler T B, Denny T, Moody M A, Haynes B F. High-throughput isolation of immunoglobulin genes from single human B cells and expression as monoclonal antibodies. Journal of virological methods. 2009; 158(1-2):171-9. Epub 2009/05/12. doi:10.1016/j.jviromet.2009.02.014. PubMed PMID:19428587; PubMed Central PMCID:PMCPmc2805188.

Figure 1B:
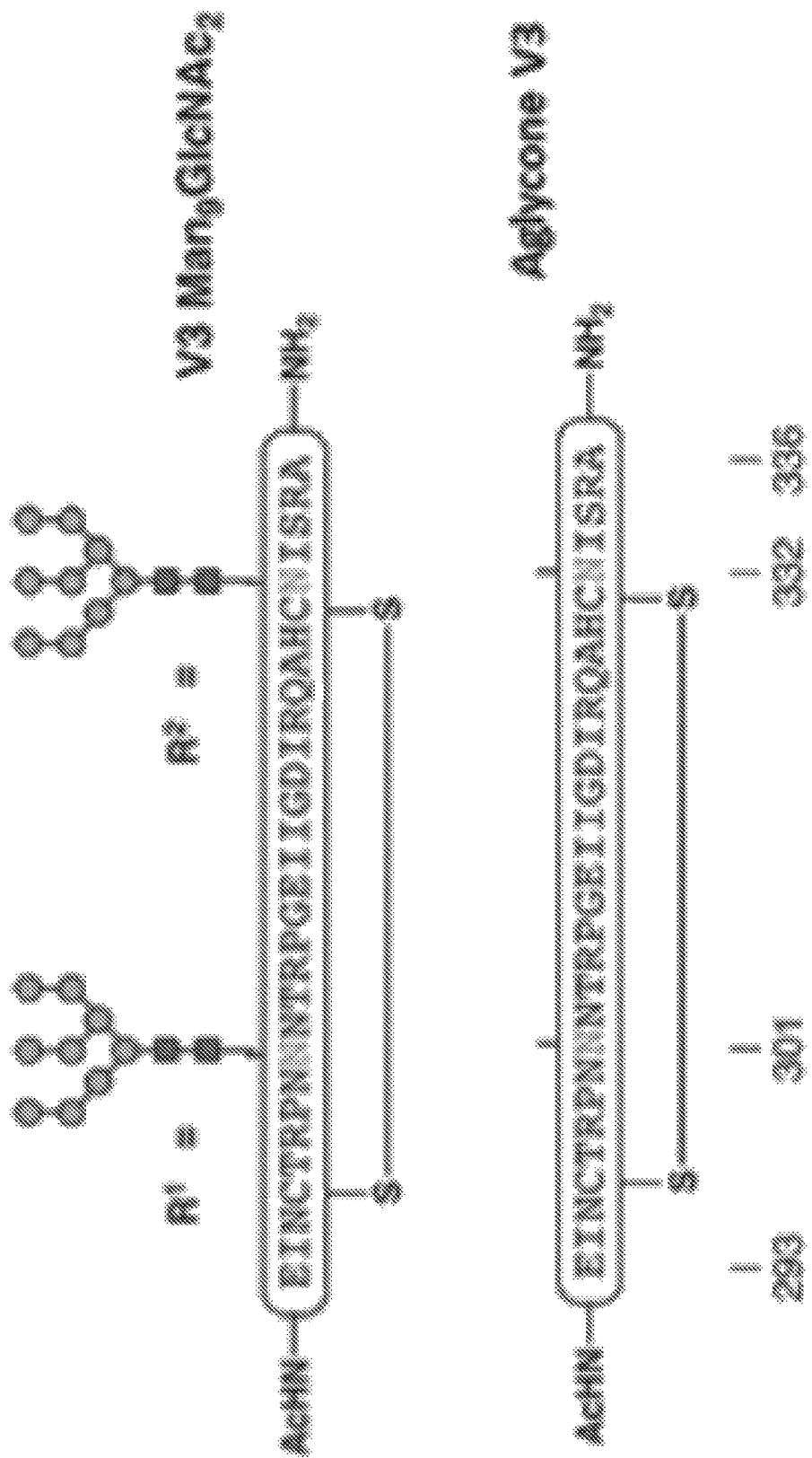
FIG. 1B shows the V3 peptide used as a hook to sort B cells from individual CH848 (SEQ ID NOS 286 and 286, respectively, in order of appearance).
Figure 3A:
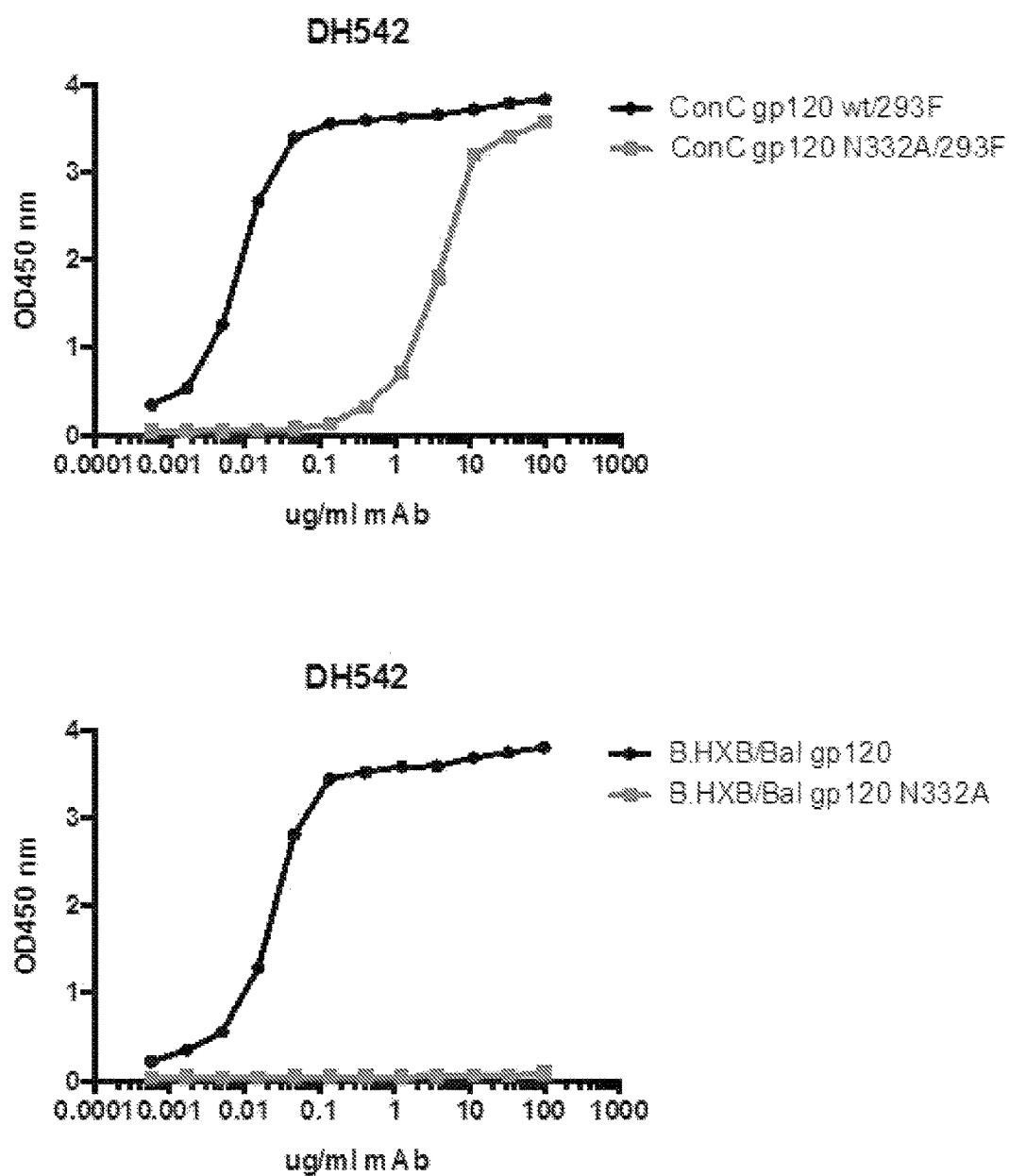
FIGS. 3A and 3B show that in an ELISA assay DH542 binding to HIV-Env depends on V3 loop glycans.
Figure 3B:
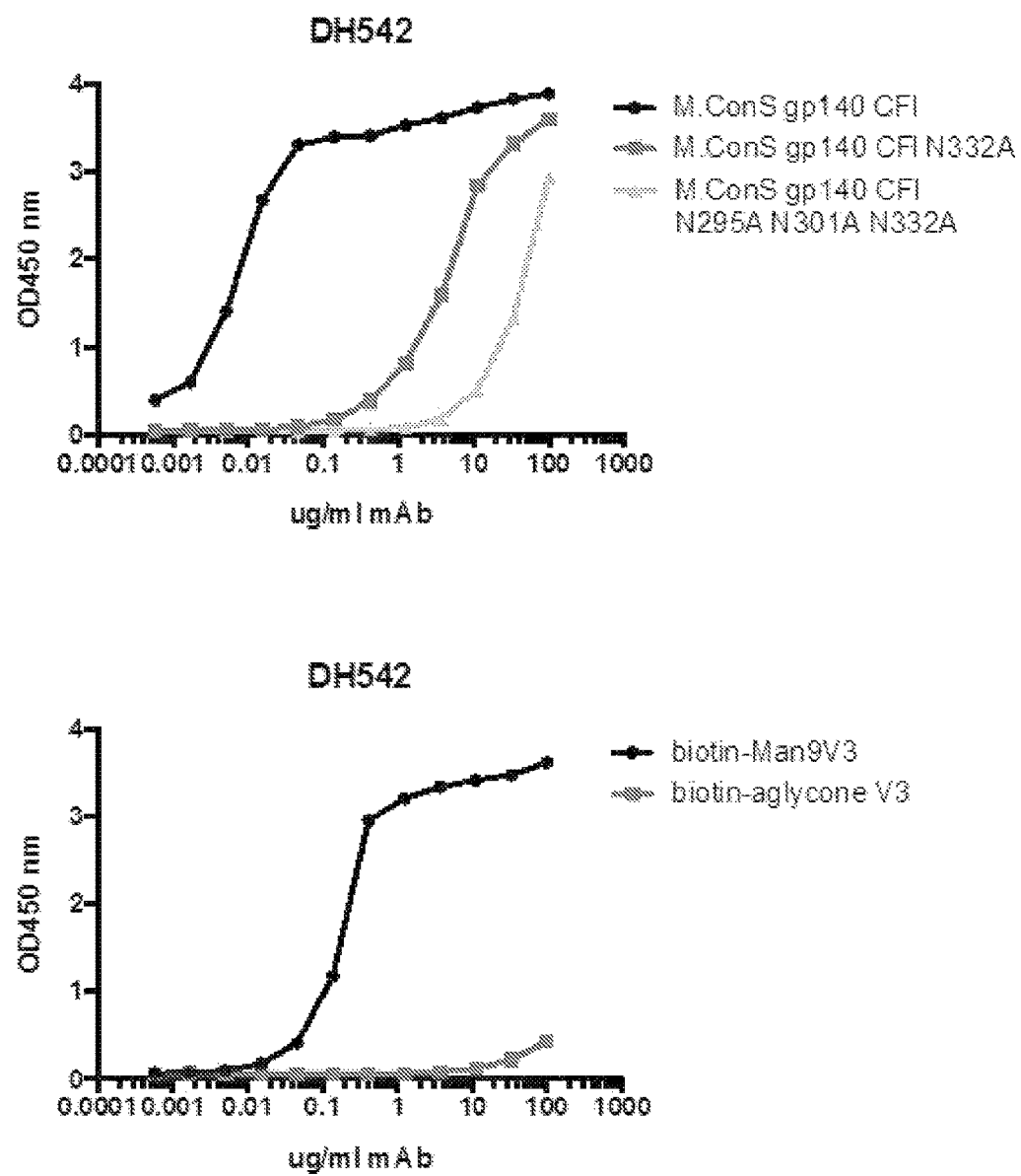
Figure 4B:
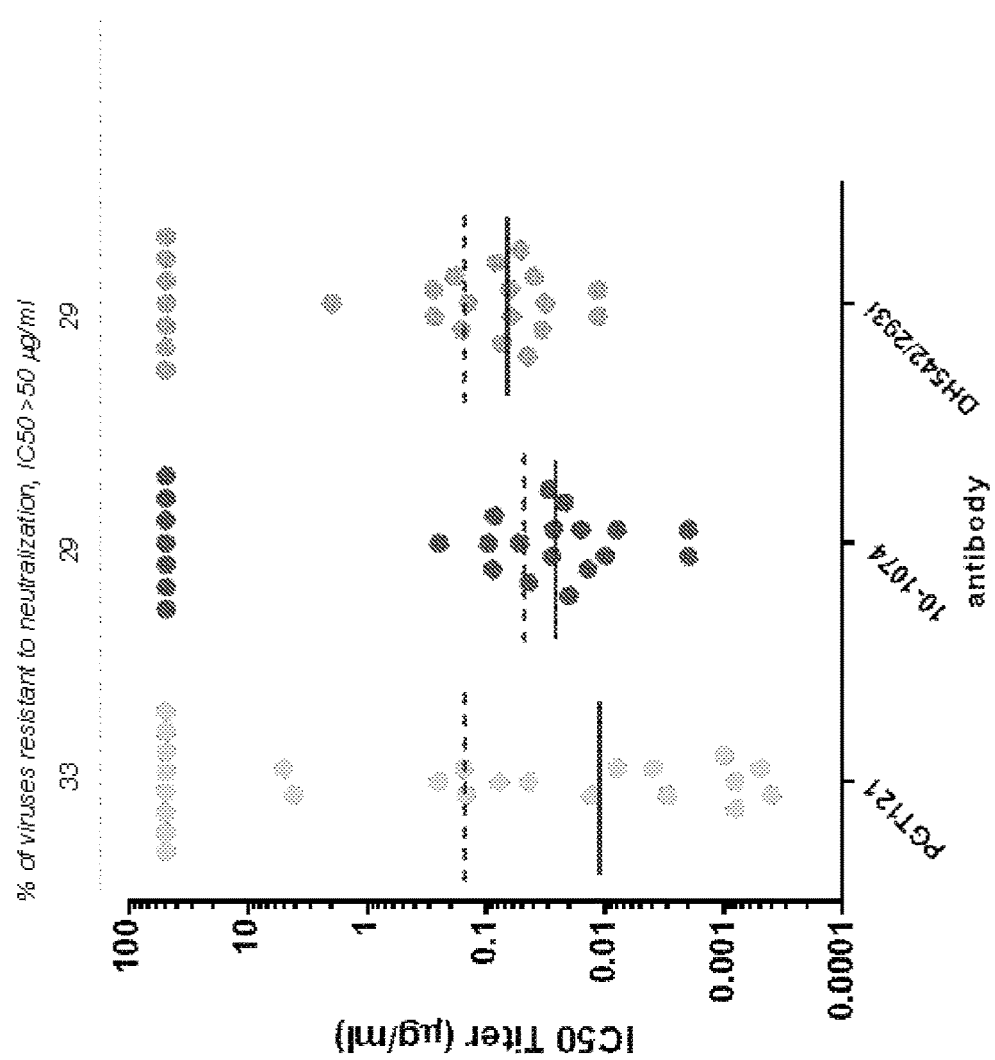
Figure 5:
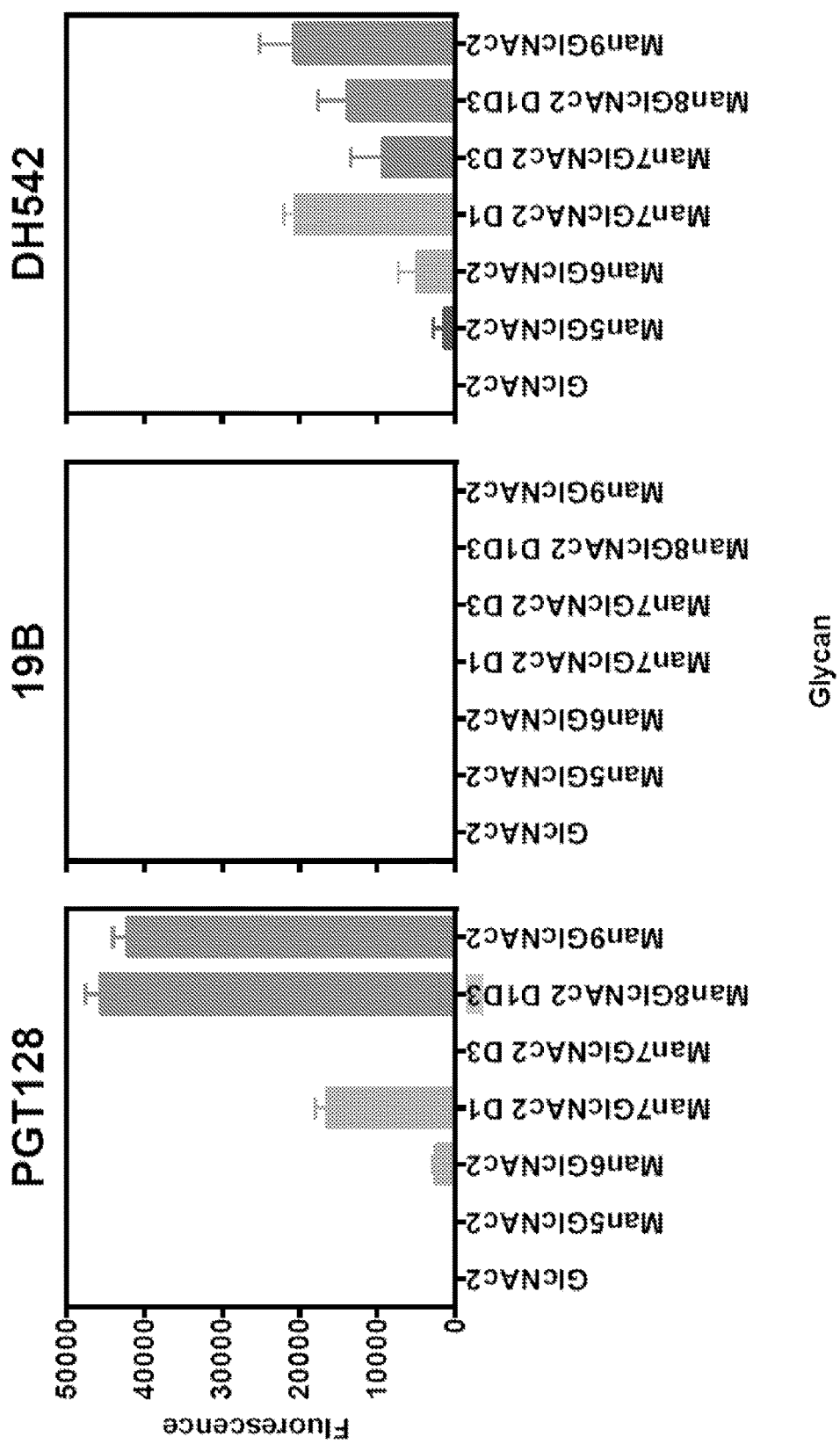
FIG. 5 shows that DH542 binds high-mannose glycans. The data represent antibody binding measured with a custom oligomanose glycan array—average from three separate glycan arrays. The glycan array is printed by Zbiotech (Aurora, CO) on polymer coated glass slides. Each glycan is printed in triplicate at three different concentrations. The antibody DH542 was diluted in PBS supplemented with 1% BSA to a final concentration of 50 ug/mL, and incubated on the glycan array for 1 h at room temperature. Unbound antibody is washed away with 5 washes with PBS-T. The binding of DH542 is detected with an anti-IgG Fc antibody conjugated to Cy3. The Cy3 intensity for each glycan is read with a GenePix 4000B array scanner and the means and standard error of the three replicates are shown in the graph. The data show that DH542 is a direct glycan binding HIV-1 antibody. It binds most strongly to Man9GlcNAc2 which is similar to known bnAbs such as PGT128 and 2G12. DH542 bound well to Man8GlcNAc2 and Man7GlcNAc2, but at a lower level than Man9GlcNAc2. Binding was also detected for two other lower forms of oligomannose, but at decreased magnitudes. DH542 did not exhibit detectable binding to the GlcNAc2 alone, meaning that it requires mannose for glycan recognition, and more specifically, binds the highest forms of oligomannose (Man9GlcNAc2) with the greatest magnitude. Overall, DH542 is a glycan-reactive antibody that binds directly to the predominant glycan, high mannose, present on HIV-1 Envelope. The figure also shows the binding by the non-glycan reactive HIV antibody 19B. It shows no binding to 100 uM glycan printed on the array. The figure also shows that the prototypic glycan-dependent HIV-1 antibody PGT128 binds well to Man7GlcNAc2, Man8, and Man9. PGT128 is reported to bind best to Man8GlcNAc2and Man9GlcNAc2, which was confirmed here as well. DH542 is shown binding to 100 uM of high mannose glycans. DH542 also binds to Man7GlcNAc2D3, which is not bound by PGT128.

DH542 is a V3 glycan bnAb from individual CH848 identified at 234 weeks post infection. This antibody was produced recombinantly from VH and VL sequences amplified by PCR from single cells sorted from PBMCs using Man9V3 glycopeptide tetramer (FIG. 1). DH542 is a member of the DH270 V3 glycan BnAb lineage (FIG. 8).

FIG. 2A shows the gene information of DH542 and FIG. 2B shows DH542 sequences.

Neutralization studies demonstrated that DH270 though containing only 5.5% VH mutations, mediated potent heterologous neutralization breadth (65.2% breadth and median IC50=0.17 ug/ml).

Example 3

TZM-bl Cells Pseudo-viruses Neutralization Assay

TZMbl neutralization assay is a standard way to evaluate antibody breadth and potency. See Montefiori, D. Methods Mol Biol. 2009; 485:395-405; HIV-1 Env-pseudoviruses infection of TZM-bl cells. Exemplary pseudovirus neutralization assays and panels of HIV-1 pseudovirus are described for example, in Li et al., J Virol 79, 10108-10125, 2005, Seaman et al, J. Virol., 84:1439-1452, 2010; Sarzotti-Kelsoe et al., J. Immunol. Methods, 409:131-46, 2014; and WO2011/038290, each of which is incorporated by reference herein. Various HIV-1 isolates, both Tier 1 and Tier 2 viruses can be included in this assay.

The TZMbl assay was conducted to determine neutralization potency and breadth of the various antibodies of the invention on different HIV-1 pseudoviruses.

Example 4

Binding Assays and Kd Determination

Kd measurements of antibody binding to HIV-1 envelope, e.g. gp120 or any other suitable peptide, will be determined by Surface Plasmon Resonance measurements, for example using Biacore, or any other suitable technology which permits detection of interaction between two molecules in a quantitative way.

Example 5

Assay for Self-reactivity

Table 3 below summarizes some of the known types of disease associated antibodies.

| Autoantibody | Disease Association (s) |
|---|---|
| SSA | SLE, Sjogrens Syndrome (SS) |
| SSB | Sjogrens Syndrome |
| Sm (Smith antigen) | SLE |
| RNP (ribonucleoprotein) | Mixed connective tissue disease (MCTD) |
| Scl-70 | Scleroderma |
| Jo-1 | Myositis |
| Centromere B | Scleroderma CREST variant (calcinosis), Raynaud's, esophogeal dysmotility, sclerodactyly and talangiectasia |
| Histones | Drug induced SLE |

Various assays for self-reactivity of human antibodies are known in the art. AtheNA Multi-Lyte ANA Plus Test System is one such assay. This is luminex-based assay, which is also used to screen patient sera. In our experiments the criteria for positivity is as follows:an antibody is positive for auto-reactivity if reactive at 25 µg/ml.

TABLE 4

Summary of immunoflourescent (IF) staining of Hep2 cells data for antibodies DH270IA1, CH491, CH493. DH270IA1 does not show self-reactivity. CH491 and CH493 show some self-reactivity in this assay.

| Antibody ID | Concentration | Score | Staining Pattern |
|---|---|---|---|
| DH270_IA1/293i | [50 ug/mL] | — | |
| DH270_IA1/293i | [25 ug/mL] | — | |
| CH491_4A/293i | [50 ug/mL] | 2+ | nuclear diffuse, cytoplasmic |
| CH491_4A/293i | [25 ug/mL] | 1+ | nuclear diffuse, cytoplasmic |
| CH493_4A/293i | [50 ug/mL] | 2+ | cytoplasmic |
| CH493_4A/293i | [25 ug/mL] | 1+ | cytoplasmic |

FIGS. 6 and 7 show a summary of binding to autoantigen in the AtheNA assay and HEp-2 cell IF staining for DH542.

TABLE 5

Summary of Athena data for DH270IA1, CH491, CH493. DH270IA1 does not show self-reactivity. CH491 and CH493 show some self-reactivity in this assay.

| Lot | Antibody ID | | SSA | SSB | Sm | RNP | Scl 70 | Jo 1 | dsDNA | Cent B | Histone |
|---|---|---|---|---|---|---|---|---|---|---|---|
| 294HC | DH270_IA1/293i | 50 | 5 | 6 | 5 | 2 | 4 | 5 | 32 | 10 | 9 |
| | | 25 | 3 | 6 | 5 | 2 | 1 | 3 | 18 | 5 | 4 |
| | | 12.5 | 3 | 6 | 5 | 3 | 2 | 6 | 11 | 3 | 4 |
| | | 6.25 | 5 | 1 | 3 | 2 | 2 | 5 | 6 | 2 | 2 |
| 21RKK | CH491_4A | 50 | 68 | 144 | 6 | 43 | 16 | 169 | 47 | 54 | 59 |
| | | 25 | 44 | 95 | 4 | 30 | 9 | 118 | 39 | 45 | 44 |
| | | 12.5 | 28 | 60 | 3 | 24 | 7 | 79 | 29 | 34 | 34 |
| | | 6.25 | 21 | 42 | 4 | 18 | 4 | 56 | 11 | 26 | 26 |
| 23RKK | CH493_4A | 50 | 155 | 70 | 37 | 69 | 36 | 198 | 0 | 94 | 166 |
| | | 25 | 100 | 38 | 53 | 55 | 34 | 167 | 0 | 129 | 202 |
| | | 12.5 | 54 | 22 | 42 | 49 | 26 | 102 | 0 | 165 | 200 |
| | | 6.25 | 22 | 15 | 46 | 32 | 17 | 54 | 0 | 177 | 174 |

Development of auto and polyreactivity during antibody maturation toward neutralization breadth is a critical aspect that may limit the ability of generating bnAbs during natural infection and upon vaccination. We have previously reported that, in subject CH505, the CD4bs CH103 bnAb lineage is polyreactive and, similarly to CD4 mimic VRC01-class bnAbs, bound to human ubiquitin ligase E3A (UBE3A) with avidity correlated with neutralization (Liao et al Nature 2013; Liu et al J Virol 2015). Since CH557 is a potent and extremely broad CD4 mimic CD4bs bnAb, we compared the auto- and polyreactivity profiles of CH557 with those of early precursors of the CH235 antibody lineage (UCA, IA4, IA3, IA2, IA1, CH235, CH236, CH239, CH240 and CH241). In line with previous observations, reactivity against autoantigens developed among early CH235 lineage members with maturation. However, bnAb CH557 itself became exquisitely HIV-1 specific:it does not react with cardiolipin or other antigens associated with autoimmune disorders, it is negative in Hep-2 IF staining, or any of 9,400 human antigens, including UBE3A. Albeit reactivity against other human antigens cannot be formally ruled out, these data demonstrate that bnAb CH557 lost the auto and poly-reactivity developed by its precursors, and demonstrates that decoupling neutralization breadth of CD4 mimic CDbs bnAbs from auto- and polyreactivity is an achievable goal.

TABLE 6

Summary of Athena assay results for CH557. Results are expressed as relative luminescence units. Readings <100 are considered negative, results between 100 and 120 are considered "indeterminate" and results >120 are considered positive. CH557 is negative for all the antigens tested at all antibody concentrations ranging from 6.25 ug/ml to 50 ug/ml.

| Antibody | ug/ml | SSA | SSB | Sm | RNP | Scl 70 | Jo 1 | dsDNA | Cent B | Histone |
|---|---|---|---|---|---|---|---|---|---|---|
| 4 e 10 | 50 | 49 | 263 | 5 | 4 | 1 | 190 | 2 | 3 | 16 |
| | 25 | 33 | 227 | 2 | 3 | 1 | 160 | 2 | 3 | 10 |
| | 12.5 | 21 | 199 | 3 | 3 | 0 | 131 | 3 | 1 | 7 |
| | 6.25 | 17 | 178 | 3 | 3 | 1 | 113 | 0 | 2 | 6 |
| synagis | 50 | 5 | 6 | 11 | 10 | 3 | 5 | 25 | 9 | 11 |
| | 25 | 3 | 7 | 3 | 4 | 2 | 2 | 11 | 4 | 5 |
| | 12.5 | 2 | 5 | 7 | 3 | 3 | 6 | 7 | 2 | 3 |
| | 6.25 | 2 | 5 | 2 | 3 | 2 | 1 | 0 | 2 | 3 |
| CH557_4A/293i | 50 | 6 | 15 | 8 | 10 | 6 | 10 | 29 | 46 | 16 |
| | 25 | 4 | 12 | 6 | 6 | 4 | 2 | 18 | 25 | 8 |
| | 12.5 | 3 | 9 | 6 | 3 | 3 | 5 | 10 | 16 | 6 |
| | 6.25 | 4 | 5 | 4 | 4 | 3 | 5 | 9 | 11 | 4 |

TABLE 7

Summary of Athena assay results for various other antibodies of the CH235 lineage. Results are expressed as relative luminescence units. Readings <100 are considered negative, results between 100 and 120 are considered "indeterminate" and results >120 are considered positive. CH236, CH239, CH235 IA1 and IA2 are positive for multiple antigens.

| Antibody ID | | SSA | SSB | Sm | RNP | Scl 70 | Jo 1 | dsDNA | Cent B | Histone |
|---|---|---|---|---|---|---|---|---|---|---|
| synagis | 50 | 13 | 9 | 6 | 2 | 1 | 4 | 3 | 3 | 0 |
| | 25 | 11 | 4 | 4 | 0 | 2 | 4 | 0 | 2 | 2 |
| 4E10 IgG1 | 50 | 99 | 207 | 55 | 28 | 5 | 227 | 14 | 14 | 32 |
| | 25 | 81 | 189 | 46 | 20 | 4 | 206 | 14 | 9 | 24 |
| CH235_4A | 50 | 12 | 7 | 16 | 11 | 8 | 7 | 25 | 11 | 14 |
| | 25 | 13 | 5 | 7 | 5 | 4 | 4 | 13 | 6 | 7 |
| | 12.5 | 13 | 5 | 8 | 6 | 2 | 3 | 0 | 5 | 5 |
| | 6.25 | 12 | 6 | 5 | 3 | 2 | 2 | 3 | 3 | 5 |

TABLE 7-continued

Summary of Athena assay results for various other antibodies of the CH235 lineage. Results are expressed as relative luminescence units. Readings <100 are considered negative, results between 100 and 120 are considered "indeterminate" and results >120 are considered positive. CH236, CH239, CH235 IA1 and IA2 are positive for multiple antigens.

| Antibody ID | | SSA | SSB | Sm | RNP | Scl 70 | Jo 1 | dsDNA | Cent B | Histone |
|---|---|---|---|---|---|---|---|---|---|---|
| CH236_4A/293i | 50 | 177 | 207 | 128 | 65 | 57 | 145 | 2 | 84 | 138 |
| | 25 | 224 | 175 | 165 | 69 | 62 | 72 | 42 | 129 | 193 |
| | 12.5 | 185 | 63 | 258 | 78 | 50 | 19 | 179 | 233 | 234 |
| | 6.25 | 44 | 15 | 184 | 40 | 31 | 7 | 228 | 208 | 154 |
| CH239_4A/293i | 50 | 289 | 10 | 250 | 93 | kriss | 15 | 38 | 173 | 228 |
| | 25 | 306 | 8 | 237 | 96 | 51 | 11 | 61 | 199 | 253 |
| | 12.5 | 277 | 6 | 277 | 85 | 48 | 8 | 108 | 216 | 263 |
| | 6.25 | 178 | 5 | 285 | 78 | 49 | 8 | 181 | 260 | 266 |
| CH240_4A/293i | 50 | 16 | 17 | 33 | 17 | 6 | 13 | 75 | 37 | 42 |
| | 25 | 16 | 11 | 22 | 11 | 6 | 11 | 50 | 24 | 27 |
| | 12.5 | 14 | 5 | 13 | 8 | 4 | 7 | 37 | 15 | 18 |
| | 6.25 | 12 | 5 | 9 | 6 | 3 | 5 | 14 | 8 | 9 |
| CH241 | 50 | 23 | 10 | 12 | 8 | 5 | 8 | 23 | 21 | 30 |
| | 25 | 15 | 6 | 11 | 6 | 4 | 5 | 18 | 14 | 20 |
| | 12.5 | 14 | 8 | 7 | 5 | 3 | 6 | 2 | 8 | 13 |
| | 6.25 | 15 | 4 | 4 | 3 | 1 | 2 | 6 | 6 | 9 |
| CH235UA/293i | 50 | 11 | 3 | 8 | 5 | 3 | 3 | 7 | 5 | 7 |
| | 25 | 9 | 3 | 6 | 4 | 3 | 5 | 0 | 3 | 3 |
| | 12.5 | 9 | 4 | 6 | 3 | 3 | 5 | 4 | 3 | 4 |
| | 6.25 | 10 | 5 | 5 | 2 | 3 | 3 | 3 | 2 | 2 |
| CH235VH_UCAtk_v2_4A/293i | 50 | 14 | 10 | 13 | 11 | 5 | 6 | 22 | 28 | 17 |
| | 25 | 11 | 6 | 10 | 6 | 3 | 4 | 13 | 18 | 11 |
| | 12.5 | 10 | 7 | 9 | 7 | 4 | 6 | 9 | 10 | 7 |
| | 6.25 | 10 | 5 | 7 | 6 | 3 | 3 | 4 | 7 | 5 |
| CH235VH_I1_v2_4A/293i | 50 | 149 | 217 | 104 | 80 | 57 | 176 | 12 | 80 | 100 |
| | 25 | 150 | 197 | 110 | 67 | 52 | 171 | 19 | 80 | 99 |
| | 12.5 | 151 | 167 | 77 | 56 | 40 | 152 | 58 | 81 | 100 |
| | 6.25 | 175 | 117 | 77 | 46 | 31 | 129 | 61 | 87 | 118 |
| CH235VH_I2_v2_4A/293i | 50 | 73 | 69 | 259 | 101 | 69 | 55 | 444 | 256 | 371 |
| | 25 | 43 | 36 | 256 | 93 | 49 | 26 | 496 | 228 | 302 |
| | 12.5 | 34 | 31 | 279 | 85 | 44 | 20 | 617 | 225 | 287 |
| | 6.25 | 18 | 15 | 204 | 66 | 28 | 12 | 599 | 183 | 207 |
| CH235VH_I3_v2_4A/293i | 50 | 14 | 10 | 18 | 10 | 5 | 6 | 35 | 37 | 17 |
| | 25 | 10 | 9 | 13 | 7 | 4 | 8 | 33 | 27 | 12 |
| | 12.5 | 12 | 6 | 12 | 5 | 3 | 3 | 23 | 15 | 7 |
| | 6.25 | 12 | 3 | 7 | 4 | 2 | 2 | 15 | 9 | 5 |
| CH235VH_I4_v2_4A/293i | 50 | 12 | 6 | 12 | 9 | 4 | 5 | 15 | 14 | 13 |
| | 25 | 12 | 4 | 12 | 5 | 2 | 2 | 7 | 10 | 9 |
| | 12.5 | 11 | 3 | 6 | 4 | 2 | 3 | 11 | 5 | 6 |
| | 6.25 | 11 | 5 | 6 | 3 | 2 | 4 | 4 | 5 | 4 |
| Cat-CH106 | 50 | 12 | 3 | 5 | 2 | 3 | 3 | 6 | 2 | 2 |
| | 25 | 8 | 3 | 1 | 3 | 2 | 2 | 3 | 2 | 3 |
| | 12.5 | 11 | 5 | 4 | 2 | 3 | 3 | 5 | 2 | 2 |
| | 6.25 | 10 | 6 | 5 | 1 | 2 | 4 | 7 | 1 | 2 |

TABLE 8

Summary of ELISA cardiolipin assay results for CH557 and various other antibodies. Antibodies were tested at concentrations ranging from 100 ug/ml to 12.5 ug/ml. Results are expressed as optical density at wavelength of 450 nm (OD450). OD450 < 0.2 are negative. Synagis is used as negative control and 4E10 is used as positive control. CH557 did not bind to cardiolipin.

| Antibody | lot | ug/ml | 100 | 50 | 25 | 12.5 |
|---|---|---|---|---|---|---|
| 4 e 10 | | 11.94 | 2.0997 | 2.346 | 1.9027 | 1.6277 |
| synagis | | 1.05 | 0.0424 | 0.0474 | 0.0408 | 0.0408 |
| Ab901754RhK/PEI | ZRJ070 | 3.86 | 0.0382 | 0.0859 | 0.0299 | 0.0394 |
| Ab901754RhKMut58_9 | ZRJ93 | 2.8 | 0.6665 | 0.428 | 0.2898 | 0.1681 |
| AbTr900114147Rh/293i | 226JAH | 7.44 | 0.4615 | 0.2596 | 0.1778 | 0.1018 |
| DH522 | 64RKK | 6.67 | 0.1206 | 0.079 | 0.0613 | 0.0491 |
| DH522UCA_Rh/293i | 362HC | 13.19 | 0.6156 | 0.415 | 0.2179 | 0.1302 |
| DH522_v2Rh/293i | 363HC | 6.93 | 0.3497 | 0.1652 | 0.1081 | 0.0828 |
| DH522I1.2Rh/293i | 372HC | 13.99 | 0.5506 | 0.2738 | 0.183 | 0.1073 |
| CH557_4A/293i | 70RKK | 11.94 | 0.0942 | 0.0761 | 0.0591 | 0.0475 |
| DH542-293i | 014RM | 2.51 | 0.062 | 0.0503 | 0.0525 | 0.0511 |

TABLE 9

Summary of binding of listed antibodies to cardiolipin in ELISA. Antibodies were tested at concentrations ranging from 100 ug/ml to 12.5 ug/ml. Results are expressed as optical density at wavelength of 450 nm (OD450). OD450 < 0.2 are negative. Synagis is used as negative control and 4E10 is used as positive control. The majority of CH235 lineage antibodies, with the exception of CH235_IA3, IA4, CH235 and CH240 (the former has borderline binding), bound to cardiolipin.

| | | 100 | 33.33333 | 11.11111 | 3.703704 | 1.234568 | 0.411523 | 0.137174 | 0.045725 |
|---|---|---|---|---|---|---|---|---|---|
| | synagis | 0.0391 | 0.0375 | 0.0359 | 0.0378 | | | | |
| | 4E10 IgG1 | 2.3179 | 2.2324 | 2.1165 | 1.941 | | | | |
| 105SJA | CH235_4A | 0.1198 | 0.0555 | 0.0423 | 0.0411 | 0.0413 | 0.0377 | 0.0378 | 0.0387 |
| 121SMI | CH236_4A/293i | 0.5104 | 0.1936 | 0.0849 | 0.0524 | 0.0423 | 0.0382 | 0.0425 | 0.0385 |
| 98JAH | CH239_4A/293i | 0.5001 | 0.2554 | 0.1078 | 0.0612 | 0.0476 | 0.0424 | 0.0386 | 0.0405 |
| 96GEH | CH240_4A/293i | 0.194 | 0.0893 | 0.0543 | 0.0434 | 0.0399 | 0.0408 | 0.0444 | 0.0421 |
| 108SJA | CH241 | 0.248 | 0.1061 | 0.0617 | 0.0491 | 0.0405 | 0.0437 | 0.0409 | 0.0384 |
| 132SMI | CH235UA/293i | 0.2337 | 0.1074 | 0.0738 | 0.0504 | 0.0436 | 0.0417 | 0.0395 | 0.0391 |
| 137SMI | DH235VH_UCAtk_v2_4A/293i | 0.5112 | 0.253 | 0.1353 | 0.0658 | 0.0486 | 0.0428 | 0.0415 | 0.0427 |
| 121JAH | DH235VH_I1_v2_4A/293i | 0.5321 | 0.2638 | 0.0955 | 0.0637 | 0.0473 | 0.0409 | 0.0414 | 0.041 |
| 138SMI | DH235VH_I2_v2_4A/293i | 0.9691 | 0.4951 | 0.1929 | 0.0894 | 0.0603 | 0.0488 | 0.0582 | 0.0442 |
| 119JAH | DH235VH_I3_v2_4A/293i | 0.1317 | 0.0743 | 0.0518 | 0.046 | 0.0439 | 0.0412 | 0.0429 | 0.0426 |
| | synagis | 0.0405 | 0.0453 | 0.0414 | 0.0414 | | | | |
| | 4E10 IgG1 | 2.249 | 2.2353 | 2.105 | 1.9205 | | | | |
| 120JAH | DH235VH_I4_v2_4A/293i | 0.1076 | 0.0609 | 0.0475 | 0.0416 | 0.0439 | 0.0399 | 0.0366 | 0.0403 |
| | Cat-CH106 | 0.0437 | 0.0443 | 0.0413 | 0.04 | 0.043 | 0.0404 | 0.0399 | 0.0407 |

Example 6

CD4 Binding Site Antibodies and MPER

Figure 23:
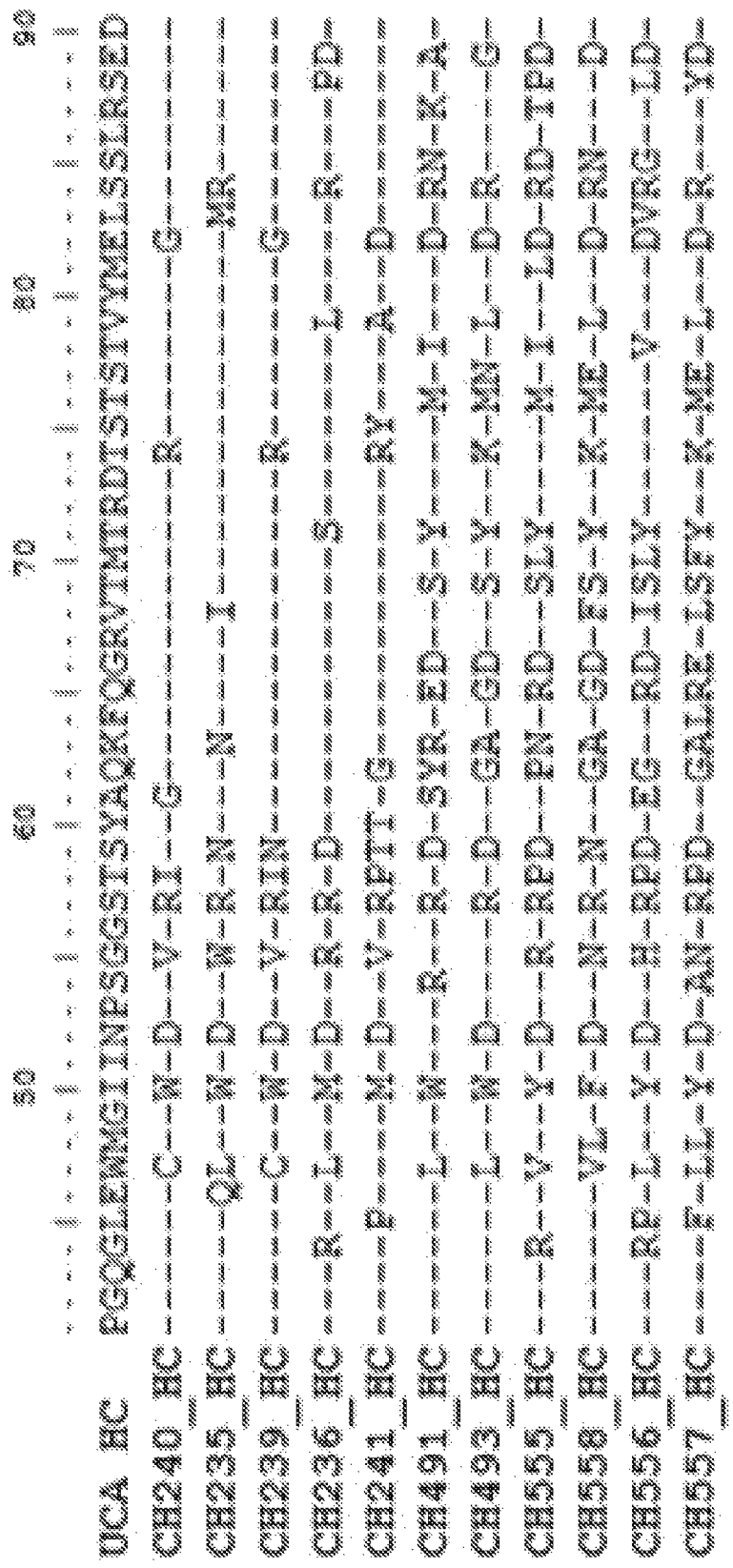
FIG. 23 shows amino acid alignment of CH235 lineage antibody heavy chain and light chain (SEQ ID NOs:179-190, in order of appearance from UCA HC to CH557_HC). Antibodies are listed in ascending order of somatic mutations and compared to the inferred unmutated common ancestor previously published (Gao, Bonsignori, Liao et al. Cell 2014)
Figure 23:
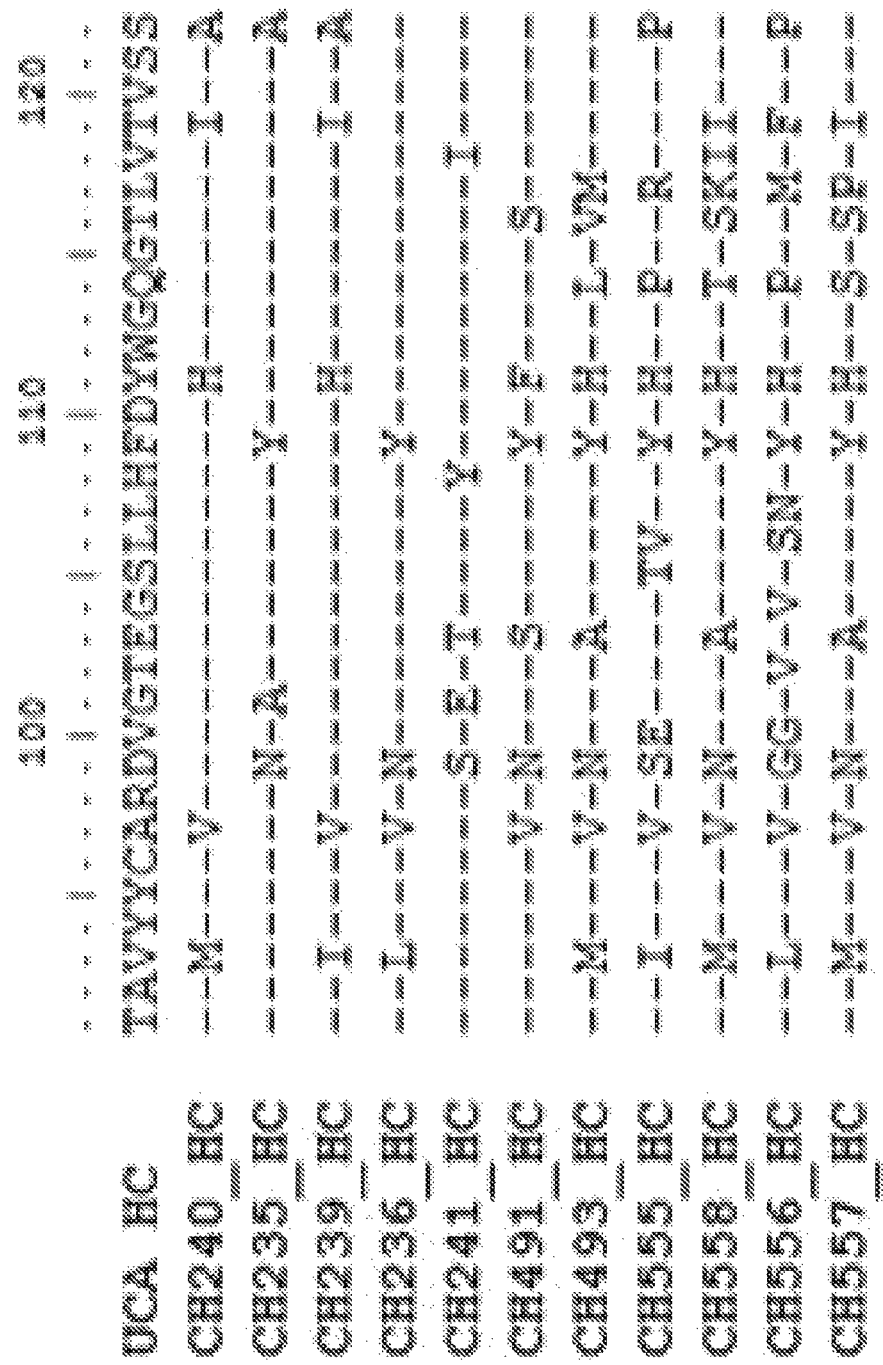

CH557 is one example of a CD4 binding site antibody which can be used in combination with the V3 glycan antibodies of the invention. VH and VL sequences of CD4 binding site antibodies are described in FIGS. 21 and 23.

MPER antibodies, from the DH511 lineage and variants as described herein, can be used in combination with the V3 antibodies of the invention. MPER antibodies sequences are described for example in FIGS. 12A and 12B, FIG. 13.

DH512_K3 is a combination of VH from DH512 and VL called DH511_2AVK

>DH511_2AVK Kappa Chain Nucleotide Sequence
(SEQ ID NO: 281)
GACATCCAGATGACCCAGTCTCCGTCTTTCCTGTACGGCTCTGTAGGCGA

TAGAGTCACCATCACTTGCCGGGCAAGTCAGAATATTAAGGACTATTTAA

ATTGGTATCAGCAGAGACCAGGGAGAGCCCCTAGACTCCTGATCTATGCT

GCATCCAATTTGCAAAGTGGGGTCCCGTCAAGGTTCAGTGGCAGTGGATA

TGGGACAGACTTTACTCTCATCATCAGCAGTCTGCAACCTGAGGACTTTG

CGACTTATTTCTGTCAAGAGAGTTATAGTTCTACGCCCACACACATTTTT

GGCCTGGGGACCAAATTGGAGAAGAAAC

>DH511_2AVK Kappa Chain Amino Acid Sequence
(SEQ ID NO: 282)
DIQMTQSPSFLYGSVGDRVTITCRASQNIKDYLNWYQQRPGRAPRLLIYA
ASNLQSGVPSRFSGSGYGTDFTLIISSLQPEDFATYFCQESYSSTPTHIF
GLGTKLEKKX Example 7

Other Assays

Epitope mapping of antibodies: Binding and/or neutralization assays using various envelope antigens can be used to determine the epitope recognized by these antibodies.

The stability and properties of the antibodies, for example as formulated in a composition for treatment will be tested.

Animal studies (PK and PD studies) could be conducted to determine the distribution and half life of the antibodies.

Various assays and experiments can be designed to analyze prevention, treatment and/or cure.

Example 8

DH540 Antibody is Described Elsewhere.

DH540 sequences are described in FIG. 22 and the antibody is described in detail in U.S. Ser. No. 62/170,558, filed Jun. 3, 2015.

Example 9

TZM-bl Neutralization Profiles of V3 Antibodies

TZM-bl neutralization assay was conducted to determine neutralization potency and breadth of different viruses by DH542-L4, DH542, PGT128, PGT121, 10-1074, DH270 and DH471. FIGS. 14 and 15 show the results of neutralization against a panel of HIV isolates in the TZM-bl pseudovirus neutralization assay. FIGS. 14 and 15 also show the mean IC50, IC80 and percent of isolates neutralized at an different IC50 or IC80 values.

Example 10

Heavy and Light Chain Chimeric V3 Antibodies

This example describes chimeric antibodies comprising non-natural VH and VL chain pairs. Recombinantly expressed VH or VL chains from naturally occurring VH:VL pairs are combined in non-natural pairs as described in FIG. 25. Lines 2-4 in FIG. 25 show antibodies having DH542 VH chain paired with VLs from other antibodies from the DH270 lineage.

In some instances VH chains (I0848_00001_L1_4A; I0848_00004_L1_4A; I0848_00005_L1_4A; I0848_00006_L1_4A; I0848_00007_L1_4A) which were identified by Illumina sequences and not as natural VH:VL pair, were paired with VL sequences from a VH:VL pair with the closest VH sequence—lines 5-9 in FIG. 25. In other instances, VH chains (I0848_00001_L1_4A; I0848_00004_L1_4A; I0848_00005_L1_4A; I0848_00006_L1_4A; I0848_00007_L1_4A) were paired with DH542_QSA which is the corrected VL chain of DH542—lines 12-15 in FIG. 25.

For Illumina sequencing RNA was isolated from patient PBMCs using an RNAeasy isolation kit (Qiagen). RNA was reverse transcribed and PCR amplified with primers targeting the IgG VH1 family of Immunoglobulin genes. Illumina adapters were added by PCR using the Nextera sample prep kit (Illumina). Illumina cDNA libraries were quantified using qPCR (Kappa biosciences) and sequenced using Illumina Miseq (2×300bp; Illumina). Analysis of Immunoglobulin sequence genetics were performed using Cloanalyst software (T. Kepler; Boston University).

```
Primer Sequences:
                                       (SEQ ID NO: 283)
AGGTGTGCACGCCGCTGGTC IgG-RT;

(SEQ ID NO: 284)
TCGTCGGCAGCGTCAGATGTGTATAAGAGACAGCCATGGACTGGACCTG
GAGG VH1-Ext_P5_1^ST;

(SEQ ID NO: 285)
GTCTCGTGGGCTCGGAGATGTGTATAAGAGACAGCGATGGGCCCTTGGT
GGA HUIGG_Deep_R_P7_1^ST
```

Figure 27:
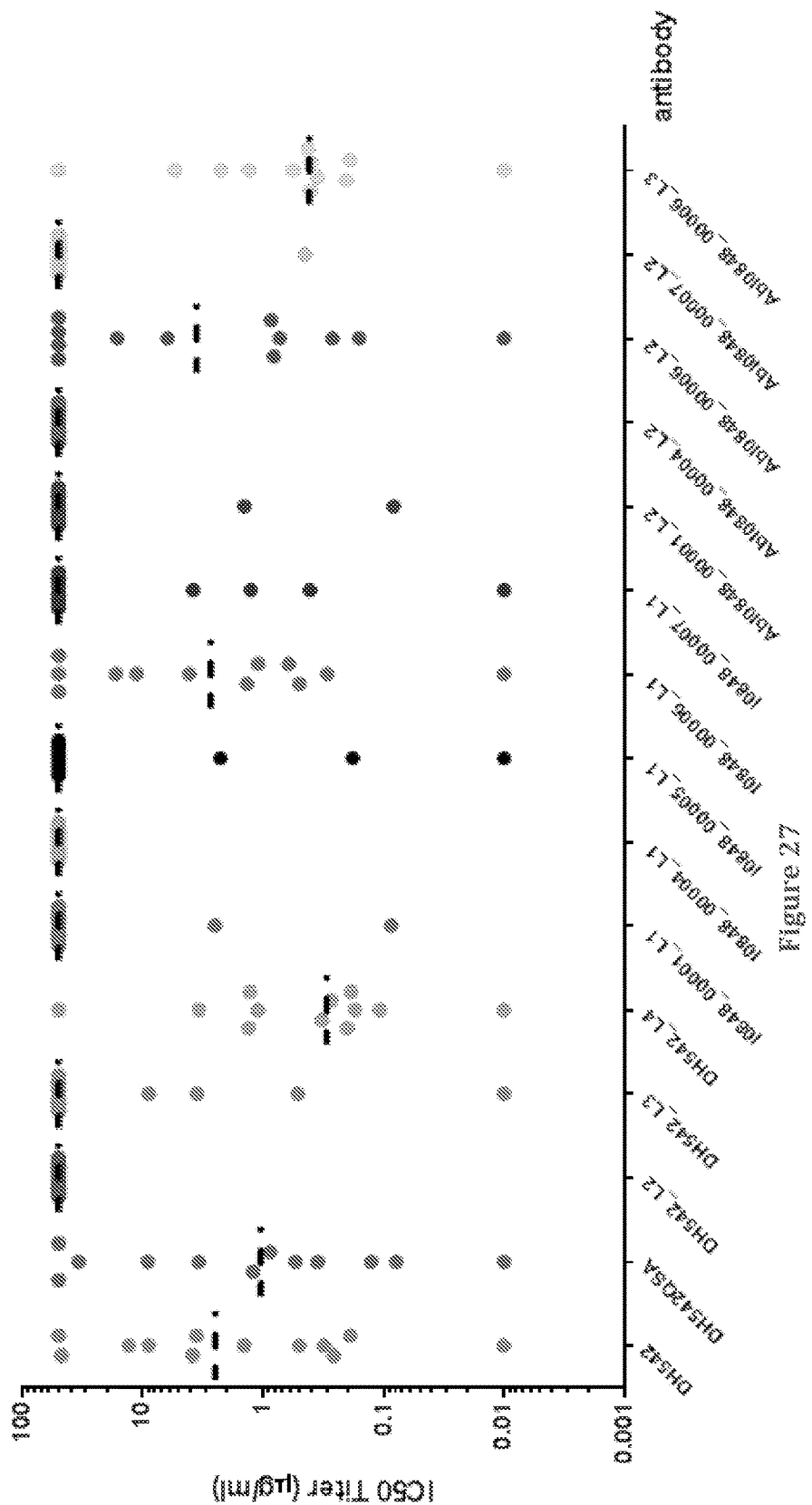
FIG. 27 shows a summary of neutralization data for the chimeric antibodies of Example 10. Dotted line shows median IC50 of all viruses including those not neutralized; <0.023 graphed as 0.01; >50 graphed as 50.

Neutralization by these antibodies was determined in the TZMB1 assay using a selection of viruses as shown in FIG. 26. Data in FIG. 26A and 26B show the neutralization profiles of these chimeric antibodies. Antibody DH542-L4-4A (also referred to as DH542-L4), comprising VH from DH542 and VL from DH429, shows improved neutralization potency compared to the DH542 antibody—FIGS. 26A and 27.

Throughout examples and figures VH sequences are referenced interchangeably as I0848_00001 or I0848_00001_L1_4A, I0848_00004 or I0848_00004_L1_4A I0848_00005 or I0848_00005_L1_4A, I0848_00006 or I0848_00006_L1_4A, I0848_00007 or I0848_00007_L1_4A.

Additional chimeric comprising non-natural VH and VL chain pairs are contemplated. In non-limiting examples, these pairings include VH and/or VL chains from antibodies DH542, DH542QSA, DH429, DH471, DH391, and/or DH473.

What is claimed is:

1. An anti-HIV-1 recombinant antibody or an antigen-binding fragment thereof, wherein the antibody or antigen-binding fragment thereof comprises:
   a VH chain that is 90%, 91%, 92%, 93%, 94%, 95%, 96%, 97%, 98%, 99% or 100% identical to the VH chain of SEQ ID NO: 3 and
   a VL chain that is 90%, 91%, 92%, 93%, 94%, 95%, 96%, 97%, 98%, 99% or 100% identical to the VL chain of SEQ ID NO: 4 or a VL chain that is 90%, 91%, 92%, 93%, 94%, 95%, 96%, 97%, 98%, 99% or 100% identical to the VL chain of SEQ ID NO: 155, or
   a VL chain that is 90%, 91%, 92%, 93%, 94, 95%, 96%, 97%, 98%, 99% or 100% identical to the VL chain of SEQ ID NO: 116.

2. An anti-HIV-1 recombinant antibody or an antigen-binding fragment thereof, wherein the antibody or antigen-binding fragment thereof comprises:
   a VH chain of SEQ ID NO: 3, 17, 19, 20, 21, 26, 27, 28, 162, 163, 164, 165 or 166 and
   a VL chain of SEQ ID NO: 41, 44, 45, 48, 50, 51, 52, 116 or 149.

3. The anti-HIV-1 recombinant antibody or antigen-binding fragment thereof of claim 1, wherein the antibody or antigen-binding fragment thereof comprises:
   a VH chain that is 90%, 91%, 92%, 93%, 94%, 95%, 96%, 97%, 98%, 99% or 100% identical to the VH chain of SEQ ID NO: 3 and
   a VL chain that is 90%, 91%, 92%, 93%, 94%, 95%, 96%, 97%, 98%, 99% or 100% identical to the VL chain of SEQ ID NO: 4.

4. The anti-HIV-1 recombinant antibody or antigen-binding fragment thereof of claim 1, wherein the antibody or antigen-binding fragment thereof comprises:
   a VH chain that is 90%, 91%, 92%, 93%, 94%, 95%, 96%, 97%, 98%, 99% or 100% identical to the VH chain of SEQ ID NO: 3 and
   a VL chain that is 90%, 91%, 92%, 93%, 94%, 95%, 96%, 97%, 98%, 99% or 100% identical to the VL chain of SEQ ID NO: 155.

5. The anti-HIV-1 recombinant antibody or antigen-binding fragment thereof of claim 1, wherein the antibody or antigen-binding fragment thereof comprises:
   a VH chain that is 90%, 91%, 92%, 93%, 94%, 95%, 96%, 97%, 98%, 99% or 100% identical to the VH chain of SEQ ID NO: 3 and
   a VL chain that is 90%, 91%, 92%, 93%, 94%, 95%, 96%, 97%, 98%, 99% or 100% identical to the VL chain of SEQ ID NO: 116.

6. The anti-HIV-1 recombinant antibody or antigen-binding fragment thereof of claim 1, wherein the antibody or fragment thereof comprises:
   a VH chain that is 90%, 91%, 92%, 93%, 94%, 95%, 96%, 97%, 98%, 99% or 100% identical to the VH chain of SEQ ID NO:3 and the VL chain of SEQ ID NO: 4, the VL chain of SEQ ID NO: 116 or the VL chain of SEQ ID NO: 155.

7. The anti-HIV-1 recombinant antibody or antigen-binding fragment thereof of claim 1 comprising the VH chain of SEQ ID NO: 3 and the VL chain of SEQ ID NO: 4.

8. The anti-HIV-1 recombinant antibody or antigen-binding fragment thereof of claim 1 comprising the VH chain of SEQ ID NO: 3 and the VL chain of SEQ ID NO: 116.

9. The anti-HIV-1 recombinant antibody or antigen-binding fragment thereof of claim 1 comprising the VH chain of SEQ ID NO: 3 and the VL chain of SEQ ID NO:155.

10. The anti-HIV-1 recombinant antibody or antigen-binding fragment thereof of claim 1, wherein the antibody or antigen-binding fragment thereof comprises a modified Fc portion.

11. The anti-HIV-1 recombinant antibody or antigen-binding fragment thereof of claim 1, wherein the antibody or antigen-binding fragment thereof is bispecific.

12. A pharmaceutical composition comprising any one of the antibodies or antigen-binding fragments thereof of claim 1.

13. A pharmaceutical composition comprising any one of the antibodies or antigen-binding fragments thereof of claim 1 and another HIV-1 broadly neutralizing antibody.

14. A composition comprising a vector comprising a nucleic acid encoding the antibody or antigen-binding fragment thereof of claim 1.

15. The composition of claim 14, wherein the vector is suitable for gene delivery and expression.

16. A method to treat HIV-1 infection in a subject comprising administering to the subject a composition comprising an anti-HIV-1 recombinant antibody or antigen-binding fragment thereof, wherein the antibody or antigen-binding fragment thereof comprises:
   a VH chain that is 90%, 91%, 92%, 93%, 94%, 95%, 96%, 97%, 98%, 99% or 100% identical to the VH chain of SEQ ID NO: 3 and
   a VL chain that is 90%, 91%, 92%, 93%, 94%, 95%, 96%, 97%, 98%, 99% or 100identical to the VL chain of SEQ ID NO: 4 or a VL chain that is 90%, 91%, 92%, 93%, 94%, 95%, 96%, 97%, 98%, 99% or 100% identical to the VL chain of SEQ ID NO:155 or
   a VL chain that is 90%, 91%, 92%, 93%, 94%, 95%, 96%, 97%, 98%, 99% or 100% identical to the VL chain of SEQ ID NO: 116 in a therapeutically effective amount.

17. The method of claim 16 wherein the pharmaceutical composition is administered in a therapeutically effective dose and regimen.

18. The method of claim 16 further comprising administering an additional HIV-1 broadly neutralizing antibody.

19. The method of claim 16, wherein the antibody or antigen-binding fragment is administered as a nucleic acid.

20. The method of claim 16, wherein the antibody or antigen-binding fragment comprises a modified Fc portion.

21. A method to treat HIV-1 infection in a subject comprising administering to the subject a composition comprising the anti-HIV-1 recombinant antibody or antigen-binding fragment thereof of claim 7 in a therapeutically effective amount.

22. A method to treat HIV-1 infection in a subject comprising administering to the subject a composition comprising the recombinant antibody or antigen-binding fragment thereof of claim 8 in a therapeutically effective amount.

23. A method to treat HIV-1 infection in a subject comprising administering to the subject a composition comprising the recombinant antibody or antigen-binding fragment thereof of claim 9 in a therapeutically effective amount.

24. The anti-HIV-1 envelope recombinant antibody or antigen-binding fragment thereof of claim 2, wherein the VL chain comprises an amino acid sequence of SEQ ID NO: 4, 147, 150, 151, 154, 155, or 156.

* * * * *